(12) United States Patent
Vo et al.

(10) Patent No.: US 11,525,119 B2
(45) Date of Patent: Dec. 13, 2022

(54) IMMUNE CELLS DERIVED FROM INDUCED PLURIPOTENT STEM CELL

(71) Applicants: THE CHILDREN'S MEDICAL CENTER CORPORATION, Boston, MA (US); PRESIDENT AND FELLOWS OF HARVARD COLLEGE, Cambridge, MA (US)

(72) Inventors: Linda Thuy Vo, Pacifica, CA (US); George Q. Daley, Weston, MA (US)

(73) Assignees: THE CHILDREN'S MEDICAL CENTER CORPORATION, Boston, MA (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 432 days.

(21) Appl. No.: 16/330,307

(22) PCT Filed: Sep. 6, 2017

(86) PCT No.: PCT/US2017/050167
§ 371 (c)(1),
(2) Date: Mar. 4, 2019

(87) PCT Pub. No.: WO2018/048828
PCT Pub. Date: Mar. 15, 2018

(65) Prior Publication Data
US 2019/0225940 A1    Jul. 25, 2019

Related U.S. Application Data

(60) Provisional application No. 62/383,984, filed on Sep. 6, 2016.

(51) Int. Cl.
| | | |
|---|---|---|
| *C12N 5/00* | (2006.01) | |
| *C12N 5/0783* | (2010.01) | |
| *C12N 15/85* | (2006.01) | |
| *A01K 67/027* | (2006.01) | |
| *C12N 5/0781* | (2010.01) | |

(52) U.S. Cl.
CPC ........ *C12N 5/0636* (2013.01); *A01K 67/0271* (2013.01); *C12N 5/0635* (2013.01); *C12N 15/85* (2013.01); *C12N 2501/065* (2013.01); *C12N 2501/42* (2013.01); *C12N 2501/60* (2013.01); *C12N 2501/602* (2013.01); *C12N 2501/603* (2013.01); *C12N 2501/604* (2013.01); *C12N 2501/606* (2013.01); *C12N 2501/608* (2013.01); *C12N 2501/65* (2013.01); *C12N 2506/11* (2013.01); *C12N 2506/45* (2013.01)

(58) Field of Classification Search
None
See application file for complete search history.

(56) References Cited

U.S. PATENT DOCUMENTS

| | | |
|---|---|---|
| 5,879,940 A | 3/1999 | Torok-Storb et al. |
| 6,103,522 A | 8/2000 | Torok-Storb et al. |
| 6,419,918 B1 | 7/2002 | Welte et al. |
| 6,838,549 B2 | 1/2005 | Welte et al. |
| 7,575,925 B2 | 8/2009 | Schmitt et al. |
| 7,883,861 B2 | 2/2011 | Rich |
| 7,989,178 B2 | 8/2011 | Rich |
| 8,034,613 B2 | 10/2011 | Slukvin et al. |
| 8,058,065 B2 | 11/2011 | Yamanaka et al. |
| 8,133,727 B2 | 3/2012 | Lou et al. |
| 8,206,979 B2 | 6/2012 | Giarratana et al. |
| 8,372,642 B2 | 2/2013 | Rajesh et al. |
| 8,772,028 B2 | 7/2014 | Zuniga-Pflucker et al. |
| 8,871,510 B2 | 10/2014 | Spangrude et al. |
| 8,926,964 B2 | 1/2015 | Hariri et al. |
| 9,045,738 B2 | 6/2015 | Yamanaka et al. |
| 9,206,394 B2 | 12/2015 | Nakauchi et al. |
| 9,273,285 B1 | 3/2016 | Wognum et al. |
| 9,452,186 B2 | 9/2016 | Shoemaker et al. |
| 9,834,754 B2 | 12/2017 | Keller et al. |
| 10,351,853 B2 * | 7/2019 | Ott .................. A61K 38/15 |
| 10,370,452 B2 | 8/2019 | Themeli et al. |
| 10,626,372 B1 | 4/2020 | Valamehr et al. |
| 10,640,570 B2 | 5/2020 | Kaufman et al. |
| 10,669,528 B2 | 6/2020 | Rossi et al. |
| 2003/0152558 A1 | 8/2003 | Luft et al. |
| 2004/0029271 A1 | 2/2004 | Busslinger et al. |
| 2005/0153443 A1 | 7/2005 | Lanza et al. |

(Continued)

FOREIGN PATENT DOCUMENTS

| | | |
|---|---|---|
| EP | 2782996 B1 | 10/2014 |
| EP | 2352816 B1 | 6/2015 |

(Continued)

OTHER PUBLICATIONS

Aptamer—Wikipedia; pp. 1-17; downloaded Jun. 14, 2021.*
Park, et al., (2008). Reprogramming of human somatic cells to pluripotency with defined factors. Nature 451, 141-146.*
Konze etal ACS Chem Biol. Jun. 21, 2013; 8(6): 1324-1334 An Orally Bioavailable Chemical Probe of the Lysine Methyltransferases EZH2 and EZH1.*
Methyltransferase From Wikipedia, the free encyclopedia pp. 1-10; downloaded Nov. 23, 2021.*

(Continued)

*Primary Examiner* — Maria G Leavitt
(74) *Attorney, Agent, or Firm* — Nixon Peabody LLP; David S. Resnick; Jeanne Jodoin

(57) ABSTRACT

Embodiments disclosed here are production methods and compositions of engineered immune cells, such as B or T lymphocytes, from limited lineage myeloid progenitor cells, or from pluripotent stem cells, or from multilineage hematopoietic progenitor cells comprising the addition of various cell differentiation transcription factors and inhibiting epigenetic histone methylations in said cells.

19 Claims, 34 Drawing Sheets

Specification includes a Sequence Listing.

(56) References Cited

U.S. PATENT DOCUMENTS

| | | |
|---|---|---|
| 2006/0003322 A1* | 1/2006 | Bentwich ............ C12N 15/113 435/6.16 |
| 2009/0217403 A1 | 8/2009 | Spits |
| 2010/0047854 A1 | 2/2010 | Mugishima et al. |
| 2011/0027881 A1 | 2/2011 | Seino et al. |
| 2011/0052554 A1 | 3/2011 | Zakrzewski et al. |
| 2011/0123502 A1 | 5/2011 | Barry et al. |
| 2011/0223669 A1 | 9/2011 | Yamanaka et al. |
| 2011/0236363 A1 | 9/2011 | Chang et al. |
| 2012/0040362 A1 | 2/2012 | Slukvin et al. |
| 2012/0129262 A1 | 5/2012 | West et al. |
| 2012/0149100 A1 | 6/2012 | Keller et al. |
| 2012/0214243 A1 | 8/2012 | Yamanaka et al. |
| 2013/0059386 A1 | 3/2013 | Yamanaka et al. |
| 2013/0078226 A1 | 3/2013 | Nakauchi et al. |
| 2013/0183759 A1 | 7/2013 | Yamanaka et al. |
| 2013/0281304 A1 | 10/2013 | Feinberg et al. |
| 2014/0037599 A1 | 2/2014 | Bhandoola et al. |
| 2014/0248248 A1 | 9/2014 | Zuniga-Pflucker et al. |
| 2014/0273211 A1 | 9/2014 | Slukvin et al. |
| 2014/0322808 A1 | 10/2014 | Keller et al. |
| 2018/0002699 A1* | 1/2018 | Ott ........................ A61K 31/19 |
| 2018/0072992 A1 | 3/2018 | Valamehr et al. |
| 2018/0298337 A1 | 10/2018 | Kaneko et al. |
| 2018/0305664 A1 | 10/2018 | Vodyanyk et al. |
| 2018/0320137 A1 | 11/2018 | Valamehr et al. |
| 2019/0161727 A1 | 5/2019 | Kawamoto et al. |
| 2019/0271005 A1 | 9/2019 | Valamehr et al. |
| 2019/0330596 A1 | 10/2019 | Kaneko et al. |
| 2020/0248142 A1 | 8/2020 | Valamehr et al. |

FOREIGN PATENT DOCUMENTS

| | | |
|---|---|---|
| WO | 2011/159684 A2 | 12/2011 |
| WO | 2017/088012 A1 | 1/2017 |
| WO | 2017/1610001 A1 | 9/2017 |

OTHER PUBLICATIONS

Vivier et al., "Innate or adaptive immunity? The example of natural killer cells." Science 331.6013 (2011): 44-49.
Beck et al., "The Notch ligands Jagged2, Deltal, and Delta4 induce differentiation and expansion of functional human NK cells from CD34+ cord blood hematopoietic progenitor cells." Biology of Blood and Marrow Transplantation 15.9 (2009): 1026-1037.
Felices et al., "Notch signaling at later stages of NK cell development enhances KIR expression and functional maturation." The Journal of Immunology 193.7 (2014): 3344-3354.
Haraguchi et al., "Notch activation induces the generation of functional NK cells from human cord blood CD34-positive cells devoid of IL-15." The Journal of Immunology 182.10 (2009): 6168-6178.
Abdalkader et al., "In aggressive variants of non-Hodgkin lymphomas, Ezh2 is strongly expressed and polycomb repressive complex PRC1.4 dominates over PRC1.2.", Virchows Arch. 463(5):697-711 (2013).
Abdalkader et al., "Aberrant differential expression of EZH1 and EZH2 in Polycomb repressive complex 2 among B- and T/NK-cell neoplasms" Pathology. 48(5):467-82 (2016).
Abel et al., "Characterization of EZH1, a human homolog of *Drosophila* Enhancer of zeste near BRCA1", Genomics. 15;37(2):161-71 (1996).
Antignano et al., "Methyltransferase G9A regulates T cell differentiation during murine intestinal inflammation", J Clin Invest. 124(5): 1945-1955 (2014).
Attema et al., "Epigenetic characterization of hematopoietic stem cell differentiation using miniChIP and bisulfite sequencing analysis", PNAS 104(30): 12371-12376 (2007).
Bachmann et al., "EZH2 expression is associated with high proliferation rate and aggressive tumor subgroups in cutaneous melanoma and cancers of the endometrium, prostate, and breast", J Clin Oncol. 10;24(2):268-273 (2006).

Baron et al., "The specification of early hematopoiesis in the mammal", Curr Opin Hematol. 12(3): 217-221 (2005).
Bertrand et al., "Characterization of purified intraembryonic hematopoietic stem cells as a tool to define their site of origin", Proc Natl Acad Sci USA 102(1):134-139 (2005).
Blaumueller et al., "Intracellular Clevage of Notch Leads to a Hereodimeric Receptor on the Plasma Membrane" Cell 90(2): 281-291 (1997).
Boiers et al., "Lymphomyeloid contribution of an immune-restricted progenitor emerging prior to definitive hematopoietic stem cells" Cell Stem Cell. 13(5):535-48 (2013).
Boisett et al., "In vivo imaging of haematopoietic cells emerging from the mouse aortic endothelium", Nature. 4;464 (7285):116-20 (2010).
Buenrostro et al., Transposition of native chromatin for fast and sensitive epigenomic profiling of open chromatin, DNA-binding proteins and nucleosome position., Nat Methods. 10(12):1213-1218 (2013).
Cacchiarelli et al., "Integrative Analyses of Human Reprogramming Reveal Dynamic Nature of Induced Pluripotency", Cell. 16;162(2):412-424 (2015).
Cedar et al., "Epigenetics of haematopoietic cell development" Nature Reviews Immunology 11(7):478-488 (2011).
Chadwick et al., "Cytokines and BMP-4 promote hematopoietic differentiation of human embryonic stem cells" Blood, 102:906-915 (2003).
Chanda et al., "Retinoic acid signaling is essential for embryonic hematopoietic stem cell development", Cell. 155 (1):215-27 (2013).
Chen et al., "Conversion of peripheral CD4+CD25- naive T cells to CD4+CD25+ regulatory T cells by TGF-β induction of transcription factor Foxp3", J. Exp. Med., vol. 198, pp. 1875-1886 (2003).
Chen et al., "G9a/GLP-dependent histone H3K9me2 patterning during human hematopoietic stem cell lineage commitment" Genes Dev. 26(22):2499-511 (2012).
Choi et al., "Human T cell development in the liver of humanized NOD/SCID/IL-2Rγ(null)(NSG) mice generated by intrahepatic injection of CD34(+) human (h) cord blood (CB) cells", Clin Immunol. 139(3):321-335 (2011).
Dallas et al., "Density of the Notch ligand Delta1 determines generation of B and T cell precursors from hematopoietic stem cells", J Exp Med. 201(9): 1361-1366 (2005).
Dambacher et al., "Epigenetic regulation of development by histone lysine methylation" Heredity (Edinb). 105 (1):24-37 (2010).
Ditadi et al., "Human definitive haemogenic endothelium and arterial vascular endothelium represent distinct lineages", Nat Cell Biol.17(5):580-591 (2015).
Dou et al., "Medial HOXA genes demarcate haematopoietic stem cell fate during human development", Nat Cell Biol. 18(6):595-606 (2016).
Doulatov et al., "Hematopoiesis: a human perspective", Cell Stem Cell. 10(2):120-36 (2012).
Doulatov et al., "Revised map of the human progenitor hierarchy shows the origin of macrophages and dendritic cells in early lymphoid development", Nat Immunol (7):585-93 (2010).
Dzierzak et al., "Of lineage and legacy: the development of mammalian hematopoietic stem cells" Nat Immunol 9(2):129-36 (2008).
Fazi et al., "A minicircuitry comprised of microRNA-223 and transcription factors NFI-A and C/EBPalpha regulates human granulopoiesis" Cell 123(5):819-31 (2005).
Ferkowicz et al., "Blood island formation: longstanding observations and modern interpretations" Exp Hematol 33(9):1041-7 (2005).
Hidalgo et al., "Ezh1 is required for hematopoietic stem cell maintenance and prevents senescence-like cell cycle arrest" Cell Stem Cell 11(5):649-62 (2012).
Holmes et al., "The OP9-DL1 system: generation of T-lymphocytes from embryonic or hematopoietic stem cells in vitro", Cold Spring Harb Protoc. 2009(2):pdb.prot5156. (2009).
Huang et al., "A network of epigenetic regulators guides developmental haematopoiesis in vivo" Nat Cell Biol. 15(12):1516-25 (2013).
Huangfu et al., "Induction of pluripotent stem cells by defined factors is greatly improved by small-molecule compounds" Nature Biotechnology 26(7):795-797 (2008).

(56) References Cited

OTHER PUBLICATIONS

Ikeda et al., "Maintenance of the functional integrity of mouse hematopoiesis by EED and promotion of leukemogenesis by EED haploinsufficiency", Sci Rep. 6:29454 (2016).
Ikawa et al., "Long-term cultured E2A-deficient hematopoietic progenitor cells are pluripotent", Immunity, vol. 20; 349-360 (2004).
Jones et al., "The Drosophila esc and E(z) proteins are direct partners in polycomb group-mediated repression", Mol Cell Biol. 18(5):2825-34 (1998).
June et al., "Adoptive cellular therapy: a race to the finish line", Sci Transl Med. 7(280):280ps7 (2015).
Kawamoto et al., "Extensive proliferation of T cell lineage-restricted progenitors in the thymus: an essential process for clonal expression of diverse T cell receptor beta chains" Eur. J. Immunol., vol. 33, 606-615 (2003).
Kennedy et al., "T lymphocyte potential marks the emergence of definitive hematopoietic progenitors in human pluripotent stem cell differentiation cultures", Cell Rep. 2(6):1722-1735. (2012).
Kinkel et al., "Jarid2 regulates hematopoietic stem cell function by acting with polycomb repressive complex 2" Blood. 125(12):1890-900(2015).
Kyba et al., "HoxB4 confers definitive lymphoid-myeloid engraftment potential on embryonic stem cell and yolk sac hematopoietic progenitors" Cell 109(1):29-37 (2002).
Laible et al., "Mammalian homologues of the Polycomb-group gene Enhancer of zeste mediate gene silencing in Drosophila heterochromatin and at S. cerevisiae telomeres" EMBO J. 16(11):3219-32 (1997).
Laurenti et al.,"The transcriptional architecture of early human hematopoiesis identifies multilevel control of lymphoid commitment" Nat Immunol. 14(7):756-63 (2013).
Lee et al., "Forced expression of HoxB4 enhances hematopoietic differentiation by human embryonic stem cells" Mol Cells.25(4):487-493 (2008).
Lee et al., "DACH1 regulates cell cycle progression of myeloid cells through the control of cyclin D, Cdk 4/6 and p21Cip1" Biochem Biophys Res Commun. 420(1):91-95 (2012).
Lee et al., "Regulation of HOXA9 activity by predominant expression of DACH1 against C/EBPa and GATA-1 in myeloid leukemia with MLL-AF9" Biochem Biophys Res Commun. 426(3):299-305 (2012).
Lee et al., "Polycomb repressive complex 2 component Suz12 is required for hematopoietic stem cell function and lymphopoiesis", Blood. 126(2):167-75 (2015).
Maes et al., "Lymphoid-affiliated genes are associated with active histone modifications in human hematopoietic stem cells" Blood, 112 (7):2722-2729 (2008).
Majewski et al., "Opposing roles of polycomb repressive complexes in hematopoietic stem and progenitor cells" Blood. 116(5):731-739 (2010).
Majewski et al., "Polycomb repressive complex 2 (PRC2) restricts hematopoietic stem cell activity", PLoS Biol. 6 (4):e93 (2008).
Margueron et al., "Ezh1 and Ezh2 maintain repressive chromatin through different mechanisms" Mol Cell. 32 (4):503-518 (2008).
Born et al., "The function of gammadelta T cells in innate immunity." Current opinion in immunology 18.1 (2006): 31-38.
Pineda et al., "Differentiation patterns of embryonic stem cells in two-versus three-dimensional culture." Cells Tissues Organs 197.5 (2013): 399-410.
Tabatabaei-Zavareh et al., "Stroma-free, serum-free differentiation and expansion of hematopoietic progenitors to the T cell lineage." Experimental Hematology 44.9 (2016): Supplement S101. Abstract.
Wang et al., "Distinct roles of IL-7 and stem cell factor in the OP9-DL1 T-cell differentiation culture system." Experimental hematology 34.12 (2006): 1730-1740.
Wu et al. "Structural biology of human H3K9 methyltransferases." PLoS One 5.1 (2010):e8570.
Greiner et al. Identification of a specific inhibitor of the histone methyltransferase SU(VAR)3-9. Nature Chemical Biology 1(3), 143-145 (2005).
Liu et al. Optimization of cellular activity of G9a inhibitors 7-aminoalkoxy-quinazolines. Journal of Medicinal Chemistry 54(17), 6139-6150 (2011).
Liu et al. Protein Lysine Methyltransferase G9a Inhibitors: Design, Synthesis, and Structure Activity Relationships of 2,4-Diamino-7-aminoalkoxy-quinazolines. J Med Chem. Aug. 12, 2010; 53(15): 5844-5857.
Liu et al., Discovery of a 2,4-Diamino-7-aminoalkoxy-quinazoline as a Potent and Selective Inhibitor of Histone Lysine Methyltransferase G9a. J Med Chem. Dec. 24, 2009; 52(24): 7950-7953.
Kondengaden et al., Discovery of novel small molecule inhibitors of lysine methyltransferase G9a and their mechanism in leukemia cell lines. Eur J Med Chem. Oct. 21, 2016;122:382-393.
Yuan et al. A Small-Molecule Probe of the Histone Methyltransferase G9a Induces Cellular Senescence in Pancreatic Adenocarcinoma, ACS Chem Biol. Jul. 20, 2012; 7(7): 1152-1157.
Chang et al. (2010). Adding a lysine mimic in the design of potent inhibitors of histone lysine methyltransferases. J Mol Biol. Jul. 2, 2010; 400(1): 1-7.
Christman et al. 5-Methyl-2'-deoxycytidine in single-stranded DNA can act in cis to signal de novo DNA methylation. Proceedings of the National Academy of Sciences of the United States of America 92(16), 7347-7351 (1995).
Margueron et al., "The Polycomb complex PRC2 and its mark in life", Nature 469:343-349 (2011).
Marson et al., "Wnt signaling promotes reprogramming of somatic cells to pluripotency" Cell Stem Cell 3(2):132-135 (2008).
McCabe et al., "EZH2 inhibition as a therapeutic strategy for lymphoma with EZH2-activating mutations" Nature. 492 (7427):108-112 (2012).
McGrath et al., "Expression of homeobox genes, including an insulin promoting factor, in the murine yolk sac at the time of hematopoietic initiation" Mol Reprod Dev. 48(2):145-153 (1997).
McKinney-Freeman et al., "The transcriptional landscape of hematopoietic stem cell ontogeny" Cell Stem Cell. 11 (5):701-14(2012).
McLean et al., "GREAT improves functional interpretation of cis-regulatory regions" Nat Biotechnol. 28(5):495-501 (2010).
Medvinsky et al., "Definitive hematopoiesis is autonomously initiated by the AGM region" Cell. 86(6):897-906 (1996).
Meerbrey et al., "The pINDUCER lentiviral toolkit for inducible RNA interference in vitro and in vivo", PNAS 108 (9):3665-3670 (2011).
Miranda-Saavedra et al., "BloodExpress: a database of gene expression in mouse haematopoiesis" Nucleic Acids Res. 37(Database issue) 873-879 (2009).
Mochizuki-Kashio et al., "Dependency on the polycomb gene Ezh2 distinguishes fetal from adult hematopoietic stem cells", Blood. 118(25):6553-6561 (2011).
Mohtashami et al., "Direct Comparison of Dll1- and Dll4-Mediated Notch Activation Levels Shows Differential Lymphomyeloid Lineage Commitment Outcome", J Immunol. 185(2):867-876 (2010).
Morin et al., "Somatic mutations altering EZH2 (Tyr641) in follicular and diffuse large B-cell lymphomas of germinal-center origin", Nat Genet. 42(2):181-185 (2010).
Mousavi et al., "Polycomb protein Ezh1 promotes RNA polymerase II elongation" Mol Cell. 45(2):255-262 (2012).
Muller et al. "Development of hematopoietic stem cell activity in the mouse embryo" Immunity. 1(4):291-301. (1994).
Muller et al., "Histone methyltransferase activity of a Drosophila Polycomb group repressor complex" Cell. 111 (2):197-208 (2002).
Nishihara et al., "A combination of stem cell factor and granulocyte colony-stimulating factor enhances the growth of human progenitor B cells supported by murine stromal cell line MS-5" Eur J Immunol. 28(3):855-864 (1998).
North et al., "Runx1 expression marks long-term repopulating hematopoietic stem cells in the midgestation mouse embryo" Immunity. 16(5):661-672 (2002).
Novershtern et al., "Densely interconnected transcriptional circuits control cell states in human hematopoiesis" Cell. 144(2):296-309(2011).

(56) References Cited

OTHER PUBLICATIONS

Ohishi et al., "Delta-1 enhances marrow and thymus repopulating ability of human CD34(+)CD38(-) cord blood cells" J Clin Invest. 110(8):1165-1174 (2002).
Ohkawara et al., "Culture system for extensive production of CD19+IgM cells by human cord blood CD34+ progenitors", Leukemia. 12(5):764-771 (1998).
Onder et al., "Chromatin-modifying enzymes as modulators of reprogramming" Nature. 483(7391):598-602 (2012).
Orkin et al., "Hematopoiesis: an evolving paradigm for stem cell biology" Cell. 132(4):631-644 (2008).
Park et al., "Disease-specific induced pluripotent stem (iPS) cells" Cell. 134(5): 877-886 (2008).
Pereira et al., "From blood to blood': de-differentiation of hematopoietic progenitors to stem cells" EMBO J. 33(14): 1511-1513(2014).
Ramos-Mejia et al., "HOXA9 promotes hematopoietic commitment of human embryonic stem cells" Blood. 124 (20):3065-3075 (2014).
Rea et al., "Regulation of chromatin structure by site-specific histone H3 methyltransferases" Nature 406:593-599 (2000).
Riolobos et al., "HLA engineering of human pluripotent stem cells" Mol Ther. 21(6):1232-1241 (2013).
Rowe et al., "Engineering Hematopoietic Stem Cells: Lessons from Development" Cell Stem Cell. 18(6):707-720 (2016).
Sarkar et al., "Small molecules enhance autophagy and reduce toxicity in Huntington's disease models" Nat Chem Biol. 3(6):331-338 (2007).
Sauvageau et al., "Differential expression of homeobox genes in functionally distinct CD34+ subpopulations of human bone marrow cells" Proc Natl Acad Sci U S A. 91(25):12223-7 (1994).
Schimtt et al., "Induction of T cell development from hematopoietic progenitor cells by delta-like-1 in vitro", Immunity 17:749-756 (2002).
Shen et al., "EZH1 mediates methylation on histone H3 lysine 27 and complements EZH2 in maintaining stem cell identity and executing pluripotency" Mol Cell. 32(4):491-502 (2008).
Shi et al., "A Combined Chemical and Genetic Approach for the Generation of Induced Pluripotent Stem Cells" Cell Stem Cell 2:525-528 (2008).
Shimizu et al., "Binding of Delta1, Jagged1, and Jagged2 to Notch2 Rapidly Induces Cleavage, Nuclear Translocation, and Hyperphosphorylation of Notch2" Mol. Cell. Biol. 20 (18): 6913-22 (2000).
Shimizu et al., "Manic Fringe and Lunatic Fringe Modify Different Sites of the Notch2 Extracellular Region, Resulting in Different Signaling Modulation", J. Biol. Chem. 276 (28): 25753-8 (2001).
Simon et al., "Mechanisms of polycomb gene silencing: knowns and unknowns" Nat Rev Mol Cell Biol. 10 (10):697-708 (2009).
Sparmann et al., "Polycomb silencers control cell fate, development and cancer", Nat Rev Cancer. 6(11):846-56 (2006).
Sridharan et al., "Proteomic and genomic approaches reveal critical functions of H3K9 methylation and heterochromatin protein-1γ in reprogramming to pluripotency" Nat Cell Biol. 15(7):872-82 (2013).
Starnes et al., "NFI-A directs the fate of hematopoietic progenitors to the erythroid or granulocytic lineage and controls beta-globin and G-CSF receptor expression" Blood. 114(9):1753-63 (2009).
Sturgeon et al., "Wnt signaling controls the specification of definitive and primitive hematopoiesis from human pluripotent stem cells" Nat Biotechnol. 32(6):554-61 (2014).
Takahashi et al., "Induction of pluripotent stem cells from mouse embryonic and adult fibroblast cultures by defined factors" Cell. 126(4):663-676 (2006).
Tashiro et al., "Promotion of hematopoietic differentiation from mouse induced pluripotent stem cells by transient HoxB4 transduction" Stem Cell Res. 8:300-311 (2012).
Tavian et al., "The changing cellular environments of hematopoiesis in human development in utero", Exp Hematol. 33(9):1062-1069 (2005).
Themeli et al., "Generation of tumor-targeted human T lymphocytes from induced pluripotent stem cells for cancer therapy", Nat Biotechnol. 31(10):928-933 (2013).

Themeli et al., "New cell sources for T cell engineering and adoptive immunotherapy", Cell Stem Cell. 16(4):357-66 (2015).
Timmermans et al., "Generation of T cells from human embryonic stem cell-derived hematopoietic zones", J Immunol. 182(11):6879-88 (2009).
Ugarte et al., "Progressive Chromatin Condensation and H3K9 Methylation Regulate the Differentiation of Embryonic and Hematopoietic Stem Cells" Stem Cell Reports. 5(5):728-40 (2015).
Van Lohuizen et al., "Interaction of mouse polycomb-group (Pc-G) proteins Enx1 and Enx2 with Eed: indication for separate Pc-G complexes" Mol Cell Biol. 18(6):3572-3579. (1998).
Varambally et al., "The polycomb group protein EZH2 is involved in progression of prostate cancer", Nature. 419 (6907):624-9 (2002).
Varnum-Finney et al. "Immobilization of Notch ligand, Delta-1, is required for induction of notch signaling", J Cell Sci. 23:4313-8 (2000).
Vo et al., "De novo generation of HSCs from somatic and pluripotent stem cell sources" Blood. 125(17):2641-8 (2015).
Wang et al. "Generation of hematopoietic repopulating cells from human embryonic stem cells independent of ectopic HOXB4 expression" J Exp Med. 201(10):1603-1614 (2005).
Wang et al., "EZH2 and STAT6 expression profiles are correlated with colorectal cancer stage and prognosis" World J Gastroenterol. 16(19):2421-7 (2010).
Warren et al., "Highly Efficient Reprogramming to Pluripotency and Directed Differentiation of Human Cells with Synthetic Modified mRNA" Cell Stem Cell, 7(5):618-30 (2010).
Watarai et al. "Murine induced pluripotent stem cells can be derived from and differentiate into natural killer T cells" J Clin Invest. 120(7):2610-2618 (2010).
Xie et al., "Polycomb repressive complex 2 regulates normal hematopoietic stem cell function in a developmental-stage-specific manner" Cell Stem Cell. 14(1):68-80 (2014).
Xu et al. "Developmental control of polycomb subunit composition by GATA factors mediates a switch to non-canonica functions" Mol Cell. 57(2):304-16 (2015).
Yap et al. "Somatic mutations at EZH2 Y641 act dominantly through a mechanism of selectively altered PRC2 catalytic activity, to increase H3K27 trimethylation" Blood. 117(8):2451-9 (2011).
Yoshimoto et al. "Autonomous murine T-cell progenitor production in the extra-embryonic yolk sac before HSC emergence" Blood. 119(24):5706-14 (2012).
Yoshimoto et al. "Embryonic day 9 yolk sac and intra-embryonic hemogenic endothelium independently generate a B-1 and marginal zone progenitor lacking B-2 potential" Proc Natl Acad Sci U S A. 108(4):1468-73. (2011).
Yu et al. "Integrative genomics analysis reveals silencing of beta-adrenergic signaling by polycomb in prostate cancer" Cancer Cell. 12(5):419-31 (2007).
Bone Marrow (Hematopoietic) Stem Cells 13-34 (2016), available on the World Wide Web at //stemcells.nih.gov/info/Regenerative_Medicine/2006Chapter2.htm.
Wognum et al., "Hematopoietic Stem and Progenitor Cells", Stemcell Technologies Doc 29068 (6.0) 2015, available on the World Wide Web at cdn.stemcell.com/media/files/minireview/MR29068-Hematopoietic_Stem_and_Progenitor_Cells.pdf.
Smith et al., "In Vitro T-Cell Generation From Adult, Embryonic, and Induced Pluripotent Stem Cells: Many Roads to One Destination", Stem Cells 33(11):3174-3180 (2015).
Kuntz et at al., "The discovery and pre-clinical development of the first clinical stage EZH2-inhibitor, EPZ-6438 (E7438)", 26th EORTC—NCI—AACR Symposium on Molecular Targets and Cancer Therapeutics, Abstract 277 (2014).
Kaniskan et al., "Selective Inhibitors of Protein Methyltransferases", Journal of Medicinal Chemistry 58(4): 1596-1629 (2014).
Doulatov et al., "Induction of multipotential hematopoietic progenitors from human pluripotent stem cells via respecification of lineage-restricted precursors" Cell Stem Cell 13(4):459-470 (2013).
Yin et al., "Ezh2 regulates differentiation and function of natural killer cells through histone methyltransferase activity." PNAS 112(52):15988-15993 (2015).

\* cited by examiner

Fig. 2E
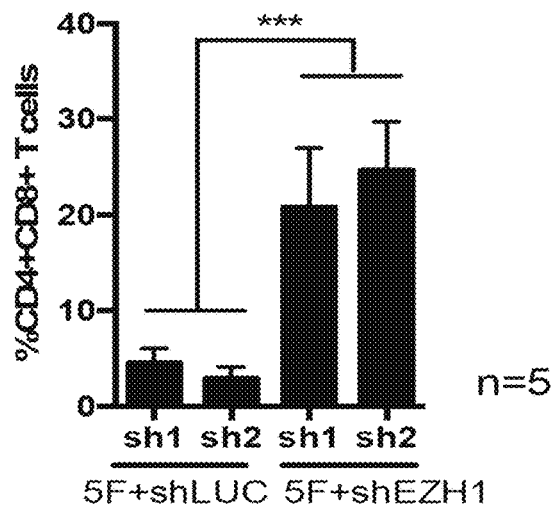
Fig. 2F
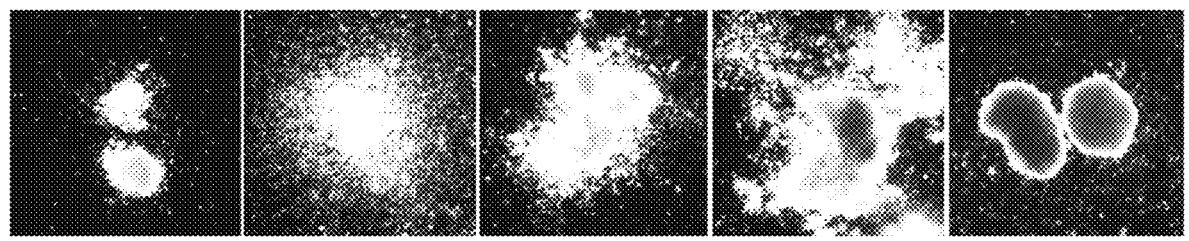
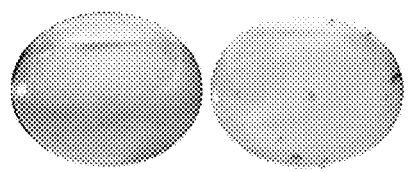
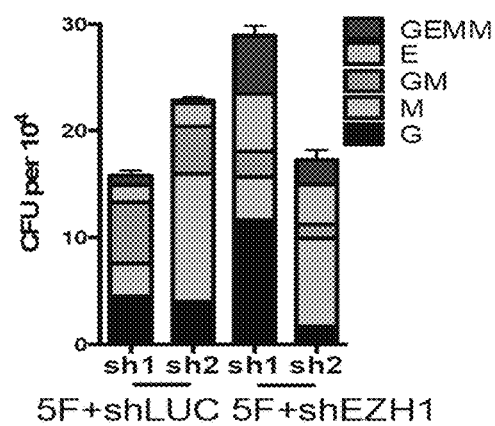

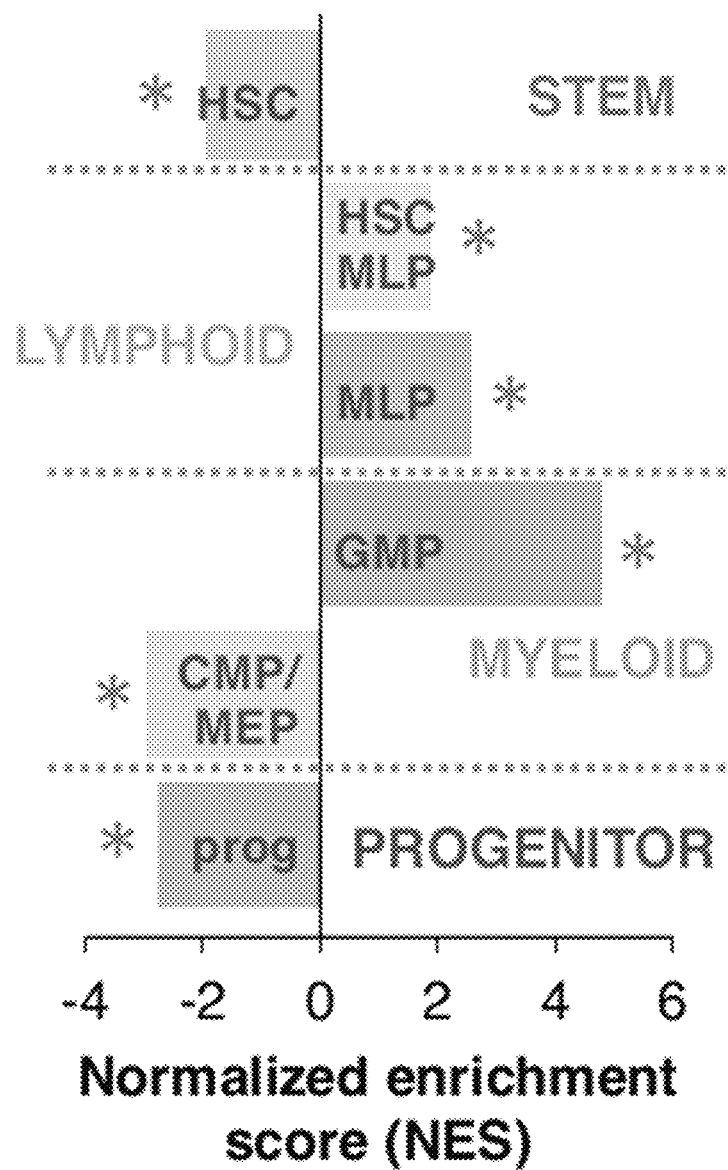

Fig. 4E

Total upregulated 1,545 peaks; Top enriched GO terms (by GREAT):

| Term | Binom Raw P-Value |
|---|---|
| T cell activation involved in immune response | 4.8659e-6 |
| Lymphocyte activation involved in immune response | 7.3480e-6 |

Fig. 4F

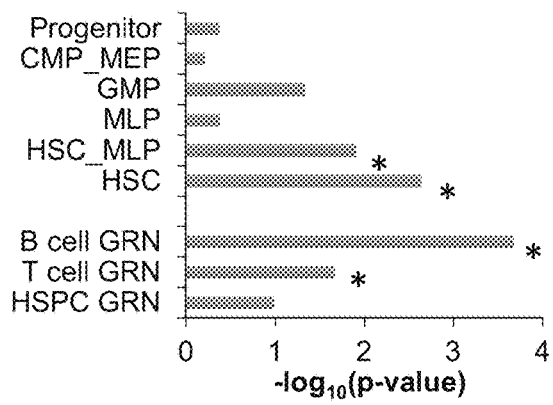

Fig. 4G

Total downregulated 1,632 peaks; Top enriched GO terms (by GREAT):

| Term name | Binom Raw P-Value |
|---|---|
| Negative regulation of reproductive process | 7.4808e-11 |
| Ventricular septum morphogenesis | 9.5057e-6 |
| Regulation of establishment of cell polarity | 3.9118e-5 |
| Commissural neuron axon guidance | 4.0169e-5 |
| Anterior/posterior axis specification, embryo | 2.5377e-4 |
| Mast cell mediated immunity | 5.9057e-4 |
| Embryonic hematopoiesis | 1.2567e-3 |
| Regulation of cell adhesion mediated by integrin | 1.2808e-3 |

-log$_{10}$(p-value)

| Histone methyltransferases | DNA methyltransferases | Methylated DNA binding proteins | Polycomb repressive complex 1/2 |
|---|---|---|---|
| SUV39H1 | DNMT3A | MECP2 | BMI1 |
| DOT1L | DNMT1 | MBD1 | RING1 |
| SMYD2 | | MBD2 | SUZ12 |
| SUV39H2 | | MBD3 | EZH2 |
| G9A | | MBD4 | EED |
| SETDB1 | | | EZH1 |
| EHMT1 | | | |

Fig. 9A

Total 988 nearest neighbor genes; Top enriched GO terms (by DAVID):

| Term | P-Value |
| --- | --- |
| Protein amino acid phospohorylation | 3.0e-4 |
| Phosphate metabolic process | 2.0e-3 |
| Intracellular signaling cascade | 2.6e-3 |
| Locomotory behavior | 4.1e-3 |
| Protein localization | 4.3e-3 |
| Intracellular transport | 7.0e-3 |
| Biological adhesion | 7.3e-3 |
| Positive regulation of T cell differentiation | 8.8e-3 |
| Behavior | 9.7e-3 |

Fig. 9B

Total 969 nearest neighbor genes; Top enriched GO terms (by DAVID):

| Term | P-Value |
| --- | --- |
| Tube development | 9.9e-5 |
| Secretion | 1.3e-3 |
| Learning or memory | 1.9e-3 |
| Positive regulation of developmental process | 2.4e-3 |
| Central nervous system neuron axonogenesis | 2.6e-3 |
| Respiratory system development | 4.6e-3 |
| Cell protection organization | 4.8e-3 |
| Di-, tri-valent inorganic cation transport | 5.8e-3 |
| Lung development | 7.2e-3 |

Fig. 9C

| title | overlap | all mRNA genes | gene signature | EZH1 KO affected genes | p value | overlap_gene_list |
|---|---|---|---|---|---|---|
| up_regulated_enriched_HSPC GRN | 3 | 20229 | 29 | 791 | 0.102742103 | FLT3;RNASE3;TRIM58 |
| up_regulated_enriched_T cell GRN | 9 | 20229 | 105 | 791 | 0.021859017 | CCDC88C;CD2;CD226;CD96;IL2RA;PCED1B;SIT1;SKAP1;TNFSF8 |
| up_regulated_enriched_B cell GRN | 16 | 20229 | 147 | 791 | 0.000921106 | AFF3;AIM2;AMKRD44;ARHGAP25;OTNBP1;EBF1;FAM65B;FGD2;KIAA0226L;MDM4;NIN;SIDT1;SP110;SSH2;WDFY4;ZCCHC7 |
| up_regulated_enriched_CMP_MEP | 5 | 20229 | 135 | 791 | 0.611908848 | CD38;FST;MAOA;OSBPL6;XK |
| up_regulated_enriched_GMP | 10 | 20229 | 139 | 791 | 0.046388341 | ASGR2;CD31D;CD38;COL4A6;IFI30;RAB27A;RNASE3;S100A9;SH3BP5;TRIM14 |
| up_regulated_enriched_HSC | 13 | 20229 | 134 | 791 | 0.002309775 | ALDH1A1;ANK3;BMP6;DPYD;GMAP2;ITGA6;KLF4;KLDBZ;LIMCH1;PDE10A;PIAS2;RPS6KA2;SKAP1 |
| up_regulated_enriched_HSC_MLP | 11 | 20229 | 129 | 791 | 0.012431679 | AMN1;ANK3;GIMAP2;HOPX;ITGA6;KLF4;LCOR;PIAS2;SCMH1;TMEM200A;TSPAN7 |
| up_regulated_enriched_MLP | 6 | 20229 | 133 | 791 | 0.419970886 | AK5;EBF1;ITGA8;KRT80;TMEM200A;TSPAN7 |
| up_regulated_enriched_progenitor | 6 | 20229 | 134 | 791 | 0.426959905 | CD38;COL4A6;LGR5;SEMA3A;TRIM3E;XK |
| down_regulated_enriched_HSPC GRN | 2 | 20229 | 29 | 781 | 0.308000069 | C8FA2T3;KIAA0125 |
| down_regulated_enriched_T cell GRN | 2 | 20229 | 106 | 781 | 0.916994856 | CLEC2D;PBX4 |
| down_regulated_enriched_B cell GRN | 7 | 20229 | 147 | 781 | 0.340445305 | BANK1;CLEC2D;GNG7;KIAA0125;PLEKHA2;PN0C;ZNF395 |
| down_regulated_enriched_CMP_MEP | 7 | 20229 | 135 | 781 | 0.266611453 | ARHGAP6;CAM1A1;CRYM;PREM1;KCNH2;PTGER3;ST6GAL2 |
| down_regulated_enriched_GMP | 3 | 20229 | 139 | 781 | 0.908170814 | CACNA2D3;FGN;METTL7B |
| down_regulated_enriched_HSC | 6 | 20229 | 134 | 781 | 0.415107586 | FXYD6;MYCT1;PRDM16;PREX2;RORA;WBP5 |
| down_regulated_enriched_HSC_MLP | 6 | 20229 | 129 | 781 | 0.380479497 | ARPGEF1;C3SALNACT1;FXYD6;IQGAP2;NCALD;SPAG1 |
| down_regulated_enriched_MLP | 9 | 20229 | 133 | 781 | 0.072616312 | ABCB5;CABP5;CNTNAP2;ERC2;IQGAP2;NCALD;OSBPL3;PAG1;PPP2R2C |
| down_regulated_enriched_progenitor | 4 | 20229 | 134 | 781 | 0.765801615 | ARHGAP6;CRYM;KCNH2;LDLRAD3 |

Fig. 14A
7 overlapping pathways UP in shEZH1/AGM/YS
| HALLMARK_TNFA_SIGNALING_VIA_NFKB |
| HALLMARK_KRAS_SIGNALING_UP |
| HALLMARK_HYPOXIA |
| HALLMARK_XENOBIOTIC_METABOLISM |
| HALLMARK_ANGIOGENESIS |
| HALLMARK_COAGULATION |
| HALLMARK_P53_PATHWAY |
Fig. 14B
3 overlapping pathways DOWN in shEZH1/AGM/YS
| HALLMARK_G2M_CHECKPOINT |
| HALLMARK_MYC_TARGETS_V1 |
| HALLMARK_E2F_TARGETS |
Fig. 14C
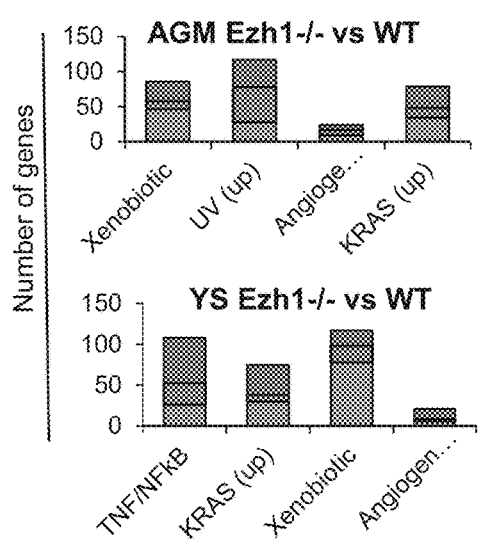
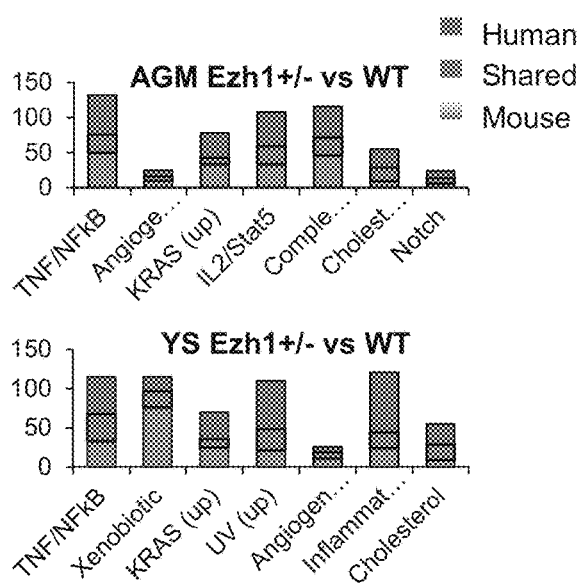

SEQUENCE LISTING

<160> NUMBER OF SEQ ID NOS: 111

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ctatctggca gtgcgagaat g                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
agacgtgcaa gcaggtcttt c                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tggatgactt atgcgtgatt t                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
caacagaact ttatggtaga a                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ccgccgtggt ttgtattcat t                                              21

<210> SEQ ID NO 6
<211> LENGTH: 128
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
attacagcaa gatggaaata ccaaatcccc ctacctccaa atgtatcact tactggaaaa    60

```
gaaaagtgaa atctgaatac atgcgacttc gacaacttaa acggcttcag gcaaatatgg    120
gtgcaaag                                                              128
```

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7

```
tcgacaactt aaacggcttc                                                 20
```

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8

```
tgcgacttcg acaacttaaa                                                 20
```

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

```
cctccaaatg tatcacttac                                                 20
```

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10

```
taaacggctt caggcaaata                                                 20
```

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11

```
aaacggcttc aggcaaatat                                                 20
```

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
catttggagg tagggggatt                                               20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ccagtaagtg atacatttgg                                               20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gtgatacatt tggaggtagg                                               20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aagtgataca tttggaggta                                               20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
agtgatacat ttggaggtag                                               20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tttccagtaa gtgatacatt                                               20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18

```
taagtgatac atttggaggt                                              20

<210> SEQ ID NO 19
<211> LENGTH: 129
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
gctttgtatg tggcaaattt tgcaaaggtt caagaaaaaa cccagatcct caatgaagaa    60
tggaagaagc ttcgtgtcca acctgttcag tcaatgaagc ctgtgagtgg acacccttttt  120 ctcaaaaag                                                          129

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gcttcattga ctgaacaggt                                              20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
acaggcttca ttgactgaac                                              20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
agaaaagggt gtccactcac                                              20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tccattcttc attgaggatc                                              20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 24
ccattcttca ttgaggatct                                               20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gtatgtggca aattttgcaa                                               20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
cagtcaatga agcctgtgag                                               20

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gcttcctctt caacctcaat a                                             21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ccgccgtggt ttgtattcat t                                             21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gctcttcttt gattacaggt a                                             21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 30
gctactcgga aaggaaacaa a                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
taatggaagg cagactattt a                                              21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ctctaatgac aagcataatt a                                              21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tcaaggttct acctatgtta a                                              21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gcccaccttc agacttctat t                                              21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gtacgtggga gagatcatta c                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 36
gactgagtcc tgccgcaaat a                                              21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
agtcgagtac ctgtgcgatt a                                              21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
cgttgggatt catggcctat t                                              21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
cggaaatctt aaaccaagaa t                                              21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gaaacagctg ccttagcttc a                                              21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tatgatggtt aacggtgatc a                                              21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
```
tattgccttc tcaccagctg c        21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
cggcaaagat catccatata t        21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gctgtgaagg agtttgaatc a        21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gctctgtgtt tgaggacagt a        21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
acttagttca gaaaccttaa a        21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gcaacggata catcttaaat a        21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
cctcggttct gagtcgtata a					21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
tcgagaagct agagatcata a					21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
acctctttga tctcgacaat a					21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
cctcttcgac ttagacaaca a					21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
cacacattcc tgaccagaga t					21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
cgagagagtt catggctctt t					21

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gctccaggaa tttaacaaga t					21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gctcagatga taacttctgt a                                              21

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
cactcggata tttgatatgt g                                              21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
agttagagac atgggtaata c                                              21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
cgtgacttca tagaggagta t                                              21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
atccctccca tcccatattt g                                              21

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gtagcaatga tgagaccctt t                                              21

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gcctagtaaa ttacagaaga a                                              21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gtacgcaaga aattggaaga a                                              21

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
cttgaataca acattgccaa t                                              21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gcccttcctc acagagttaa a                                              21

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
acgctgagta cttcgaaatg t                                              21

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
gatgattctg cctccaaatt g                                              21

```
<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ccgggaacag agaatgttta a                                              21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
cacccgtgat cacggagatt t                                              21

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
ccagtgaatc taatgtgact a                                              21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
ccagagacat acataggaat t                                              21

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
gtgcgatggt taggcgattt g                                              21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
gcaaacttta tgtttgggat t                                              21

<210> SEQ ID NO 73
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
ctggagctgg tgaatgagaa a                                              21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
gccctgatct ctaagatcta t                                              21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gtcagatcag accacaacga t                                              21

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
agacgaggta tgtgaagaca a                                              21

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
attgatgcca caaccataat a                                              21

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
cagattggat cggaaagtaa a                                              21

<210> SEQ ID NO 79
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
cctaatactt tccagattga t                                              21

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
taatggatat tgcctacatt t                                              21

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
caagatgctg atgagcaaga t                                              21

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
cggcctgaac gccttcgaca t                                              21

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
gacctgagca ccttcgactt c                                              21

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
gccggtgacc aagattacca a                                              21

<210> SEQ ID NO 85
<211> LENGTH: 21
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 85
gctgacaatc aaatgaatca t                                             21

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
cggaatctca tagcaccaat a                                             21

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
gcttacgttt actggtttct t                                             21

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
ccaaacctct tgccactaga a                                             21

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
gcctagtgtg tgtgctttct t                                             21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
gcaacgactc ttaccgaatt t                                             21

<210> SEQ ID NO 91
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 91
cccacgacgt aaagccttta a                                              21

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
gccaagtagt agttcagagt t                                              21

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
gcccaatgag actgacatca a                                              21

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
agaatcgtcg tatgcagtga a                                              21

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
cgactacatc aaaggcagca a                                              21

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
gaggttcgct tatcaactaa t                                              21

<210> SEQ ID NO 97
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 97
cccgagtatg cgcccatatt t                                              21

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
tcgccaacac gagtgttata t                                              21

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
ccgcaagaag aagctaaaca a                                              21

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
cacattggag agaggcgatt t                                              21

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
cccggatctc aagctcgcta t                                              21

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
ccagatgttc ttcgctaata a                                              21

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 103
gcctcagagc tattacccaa t                                              21

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
cccaaggtca aggagattat t                                              21

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
ccaccagaag aagagaagaa t                                              21

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
cgtctgcaaa gaggagaaga t                                              21

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
gagagcgcaa agacattgtt t                                              21

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
ctgggaagta tgatgtgtat t                                              21

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 109
accacctaag aagcccaaat c                                              21

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
cccagatcct caatgaagaa                                                20

<210> SEQ ID NO 111
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: a, c, t, g, unknown or other

<400> SEQUENCE: 111
ttggcnnnnn gccaa                                                     15
```

IMMUNE CELLS DERIVED FROM INDUCED PLURIPOTENT STEM CELL

CROSS REFERENCE TO RELATED APPLICATIONS

This application is a 35 U.S.C. § 371 National Phase Entry Application of International Application No. PCT/US2017/050167 filed Sep. 6, 2017, which designated the U.S., and which claims the benefit under 35 U.S.C. § 119(e) of U.S. Provisional Application No. 62/383,984 filed on Sep. 6, 2016, the contents of each of which are incorporated herein by reference in their entireties.

GOVERNMENT SUPPORT

This invention was made with government support under grant numbers HL100001 and DK092760 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Oct. 9, 2017, is named 701039-087011-PCT_SL.txt and is 26,848 bytes in size.

FIELD OF THE DISCLOSURE

The present disclosure relates generally to the fields of medicine, cell biology, and molecular biology. This disclosure relates to production methods of immune cells such as B or T lymphocytes from limited lineage myeloid progenitor cells, or from pluripotent stem cells (PSCs), or from multi-lineage hematopoietic progenitor cells (MHPCs).

BACKGROUND

There is a lack of supply of functional immune cells for the in vivo cellular replacement therapy, therapy for a host of diseases, disorders and conditions, and for the in vitro studies of disease modeling, drug screening, and hematological diseases. Bone marrow transplantation is by far the most established cellular replacement therapy for a variety of hematological disorders. The functional unit of a bone marrow transplant is the hematopoietic stem cell (HSC), which resides at the apex of a complex cellular hierarchy and replenishes blood development throughout life. However, the scarcity of HLA-matched HSCs or patient-specific HSCs severely limits the ability to carry out transplantation, disease modeling, drug screening, and in vitro studies of hematological diseases. Often, there is not a large enough cell population transplanted into a recipient subject to ensure sufficient engraftment and reconstitution in vivo in the recipient subject.

As such, many studies have been developed to generate HSCs from alternative sources. For example, reprogramming of somatic cells to induced pluripotent stem cells (iPSCs) has provided access to a wide array of patient-specific pluripotent cells, a promising source for disease modeling, drug screens and cellular therapies. Pluripotent cells are induced in human and mouse somatic cells by the forced expression of OCT4 (Oct4) and SOX2 (Sox2) with either the combinations of KLF4 (Klf4) and optionally c-MYC (c-Myc), or the combinations of NANOG (Nanog) and LIN28 (Lin28). Alternative combinations of transactivating factors include OCT4, SOX2, NANOG and LIN28. Mouse iPS cell lines derived from bone marrow hematopoietic progenitor cells (HPCs) has been reported. Derivation of human iPS cells from postnatal human blood cells, from granulocyte colony-stimulating factor (G-CSF) mobilized peripheral blood CD34+ cells, and from human cord blood and adult bone marrow CD34+ cells without any pretreatment such as G-CSF mobilization has been also reported. These reports all employed HPCs, stem cells as the source of iPSCs. Somatic cells such as T lymphocyte cells, B lymphocyte cells, fibroblasts and keratinocytes are also used as the alternative sources of iPSCs.

The iPSCs have been shown to differentiate into various cells belonging to the three germ layers, as demonstrated by the analysis of teratomas generated from human iPSCs and mouse iPSCs. In addition, the pluripotency of iPSCs is confirmed by the contribution of iPS cell-derived cells to various organs of the chimeric mice developed from iPSC-introduced blastocysts.

However, in addition to the cell quantity and cell source problems, there is still a big hurdle in producing iPSCs-derived hematopoietic stem and progenitor cells (iPSCs-HSPC) or the differentiated cells therefrom where the progeny cells would engraft in vivo. As described above, the various studies aimed at in vitro generating HSCs from alternative sources produced hematopoietic progenitor or stem cells that do not engraft well in vivo.

SUMMARY

Embodiments of the present disclosure relate to methods for producing patient-specific, histocompatible, multipotent hematopoietic progenitor cells (MHPCs) that can be subjected to specific, directed differentiation to provide functional immune cells in quantities larger than what has been traditionally possible in in vitro culture conditions. Embodiments of the present disclosure also relate compositions comprising these MHPCs, and progeny cells resulting from the specific, directed differentiation process, and the uses of these cells.

There is a lack of supply of functional HLA-matched immune cells for the in vivo cellular replacement therapy, the treatment of diseases, disorders and medical conditions, and for the in vitro studies of disease modeling, drug screening, and hematological diseases. Mostly, the immune cells are differentiated from hematopoietic stem cell (HSC) but there is a scarcity of HLA-matched HSCs. The present method solves this problem by reversing the lineage potentials of previously non-lymphoid lineage committed myeloid progenitor cells back to MHPCs, and then subsequently specifically promoting and directing differentiation of the hematopoietic progenitor cells (HPCs) into the lymphoid lineage. In addition, the MHPCs, having reversed lineage potentials, are modified to have enhanced in vivo engraftment and reconstitution properties. The production method is useful, for example, as a cell preparation method in immunotherapy.

Abbreviations used herein:
HPCs=hematopoietic progenitor cells
MHPCs=multilineage hematopoietic progenitor cells or multipotent hematopoietic progenitor cells
iPSCs=induced pluripotent stem cells
HSCs=hematopoietic stem cells The inventors, by introducing at least three exogenous transcription factors, ERG, HOXA9, and RORA, into non-lymphoid lineage committed myeloid progenitor cells, were able to reversed the lineage potential of these cells. The resultant cells were MHPCs.

The blood cells produced during hematopoiesis are divided into the following three cell lineages: (1) erythroid cells, (2) lymphoid cells, and (3) myeloid cells. Erythroid cells, including normoblasts, erythroblasts and mature red blood cells (RBCs), are the most common type of blood cell and are a principal means of delivering oxygen from the lungs to body tissues. Lymphoid cells, including B-cells and T-cells, are a type of white blood cell that play a significant role in the body's immune defenses. Myeloid cells, including granulocytes, megakaryocytes, and macrophages, are a diverse group of cells comprising other white blood cells (e.g., neutrophils, eosinophils and basophils) and platelets.

Myeloid progenitor cells are committed to the myeloid linage, which is a non-lymphoid lineage. Myeloid progenitor cells in the myeloid lineage undergo further cell division, differentiation and maturation, and the myeloid lineage produces the following cell types: megakaryocytes, thrombocytes, erythrocytes, mast cells, myeloblast, basophils, neutrophils, eosinophils, monocytes and macrophages. The myeloid lineage is different from the lymphoid lineage, which produces immune cells such as T and B lymphocytes. By further inhibiting a histone methyltransferase EZH1 in these reversed lineage MHPCs, the inventors were able to direct the differentiation of these cells into immune cells by co-culture with OP9-DL1/4 cells or by activating the Notch signaling pathway in these cells. Moreover, the inventors found that by incorporating two additional exogenous transcription factors, DACH1 and NFIA, into these cells enhanced the lymphoid potential of these cells upon co-culture with OP9-DL1/4 cells or by activating the Notch signaling pathway. Furthermore, the inventors found that by incorporating two other exogenous transcription factors, SOX4 and MYB, into these cells enhanced the engraftment and reconstitution of these cells in vivo in a recipient subject.

The advantage of the disclosure protocol is that the method now enables semi-permanent bulk production of desired and specific immune cells from a source of cells, which can be readily collected from the patient's body. For example, somatic cells such as blood cells, immune cells, skin cells etc. The production of function immune cells is not restricted to using only stem or progenitor cells obtained from a patient. The produced immune cells can then be used for immunotherapy.

Accordingly, it is an object of the present disclosure to provide production methods of immune cells which include the step of reversing the lineage potentials of previously non-lymphoid lineage committed myeloid progenitor cells to MHPCs, and specific and directed differentiating the reversed-lineage MHPCs into desired immune cells. The non-lymphoid lineage committed myeloid progenitor cells can be made from iPSCs, which are generated from any cells in the patient's body, e.g.somatic cells. Such cells can be readily collected from the patient's body. For example, cells from a blood sample, a skin sample, a buccal mouth swab etc. The non-lymphoid lineage committed myeloid progenitor cells may be harvested from the patient's bone marrow.

It is also the objective of this the present disclosure to provide methods for enhancing or improving the in vivo engraftment, or reconstitution, or both of hematopoietic related cells that have been implanted into a subject.

It is also the objective of this the present disclosure to provide compositions of modified (also referred to as engineered) cells for use in in vivo cellular replacement therapy, medical therapy such as cancer immune therapy, and for the in vitro studies of disease modeling, drug screening, and hematological diseases.

Accordingly, disclosed here is (1) a method for preparing modified immune cells, such as T or B cells, the method which comprises a step of reversing the lineage potentials of myeloid progenitor cells to HPCs using exogenous copies of transcription factors and a step of specific and directed differentiation of the reversed lineage HPCs into immune cells; (2) modified myeloid progenitor cells having reversed lineage and have increased lymphoid lineage potential; (3) compositions which contain the modified myeloid progenitor cells having reversed lineage that include increased lymphoid lineage potential; (4) modified myeloid progenitor cells described herein and compositions thereof for use in the manufacture/production of described modified immune cells; (5) modified myeloid progenitor cells described herein and compositions thereof for use in cellular replacement therapy, or for the treatment of cancer, autoimmune disorders, hematological diseases or other genetic diseases and disorders; (6) a pharmaceutical composition which contains the modified immune cells that are prepared by the method described herein; and (7) a method for treatment uses with the immune cells made with the above-described method, such as bone marrow transplant and cancer immune therapy, autoimmune disorders, hematological diseases or other genetic diseases and disorders. The modified immune cells are mammalian cells, such as human cells.

In one embodiment, this disclosure provides a modified or an engineered myeloid progenitor cell having reversed lineage that include increased lymphoid lineage potential. In one embodiment, this disclosure provides a modified or an engineered myeloid progenitor cell having reversed lineage to include increased lymphoid lineage potential that is produced by a method described herein. In some embodiment, the modified or an engineered myeloid progenitor cell has an exogenous gene coding copy of each of the following transcription factors: ERG, HOXA9, and RORA, via ERA transfections. In one embodiment, the modified or engineered myeloid progenitor cell further comprises an exogenous gene coding copy of SOX4, or MYB, or both SOX4 and MYB. In another embodiment, the modified or engineered myeloid progenitor cell further comprises an exogenous gene coding copy of DACH1, or NFIA, or both DACH1 and NFIA. In some embodiment, the modified myeloid progenitor cells are derived from lineage-restricted $CD34^+CD45^+$ myeloid precursor cells.

In another embodiment, this disclosure provides a composition comprising modified or engineered myeloid progenitor cell described herein.

In another embodiment, this disclosure provides modified myeloid progenitor cells described herein and compositions thereof for use in the manufacture/production of described modified immune cells, wherein the modified myeloid progenitor cell comprises an exogenous gene coding copy of each of the following transcription factors: ERG, HOXA9, and RORA. In one embodiment, the modified or engineered modified myeloid progenitor cell further comprises an exogenous gene coding copy of SOX4, or MYB, or both SOX4 and MYB. In another embodiment, the modified or engineered modified myeloid progenitor cell further comprises an exogenous gene coding copy of DACH1, or NFIA, or both DACH1 and NFIA.

In another embodiment, this disclosure provides modified myeloid progenitor cells described herein and compositions thereof for use in cellular replacement therapy, or for the treatment of cancer, autoimmune disorders, hematological diseases, or other genetic diseases and disorders, wherein the modified myeloid progenitor cell comprises an exogenous gene coding copy of each of the following transcription factors: ERG, HOXA9, and RORA. In one embodiment, the modified or engineered modified myeloid progenitor cell further comprises an exogenous gene coding copy of SOX4, or MYB, or both SOX4 and MYB. In another embodiment, the modified or engineered modified myeloid progenitor cell further comprises an exogenous gene coding copy of DACH1, or NFIA, or both DACH1 and NFIA.

Accordingly, in one embodiment, provided herein is a method comprising (a) in vitro or ex vivo generating multilineage hematopoietic progenitor cells (MHPCs) from myeloid progenitor cells; (b) inhibiting a histone methyltransferase in the resultant population of MHPCs; and, (c) differentiating the resultant population of MHPCs in the presence of a notch ligand or defined stromal cells or both to promote differentiation into the lymphoid lineage. In some embodiments, in vitro culturing of the cells occurs between step (a) and step (b). In some embodiments, selection of cells occurs between step (a) and step (b).

In another embodiment, provided herein is a method comprising (a) in vitro transfecting myeloid progenitor cells with an exogenous gene coding copy of each of the following transcription factors, ERG, HOXA9, and RORA, wherein the transcription factors are expressed in the transfected cells to produce a resultant population of multilineage hematopoietic progenitor cells (MHPCs) that have myeloid and erythroid potential; (b) (i) inhibiting a histone methyltransferase in the resultant population of MHPCs to expand lymphoid potential, or (ii) in vitro transfecting resultant population of MHPCs with an exogenous gene coding copy of DACH1 and NFIA to expand lymphoid potential, or (iii) both (i) and (ii); and (c) differentiating the resultant population of MHPCs in the presence of a notch ligand or supportive stroma or both to promote differentiation into the lymphoid lineage.

In another embodiment, this disclosure provides a method of generating of modified immune cells from a population of myeloid progenitor cells comprising: (a) in vitro transfecting the myeloid progenitor cells with an exogenous copy of each of the following transcription factors ERG, HOXA9, and RORA, wherein the transfected transcription factors are expressed in vivo in the cells to produce a population of multilineage progenitor cells (MHPCs) that having myeloid, and erythroid potential; (b) (i) inhibiting a histone methyltransferase enzyme that targets the histone protein at H3K9 and/or H3K27 in the resultant population of MHPCs to expand lymphoid potential, or (ii) in vitro transfecting resultant population of MHPCs with an exogenous gene coding copy of DACH1 and NFIA to expand lymphoid potential, or (iii) both (i) and (ii); and (c) differentiating the resultant population of MHPCs in the presence of a notch ligand to promote differentiation into the lymphoid lineage. These immune cells are genetically modified to have exogenous copies of ERG, HOXA9, and RORA compared to the original myeloid progenitor cells.

In another embodiment, provided herein is a method comprising (a) in vitro contacting or introducing to a population of myeloid progenitor cells a vector or more, the vector(s) collectively carrying an exogenous gene coding copy of each of the following transcription factors, ERG, HOXA9, and RORA, for the in vivo expression of the exogenous copies of genes in the contacted cells, wherein the transfected transcription factors are expressed in vivo in the contacted cells to produce a population of multilineage hematopoietic progenitor cells (MHPCs) that having myeloid and erythroid potential; (b) contacting the MHPCs with an inhibitor of a histone methyltransferase enzyme; and (c) contacting the MHPCs a notch ligand or defined stromal cells or both. In some embodiments, in vitro culturing of the cells occurs between step (a) and step (b). In some embodiments, the selection of cells occurs between step (a) and step (b). In one embodiment of the method, step (c) consists of activating the Notch signaling pathway in the MHPCs by any method known in the art.

In another embodiment, this disclosure provides a method of improving in vivo engraftment (also the reconstitution) of hematopoietic stem cells in a recipient host comprising: (a) in vitro or ex vivo generating multilineage hematopoietic progenitor cells (MHPCs) from myeloid progenitor cells; (b) inhibiting a histone methyltransferase in the resultant population of MHPCs; and (c) transplanting said resultant MHPCs into the recipient host.

In another embodiment, this disclosure provides a modified or engineered immune cell produced by a method described herein.

In another embodiment, this disclosure provides a composition comprising modified or engineered immune cells produced by a method described herein.

In another embodiment, this disclosure provides a modified or engineered immune cell derived from a population of myeloid progenitor cells, wherein the immune cell comprises an exogenous gene coding copy of each of the following transcription factors: ERG, HOXA9, and RORA. In one embodiment, the modified or engineered immune cell further comprises an exogenous gene coding copy of SOX4, or MYB, or both SOX4 and MYB. In another embodiment, the modified or engineered immune cell further comprises an exogenous gene coding copy of DACH1, or NFIA, or both DACH1 and NFIA.

In another embodiment, this disclosure provides a modified or engineered immune cell derived from a population of myeloid progenitor cells, wherein the immune cell comprises an exogenous gene coding copy of each of the following transcription factors: ERG, HOXA9, RORA, DACH1 and NFIA.

In another embodiment, this disclosure provides a modified or engineered immune cell derived from a population of myeloid progenitor cells, wherein the immune cell comprises an exogenous gene coding copy of each of the following transcription factors: ERG, HOXA9, and RORA, and an exogenous gene coding copy of each of the following reprogramming factors OCT4, SOX2, KLF4 and optionally c-MYC or NANOG and LIN28, or the four reprogramming factors: OCT4, SOX2, NANOG and LIN28. In another embodiment, the modified cells further comprise an exogenous gene coding copy of two addition transcription factors, SOX4 and MYB. In another embodiment, the modified cells further comprise an exogenous gene coding copy of two addition transcription factors, DACH1 and NFIA.

In one embodiment, this disclosure provides a composition of modified cells derived from a population of myeloid progenitor cells, wherein the modified cell comprises an exogenous copy of each of the following transcription factors ERG, HOXA9, and RORA. In another embodiment, the modified cells further comprise an exogenous gene coding copy of two addition transcription factors, SOX4 and MYB.

In one embodiment, this disclosure provides a composition of modified cells derived from a population of myeloid progenitor cells, wherein the modified cell comprises an exogenous gene coding copy of each of the following transcription factors ERG, HOXA9, RORA, SOX4, and MYB.

In one embodiment, this disclosure provides a composition of modified cells derived from a population of myeloid progenitor cells, wherein the modified cell comprises an exogenous gene coding copy of each of the following transcription factors ERG, HOXA9, RORA, DACH1, NFIA, SOX4, and MYB.

In one embodiment, this disclosure provides a composition of modified cells derived from a population of myeloid progenitor cells, wherein the modified cell comprises an exogenous gene coding copy of each of the following transcription factors ERG, HOXA9, and RORA, and an exogenous gene coding copy of each of the following reprogramming factors OCT4, SOX2, KLF4 and optionally c-MYC or nanog and LIN28. Alternative combinations of reprogramming factors include these four factors: OCT4, SOX2, NANOG and LIN28.

In one embodiment, this disclosure provides a composition of modified cells derived from a population of myeloid progenitor cells, wherein the modified cell comprises an exogenous gene coding copy of each of the following transcription factors ERG, HOXA9, and RORA, SOX4 and MYB, and an exogenous gene coding copy of each of the following reprogramming factors OCT4, SOX2, KLF4 and optionally c-MYC or nanog and LIN28. Alternative combinations of reprogramming factors include these four factors: OCT4, SOX2, NANOG and LIN28.

In one embodiment of any method, cells or composition described, the myeloid progenitor cells, HPCs, MHPCs, iPSCs, modified or engineered cell, or modified or engineered immune cell is a mammalian cell. For example, the immune cell is a human, rat, mouse, rabbit, or hamster cell.

In one embodiment of any method, cells or composition described, the myeloid progenitor cells, HPCs, MHPCs, iPSCs, modified or engineered mammalian cell is a primate cell.

In one embodiment of any method, cells or composition described, the myeloid progenitor cells, HPCs, MHPCs, iPSCs, modified or engineered primate cell or immune cell is a human cell.

In one embodiment of any method, cells or composition described, the MHPCs are generated by introducing in vitro or ex vivo each of the following transcription factors ERG, HOXA9, and RORA, in the myeloid progenitor cells, such as the common myeloid progenitor cell (CMP). For example, by transfecting with a vector or more, the vector(s) collectively carry an exogenous gene coding copy of each of the following transcription factors, ERG, HOXA9, and RORA, for in vivo expression of the transcription factors in the transfected cells.

In one embodiment of any method, cells or composition described, the MHPCs are generated by contacting a population of myeloid progenitor cells with a vector or more, wherein the vector(s) collectively carrying an exogenous gene coding copy of each of the following transcription factors, ERG, HOXA9, and RORA, for the in vivo expression of the factors in the contacted cells, and wherein the transfected transcription factors are expressed in vivo in the contacted cells. For example, a first vector carrying a nucleic acid sequence of an exogenous gene coding copy of ERG, a second vector carrying a nucleic acid sequence of an exogenous gene coding copy of HOXA9, and a third vector carrying a nucleic acid sequence of an exogenous gene coding copy of RORA. Alternatively, a single vector carrying all the three exogenous genes coding for ERG, HOXA9, and RORA transcription factors.

In one embodiment of any method, cells or composition described, the method further comprising in vitro transfecting the myeloid progenitor cells with an exogenous gene coding copy of the transcription factors, SOX4, wherein the transfected transcription factor is expressed in vivo in the transfected cells.

In one embodiment of any method, cells or composition described, the method further comprising in vitro transfecting the myeloid progenitor cells with an exogenous gene coding copy of the transcription factors, MYB, wherein the transfected transcription factor is expressed in vivo in the transfected cells.

In one embodiment of any method, cells or composition described, the myeloid lineage progenitor cells are at least CD45$^+$. In one embodiment of any method, cells or composition described, the myeloid lineage progenitor cells are CD34$^+$ CD45$^+$. In one embodiment of any method, cells or composition described, the myeloid lineage progenitor cells are at least CD45$^+$ and CD11 b$^+$. In some embodiment, the myeloid lineage progenitor cells are negative for lymphoid lineage markers such as IL-7 R alpha/CD127, CD3, CD4, CD8 and CD19.

In one embodiment of any method, cells or composition described, the myeloid lineage progenitor cells are non-lymphoid lineage committed.

In one embodiment of any method, cells or composition described, the resultant MHPCs are CD34+ CD38 negative/low.

In one embodiment of any method, cells or composition described, the resultant MHPCs have myeloid and erythroid but no or very limited lymphoid potential, less than 5%.

In one embodiment of any method, cells or composition described, the myeloid lineage progenitor cells are progenitor cells are derived from embryoid bodies obtained from a population of pluripotent stem cells.

In one embodiment of any method, cells or composition described, the population of pluripotent stem cells is iPSCs or embryonic stem cells (ESC).

In one embodiment of any method, cells or composition described, the iPSCs are produced by in vitro or ex vivo introducing exogenous copies of only three reprogramming factors OCT4, SOX2, and KLF4 into mature or somatic cells. Alternatively, the iPSC having exogenous copies of the four reprogramming factors include OCT4, SOX2, NANOG and LIN28.

In one embodiment of any method, cells or composition described, the iPSC having exogenous copies of OCT4, SOX2, and KLF4 is further introduced in vitro or ex vivo with exogenous copies of c-MYC or nanog and LIN28 into the cells.

In one embodiment of any method, cells or composition described, the iPSC are produced by introducing in vitro or ex vivo exogenous copies of reprogramming factors OCT4, SOX2, and KLF4, and optionally with c-MYC or nanog and LIN28 into mature or somatic cells.

In one embodiment of any method, cells or composition described, the iPSC are produced by in vitro or ex vivo contacting mature cells with a vector or more, wherein the vector(s) collectively carry exogenous copies of reprogramming factors OCT4, SOX2, and KLF4, and optionally with c-MYC or nanog and LIN28 into mature cells, and wherein the reprogramming factors are expressed in vivo in the contacted mature or somatic cells.

In one embodiment of any method, cells or composition described, the cells from which iPSC are made can be from any cell type in a donor subject, any mature or somatic cells. For examples, cells is a blood sample, or bone marrow sample, B lymphocytes (B-cells), T lymphocytes, (T-cells), fibroblasts, keratinocytes etc.

In one embodiment of any method, cells or composition described, the iPSC are produced by in vitro or ex vivo introducing the disclosed reprogramming factors two or more times into the mature or somatic cells.

In one embodiment of any method, cells or composition described, the iPSC are produced by in vitro or ex vivo contacting mature cells with the disclosed vector(s) factors two or more times into the mature or somatic cells.

In one embodiment of any method, cells or composition described, the notch ligand is Delta-like-1, Delta-like-4, and immobolized Deltaext-IgG, consisting of the extracellular domain of human Delta-like-1 fused to the Fc domain of human IgG1.

In one embodiment of any method, cells or composition described, the Delta-like-1 or Delta-like-4 is supplied with co-culturing the MHPCs with immobolized Deltaext-IgG, OP9-DL1 cells or OP9-DL4 cells. OP9-DL1 cells are a bone-marrow-derived stromal cell line that ectopically expresses the Notch ligand, Delta-like 1 (Dll1).

In one embodiment of any method, cells or composition described, the Notch signaling pathway of the inhibited MHPCs is stimulated in culture.

In one embodiment of any method, cells or composition described, the histone methyltransferase catalysis the addition of methyl group to the histone H3 lysine residue 9 (H3K9) and/or histone H3 lysine residue 27 (H3K27).

In one embodiment of any method, cells or composition described, the histone methyltransferase inhibitor inhibits the G9a/GLP heteromeric complex.

In one embodiment of any method, cells or composition described, the histone methyltransferase inhibitor inhibits EZH1 (Enhancer Of Zeste 1 Polycomb Repressive Complex 2 Subunit).

In one embodiment of any method, cells or composition described, the H3K9 or H3K27 histone methyltransferase is inhibited by a small molecule or a nucleic acid or a CRISPR-mediated target genetic interference.

In one embodiment of any method, cells or composition described, the H3K27 histone methyltransferase is EZH1.

In one embodiment of any method, cells or composition described, the H3K27 histone methyltransferase is not EZH2.

In one embodiment of any method, cells or composition described, the histone methyltransferase small molecule inhibitor that is specific to EZH1 and not to EZH2.

In one embodiment of any method, cells or composition described, the histone methyltransferase small molecule inhibitor include but are not limited to AMI-1, A-366, BIX-01294, BIX01338, BRD4770, chaetocin, UNC0224, UNC0631, UNC0638, UNC0642, UNC0646, EPZ5676, EPZ005687, GSK343, EPZ-6438, 3-deazaneplanocin A (DZNeP) HCl, UNC1999, MM-102, SGC 0946, Entacapone, EPZ015666, UNC0379, E11, MI-2 (Menin-MLL Inhibitor), MI-3 (Menin-MLL Inhibitor), PFI-2, GSK126, EPZ004777, BRD4770, and EPZ-6438.

In one embodiment of any method, cells or composition described, the histone methyltransferase nucleic acid inhibitor is a nucleic acid targeting the expression of the histone methyltransferase.

In one embodiment of any method, cells or composition described, the nucleic acid inhibitor is a RNA interference inhibitor.

In one embodiment of any method, cells or composition described, the nucleic acid is a selected from the group consisting of CTATCTGGCAGTGCGAGAATG (SEQ. ID. NO: 1), AGACGTGCAAGCAGGTCTTTC (SEQ. ID. NO: 2), TGGATGACTTATGCGTGATTT (SEQ. ID. NO: 3), CAACAGAACTTTATGGTAGAA (SEQ. ID. NO: 4), CCGCCGTGGTTTGTATTCATT (SEQ. ID. NO: 5), GCTTCCTCTTCAACCTCAATA (SEQ. ID. NO: 27), CCGCCGTGGTTTGTATTCATT (SEQ. ID. NO: 28), GCTCTTCTTTGATTACAGGTA (SEQ. ID. NO: 29), and GCTACTCGGAAAGGAAACAAA (SEQ. ID. NO: 30).

In one embodiment of any modified immune cell described, the immune cell further comprises an exogenous gene coding copy of SOX4 or MYB or both SOX4 and MYB.

In one embodiment of any modified immune cell described, the immune cell further comprises an exogenous gene coding copy of DACH1 or NFIA or both DACH1 and NFIA.

In one embodiment of any method, cells or composition described, specific and directed differentiation of the histone methyltransferase-inhibited MHPCs comprises contacting the cells with cytokines selected from the group consisting of IL-7, IL-2, IL-15, and IL-4.

In one embodiment, provided herein is a method of cellular replacement therapy, or for the treatment of cancer, autoimmune disorders, hematological diseases, or other genetic diseases and disorders in a subject, comprising (a) providing a somatic cell from a donor subject, (b) generating multilineage hematopoietic progenitor cells from myeloid progenitor cells derived from the somatic cell as described in any of the preceding paragraphs; (c) inhibiting a histone methyltransferase in the resultant population of multilineage hematopoietic progenitor cells as described in any of the preceding paragraphs; (d) differentiating the resultant population of multilineage hematopoietic progenitor cells in the presence of a notch ligand or a stromal cell or both to promote differentiation into the lymphoid lineage as described in any of the preceding paragraphs, and implanting the resultant differentiated lymphoid cells into a recipient subject.

In one embodiment of the treatment method described above, the host subject and the recipient subject are the same individual.

In one embodiment of the treatment method described above, the host subject and the recipient subject are not the same individual, but are at least HLA compatible.

Definitions

As used herein, in one embodiment, the term "hematopoietic stem cell" or "HSC" refers to a stem cell that has self-renewal capacity and also give rise to all the blood cell types of the three hematopoietic lineages, erythroid, lymphoid, and myeloid. These cell types include the myeloid lineages (monocytes and macrophages, neutrophils, basophils, eosinophils, erythrocytes, megakaryocytes/platelets, dendritic cells), and the lymphoid lineages (T-cells, B-cells, NK-cells). Human HSCs are determined as $CD34^+$, $CD59^+$, $CD90/Thy1^+$, $CD38^{low/-}$, $c-kit/CD117^{-/low}$, and $Lin^-$. Mouse HSC- are considered $CD34^{low/-}$, $SCA-1^+$, $CD90/Thy1^{+/low}$, $CD38^+$, $c-Kit/CD117^+$, and $Lin^-$. Detecting the expression of these marker panels allows separation of specific cell populations via techniques like fluorescence-activated cell sorting (FACS). In one embodiment, the term "hematopoietic stem cell" or "HSC" refers to a stem cell that has self-renewal capacity and that have the following cell surface markers: CD34+, CD59+, Thy1/CD90+, CD38$^{lo/-}$, CD133+, c-Kit/CD117$^{-/lo}$, and Lin$^-$. In one embodiment, the term "hematopoietic stem cell" or "HSC" refers to a stem cell that is at least CD34+. In one embodiment, the term "hematopoietic stem cell" or "HSC" refers to a stem cell that has self-renewal capacity and that is at least CD34$^+$ and c-kit/CD117$^{lo/-}$. In one embodiment, the term "hematopoietic stem cell" or "HSC" refers to a stem cell that has self-renewal capacity and that is at least CD38$^{low/-}$, c-kit/CD117$^{-/low}$.

As used herein, the terms "iPS cell", "iPSC", and "induced pluripotent stem cell" are used interchangeably and refers to a pluripotent cell artificially derived by the transfection of following reprogramming factors OCT4, SOX2, KLF4, and optionally c-MYC or nanog and LIN28, into a from a differentiated cell, e.g., a somatic cell. Alternative combinations of reprogramming factors include OCT4, SOX2, NANOG and LIN28.

As used herein, the term "lineage" when used in the context of stem and progenitor cell differentiation and development refers to the cell differentiation and development pathway, which the cell can take to becoming a fully differentiated cell. For example, a HSC has three hematopoietic lineages, erythroid, lymphoid, and myeloid; the HSC has the potential, ie., the ability, to differentiate and develop into those terminally differentiated cell types known for all these three lineages. When the term "multilineage" used, it means the cell is able to, in the future, differentiate and develop into those terminally differentiated cell types known for more than one lineage. For example, the HSC has multilineage potential. When the term "limited lineage" used, it means the cell can differentiate and develop into those terminally differentiated cell types known for one lineage. For example, a common myeloid progenitor cell (CMP) or a megakaryocyte-erythroid progenitor (MEP) has a limited lineage because the cell can only differentiate and develop into those terminally differentiated cell types of the myeloid lineage and not that of the lymphoid lineage. Terminally differentiated cells of the myeloid lineage include erythrocytes, monocytes, macrophages, megakaryocytes, myeloblasts, dendritic cells, and granulocytes (basophils, neutrophils, eosinophils, and mast cells); and terminally differentiated cells of the lymphoid lineage include T lymphocytes/T cells, B lymphocytes/B cells, dendritic cells, and natural killer cells.

As used herein, the term "a progenitor cell" refers to an immature or undifferentiated cell that has the potential later on to mature (differentiate) into a specific cell type (a fully differentiated or terminally differentiated cell), for example, a blood cell, a skin cell, a bone cell, or hair cells. Progenitor cells have a cellular phenotype that is more primitive (e.g., is at an earlier step along a developmental pathway or progression than is a fully differentiated cell) relative to a cell, which it can give rise to by differentiation. Often, progenitor cells also have significant or very high proliferative potential. Progenitor cells can give rise to multiple distinct differentiated cell types or to a single differentiated cell type, depending on the developmental pathway and on the environment in which the cells develop and differentiate. A progenitor cell also can proliferate to make more progenitor cells that are similarly immature or undifferentiated.

As used herein, the term "multilineage hematopoietic progenitor cells", "multipotent hematopoietic progenitor cells" and "MHPCs" are used interchangeably and refer to hematopoietic cells (cell that form the blood) that have the ability or potential to generate, or differentiate into, multiple types of hematopoietic lineage cells. In one embodiment, the term includes the "reverse multilineage hematopoietic progenitor cells" "reverse MHPCs" or described herein. Such cells are derived from myeloid progenitor cells after the in vitro or ex vivo transfection to incorporate several exogenous copies of gene coding nucleic acids of the transcription factors: ERG, HOXA9, and RORA into the cell. In one embodiment, the term includes "embryonic body-derived progenitors" and "EB-derived progenitors."

As used herein, in one embodiment, the term "myeloid progenitor cells" or "myeloid lineage progenitor cells" refer to an immature or undifferentiated cell that is committed to the myeloid lineage and can only differentiate and develop into those terminally differentiated cell types of the myeloid lineage. Examples are CMP, MEP, and GMPs of the myeloid lineages. In one embodiment, the term "myeloid progenitor cells" or "myeloid lineage progenitor cells" refer to the CD34+ CD45+ cells derived from embryonic bodies obtained pluripotent stem cells. In one embodiment, the term "myeloid progenitor cells" or "myeloid lineage progenitor cells" refer to cells that only differentiate and develop into granulocytes and macrophages.

The term "differentiated cell" is meant any primary cell that is not, in its native form, pluripotent as that term is defined herein. The term a "differentiated cell" also encompasses cells that are partially differentiated, such as multipotent cells (e.g. adult somatic stem cells). In some embodiments, the term "differentiated cell" also refers to a cell of a more specialized cell type derived from a cell of a less specialized cell type (e.g., from an undifferentiated cell or a reprogrammed cell) where the cell has undergone a cellular differentiation process.

In the context of cell ontogeny, the term "differentiate", or "differentiating" is a relative term meaning a "differentiated cell" is a cell that has progressed further down the developmental pathway than its precursor cell. Thus in some embodiments, a reprogrammed cell as this term is defined herein, can differentiate to lineage-restricted precursor cells (such as a mesodermal stem cell or a endodermal stem cell), which in turn can differentiate into other types of precursor cells further down the pathway (such as an tissue specific precursor, for example, a cardiomyocyte precursor, or a pancreatic precursoe), and then to an end-stage differentiated cell, which plays a characteristic role in a certain tissue type, and may or may not retain the capacity to proliferate further.

The term "multipotent" when used in reference to a "multipotent cell" refers to a cell that is able to differentiate into some but not all of the cells derived from all three germ layers. Thus, a multipotent cell is a partially differentiated cell. Multipotent cells are well known in the art, and examples of muiltipotent cells include adult somatic stem cells, such as for example, hematopoietic stem cells and neural stem cells, hair follicle stem cells, liver stem cells etc. Multipotent means a stem cell may form many types of cells in a given lineage, but not cells of other lineages. For example, a multipotent blood stem cell can form the many different types of blood cells (red, white, platelets, etc. . . . ), but it cannot form neurons; cardiovascular progenitor cell (MICP) differentiation into specific mature cardiac, pacemaker, smooth muscle, and endothelial cell types; pancreas-derived multipotent progenitor (PMP) colonies produce cell types of pancreatic lineage (cells that produces insulin, glucagon, amylase or somatostatin) and neural lineage (cells that are morphologically neuron-like, astrocytes-like or oligodendrocyte-like).

The term a "reprogramming gene", as used herein, refers to a gene whose expression, contributes to the reprogramming of a differentiated cell, e.g. a somatic cell to an undifferentiated cell (e.g. a cell of a pluripotent state or partially pluripotent state, multipotent state). A reprogramming gene can be, for example, genes encoding master transcription factors Sox2, Oct3/4, Klf4, Nanog, Lin-28, c-myc and the like. The term "reprogramming factor" refers to the protein encoded by the reprogramming gene.

The term "exogenous" refers to a substance present in a cell other than its native source. The terms "exogenous" when used herein refers to a nucleic acid (e.g. a nucleic acid encoding a reprogramming transcription factor, e.g. Sox2, Oct3/4, Klf4, Nanog, Lin-28, c-myc and the like) or a protein (e.g., a transcription factor polypeptide) that has been introduced by a process involving the hand of man into a biological system such as a cell or organism in which it is not normally found or in which it is found in lower amounts. A substance (e.g. a nucleic acid encoding a sox2 transcription factor, or a protein, e.g., a SOX2 polypeptide) will be considered exogenous if it is introduced into a cell or an ancestor of the cell that inherits the substance.

The term "isolated" as used herein signifies that the cells are placed into conditions other than their natural environment. The term "isolated" does not preclude the later use of these cells thereafter in combinations or mixtures with other cells.

As used herein, the term "expanding" refers to increasing the number of like cells through cell division (mitosis). The term "proliferating" and "expanding" are used interchangeably.

As used herein, a "cell-surface marker" refers to any molecule that is expressed on the surface of a cell. Cell-surface expression usually requires that a molecule possesses a transmembrane domain. Some molecules that are normally not found on the cell-surface can be engineered by recombinant techniques to be expressed on the surface of a cell. Many naturally occurring cell-surface markers are termed "CD" or "cluster of differentiation" molecules. Cell-surface markers often provide antigenic determinants to which antibodies can bind to. A cell-surface marker of particular relevance to the methods described herein is CD34. The useful hematopoietic progenitor cells according to the present disclosure preferably express DC34 or in other words, they are CD34 positive.

A cell can be designated "positive" or "negative" for any cell-surface marker, and both such designations are useful for the practice of the methods described herein. A cell is considered "positive" for a cell-surface marker if it expresses the marker on its cell-surface in amounts sufficient to be detected using methods known to those of skill in the art, such as contacting a cell with an antibody that binds specifically to that marker, and subsequently performing flow cytometric analysis of such a contacted cell to determine whether the antibody is bound the cell. It is to be understood that while a cell may express messenger RNA for a cell-surface marker, in order to be considered positive for the methods described herein, the cell must express it on its surface. Similarly, a cell is considered "negative" or "negative/low" (abbreviated as "–/lo" or "lo/–") for a cell-surface marker if the cell does not express the marker on its cell surface in amounts sufficient to be detected using methods known to those of skill in the art, such as contacting a cell with an antibody that binds specifically to that marker and subsequently performing flow cytometric analysis of such a contacted cell to determine whether the antibody is bound the cell. In some embodiments, where agents specific for cell-surface lineage markers used, the agents can all comprise the same label or tag, such as fluorescent tag, and thus all cells positive for that label or tag can be excluded or removed, to leave uncontacted hematopoietic stem or progenitor cells for use in the methods described herein.

As used herein, the term "a histone methyltransferase inhibitor" or "inhibitor" is any molecule that inhibits of expression of a histone methyltransferase (e.g., G9a, GLP, EZH1), or inhibits the catalytic activity of the enzyme to methylate lysine resides on the substrate histone protein. For example, a histone methyltransferase inhibitor can be an siRNA or dsRNA that inhibits of expression of G9a, GLP, or EZH1 in the inhibited cell, or a gRNA that promotes the degradation of the mRNA of G9a, GLP, or EZH1 in the inhibited cell. For example, a histone methyltransferase inhibitor is a small molecule that antagonizes the enzyme activity. Examples include but are not limited to small molecules AMI-1, A-366, BIX-01294, BIX01338, BRD4770, chaetocin, UNC0224, UNC0631, UNC0638, UNC0642, UNC0646, EPZ5676, EPZ005687, GSK343, EPZ-6438, 3-deazaneplanocin A (DZNeP) HCl, UNC1999, MM-102, SGC 0946, Entacapone, EPZ015666, UNC0379, EI1, MI-2 (Menin-MLL Inhibitor), MI-3 (Menin-MLL Inhibitor), PFI-2, GSK126, EPZ004777, BRD4770, and EPZ-6438 as described herein.

As used herein, the term "small molecule" refers to a chemical agent including, but not limited to, peptides, peptidomimetics, amino acids, amino acid analogs, polynucleotides, polynucleotide analogs, aptamers, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. In some embodiments, the small molecule is a heterorganic compound or an organometallic compound.

The term "inhibitory RNA" is meant to include a nucleic acid molecule that contains a sequence that is complementary to a target nucleic acid (e.g., a target microRNA) that mediates a decrease in the level or activity of the target nucleic acid. Non-limiting examples of inhibitory RNAs include interfering RNA, shRNA, siRNA, ribozymes, antagomirs, and antisense oligonucleotides. Methods of making inhibitory RNAs are described herein. Additional methods of making inhibitory RNAs are known in the art. In one embodiment, the BCL11A microRNA described herein is an inhibitory RNA that causes a decrease in the activity of BCL11A mRNA.

As used herein, "an interfering RNA" refers to any double stranded or single stranded RNA sequence, capable—either directly or indirectly (i.e., upon conversion) of inhibiting or down-regulating gene expression by mediating RNA interference. Interfering RNA includes, but is not limited to, small interfering RNA ("siRNA") and small hairpin RNA ("shRNA"). "RNA interference" refers to the selective degradation of a sequence-compatible messenger RNA transcript.

As used herein "an shRNA" (small hairpin RNA) refers to an RNA molecule comprising an antisense region, a loop portion and a sense region, wherein the sense region has complementary nucleotides that base pair with the antisense region to form a duplex stem. Following post-transcriptional processing, the small hairpin RNA is converted into a small interfering RNA by a cleavage event mediated by the enzyme Dicer, which is a member of the RNase III family. As used herein, the phrase "post-transcriptional processing" refers to mRNA processing that occurs after transcription and is mediated, for example, by the enzymes Dicer and/or Drosha.

A "small interfering RNA" or "siRNA" as used herein refers to any small RNA molecule capable of inhibiting or down regulating gene expression by mediating RNA interference in a sequence specific manner. The small RNA can be, for example, about 18 to 21 nucleotides long. Each siRNA duplex is formed by a guide strand and a passenger strand. The endonuclease Argonaute 2 (Ago 2) catalyzes the unwinding of the siRNA duplex. Once unwound, the guide strand is incorporated into the RNA Interference Specificity Complex (RISC), while the passenger strand is released. RISC uses the guide strand to find the mRNA that has a complementary sequence leading to the endonucleolytic cleavage of the target mRNA.

Retroviruses are RNA viruses that utilize reverse transcriptase during their replication cycle. The term "retrovirus" refers to any known retrovirus (e.g., type c retroviruses, such as Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus The retroviral genomic RNA is converted into double-stranded DNA by reverse transcriptase. This double-stranded DNA form of the virus is capable of being integrated into the chromosome of the infected cell; once integrated, it is referred to as a "provirus." The provirus serves as a template for RNA polymerase II and directs the expression of RNA molecules, which encode the structural proteins and enzymes needed to produce new viral particles.

At each end of the provirus are structures called "long terminal repeats" or "LTRs." The term "long terminal repeat (LTR)" refers to domains of base pairs located at the ends of retroviral DNAs which, in their natural sequence context, are direct repeats and contain U3, R, and U5 regions. LTRs generally provide functions fundamental to the expression of retroviral genes (e.g., promotion, initiation and polyadenylation of gene transcripts) and to viral replication. The LTR contains numerous regulatory signals including transcriptional control elements, polyadenylation signals and sequences needed for replication and integration of the viral genome. The viral LTR is divided into three regions called U3, R and U5. The U3 region contains the enhancer and promoter elements. The U5 region is the sequence between the primer binding site and the R region and contains the polyadenylation sequence. The R (repeat) region is flanked by the U3 and U5 regions. The LTR composed of U3, R, and U5 regions, appears at both the both the 5' and 3' ends of the viral genome. In one embodiment of the invention, the promoter within the LTR, including the 5' LTR, is replaced with a heterologous promoter. Examples of heterologous promoters that can be used include, for example, a spleen focus-forming virus (SFFV) promoter, a tetracycline-inducible (TET) promoter, a β-globin locus control region and a β-globin promoter (LCR), and a cytomegalovirus (CMV) promoter.

The term "lentivirus" refers to a group (or genus) of retroviruses that give rise to slowly developing disease. Viruses included within this group include HIV (human immunodeficiency virus; including HIV type 1, and HIV type 2), the etiologic agent of the human acquired immunodeficiency syndrome (AIDS); visna-maedi, which causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates. Diseases caused by these viruses are characterized by a long incubation period and protracted course. Usually, the viruses latently infect monocytes and macrophages, from which they spread to other cells. HIV, FIV, and SIV also readily infect T lymphocytes, i.e., T-cells.

The term "R region" refers to the region within retroviral LTRs beginning at the start of the capping group (i.e., the start of transcription) and ending immediately prior to the start of the poly A tract. The R region is also defined as being flanked by the U3 and U5 regions. The R region plays an important role during reverse transcription in permitting the transfer of nascent DNA from one end of the genome to the other.

The term "promoter/enhancer" refers to a segment of DNA which contains sequences capable of providing both promoter and enhancer functions. For example, the long terminal repeats of retroviruses contain both promoter and enhancer functions. The enhancer/promoter may be "endogenous," "exogenous," or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

A "nucleic acid," as described herein, can be RNA or DNA, and can be single or double stranded, and can be selected, for example, from a group including: nucleic acid encoding a protein of interest, oligonucleotides, nucleic acid analogues, for example peptide-nucleic acid (PNA), pseudo-complementary PNA (pc-PNA), and locked nucleic acid (LNA). Such nucleic acid sequences include, for example, but are not limited to, nucleic acid sequence encoding proteins, for example that act as transcriptional repressors, antisense molecules, ribozymes, small inhibitory nucleic acid sequences, for example but are not limited to RNAi, shRNAi, siRNA, microRNAi (miRNA), and antisense oligonucleotides.

As used herein, the term "engraftment" in reference to a recipient host is when the new blood-forming cells start to grow and which are derived from the implanted cells and make healthy blood stem cells that show up in recipient's blood after a minimum period of 10 days after implantation. Engraftment can occur as early as 10 days after transplant but is more common around 14-20 days.

As used herein, the term "reconstitution" with respect to the immune system or the blood system in a recipient host refers to the rebuilding the innate reservoir or working system, or part thereof within the body of recipient host to a natural or a functionally state. For example, such as bone marrow after chemotherapy had obliterated the bone marrow stem cells.

BRIEF DESCRIPTION OF THE DRAWINGS

FIG. 1A shows the scheme for embryoid body (EB) differentiation of human iPSC into hematopoietic progenitors. EBs cultured in serum, BMP4 and hematopoietic cytokines were dissociated after 14 days. CD34+ progenitors were isolated by MACS sorting and transduced with HOXA9, ERG, RORA, SOX4 and MYB in doxycycline (Dox)-inducible lentiviral vectors (5F). 5F cells were then transduced with individual shRNAs targeting each epigenetic modifier, then seeded onto OP9-DL1 stromal co-culture in a 96-well plate to induce T cell differentiation. Dox was added to cultures for 20 days to sustain transgene expression and then removed thereafter. T cell potential was assessed by flow cytometry on day 35.

FIG. 1B shows the Venn diagram summarizing the candidate hits from two independent experiments using two different IPSC lines, CD45-IPS and MSC-IPS. The screen was performed by transduction with 5F followed by superinfection of shRNAs, then the transduced cells were co-cultured with OP-DL1 stroma. The top candidates from the screen are listed. Each candidate was scored as a hit if at least 2 of 4 shRNAs produced CD4+CD8+ T cells at higher frequency and higher absolute cell counts compared to control shRNAs targeting luciferase (shLUC).

FIG. 1C shows the relative expansion of 5F+shRNA cells after 14 days respecification in +Dox culture.

FIG. 1D shows the prospective analysis of CD4+CD8+ T cell frequencies from 5F+shRNA targeting indicated epigenetic modifier.

FIG. 1E shows the prospective analysis of CD19+ B cell frequencies from indicated 5F+shRNA cells.

FIG. 1F shows the expansion and differentiation potential of 5F+shEZH1 cells after long-term in vitro culture. 5F+shEZH1 cells were maintained in +Dox cultures for the normal 14 days respecification ($\sim 10^2$-fold expansion), plus an additional 6 weeks ($\sim 10^4$-fold expansion) and then plated into OP9-DL1 stromal coculture. Representative flow cytometric analyses of T cell potential of 5F+shLUC and 5F+shEZH1 cells after long-term culture and differentiation (13 weeks) are shown.

FIGS. 2A-2F collectively show that the repression of EZH1 unlocks multilymphoid potential with minimal effects on myeloerythroid differentiation.

FIG. 2A shows the flow cytometry analysis of CD4+ CD8+ T cell development of 5F cells with two different shRNAs targeting luciferase (shLUC) or EZH1 (shEZH1). Cells were assessed at 35 days following of co-culture with OP9-DL1.

FIG. 2B shows that the knockdown of EZH1 robustly promotes B cell (CD19+) potential in iPSC-derived 5F cells as assessed by flow cytometry.

FIG. 2C shows that the myeloid (CD11b) cells differentiation are not impaired in 5F+shEZH1 cells.

FIG. 2D shows that the erythroid (CD71+GLYA+) cells differentiation are not impaired in 5F+shEZH1 cells.

FIG. 2E shows the quantitation of T cell potential of 5F+shEZH1 cells compared to 5F+shLUC cells. Graph is shown as mean f SEM of 5 independent replicates using CD34-iPS, CH45-iPS and MSC-iPS lines. ***$p<0.001$.

FIG. 2F shows the colony-forming potential of 5F+shLUC or 5F+shEZH1 cells plated without Dox. (Top Row) Representative images of CFU-G, CFU-M, CFU-GM, CFU-GEMM and CFU-E colonies on plates without Dox. (Bottom Row, Left) Representiatve images of 5F+shLUC or 5F+shEZH1 plates. (Bottom Row, Right) Quantitation of colony-forming potential of 5F+shLUC or 5F+shEZH1 cells in two independent experiments (n=2).

FIG. 3A shows the representative flow cytometry plots of 5F cells with each indicated PRC2 subunit knocked down using two different shRNAs.

FIG. 3B shows the quantitative PCR of mRNA knockdown efficiency of individual shRNAs.

FIG. 3C shows the quantitation of T cell frequencies from 5F plus shRNA targeting the indicated subunit shown as mean±SEM of two independent experiments.

FIG. 3D shows the schematic for rescue experiments. 5F cells are GFP+ and shRNAs are selectable by puromycin. 5F+shEZH1 cells were transduced with murine EZH1 ORF (mEzh1) or mEzh1 with the catalytic SET domain deleted (mEzh1ΔSet), both marked by mCherry fluorescence. GFP+, puro-resistant, mCherry+ cells were sorted and seeded into OP9-DL1 stromal co-culture for T cell differentiation.

FIG. 3E shows the representative flow cytometric plots of rescue experiments detailed in FIG. 3D. All plots are gated on CD45+.

FIG. 3F shows the quantitation of flow cytometric analysis in FIG. 3E, data presented as mean f SEM of two independent experiments.

FIG. 3G shows the dose-dependent decrease in EZH2 and EZH1 enzymatic activity with increasing concentration of GSK126 as monitored by total protein levels of the H3K27me3 in 5F cells. At 3 uM, protein levels of total H3K27me3 begins to decrease relative to DMSO control, indicating effective dose for EZH2 and EZH1 inhibition.

FIG. 3H shows the flow analysis of T cell potential after treatment of CD34+ d9 hemogenic endothelial (HE) cells without 5F treated with an escalating dose GSK126.

FIG. 3I shows the representative images of colony assays plated with 5F cells treated with the indicated GSK126 concentration.

FIG. 3J shows the quantitation of colonies in (G) as f SEM of two replicates.

FIGS. 4A-4H collectively show that gene expression and chromatin accessibility of definitive respecified progenitors.

FIG. 4A shows the 104 genes were significantly upregulated and 49 genes were significantly downregulated (>2-fold; t-test, $p<0.1$) upon EZH1 knockdown compared to control knockdown in 5F cells.

FIG. 4B shows the GO analysis of the most significantly upregulated genes in FIG. 4A.

FIG. 4C shows the GSEA analysis of human HSC and progenitor signatures in 5F+shEZH1 compared with 5F+shLUC cells. HSC_MLP, MLP and GMP signatures are significantly enriched (FDR<0.25) in 5F+shEZH1 cells.

FIG. 4D shows the plot of all ATAC-seq peaks in 5F+shEZH1 and 5F+shLUC cells.

FIG. 4E shows the GO analysis of enriched pathways of regions associated with upregulated ATAC-seq peaks.

FIG. 4F shows the comparison of genomic regions associated with upregulated ATAC-seq peaks and HSPC, T, B cell GRNs and HSPC signa-tures. *$p<0.05$.

FIG. 4G shows the GO analysis of enriched pathways of regions associated with downregulated ATAC-seq peaks.

FIG. 4H shows the comparison of genomic regions associated with upregulated ATAC-seq peaks and HSPC, T, B cell GRNs and HSPC signatures. *$p<0.05$.

FIG. 5A shows that the EZH1 or EZH2 tagged with V5 epitope was overexpressed in 5F cells and subjected to ChIP-sequencing analysis. ChIP-seq peaks were defined within proximal promoter re-gions (−1 to +1 kb of TSS). EZH1 and EZH2 ChIP-seq peaks were overlapped to identify unique EZH1-bound promoters.

FIG. 5B is the ChIP-seq density heatmaps for H3K4me3, H3K27me3, EZH1 and EZH2.

FIG. 5C shows the proportion of histone marks associated with EZH1 and EZH2 promoters.

FIG. 5D shows the mRNA expression heatmap of unique EZH1 bound TFs, 152 out of 1069 total genes, and their regulated network.

FIG. 5E shows that the significantly upregulated networks of EZH1-bound TFs (FDR<0.25) are enriched in HSPC, B and T cell GRNs.

FIG. 5F shows that EZH1-bound TFs are specifically expressed in HSC, MLP and Pro-B cell populations of the HSPC hierarchy.

FIG. 5G shows that the enrichment of EZH1-bound genes to each population of HSPC hierarchy (left) and the breakdown of their associated histone marks (right).

FIG. 5H shows that the EZH1-bound, bivalent genes are highly expressed in B, T, NK, granulocyte and monocyte lineages.

FIG. 6A shows the representative images of E9.5 embryo proper (top) and yolk sac (bottom).

FIG. 6N shows the lineage distribution of secondary recipients in FIG. 6M. *p<0.05, ** p<0.01, N.E.=not engrafted.

FIG. 7A shows the of candidate chromatin factors. Four shRNAs targeting each factor were used in the screen.

FIG. 7B shows the representative flow plots showing T cell potential of 5F cells with each top candidate factor knocked down with shRNAs.

FIGS. 9A-9C collectively show the ATAC-sequencing analysis of 5F+shEZH1 versus 5F+shLUC cells.

FIG. 9A. GO analysis of enriched pathways of nearest neighbor genes associated with upregulated ATAC-seq peaks.

FIG. 9B GO analysis of nearest neighbor genes associated with upregulated ATAC peaks.

FIG. 9C. Comparison of upregulated and downregulated ATAC-seq peaks in 5F+shEZH1 cells with HSPC, B, T cell GRN and HSPC hierarchy signatures.

FIGS. 10A-11F collectively show the characterization of adult Ezh1-deficient mice.

FIG. 10A shows the quantification of LSK SLAM HSCs in adult bone marrow.

FIG. 11A shows the gating scheme for (embryo proper) EP and (yolk sac) YS.

FIG. 11B shows the representative flow plots of B cells in EP and YS from multiple pooled embryos (left) and quantitation from two replicates (right).

FIG. 11C shows the representative flow plots of T cells in EP and YS from multiple pooled embryos (left) and quantitation from two replicates (right).

FIG. 12A shows the representative flow plots of B1 and B2 progenitor frequencies after 9 days differentiation on OP9-DL stroma.

FIG. 12B shows the representative images of CD19+ B cells (left) isolated from (FIG. 13A) and after 4 days in class switch recombination-promoting conditions (right).

FIG. 12C shows the flow analysis of class-switch recombination efficiencies.

FIG. 13A shows the representative flow analysis of B1 and B2 progenitors in the peritoneal cavity of engrafted primary recipients.

FIG. 13B shows the representative flow analysis of TCRβ and TCRγδ frequencies of donor-derived peripheral CD3+ T cells from engrafted primary recipients.

FIGS. 14A-14D collectively show that the EZH1-regulated networks shared between mouse and human HSPCs.

FIG. 14A shows the 7 significantly upregulated pathways shared between all mouse and human Ezh1-deficient HSPCs.

FIG. 14B shows the three significantly downregulated pathways shared between all mouse and human Ezh1-deficient HSPCs.

FIG. 14C shows the number of genes in each GSEA network shared between human 5F+shEZH1 and mouse HSPCs sorted from indicated tissue/genotype.

FIG. 14D shows the GO analysis of all shared genes in FIG. 5C.

FIG. 16A shows the Venn diagram of 23 candidate transcription factors (TFs) that are specifically expressed in HSCs, downregulated in EB-derived CD34+ progenitors and not induced in ERG, HOXA9, RORA-transduced hematopoietic progenitors.

FIG. 16B shows the new library of 23 TFs and 5F (HOXA9, ERG, RORA, SOX4, MYB) were cloned into doxycycline-inducible lentiviral vectors and transduced in EB-derived CD34+ hematopoietic progenitors and plated into colony assays. Colonies were picked and analyzed for TF integration by genomic PCR using gene-specific primers.

FIG. 16C shows the schematic for assessing lymphoid potential of EB-CD34+ cells transduced with 28 or 13 TF subset. The 13 TFs (including 5F) that were integrated at the highest frequencies were chosen to assess T and B cell potential by stromal co-culture.

FIG. 16D shows the flow cytometic analysis of T cell potential of 28 TF or 13 TF in two different IPS lines (MSC-IPS1, CD34-IPS).

FIG. 16E shows the flow cytometric analysis of B cell potential of 28 TF or 13 TF in two IPS lines. The 13 TFs are sufficient to uncoverT and B cell potential.

FIG. 16F shows the reductive strategy to determine minimal TF requirement for multilymphoid potential. Flow cytometric analysis of lymphoid potential of EB-derived CD34+ cells transduced with all 13 TF or with one TF subtracted at a time. In addition to ERG and RORA, NFIA and DACH1 are required for both T and B cell potential.

DETAILED DESCRIPTION

Figure 1A:
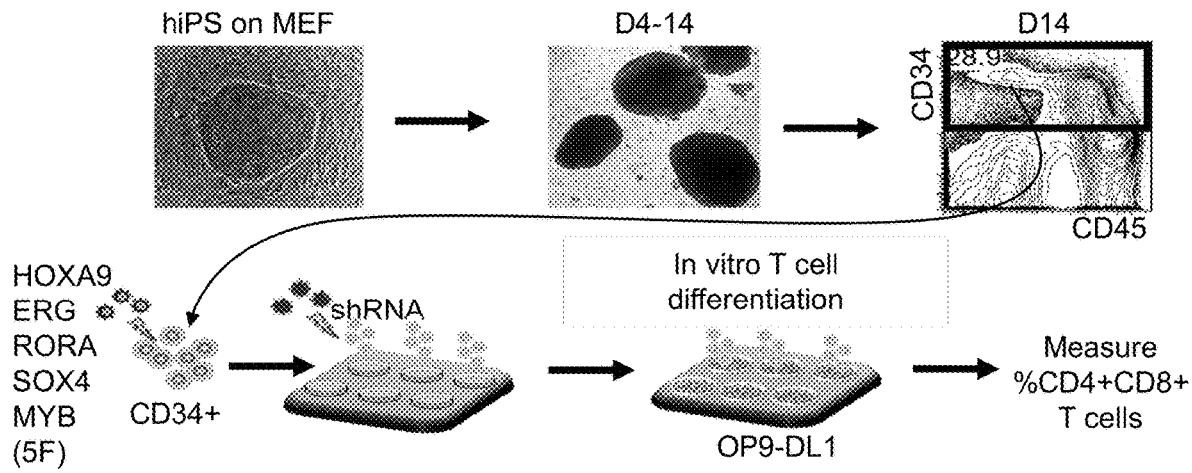
FIGS. 1A-1F collectively show the in vitro screen for epigenetic modifiers that restrict definitive lymphoid potential.

Unless otherwise explained, all technical and scientific terms used herein have the same meaning as commonly understood by one of ordinary skill in the art to which this disclosure belongs. It should be understood that this disclosures is not limited to the particular methodology, protocols, and reagents, etc., described herein and as such can vary. The terminology used herein is for the purpose of describing particular embodiments only, and is not intended to limit the scope of the present invention, which is defined solely by the claims.

Definitions of common terms in molecular biology can be found in The Merck Manual of Diagnosis and Therapy, 19th Edition, published by Merck Sharp & Dohme Corp., 2011 (ISBN 978-0-911910-19-3) or the 2015 digital online edition at merckmanuals.com; Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties. Further, unless otherwise required by context, singular terms shall include pluralities and plural terms shall include the singular.

Unless otherwise stated, the present disclosure was performed using standard procedures known to one skilled in the art, for example, in Michael R. Green and Joseph Sambrook, Molecular Cloning: A Laboratory Manual, Cold Spring Harbor Laboratory Press, Cold Spring Harbor, N.Y., USA (2012); Davis et al., Basic Methods in Molecular Biology, Elsevier Science Publishing, Inc., New York, USA (1986); Current Protocols in Molecular Biology (CPMB) (Fred M. Ausubel, et al. ed., John Wiley and Sons, Inc.), Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998), Methods in Molecular biology, Vol. 180, Transgenesis Techniques by Alan R. Clark editor, second edition, 2002, Humana Press, and Methods in Meolcular Biology, Vo. 203, 2003, Transgenic Mouse, edited by Marten H. Hofker and Jan van Deursen, which are all herein incorporated by reference in their entireties.

Other than in the operating examples, or where otherwise indicated, all numbers expressing quantities of ingredients or reaction conditions used herein should be understood as modified in all instances by the term "about." The term "about" when used in connection with percentages will mean±1%.

All patents and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The disclosure described herein, in a preferred embodiment, does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

The present disclosure relates to in vitro or ex vivo methods for producing functional immune cells from progenitor cells that have little or no lymphoid potential. For example, myeloid progenitor cells have no lymphoid potential and they do not proliferate and differentiate to lymphoid cells such as natural killer lymphocytes, dendritic cells, T lymphocytes, and B lymphocytes. Myeloid progenitor cells are committed in the myeloid lineage; they undergo further cell division, differentiation and maturation, and produce the following cell types: megakaryocytes, thrombocytes, granulocytes, erythrocytes, mast cells, myeloblast, basophils, neutrophils, eosinophils, monocytes and macrophages. The functional immune cells derived from non-lymphoid lineage progenitor cells are modified to carry exogenous DNA copies that encode for certain transcription factors. In one embodiment, patient-specific functional immune cells can be produced according the methods. The cells are functional because they express T- or B-cell specific markers and also undergone T cell receptor (TCR) gene rearrangement.

Accordingly, in one embodiment, provided herein is an in vitro or ex vivo method comprising (a) generating multilineage hematopoietic progenitor cells (MHPCs) from myeloid progenitor cells; (b) inhibiting a histone methyltransferase in the resultant population of MHPCs; and, (c) differentiating the resultant population of MHPCs in the presence of a notch ligand or defined stromal cells or both to promote differentiation into the lymphoid lineage. In some embodiments, in vitro culturing of the cells occurs between the steps. In some embodiments, the cell culturing serves to expand the number of cells of interest at each step prior to performing the next step of the method. In some embodiments, selection of cells occurs between steps.

In another embodiment, provided herein is a method comprising (a) in vitro transfecting myeloid progenitor cells with an exogenous gene coding copy of each of the following transcription factors, ERG, HOXA9, and RORA, wherein the transcription factors are expressed in the transfected cells to produce a resultant population of MHPCs that have both myeloid and erythroid potential; (b) inhibiting a histone methyltransferase in the resultant population of MHPCs to expand lymphoid potential therein; and (c) differentiating the resultant population of MHPCs in the presence of a notch ligand or supportive stroma or both to promote differentiation into the lymphoid lineage. In some embodiments, in vitro culturing of the cells occurs between the steps at each step prior to performing the next step of the method. In some embodiments, selection of cells occurs between steps. In some embodiments, the culturing serves to expand the number of cells of interest.

In another embodiment, this disclosure provides a method of generating of modified immune cells or modified hematopoietic progenitor cells (HPCs) from a population of myeloid progenitor cells comprising: (a) in vitro transfecting the myeloid progenitor cells with an exogenous copy of each of the following transcription factors ERG, HOXA9, and RORA, wherein the transfected transcription factors are expressed in vivo in the cells to produce a population of MHPCs that having myeloid and erythroid potential; (b) inhibiting a histone methyltransferase that methylate histone 3 lysine 9 or lysine 27 residue in the histone (H3K9 or H3K27 or both) in the resultant population of MHPCs; and (c) differentiating the resultant population of MHPCs in the presence of a notch ligand to promote differentiation into the lymphoid lineage. These immune cells are genetically modified. In some embodiments, in vitro culturing of the cells occurs between the steps. In some embodiments, selection of cells occurs between steps. In some embodiments, the culturing serves to expand the number of cells of interest at each step prior to performing the next step of the method.

In another embodiment, provided herein is a method comprising (a) introducing or contacting a population of myeloid progenitor cells with a vector or more, the vector(s) collectively carrying an exogenous gene coding copy of each of the following transcription factors, ERG, HOXA9, and RORA, for in vivo expression in the contacted cells, wherein the transfected transcription factors are expressed in vivo in the contacted cells to produce a population of MHPCs that having myeloid and erythroid potential; (b) contacting the MHPCs with an inhibitor of a histone methyltransferase; and (c) contacting the MHPCs a notch ligand or defined stromal cells or both. In some embodiments, in vitro culturing of the cells occurs between the steps. In some embodiments, selection of cells occurs between steps. In some embodiments, the culturing serves to expand the number of cells of interest at each step prior to performing the next step of the method.

In another embodiment, this disclosure provides a method of improving in vivo engraftment of hematopoietic stem cells (HSCs) or HPCs in a recipient host comprising: (a) generating MHPCs from myeloid progenitor cells; (b) inhibiting a histone methyltransferase in the resultant population of MHPCs; and (c) transplanting said resultant MHPCs into the host. In some embodiments, in vitro culturing of the cells occurs between the steps. In some embodiments, selection of cells occurs between steps. In some embodiments, the culturing serves to expand the number of cells of interest at each step prior to performing the next step of the method. The myeloid progenitor cells have no or limited lymphoid potential. In one embodiment, co-culturing the myeloid progenitor cells in OP9-DL1/4 cells does not produce any $CD4^+/CD8^+$ cells.

In another embodiment, this disclosure provides a modified or engineered immune cell produced by a method described herein. These immune cells are genetically modified to have exogenous copies of ERG, HOXA9, and RORA compared to the original myeloid progenitor cells.

In another embodiment, this disclosure provides a composition comprising engineered immune cells produced by a method described herein. In one embodiment, the composition further comprises a pharmacological acceptable carrier. In one embodiment, the pharmacological acceptable carrier is not cell culture media.

In one embodiment, this disclosure provides a modified myeloid progenitor cells having reversed lineage to include increased lymphoid lineage potential.

In one embodiment, this disclosure provides a composition which contain the modified modified myeloid progenitor cells having reversed lineage to include increased lymphoid lineage potential.

In one embodiment, this disclosure provides modified myeloid progenitor cells described herein and compositions thereof for use in the manufacture/production of described modified immune cells.

In one embodiment, this disclosure provides modified myeloid progenitor cells described herein and compositions thereof for use in the cellular replacement therapy, or for the treatment of cancer, autoimmune disorders, hematological diseases or other genetic diseases and disorders.

In one embodiment, this disclosure provides an engineered immune cell derived from a population of myeloid progenitor cells, wherein the immune cell comprises an exogenous gene coding copy of each of the following transcription factors: ERG, HOXA9, and RORA. In another embodiment, the immune cell consists essentially of an exogenous gene coding copy of each of the following transcription factors: ERG, HOXA9, and RORA. In a further embodiment, the immune cell consists of an exogenous gene coding copy of each of the following transcription factors: ERG, HOXA9, and RORA. In one embodiment, the immune cell further comprise of an exogenous gene coding copy of following transcription factor SOX4 or MYB or both SOX4 and MYB. In one embodiment, the immune cell further comprise of an exogenous gene coding copy of following transcription factor DACH1 or NFIA or both DACH1 and NFIA.

In another embodiment, this disclosure provides an engineered immune cell or modified myeloid progenitor cell derived from a population of myeloid progenitor cells, wherein the immune cell or modified myeloid progenitor cell comprises an exogenous gene coding copy of each of the following transcription factors ERG, HOXA9, and RORA, and an exogenous gene coding copy of each of the following reprogramming factors OCT4, SOX2, KLF4 and optionally c-MYC or nanog and LIN28. Alternatively, the reprogramming factors are OCT4, SOX2, NANOG and LIN28. In another embodiment, the immune cell or modified myeloid progenitor cell consists essentially of an exogenous gene coding copy of each of the following transcription factors: ERG, HOXA9, and RORA, and an exogenous gene coding copy of each of the following reprogramming factors OCT4, SOX2, KLF4 and optionally c-MYC or nanog and LIN28. In a further embodiment, the immune cell or modified myeloid progenitor cell consists of an exogenous gene coding copy of each of the following transcription factors: ERG, HOXA9, and RORA, and an exogenous gene coding copy of each of the following reprogramming factors OCT4, SOX2, KLF4 and optionally c-MYC or nanog and LIN28. Alternatively, the reprogramming factors introduced into the modified cell are OCT4, SOX2, NANOG and LIN28.

In one embodiment, this disclosure provides a composition of modified or engineered immune cells or modified myeloid progenitor cell derived from a population of myeloid progenitor cells, wherein the modified cell comprises an exogenous copy of each of the following transcription factors ERG, HOXA9, and RORA. In another embodiment, the modified cell or modified myeloid progenitor cell consists essentially of an exogenous gene coding copy of each of the following transcription factors: ERG, HOXA9, and RORA. In a further embodiment, the modified cell or modified myeloid progenitor cell consists of an exogenous gene coding copy of each of the following transcription factors: ERG, HOXA9, and RORA.

In one embodiment, the modified cells described further comprise an exogenous gene coding copy of one or both of two addition transcription factors, SOX4 and MYB. In another embodiment, the modified cells further consists essentially an exogenous gene coding copy of one or both of two addition transcription factors, SOX4 and MYB. In a further embodiment, the modified cell consists of an exogenous gene coding copy of two addition transcription factors, SOX4 and MYB.

In one embodiment, the modified cells described further comprise an exogenous gene coding copy of one or both of two addition transcription factors, DACH1 and NFIA. In another embodiment, the modified cells further consists essentially an exogenous gene coding copy of two addition transcription factors, DACH1 and NFIA. In a further embodiment, the modified cell consists of an exogenous gene coding copy of one or both of two addition transcription factors, DACH1 and NFIA.

In another embodiment, this disclosure provides a modified or engineered MHPC produced by a method described herein. In another embodiment, this disclosure provides a composition comprising engineered MHPCs produced by a method described herein. The engineered MHPC has exogenous gene coding copy of one or more of the following transcription factors: ERG, HOXA9, RORA, SOX4, MYB, DACH1, NFIA, OCT4, SOX2, KLF4, c-MYC, NANOG and LIN28. Combinations of exogenous transcription or reprogramming factors in the engineered MHPC include ERG, HOXA9, and RORA; ERG, HOXA9, RORA, SOX4 and MYB; ERG, HOXA9, RORA, DACH1, and NFIA; ERG, HOXA9, RORA, SOX4, MYB, DACH1, and NFIA; ERG, HOXA9, RORA, OCT4, SOX2, KLF4 and optionally c-MYC or NANOG and LIN28; ERG, HOXA9, RORA, SOX4, MYB, OCT4, SOX2, KLF4 and optionally c-MYC or nanog and LIN28; ERG, HOXA9, RORA, SOX4, MYB, DACH1, NFIA, OCT4, SOX2, KLF4 and optionally c-MYC or NANOG and LIN28; ERG, HOXA9, RORA, DACH1, NFIA, OCT4, SOX2, KLF4 and optionally c-MYC or nanog and LIN28; ERG, HOXA9, RORA, DACH1, NFIA, OCT4, SOX2, NANOG and LIN28; ERG, HOXA9, RORA, SOX4, MYB, OCT4, SOX2, NANOG and LIN28; and ERG, HOXA9, RORA, DACH1, NFIA, SOX4, MYB, OCT4, SOX2, NANOG and LIN28. In one embodiment, the composition further comprises a pharmacological acceptable carrier. In one embodiment, the pharmacological acceptable carrier is not cell culture media.

In one embodiment, this disclosure provides a composition of modified cells derived from a population of myeloid progenitor cells, wherein the modified cell comprises an exogenous gene coding copy of each of the following transcription factors ERG, HOXA9, RORA, SOX4 and MYB. In another embodiment, the modified cells further consists essentially an exogenous gene coding copy of each of the following transcription factors, ERG, HOXA9, RORA, SOX4 and MYB. In a further embodiment, the modified cell consists of an exogenous gene coding copy of each of the following transcription factors, ERG, HOXA9, RORA, SOX4 and MYB.

In one embodiment, this disclosure provides a composition of modified cells derived from a population of myeloid progenitor cells, wherein the modified cell comprises an exogenous gene coding copy of each of the following transcription factors ERG, HOXA9, RORA, DACH1 and NFIA. In another embodiment, the modified cells further consists essentially an exogenous gene coding copy of each of the following transcription factors, ERG, HOXA9, RORA, DACH1 and NFIA. In a further embodiment, the modified cell consists of an exogenous gene coding copy of each of the following transcription factors, ERG, HOXA9, RORA, DACH1 and NFIA.

In one embodiment, this disclosure provides a composition of modified cells derived from a population of myeloid progenitor cells, wherein the modified cell comprises an exogenous gene coding copy of each of the following transcription factors ERG, HOXA9, and RORA, and an exogenous gene coding copy of each of the following reprogramming factors OCT4, SOX2, KLF4 and optionally c-MYC or nanog and LIN28. In another embodiment, the modified cell consists essentially of an exogenous gene coding copy of each of the following transcription factors: ERG, HOXA9, and RORA, and an exogenous gene coding copy of each of the following reprogramming factors OCT4, SOX2, KLF4 and optionally c-MYC or nanog and LIN28. In a further embodiment, the modified cell consists of an exogenous gene coding copy of each of the following transcription factors: ERG, HOXA9, and RORA, and an exogenous gene coding copy of each of the following reprogramming factors OCT4, SOX2, KLF4 and optionally c-MYC or nanog and LIN28. Alternatively, the combinations of four reprogramming factors, OCT4, SOX2, NANOG and LIN28, are in the modified cell.

In one embodiment, this disclosure provides a composition of modified cells derived from a population of myeloid progenitor cells, wherein the modified cell comprises an exogenous gene coding copy of each of the following transcription factors ERG, HOXA9, RORA, SOX4 and MYB, and an exogenous gene coding copy of each of the following reprogramming factors OCT4, SOX2, KLF4 and optionally c-MYC or nanog and LIN28. In another embodiment, the modified cell consists essentially of an exogenous gene coding copy of each of the following transcription factors: ERG, HOXA9, RORA, SOX4 and MYB, and an exogenous gene coding copy of each of the following reprogramming factors OCT4, SOX2, KLF4 and optionally c-MYC or nanog and LIN28. In a further embodiment, the modified cell consists of an exogenous gene coding copy of each of the following transcription factors: ERG, HOXA9, RORA, SOX4 and MYB, and an exogenous gene coding copy of each of the following reprogramming factors OCT4, SOX2, KLF4 and optionally c-MYC or nanog and LIN28. Alternatively, the combinations of four reprogramming factors, OCT4, SOX2, NANOG and LIN28, are in the modified cell.

In one embodiment, this disclosure provides a composition of modified cells derived from a population of myeloid progenitor cells, wherein the modified cell comprises an exogenous gene coding copy of each of the following transcription factors ERG, HOXA9, RORA, DACH1 and NFIA, and an exogenous gene coding copy of each of the following reprogramming factors OCT4, SOX2, KLF4 and optionally c-MYC or nanog and LIN28. In another embodiment, the modified cell consists essentially of an exogenous gene coding copy of each of the following transcription factors: ERG, HOXA9, RORA, DACH1 and NFIA, and an exogenous gene coding copy of each of the following reprogramming factors OCT4, SOX2, KLF4 and optionally c-MYC or nanog and LIN28. In a further embodiment, the modified cell consists of an exogenous gene coding copy of each of the following transcription factors: ERG, HOXA9, RORA, DACH1 and NFIA, and an exogenous gene coding copy of each of the following reprogramming factors OCT4, SOX2, KLF4 and optionally c-MYC or nanog and LIN28. Alternatively, the combinations of four reprogramming factors, OCT4, SOX2, NANOG and LIN28, are in the modified cell.

In one embodiment, this disclosure provides a composition of modified cells derived from a population of myeloid progenitor cells, wherein the modified cell comprises an exogenous gene coding copy of each of the following transcription factors ERG, HOXA9, RORA, SOX4, MYB, DACH1 and NFIA, and an exogenous gene coding copy of each of the following reprogramming factors OCT4, SOX2, KLF4 and optionally c-MYC or nanog and LIN28. In another embodiment, the modified cell consists essentially of an exogenous gene coding copy of each of the following transcription factors: ERG, HOXA9, RORA, SOX4, MYB, DACH1 and NFIA, and an exogenous gene coding copy of each of the following reprogramming factors OCT4, SOX2, KLF4 and optionally c-MYC or nanog and LIN28. In a further embodiment, the modified cell consists of an exogenous gene coding copy of each of the following transcription factors: ERG, HOXA9, RORA, SOX4, MYB, DACH1 and NFIA, and an exogenous gene coding copy of each of the following reprogramming factors OCT4, SOX2, KLF4 and optionally c-MYC or nanog and LIN28. Alternatively, the combinations of four reprogramming factors, OCT4, SOX2, NANOG and LIN28, are in the modified cell.

In one embodiment, this disclosure provides a pharmacological composition comprising modified immune cells described herein and a pharmacological acceptable carrier, wherein the modified immune cell comprises an exogenous gene coding copy of each of the following transcription factors ERG, HOXA9, RORA, and optionally each of the following transcription factors SOX4, MYB, DACH1 and NFIA. In one embodiment, the pharmacological acceptable carrier is not cell culture media. In one embodiment, the pharmacological composition is a cryopreserved composition comprising at least one cryopreservative agent known in the art.

Pluripotent stem cells (PSCs) have the potential to give rise to all the somatic tissues. Directed differentiation of PSCs aims to recapitulate embryonic development to generate patient-matched tissues by specifying the three germ layers. A common theme in directed differentiation across all germ layers is the propensity of PSCs to give rise to embryonic- and fetal-like cell types, which poses a problem for integration and function in an adult recipient. This distinction is particularly striking in the hematopoietic system, which emerges in temporally and spatially separated waves at during ontogeny (Dzierzak and Speck, 2008). The earliest "primitive" progenitors emerge in the yolk sac at 8.5 dpc and give rise to a limited repertoire of macrophages, megakaryocytes and nucleat-ed erythrocytes (Baron et al 2005, Tavian and Peault 2005, Ferkowicz et al 2005). These early embryonic-like progenitors are generally myeloid-based and cannot func-tionally repopulate the bone marrow of adult recipients. By contrast, "definitive" cells with hematopoietic stem cell (HSC) potential emerge later in arterial endothelium within the aorta-gonad-mesonephros (AGM) and other anatomical sites (Dzierzak and Speck, 2008). Directed differentiation of PSCs gives rise to hematopoietic progenitors, which resemble those found in the yolk sac of the early embryo. These lack functional reconstitution potential, are biased to myeloid lineages, and express embryonic globins. Thus, understanding key fate determining mechanisms that promote development of either primitive or definitive lineages is critical for specifying HSCs, and other adult-like cell types (e.g., red blood cells) from PSCs.

Activation of Wnt pathway in the early mesoderm, and Notch in hemogenic endothelium, are critical for enhancing definitive potential (Kennedy et al. 2012, Sturgeon et al. 2013, Ditadi et al. 2015). Definitive potential is marked by B and T lymphopoiesis. While lymphoid activity emerges prior to HSCs (Böiers et al 2013, Yoshimoto et al. 2012, Yoshimoto et al 2011), robust B and T cell potential remains a useful marker of definitive fate in vitro. Comprehensive gene expression profiling has shed light on the molecular distinctions between hematopoietic progenitors throughout ontogeny (Mckinney-Freeman et al. 2012, Miranda-Saavedra et al. 2009). Several classes of homeobox (Hox) A and B cluster genes are expressed in definitive, but not yolk sac cells (Sauvageau et al. 1994, McGrath and Palis 1997). Accordingly, overexpression of HoxB4 is sufficient to generate cells with engraftment potential from mouse PSCs. Moreover, HOXA cluster genes enhance hematopoietic commitment from human PSCs (Doulatov et al. 2013, Ramos-Mejia et al. 2015, Dou et al. 2016). Despite these advances, definitive hematopoietic potential of PSCs remains limited.

Epigenetic regulation maintains cell identity during development. Differentiation is marked by progressive silencing of alternative lineage programs by repressive mecha-nisms, including methylation of DNA and histone residues associated with heterochromatin (Dambacher et al 2010). For instance, tri-methylation of histone H3 on lysine 27 (H3K27) by Polycomb repressive complex 2 (PRC2) is required for blood development (Majewski et al. 2008, Majewski et al. 2010, Mochizuki-Kashio et al. 2011, Hidalgo et al. 2012, Xie et al. 2014, Kinkel et al. 2015, Lee et al. 2015, Ikeda et al. 2016). The inventors tested that primitive and definitive hematopoietic programs are co-excluded by epigenetic mechanisms, similarly to alternative lineage fates. The primitive program that emerges in the yolk sac and during directed differentiation of PSCs is cemented by repressive mechanisms that preclude master transcription factors: SCL, RUNX1, GATA2, HOXA, from activating stem cell and lymphoid genes that characterize definitive progenitors. The inventors found that alleviating this repression would establish definitive potential from PSCs in vitro and early embryonic progenitors in vivo. The inventors here report that haploinsufficient reduction in Polycomb group protein EZH1 enables multi-lymphoid output from PSCs, and emergence of HSCs in sites of primitive hematopoiesis in vivo. Thus, EZH1 is a novel regulator of definitive hematopoietic potential in vitro and in vivo.

The object of the present disclosure is to provide a solution to the problem of a scarcity of HLA-matched HSCs for the in vivo cellular replacement therapy, treatment of various medical diseases/conditions, and for the in vitro studies of disease modeling, drug screening, and hematological diseases, particularly for HLA-matched HSCs that would eventually produce immune cells. Another objective is to enhance the engraftment and reconstitution a transplanted hematopoietic related cell or hematopoietic-derived cells in a subject.

The inventors, by introducing at least three transcription factors, ERG, HOXA9, and RORA, into lineage-restricted myeloid progenitor cells, were able to reverse the lineage potential of these cells, so that the resultant cells now have the capability to proliferate to produce more progeny cells, self-renew to progenitor cells, and also to differentiate into cell types of more than one lineage. This step provides another source of cell type for making lymphoid cells and also erythroid cells. Myeloid progenitor cells are committed to the myeloid lineage for further differentiation and maturation, and the myeloid lineage produces the following cell types: megakaryocytes, thrombocytes, erythrocytes, mast cells, myeloblast, basophils, neutrophils, eosinophils, monocytes and macrophages. The myeloid lineage is different from a lymphoid lineage which produces immune cells such as T and B lymphocytes.

The inventors have shown previously that it is possible to make large bulk amounts of lineage-restricted $CD34^+CD45^+$ myeloid precursor cells from iPSC. (See S. Doulatov, et al. 2013, Cell Stem Cell. 13: 459-470, this reference is incorporated herein in its entirety). Human iPSCs were differentiated as embryoid bodies (EBs) in the presence of BMP4 and cytokines, as previously described (Chadwick et al., 2003, Blood, 102:906-915). Briefly, iPSC colonies were scraped into non-adherent rotating 10 cm plates. EB media was KO-DMEM+20% FBS (Stem Cell Technologies), 1 mM L-glutamine, 1 mM NEAA, penicillin/streptomycin, 0.1 mM β-mercaptoethanol, 200 µg/ml h-transferrin, and 50 µg/ml ascorbic acid. After 24 hrs, media was changed by allowing EBs to settle by gravity, and replaced with EB media supplemented with growth factors: 50 ng/ml BMP4 (R&D Systems), 300 ng/ml SCF, 300 ng/ml FLT3, 50 ng/ml G-CSF, 20 ng/ml IL-6, 10 ng/ml IL-3 (all Peprotech). Media was changed on day 5, and day 10. EBs were dissociated on day 14 by digesting with collagenase B (Roche) for 2 hrs, followed by treatment with enzyme-free dissociation buffer (Gibco), and filtered through an 80 µm filter. Dissociated EBs can be frozen in 10% DMSO, 40% FBS freezing solution.

EBs are three-dimensional aggregates of pluripotent stem cells produced and cultured in vitro in the presence of serum. The EBs then would proceed to generate a mixture of primitive and definitive hematopoietic progenitor cell types. Primitive progenitors equate to those that arise in vivo naturally in the earliest stages of embryonic development, whereas at later stages of maturation the embryonic populations give rise to definitive progenitors cells, which behave similarly to the cells typical of adult hematopoiesis. Lineage-restricted CD34+CD45$^+$ myeloid precursor cells appear at day 10 and are expanded until day 14, and then isolated by cell sorting by CD34+CD45+ surface markers after dissociation of the cells aggregated in the EB. These myeloid progenitors showed robust myeloid colony-forming activity: macrophage colonies (CFU-M), and granulocyte colony (CFU-G), but produce few erythroid colonies (CFU-E and BFU-E) or mixed colonies:
granulocyte/erythrocyte/macrophage/megakaryocyte colonies (multilineage myeloid progenitors: CFU-GEMM), and granulocyte/macrophage colonies (CFU-GM). These lineage-restricted $CD34^+CD45^+$ myeloid precursor cells had no capacity to proliferate or self-renew in culture in the absence of serum. These $CD34^+CD45^+$ progenitors in serum free media completely differentiate into $CD34^-$ cells after 7 days of culture and this is consistent with loss of clonogenic capacity.

From the bulk produced lineage-restricted $CD34^+CD45^+$ myeloid precursors cells, the inventors showed that it was possible to reverse the myeloid restricted lineage of these cells and induce cell proliferation and self-renewal capability by expressing three transcription factors, ERG, HOXA9 and RORA, (abbreviated herein as the EAR factors) in these cells. (See S. Doulatov, et al. 2013, Cell Stem Cell. 13: 459-470, this reference is incorporated herein in its entirety). Briefly, open reading frames encoding the three transcription factors, ERG, HOXA9 and RORA were cloned into lentiviral vectors using LR Clonase (INVITROGEN™). Two lentiviral vectors were used: pSMAL-GFP (constitutive) and pINDUCER-21 (doxycycline-regulated) (Meerbrey et al., 2011, 108:3665-3670, this reference is incorporated herein in its entirety). Lentiviral particles were produced by transfecting 293T-17 cells (ATCC) with the 3rd-generation packaging plasmids. Virus was harvested 12 and 36 hrs after transfection and concentrated by ultracentrifugation at 23,000 rpm for 2 hrs. Constructs were titered by serial dilution on 293T cells. Sorted $CD34^+CD45^+$ progenitors were seeded on fibronectin-coated (10 ug/cm$^2$) 96 well plates at a density of 2-5×10$^4$ cells per well. The infection media was IMDM+20% BIT (StemCell Technologies), 1 mM L-glutamine, and 0.1 mM P-mercaptoethanol, with 300 ng/ml SCF, 300 ng/ml FLT3, 50 ng/ml G-CSF, 20 ng/ml IL-6, 10 ng/ml IL-3 (all Peprotech). Lentiviral infections were carried out in a total volume of 150 ul. Following gene transfer, progenitors were cultured in suspension in infection media supplemented with 50 ng/ml SCF, 50 ng/ml FLT3, 50 ng/ml TPO, 50 ng/ml IL6, and 10 ng/ml IL-3 (all R&D Systems). All experiments with inducible constructs (including all transplantation experiments), infection media was replaced with StemSpan SFEM (StemCell Technologies). Dox was added at 2 ng/ml (Sigma). Culture media was same as above. Cultures were maintained at a density of <1×10$^6$ cells/ml, and media was changed every 3-4 days. Single lentiviral systems can also be used to introduce the open reading frames encoding the three transcription factors, ERG, HOXA9 and RORA into the selected myeloid progenitor cells. Single lentiviral expression systems and vector cassettes are known in the art. For example, as taught in U.S. Pat. No. 8,865,467, the contents are incorporated herein by reference in its entirety. Alternatively, gene transfer can be performed by episomal vectors. Episomal expression vector systems are known in the art. For example, as taught in U.S. Pat. Nos. 5,624,820; 5,674,703; 6,339,065; 6,410,314; 6,479,279; 6,797,494; 6,808,923; 7,294,505; 7,790,446; 8,703,481; 8,187,836; and 9,068,200, the contents of which are incorporated herein by reference in their entirety.

The resultant transfected lineage-restricted CD34$^+$CD45$^+$ myeloid precursor cells produced a CD34$^+$ population of cells after 7 days of culture in serum-free media and this CD34$^+$ population of cells continued to expand from 7-14 days in culture. The production of a population of cells in a serum-free media indicates the recovery of the self-renewal capability of multilineage hematopoietic progenitor cells. Within this expanded population of CD34$^+$ population of cells are cells that are also CD38 negative or low, and are CD90$^+$ and CD 49$^+$. It is well known that the multipotent hematopoietic progenitor cells found in cord blood and hematopoietic stem cells are CD34$^+$/CD 38$^-$. Therefore, by transfecting lineage-restricted CD34$^+$CD45$^+$ myeloid precursors cells with EAR, a new population of cells that can proliferate and self-renew in serum free-media and also exhibit cell surface markers that are characteristics of multilineage multipotent hematopoietic progenitor cells instead of the original lineage-restricted CD34$^+$CD45$^+$ myeloid precursors cells used for the EAR transfection.

Accordingly, the inventors were able to produce multilineage multipotent CD34$^+$/CD 38$^{lo/-}$ hematopoietic progenitor cells from lineage-restricted CD34$^+$CD45$^+$ myeloid precursor cells by EAR transfection.

In one embodiment, provided herein are modified myeloid progenitor cells derived from lineage-restricted CD34$^+$CD45$^+$ myeloid precursor cells, the modified myeloid progenitor cells have reversed lineage that include increased lymphoid lineage potential. In one embodiment, the increased lymphoid lineage potential is at least 5% compared to prior EAR transfection. In other embodiments, the increased lymphoid lineage potential is at least 10%, at least 20%, at least 30%, at least 40%, at least 50%, at least 60%, at least 70%, at least 80%, at least 90%, at least 95%, at least 99%, or more compared to prior to EAR transfection.

The reversed-lineage hematopoietic progenitor cells have myeloid and erythroid lineage potentials and give rise to myelo-erythroid colonies. Moreover, the inventors found that by expressing two additional transcription factors, SOX4 and MYB, in the progenitor cells, the in vivo engraftment of the reversed-lineage hematopoietic progenitor cells was enhanced, and there was an increase in the number of mixed myelo-erythroid colonies from the the reversed-lineage CD34$^+$CD45$^+$ hematopoietic progenitor cells. In one embodiment, the enhanced in vivo engraftment is at least 0.1% compared to in the absence of any additional transcription factors selected from the group consisting of SOX4 and MYB. In other embodiments, the enhanced in vivo engraftment is at least 0.2%, at least 0.5%, at least 1%, at least 2%, at least 3%2 at least 4%, at least 5%, at least 10%, at least 20%, at least 30%, at least 40%, at least 50%, at least 60%, at least 70%, at least 80%, at least 90%, at least 95%, at least 99%, or more compared to in the absence of any additional transcription factors selected from the group consisting of SOX4 and MYB.

In addition, the inventors also found that another two transcription factors, DACH1 and NFIA, enhanced lymphoid potential. In one embodiment, the enhanced in vivo lymphoid potential is at least 0.1% compared to in the absence of any additional transcription factors selected from the group consisting of DACH1 and NFIA. In other embodiments, the enhanced in vivo lymphoid potential is at least 0.2%, at least 0.5%, at least 1%, at least 2%, at least 3%2 at least 4%, at least 5%, at least 10%, at least 20%, at least 30%, at least 40%, at least 50%, at least 60%, at least 70%, at least 80%, at least 90%, at least 95%, at least 99%, or more compared to in the absence of any additional transcription factors selected from the group consisting of DACH1 and NFIA.

By further inhibiting a histone methyltransferase in these reversed lineage multipotent CD34$^+$/CD38$^{lo/-}$ hematopoietic progenitor cells, the inventors were able differentiate these cells into immune cells by co-culturing the reversed lineage multipotent hematopoietic progenitor cells with OP9-DL1/4 cells. The OP9-DL1/4 cells express and secrete the Notch ligand which is a factor known of promoting differentiation of HSCs to T lymphocytes. The Notch ligand activates the Notch signaling pathway in the histone methyltransferase-inhibited, CD34$^+$/CD38$^{lo/-}$ hematopoietic progenitor cells. Normally, in the absence of a histone methyltransferase inhibitor, the reversed lineage multipotent CD34$^+$/CD 38$^{lo/-}$ hematopoietic progenitor cells produce about 0-5% colonies or cells with T cell potential when cultured with OP9-DL1/4 cells. In contrast, with EZH1 knockdown (e.g., by using siRNA or a histone methyltransferase inhibitor) the frequency of T cell potential increased to 25-30%, at least a five-fold increase. See FIGS. 2A and 2B. In some embodiments, the term "OP9" cells referenced herein refers to OP9-DL1 or OL9-DL4 cells that secrete Notch ligand that activate the Notch signaling pathway.

In one embodiment of any method, cells, or composition described herein, the MHPCs exhibit increased frequency of T cell potential compared to in the absence of a histone methyltransferase inhibitor. In one embodiment, the increased frequency of T cell potential is at least 5% compared to prior to in the absence of a histone methyltransferase inhibitor. In other embodiments, the increased frequency of T cell potential is at least 10%, at least 20%, at least 30%, at least 40%, at least 50%, at least 60%, at least 70%, at least 80%, at least 90%, at least 95%, at least 99%, or more compared to prior to in the absence of a histone methyltransferase inhibitor.

Figure 16B:
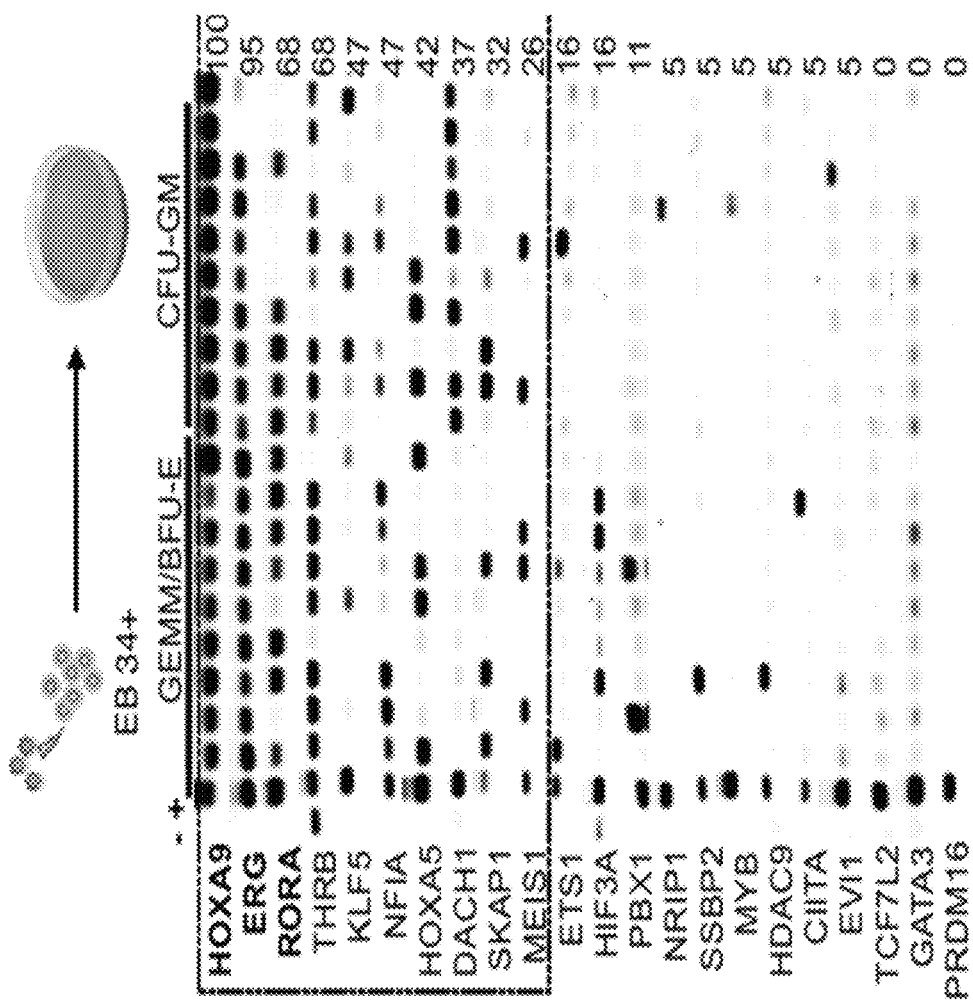
FIGS. 16A-16F shows that NFIA and DACH1 are for lymphoid development from hPSCs.
Figure 16A:
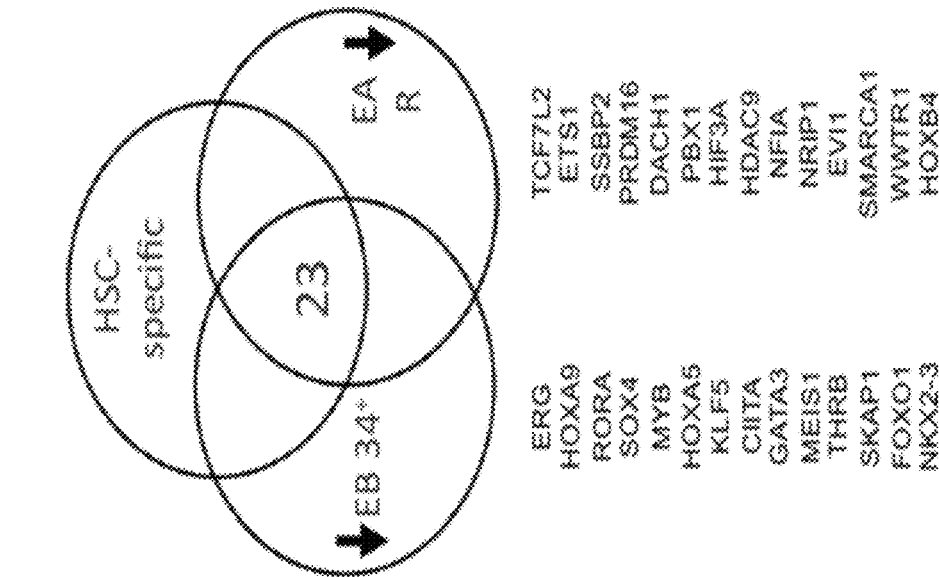
Figure 16C:
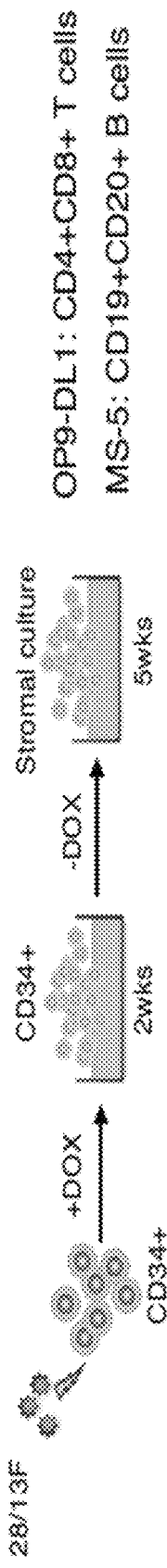
Figure 16D:
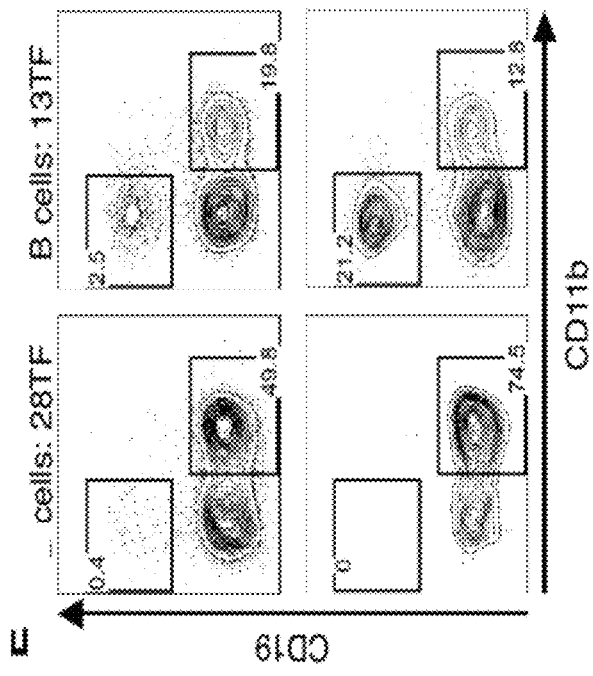
Figure 16E:
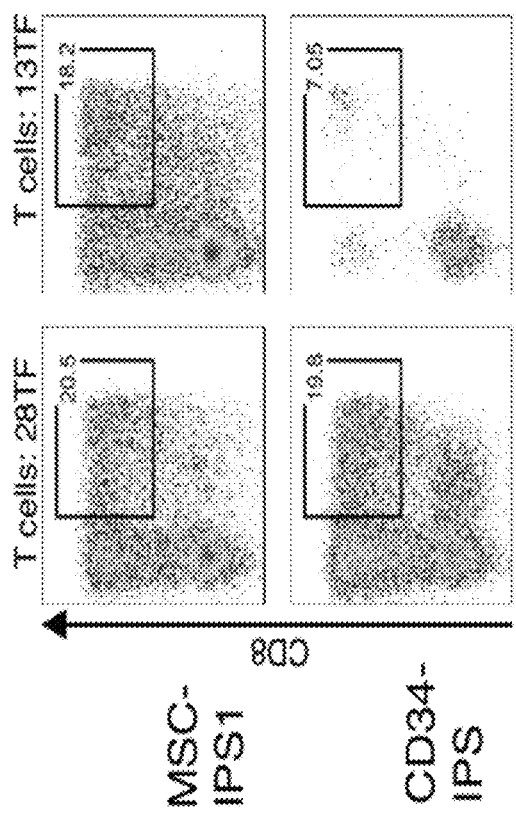
Figure 16F:
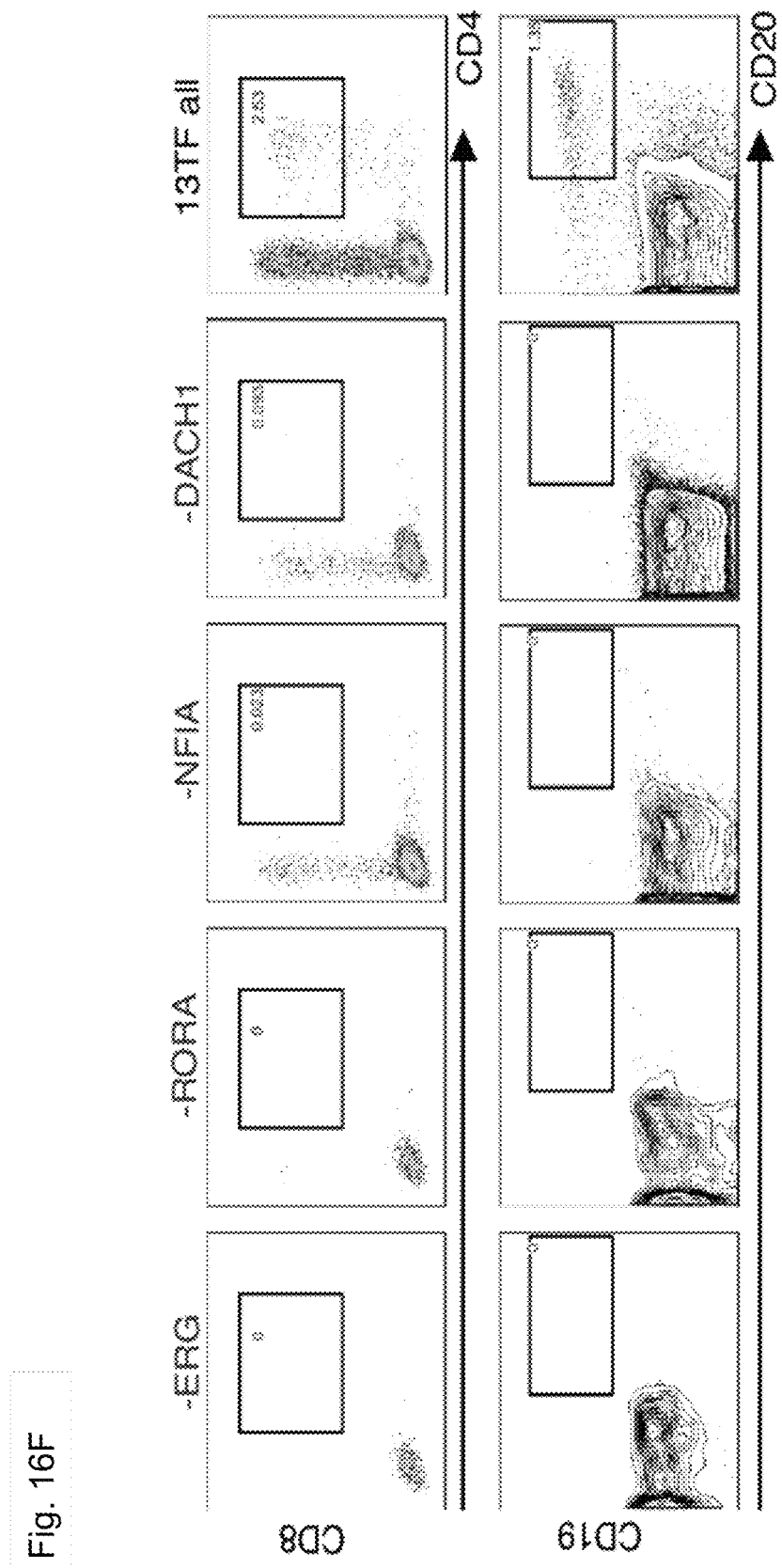

Moreover, by further incorporating the in vivo expression of two other transcription factors, SOX4 and MYB, into these cells, engraftment and reconstitution of these cells in vivo is enhanced. The inventors also found that by further incorporating the in vivo expression of two other transcription factors, DACH1 and NFIA, into these cells, the lymphoid potential of these cells is enhanced. See FIG. 16F.

To understand the gene regulatory networks of definitive lymphoid development from human pluripotent stem cells (hPSCs), in parallel, the inventors screened additional transcription factors that are known to be highly expressed in hematopoietic stem cells (HSCs). The inventors selected 23 additional transcription factors (TFs) in addition to HOXA9, ERG, RORA, SOX4 and MYB that were HSC-specific, not induced by HOXA9, ERG, and RORA, and downregulated in CD34+ cells differentiated from embryoid bodies (EBs). The library of 28 transcription factors were introduced into CD34+ EBs and the EBs were plated used in colony-forming assays. Integration-site analysis by PCR of colonies revealed enrichment in 13 TFs. To test these libraries prospectively, CD34+ EBs were transduced with the 13 TF subset or 28 TF library and plated the cells onto stromal co-culture to induce T or B cell differentiation. The 13 TF library was sufficient to induce multilymphoid potential from CD34+ EBs. To identify the necessary TFs for lymphoid potential, one TF was removed at a time from the 13 TF cocktail, and T and B cell differentiation were performed in the transduced EB. The inventors found that the addition of NFIA and DACH1, together with HOXA9, ERG, RORA, were required for T and B cell development from hPSCs.

NFI genes function as both positive and regulators of gene transcription. NFIA has been shown to regulate erythrocytic/granulocytic lineage switching (Fazi et al 2005, Starnes et al 2009). DACH1 regulates cell cycle progression of myeloid cells and maintain the colonogenic activity and block the differentiation of myeloid progenitors (Lee et al 2012, Lee et al 2012). However, their roles in hematopoietic stem cell and definitive lymphoid development have not been previously explored. Here, the inventors demonstrated that these TFs are part of a regulatory network that is required for lymphoid development from hPSCs.

The advantage of the disclosure protocols is the methods enable semi-permanent bulk production of desired immune cells or other types of hematopoietic cells (i.e. cells differentiated from multipotent HSCs) from a variety of types of cell source, from stem cells, hematopoietic progenitor cells, and mature and differentiated somatic cells, all of which can be readily collected from the patient's body.

The produced engineered immune cells or engineered histone methyltransferase-inhibited, CD34+/CD 38l$^{o/-}$ hematopoietic progenitor cells can be transplanted into a patient for various medical treatments such as immune system reconstruction therapy (e.g., after bone marrow ablation) or immunotherapy (e.g., in cancer therapy or autoimmune diseases). One added advantage is that if the donor of the source cells and recipient of the engineered immune cells are the same person, the produced engineered immune cells have HLA that are identical to the recipient and this avoids host-graft immune rejection after the transplantation. For recipient patients that are HLA allogeneic to the donor person of the source cells, host-graft immune rejection is greatly reduced.

The produced engineered immune cells or engineered histone methyltransferase-inhibited, CD34+/CD 38− hematopoietic progenitor cells can also be cryopreserved till needed in the future.

Currently, bone marrow transplantation is the most established cellular replacement therapy for a variety of hematological disorders. The functional unit of a bone marrow transplant is the hematopoietic stem cell (HSC), which resides at the apex of a complex cellular hierarchy and replenishes blood development throughout life[1]. The scarcity of HLA-matched HSCs severely limits the ability to carry out transplantation, disease modeling and drug screening. As such, many studies have aimed to generate HSCs from alternative sources. Advances in reprogramming to induced pluripotent stem cells (iPSCs)[2] has provided access to a wide array of patient-specific pluripotent cells, a promising source for disease modeling, drug screens and cellular therapies. However, the inability to derive engraftable hematopoietic stem and progenitor cells from human pluripotent stem cells (hPSCs) has limited the characterization of hematological diseases to in vitro assays. Generation of HSCs by directed differentiation has remained elusive, and there is a need for novel approaches to this problem.

One approach to generate HSCs from hPSCs is to specify HSCs from its ontogenetic precursors. It is now widely accepted that HSCs originate from hemogenic endothelium (HE) in the aorta-gonad-mesonephros (AGM)[3] and arterial endothelium in other anatomical sites. Recent work on the directed differentiation of HE from hPSCs have provided valuable insights into some of the signaling pathways that control the emergence of primitive or definitive populations[4,5]; however, the endothelial-to-hematopoietic transition remains incompletely understood in human hematopoietic development, making rational intervention challenging.

An alternative to specifying HSCs from its precursor HE is to start with the short-lived progenitors and convert them to a stem cell state, a strategy that that is define as "respecification"[6]. Respecification combines directed differentiation with transcription-based reprogramming to re-establish HSC fate. The molecular differences between primary human HSCs and progenitors have been well characterized by gene expression profiling[7,8], providing a rational approach to introduce stem cell genes back into progenitors. The inventors were able to obtain transplantable HSC by restoring the HSC transcription factor network in primitive progenitors derived from hPSCs. The proof-of-principle for this approach is seminal experiments that demonstrate that HoxB4 can restore HSC properties in murine primitive progenitors[9].

For the human system[10,11], a different set of factors were need to restore hHSC properties in human primitive progenitors due to species-specific differences. The inventors tailored transcription factor combinations for hPSCs. The inventors had previously reported that five transcription factors: ERG, HOXA9, RORA, SOX4, and MYB (abbreviated as 5F) can convert hPSC-derived myeloid-restricted precursors into reversibly immortalized multilineage hematopoietic progenitors[6]. Doxycycline (Dox)-regulated conditional induction of 5F expands and maintains an immature CD34+CD38− self-renewing state while Dox withdrawal initiates differentiation. The immature CD34+CD38− self-renewing state is a hHSC property. These cells are abbreviated as CD34-5F cells. The CD34-5F cells give rise to short-term engraftment after transplantation in immunodeficient mice, with erythroid progenitors undergoing maturation and hemoglobin switching in vivo. This system presents a useful platform for modeling hematological disorders due to its capacity to generate large numbers of engraftable disease cells for in vitro and in vivo screens.

Generation of iPSCs by somatic cell reprogramming involves global epigenetic remodeling, and chromatin-modifying enzymes have been characterized as barriers or facilitators of reprogramming[12,13,14]. Within the hematopoietic system, there are many epigenetic changes that mediate blood development during ontogeny and differentiation from HSCs to mature progeny. The progression from HSCs to differentiated progeny involves coordinated control of gene expression programs leading to the activation or repression of lineage-specific genes. See FIG. 5. The events that lead to the formation of mature lymphocytes that express antigen receptors involve regulation of both gene expression and DNA recombination, mainly through the control of chromatin accessibility[15]. HSC state is controlled by a large number of transcription factors and epigenetic modifiers. The inventors used screening strategies find additional factors that regulate of the HSC fate. The inventors used shRNA libraries that repress potential negative regulators of HSC fate to screen for transcription factors and epigenetic modifiers.

Accordingly, in one embodiment of any method, cells, or composition described herein, the MHPCs are generated by introducing in vitro an exogenous gene coding copy each of the following transcription factors: ERG, HOXA9, and RORA, into the myeloid progenitor cells. In one embodiment, a vector is used as the transport vehicle to introduce any of the herein described exogenous gene coding copies into the myeloid progenitor cells. For example, by transfecting the myeloid progenitor cells with a vector or more, wherein the vector(s) collectively carry an exogenous gene coding copy of each of the following transcription factors, ERG, HOXA9, and RORA, for the in vivo expression of the transcription factor in the transfected cells. For example, by contacting the myeloid progenitor cells with a vector or more, wherein the vector(s) collectively carry an exogenous gene coding copy of each of the following transcription factors, ERG, HOXA9, and RORA, for the in vivo expression of the transcription factor in the contacted cells. For example, by contacting the myeloid progenitor cells with a nucleic acid or more, wherein the nucleic acid (s) collectively carry an exogenous gene coding copy of each of the following transcription factors, ERG, HOXA9, and RORA, for the in vivo expression of the transcription factor in the contacted cells. In one embodiment, a single vector is used as the transport vehicle to introduce the exogeneous gene coding copies of all three transcription factors, ERG, HOXA9, and RORA into the myeloid progenitor cells. In one embodiment, one or more episomal vectors are used as the transport vehicle to introduce the exogeneous gene coding copies of the three transcription factors, ERG, HOXA9, and RORA into the myeloid progenitor cells.

In one embodiment of any method, cells, or composition described herein, the MHPCs are generated by contacting a population of myeloid progenitor cells with a vector or more, wherein the vector(s) collectively carrying an exogenous gene coding copy of each of the following transcription factors, ERG, HOXA9, and RORA, for the in vivo expression of the factors in the contacted cells, and wherein the transfected transcription factors are expressed in vivo in the contacted cells. The contacting is in vitro or ex vivo. In one embodiment, a single vector is used as the transport vehicle to introduce the exogeneous gene coding copies of all three transcription factors, ERG, HOXA9, and RORA into the myeloid progenitor cells. In one embodiment, one or more episomal vectors are used as the transport vehicle to introduce the exogeneous gene coding copies of the three transcription factors, ERG, HOXA9, and RORA into the myeloid progenitor cells.

In one embodiment of any method, cells, or composition described herein, the MHPCs are generated by contacting the myeloid progenitor cells with a nucleic acid or more, wherein the nucleic acid (s) collectively comprises an exogenous gene coding copy of each of the following transcription factors, ERG, HOXA9, and RORA, for the in vivo expression of the transcription factor in the contacted cells. The contacting is in vitro or ex vivo.

In one embodiment of any method, cells, or compositions described herein, the contacting of the myeloid progenitor cells with any vector(s), nucleic acid(s) or compositions comprising the vector(s) or nucleic acid(s) described herein occurs in vitro or ex vivo.

In one embodiment of any methods, cells, or composition described herein, the contacting or introduction is repeated at least once.

In one embodiment of any method, cells, or composition described herein, the method further comprising transfecting the myeloid progenitor cells with an exogenous gene coding copy of SOX4 or MYB or both SOX4 and MYB, wherein the transfected transcription factor(s) is/are expressed in vivo in the transfected cells. The transfecting is in vitro or ex vivo.

In one embodiment of any method, cells, or composition described herein, the method further comprising transfecting the myeloid progenitor cells with an exogenous gene coding copy of DACH1 or NFIA or both DACH1 and NFIA, wherein the transfected transcription factor is expressed in vivo in the transfected cells. The transfecting is in vitro or ex vivo.

Transcription Factors

ERG (ETS-related gene) is an oncogene meaning that it encodes a protein that typically is mutated in cancer. ERG is a member of the ETS (erythroblast transformation-specific) family of transcription factors. The ERG gene encodes for a protein, also called ERG, that functions as a transcriptional regulator. Genes in the ETS family regulate embryonic development, cell proliferation, differentiation, angiogenesis, inflammation, and apoptosis. The external idenifications for ERG gene are as follows: HGNC: 3446; Entrez Gene: 2078; Ensembl: ENSG00000157554; OMIM: 165080; UniProtKB: P11308; EMBL: AY204741 mRNA and the corresponding mRNA translation: AAP41719.1; and GENBANK: AY204742 mRNA and the corresponding mRNA translation: AAP41720.1.

Homeobox protein Hox-A9 is a protein that in humans is encoded by the HOXA9 gene. In vertebrates, the genes encoding the homeobox genes class of transcription factors are found in clusters named A, B, C, and D on four separate chromosomes. Expression of these proteins is spatially and temporally regulated during embryonic development. Hox-A9 is part of the A cluster on chromosome 7 and encodes a DNA-binding transcription factor which may regulate gene expression, morphogenesis, and differentiation. The external idenifications for HOXA9 gene are as follows: HGNC: 5109; Entrez Gene: 3205; Ensembl: ENSG00000078399; OMIM: 142956; UniProtKB: P31269; EMBL: BT006990 mRNA and the corresponding mRNA translation: AAP35636.1; and GENBANK:AC004080 Genomic DNA.

RAR-related orphan receptor alpha (RORα), also known as NR1F1 (nuclear receptor subfamily 1, group F, member 1) or RORA is a nuclear receptor that in humans is encoded by the RORA gene. RORα participates in the transcriptional regulation of some genes involved in circadian rhythm. This nuclear receptor binds DNA as a monomer to ROR response elements (RORE) containing a single core motif half-site 5'-AGGTCA-3' preceded by a short A-T-rich sequence. In is a key regulator of embryonic development, cellular differentiation, immunity, circadian rhythm as well as lipid, steroid, xenobiotics and glucose metabolism. It is considered to have intrinsic transcriptional activity, have some natural ligands like oxysterols that act as agonists (25-hydroxycholesterol) or inverse agonists (7-oxygenated sterols), enhancing or repressing the transcriptional activity, respectively. It is involved in recruiting distinct combinations of cofactors to target genes regulatory regions to modulate their transcriptional expression, depending on the tissue, time and promoter contexts. It regulates genes involved in photoreceptor development including OPN1SW, OPN1SM and ARR3 and skeletal muscle development with MYOD1. It is required for proper cerebellum development, regulates SHH gene expression, among others, to induce granule cells proliferation as well as expression of genes involved in calcium-mediated signal transduction. It regulates the circadian expression of several clock genes, including CLOCK, ARNTL/BMAL1, NPAS2 and CRY1. It competes with NR1D1 for binding to their shared DNA response element on some clock genes such as ARNTL/BMAL1, CRY1 and NR1D1 itself, resulting in NR1D1-mediated repression or RORA-mediated activation of clock genes expression, leading to the circadian pattern of clock genes expression. Therefore influences the period length and stability of the clock. It also regulates genes involved in lipid metabolism such as apolipoproteins APOA1, APOA5, APOC3 and PPARG. In liver, has specific and redundant functions with RORC as positive or negative modulator of expression of genes encoding phase I and phase II proteins involved in the metabolism of lipids, steroids and xenobiotics, such as CYP7B1 and SULT2A1. It induces a rhythmic expression of some of these genes. In addition, interplays functionally with NR1H2 and NR1H3 for the regulation of genes involved in cholesterol metabolism. It is also involved in the regulation of hepatic glucose metabolism through the modulation of G6PC and PCK1. In adipose tissue, it plays a role as negative regulator of adipocyte differentiation, probably acting through dual mechanisms. May suppress CEBPB-dependent adipogenesis through direct interaction and PPARG-dependent adipogenesis through competition for DNA-binding. Downstream of IL6 and TGFB and synergistically with RORC isoform 2, is implicated in the lineage specification of uncommitted CD4$^+$ T-helper (T(H)) cells into T(H)17 cells, antagonizing the T(H)1 program. Probably regulates IL17 and IL17F expression on T(H) by binding to the essential enhancer conserved non-coding sequence 2 (CNS2) in the IL17-IL17F locus. Involved in hypoxia signaling by interacting with and activating the transcriptional activity of HIF1A. May inhibit cell growth in response to cellular stress. RORA may exert an anti-inflammatory role by inducing CHUK expression and inhibiting NF-kappa-B signaling. The external idenifications for RORA gene are as follows: HGNC: 10258; Entrez Gene: 6095; Ensembl: ENSG00000069667; OMIM: 600825; UniProtKB: P35398; EMBL: U04899 mRNA and the corresponding mRNA: AAA62660.1; GENBANK: L14611 mRNA and the corresponding mRNA translation: AAA02963.1.

HOX- and ETS-family transcription factors HOXA9 and ERG are inducers of self-renewal and multilineage potential in hematopoietic progenitors differentiated from hPSCs. RORA is a nuclear receptor that plays a role in maintaining quiescence of hematopoietic progenitors. The addition of SOX4 and MYB modulates this network to enable myeloid and erythroid engraftment in vivo.

OCT4, SOX2, KLF4 and c-MYC are the original four transcription factors identified to reprogram mouse fibroblasts into iPSCs. These same four factors were also sufficient to generate human iPSCs. OCT3/4 and SOX2 function as core transcription factors of the pluripotency network by regulating the expression of pluripotency-associated genes. Kruppel-like factor 4 (KLF4) is a downstream target of LIF-STAT3 signaling in mouse ES cells and regulates self-renewal. Human iPSCs can also be generated using four alternative factors; OCT4 and SOX2 are required but KLF4 and c-MYC could be replaced with NANOG, a homeobox protein important for the maintenance of pluripotency in both ES cells and early embryos, and LIN28, an RNA binding protein. The combination of OCT4, SOX2, NANOG and LIN28 reprogramming factors have been reported to be also sufficient to generate human iPSCs.

Transcription factor SOX-4 (SOX4). This intronless gene encodes a member of the SOX (SRY-related HMG-box) family of transcription factors involved in the regulation of embryonic development and in the determination of the cell fate. The encoded protein act as a transcriptional regulator after forming a protein complex with other proteins, such as syndecan binding protein (syntenin). The protein may function in the apoptosis pathway leading to cell death as well as to tumorigenesis and may mediate downstream effects of parathyroid hormone (PTH) and PTH-related protein (PTHrP) in bone development. The external idenifications for *Homo sapiens* (Human) SOX4 gene are as follows: HGNC: 11200; Entrez Gene: 6659; Ensembl: ENSG00000124766; OMIM: 184430; UniProtKB: Q06945; EMBL: BC072668 mRNA and the corresponding mRNA translation: AAH72668.1; GENBANK: X65661 mRNA and the corresponding mRNA translation: CAA46612.1.

MYB Proto-Oncogene, Transcription Factor (MYB). This gene encodes a protein with three HTH DNA-binding domains that functions as a transcription regulator. This protein plays an essential role in the regulation of hematopoiesis. This gene may be aberrantly expressed or rearranged or undergo translocation in leukemias and lymphomas, and is considered to be an oncogene. The external idenifications for the MYB gene are as follows: HGNC: 7545; Entrez Gene: 4602; Ensembl: ENSG00000118513; OMIM: 189990; UniProtKB: P10242; EMBL: AJ606319 mRNA and the corresponding mRNA translation: CAE55170.1; GENBANK: AJ606320 mRNA and the corresponding mRNA translation: CAE55171.1.

NF1 genes function as both positive and regulators of gene transcription. Nuclear factor 1 A-type (NFIA) has been shown to regulate erythrocytic/granulocytic lineage switching (Fazi et al 2005, Starnes et al 2009). NFIA has been shown to recognize and bind to the palindromic sequence 5'-TTGGCNNNNNGCCAA-3' (SEQ ID NO: 111) present in viral and cellular promoters and in the origin of replication of adenovirus type 2. NFIA proteins are individually capable of activating transcription and replication. The external idenifications for NFIA gene are as follows: HGNC: 7784; Entrez Gene: 4774; Ensembl: ENSG00000162599; OMIM: 600727; UniProtKB: Q12857; EMBL: AK299579 mRNA and the corresponding mRNA translation: BAG61515.1; GENBANK: AC092784 Genomic DNA.

Dachshund Family Transcription Factor 1 (DACH1). This gene encodes a chromatin-associated protein that associates with other DNA-binding transcription factors to regulate gene expression and cell fate determination during development. The protein contains a Ski domain that is highly conserved from *Drosophila* to human. DACH1 regulates cell cycle progression of myeloid cells and maintain the colonogenic activity and block the differentiation of myeloid progenitors (Lee et al 2012, Lee et al 2012). The transcription factor is involved in regulation of organogenesis and may be a regulator of SIX1, SIX6 and probably SIX5. Corepression of precursor cell proliferation in myoblasts by SIX1 is switched to coactivation through recruitment of EYA3 to the SIX1-DACH1 complex. Transcriptional activation seems also to involve the association of CREBBP. DACH1 also act as a corepressor of SIX6 in regulating proliferation by directly repressing cyclin-dependent kinase inhibitors, including the p27Kip1 promoter. Furthermore, DACH1 inhibits TGF-beta signaling through interaction with SMAD4 and NCOR1, and binds to chromatin DNA via its DACHbox-N domain. However, their roles in hematopoietic stem cell and definitive lymphoid development have not been previously explored. The external idenifications for for DACH1 gene as follows: HGNC: 266; Entrez Gene: 1602; Ensembl: ENSG00000276644; OMIM: 603803; UniProtKB: Q9UI36; EMBL: AF356492 mRNA and the corresponding mRNA translation: AAL08487.1.

The cDNA encoding the described and desired transcription factors can be cloned by methods known in the art into expression vectors for in vivo expression in the cells. The expression vectors can be constitutive or inducible vectors. The protein and DNA information for transcription factors can be found in the publically available databases such as the GenBank™ database on the National Institute of Health, the UniProt at the Protein knowledgebase, and GeneCard database at the Weizmann Institute for Science. The cDNA clones or plasmids carrying the cDNA can be purchased at BioCat GmbH, and the lentivirus carrying the cDNAs for expression can also be purchased at Applied Biological Materials (ABM) Inc.

Accordingly, in one embodiment, provided herein is a population of modified myeloid lineage progenitor cells having exogenous gene encoding copies of the transcription factors ERG, HOXA9, and RORA. In one embodiment, the modified myeloid lineage progenitor cells further comprise an exogenous gene coding copy of SOX4, or MYB, or both SOX4 and MYB. In another embodiment, the modified myeloid lineage progenitor cells further comprise an exogenous gene coding copy of DACH1, or NFIA, or both DACH1 and NFIA. In another embodiment, the modified myeloid lineage progenitor cells further comprise exogenous gene coding copies of reprogramming factors OCT4, SOX2, and KLF4, and optionally with c-MYC or nanog and LIN28, or the exogenous gene coding copies for four reprogramming factors consisting of OCT4, SOX2, NANOG, and LIN 28. In another embodiment, the modified myeloid lineage progenitor cells can be cultured expanded in serum-free media, i.e., the modified myeloid lineage progenitor cells under mitosis and self-renewal in serum-free media.

Accordingly, in one embodiment, provided herein is a population of modified myeloid lineage progenitor cells having exogenous gene encoding copies of the transcription factors ERG, HOXA9, and RORA, for use in producing blood cells, such as immune cells, for medical treatments such as transplant therapy and cancer immune therapy, or for in vitro research purposes described herein. In one embodiment, the modified myeloid lineage progenitor cells further comprise an exogenous gene coding copy of SOX4, or MYB, or both SOX4 and MYB. In another embodiment, the modified myeloid lineage progenitor cells further comprise an exogenous gene coding copy of DACH1, or NFIA, or both DACH1 and NFIA. In another embodiment, the modified myeloid lineage progenitor cells further comprise exogenous gene coding copies of reprogramming factors OCT4, SOX2, and KLF4, and optionally with c-MYC or nanog and LIN28, or the exogenous gene coding copies for four reprogramming factors consisting of OCT4, SOX2, NANOG, and LIN 28. In another embodiment, the modified myeloid lineage progenitor cells can be cultured expanded in serum-free media, i.e., the modified myeloid lineage progenitor cells under mitosis and self-renewal in serum-free media.

In one embodiment of any method, cells, or composition described herein, the myeloid lineage progenitor cells are progenitor cells derived from embryoid bodies (EB) obtained from a population of pluripotent stem cells. In one embodiment, the pluripotent stem cells are iPSCs. In one embodiment, the iPSCs are derived from mature, differentiated, somatic cells.

Accordingly, in one embodiment of any method, cells, or composition described, the method further comprises providing a population of pluripotent stem cells (PSCs) for generating the myeloid lineage progenitor cells. In one embodiment, the PSCs are human cells.

In one embodiment of any method, cells, or composition described, the method further comprises producing myeloid lineage progenitor cells from the population of pluripotent stem cells (PSCs). In one embodiment, the PSCs are human cells.

In one embodiment of any method, cells, or composition described herein, the myeloid lineage progenitor cells are produced by first culturing in vitro a population of pluripotent stem cells in bone morphogenetic protein 4 (BMP4), stem cell factor (SCF), Fms-like tyrosine kinase 3 (FLT3/CD135), granulocyte-colony stimulating factor (G-CSF/CSF 3), IL-6, and IL-3 for a period of about 10-21 days to form EB from the pluripotent stem cells, dissociating the EB aggregates of cells into single cells, and positively selecting for $CD34^+$ and $CD45^+$ cells from the dissociated cells. The positively selected $CD34^+$ and $CD45^+$ cells are the myeloid lineage progenitor cells. In one embodiment, the PSCs are cultured for at least 10 days. In other embodiments, the PSCs are cultured for days, at least 11 days, at least 12 days, at least 13 days, at least 14 days, at least 15 days, at least 16 days, at least 17 days, at least 18 days, at least 19 days, at least 20 days or at least 21 days. In one embodiment, the transfected or contacted myeloid progenitor cells are cultured for about 7-21 days. In other embodiment, the PSCs are cultured for about 10-20 days, about 10-18 days, about 10-16 days, about 10-14 days, about 10-12 days, about 11-21 days, 11-20 days, about 11-18 days, about 11-16 days, about 11-14 days, about 11-13 days, about 11-12 days, about 12-21 days, about 12-20 days, about 12-18 days, about 12-16 days, about 12-14 days, about 13-21 days, 13-20 days, about 12-18 days, about 13-16 days, about 14-20 days, about 14-18 days, about 14-16 days, 10-19 days, about 10-17 days, about 10-15 days, about 10-13 days, about 10-11 days, about 11-19 days, 11-19 days, about 11-17 days, about 11-15 days, about 12-19 days, about 12-17 days, about 12-15 days, 12-13 days, about 14-21 days, about 13-18 days, about 13-17 days, about 13-15 days, about 13-14 days, about 15-21 days, about 15-20 days, about 15-19 days, about 15-17 days, about 15-16 days, about 16-21 days, about 16-20 days, about 16-19 days, about 16-18 days, about 16-17 days, about 17-21 days, about 17-20 days, about 17-19 days, about 17-18 days, about 18-21 days, about 18-20 days, about 18-19 days, about 19-21 days, about 19-20 days, and about 20-21 days.

In one embodiment of any method, cells, or composition described herein, the myeloid lineage progenitor cells are $CD34^+$ and $CD45^+$. In other embodiments of any method, cells, or composition described herein, the myeloid lineage progenitor cells are further CD14 positive, or CD15 positive, or CD11 b positive or positive for a combination of two or three of these cell surface CD antigens.

In one embodiment of any method, cells, or composition described herein, the myeloid lineage progenitor cells are non-lymphoid lineage committed. In one embodiment, the myeloid lineage progenitor cells exhibit primarily (>80% of the CFU of the total CFU is a colony forming assay) the following colony-forming activity in culture: CFU-M and CFU-G colonies. In other embodiments, the myeloid lineage progenitor cells produce more than 82%, more than 84%, more than 86%, more than 88%, more than 90%, more than 92%, more than 95%, more than 97%, or more than 99% CFU-M and CFU-G colonies out of the total CFU is a colony forming assay. In one embodiment, the myeloid lineage progenitor cells produce few CFU-E, BFU-E, CFU-GEMM, and CFU-GM colonies (<20% of the total CFU is a colony forming assay). In one embodiment, the myeloid lineage progenitor cells produce less than 18%, less than 16%, less than 14%, less than 12%, less than 10%, less than 8%, less than 6%, less than 4%, or less than 2%, CFU-E, BFU-E, CFU-GEMM, and CFU-GM colonies out of the total CFU is a colony forming assay. In vitro colony forming assay can be performed by any method known in the art. For example, as taught in Tashiro K, et al. 2012, Stem Cell Res. 8:300-311, U.S. Pat. Nos. 6,103,522, 6,419,918, 683,854, 7,883,861, 7,989,178 9, 9,273,285. These references are incorporated herein in their entirety. For example, using a commercially available kit such as Hematopoietic CFC Assays from Cell Biolabs Inc. and The Human Colony Forming Cell (CFC) Assay using Methylcellulose-based Media from R&D Systems.

In another embodiment of any method, cells, or composition described herein, the myeloid lineage progenitor cells are harvested from collected from peripheral blood, cord blood, chorionic villi, amniotic fluid, placental blood, or bone marrow. Myeloid lineage progenitor cells that are $CD34^+$ and $CD45^+$ cells are positively selected from these sources.

Peripheral blood progenitor cells (PBPC) have become the preferred source of hematopoetic progenitor cells for allogeneic and autologous transplantation because of technical ease of collection and shorter time required for engraftment. Traditionally, granulocyte-colony stimulating factor (G-CSF) has been used to stimulate more PBPC and release of hematopoetic progenitor cells from the bone marrow. Although regimens using G-CSF usually succeed in collecting adequate numbers of PBPC from healthy donors, 5%-10% will mobilize stem cells poorly and may require multiple large volume apheresis or bone marrow harvesting.

In one embodiment of any method, cells, or composition described herein, the population of pluripotent stem cells is induced pluripotent stem cells (iPSCs) or embryonic stem cells (ESC). IPCS and ESC can be produced by any method known in the art. Methods of producing iPS cell are known in the art, e.g., U.S. Pat. No. 8,058,065, and U.S. Patent Application Nos: 20110223669, 20120214243, 20130059386, and 20130183759, all of which are incorporated herein by reference in their entireties.

In one embodiment of any method, cells, or composition described herein, the iPSCs are produced by introducing exogenous copies of only three reprogramming factors OCT4, SOX2, and KLF4 into mature or somatic cells.

In one embodiment of any method, cells, or composition described herein, the iPSCs having exogenous gene coding copies of OCT4, SOX2, and KLF4 is further introduced with c-MYC or nanog and LIN28 into mature or somatic cells.

In one embodiment of any method, cells, or composition described herein, the iPSCs are produced by introducing exogenous copies of reprogramming factors OCT4, SOX2, and KLF4, and optionally with c-MYC or nanog and LIN28 into mature or somatic cells.

In one embodiment of any method, cells, or composition described herein, the iPSCs are produced by contacting mature cells with a vector or more, wherein the vector(s) collectively carry exogenous gene coding copies of reprogramming factors OCT4, SOX2, and KLF4, and optionally with c-MYC or nanog and LIN28 into mature or somatic cells, and wherein the reprogramming factors are expressed in vivo in the contacted mature or somatic cells. The contacting is in vitro or ex vivo.

In one embodiment of any disclosed methods, the iPS cell comprises at least an exogenous copy of a nucleic acid sequence encoding a reprogramming factor selected from the group consisting of genes Oct4 (Pou5f1), Sox2, cMyc, Klf4, Nanog, Lin 28 and Glis1. In some embodiments, combinations of reprogramming factors are used. For example, a combination of four reprogramming factors consisting of Oct4, Sox2, cMyc, and Klf4, or a combination of four reprogramming factors consisting of Oct4, Sox2, Nanog, and Lin 28.

In one embodiment of any method, cells, or composition described herein, the mature cells from which iPS cells are made include any somatic cells such as B lymphocytes (B-cells), T lymphocytes, (T-cells), and fibroblasts and keratinocytes.

In one embodiment of any method, cells, or composition described herein, the iPSCs are produced by introducing the disclosed reprogramming factors two or more times into the mature or somatic cells.

In one embodiment of any method, cells, or composition described herein, the iPSCs are produced by contacting mature cells with the disclosed vector(s) factors two or more times into the mature/somatic cells.

In some embodiments, in vitro culturing of the cells occur between the step (a) of generating MHPCs and the step (b) of inhibiting the histone methyltransferase in the multilineage hematopoietic progenitor cells. In some embodiments, selection of desired cells occurs between step (a) of generating MHPCs and the step (b) of inhibiting the histone methyltransferase in the MHPCs.

In one embodiment of any method, cells, or composition described herein, the transfected or contacted myeloid progenitor cells carrying the added exogenous gene coding copy of the described transcription factors are further cultured in vitro for a period of time to expand the number of cells prior to inhibiting the histone methyltransferase. In one embodiment of any method, cells, or composition described herein, the transfected or contacted myeloid progenitor cells are cultured for at least 7 days. In other embodiments, the transfected or contacted myeloid progenitor cells are cultured for at least 7 days, at least 8 days, at least 9 days, at least 10 days, at least 11 days, at least 12 days, at least 13 days, or at least 14 days. In one embodiment, the transfected or contacted myeloid progenitor cells are cultured for about 7-21 days. In other embodiment, the transfected or contacted myeloid progenitor cells are cultured for about 7-20 days, about 7-18 days, about 7-16 days, about 7-14 days, about 7-12 days, about 7-10 days, 8-20 days, about 8-18 days, about 8-16 days, about 8-14 days, about 8-12 days, about 8-10 days, 9-20 days, about 9-18 days, about 9-16 days, about 9-14 days, about 9-12 days, about 9-10 days, 10-20 days, about 10-18 days, about 10-16 days, about 10-14 days, about 10-12 days, 11-20 days, about 11-18 days, about 11-16 days, about 11-14 days, about 11-13 days, about 11-12 days, about 12-20 days, about 12-18 days, about 12-16 days, about 12-14 days, 13-20 days, about 12-18 days, about 13-16 days, about 14-20 days, about 14-18 days, and about 14-16 days.

In one embodiment of any method, cells, or composition described herein, the culture expanded myeloid progenitor cells carrying the added exogenous gene coding copy of the described transcription factors are further selected for the presence of cell surface marker CD34 (CD34 positive) and for the absence or low expression of cell surface marker CD 38 (CD38 low/negative). In other words, the cells obtained after culture expansion for a period of time described herein are positively selected for CD34 and negatively selected against CD38. The selected CD34$^+$ CD38$^{lo/-}$ cells are the reverse lineage MHPCs. Selection can be performed by any method know, for example, by fluorescence activated cell sorting (facs) as described in US Patent Publication Nos: 20090239235, 20090061513, 20140075593, and U.S. Pat. Nos. 5,985,216, 6,455,263, 6,461,813, and 6,897,031. These references are incorporated herein by reference in their entirety.

In one embodiment of any method, cells, or composition described herein, the MHPCs have myeloid and erythroid potential with low or undetectable lymphoid potential. Lymphoid potential is determined by any method known in the art, e.g., as taught in the Example Section, or as measured during in vitro differentiation protocols or following engraftment in receptive murine hosts.

In one embodiment of any method, cells, or composition described herein, the MHPCs are CD34$^+$ CD38 low/negative. In one embodiment of any method, cells, or composition described herein, the MHPCs are CD90 positive or CD49f positive or both. In one embodiment of any method, cells, or composition described herein, the MHPCs exhibit increased expression of the HSC-specific transcription factors HLF, or NF1B, or HOPX, or HMGA2 or RBPMS or combinations thereof compared to prior to the introduction of the EAR into the cell. In one embodiment, the increased expression is at least 5% compared to prior to the introduction of the EAR into the cell. In other embodiments, the increased expression is at least 10%, at least 20%, at least 30%, at least 40%, at least 50%, at least 60%, at least 70%, at least 80%, at least 90%, at least 95%, at least 99%, or more compared to prior to the introduction of the EAR into the cell.

In some embodiment of any methods, cells, or composition described herein, the MHPC has at least one of the cell surface marker characteristic of the human hematopoietic progenitor cells: CD34$^+$, CD59$^+$, Thy1/CD90$^+$, CD38$^{lo/-}$, C-kit/CD117$^{lo/-}$ and Lin$^-$. Preferably, the multilineage hematopoietic progenitor cells have several of these markers.

In some embodiment of any methods, cells, or composition described herein, the MHPCs have the cell surface marker characteristic of the erythroid lineage: CD71 and Ter119.

In some embodiments of any methods, cells, or composition described herein, the myeloid lineage progenitor cell or the MHPC is selected for the CD34$^+$ surface marker prior to any contacting.

Inhibition of Histone H3 Methylation to Promote and Enhance Lymphoid Potential

In the course of these experiments, the inventors discovered that inhibition of specific histone modifying enzymes targeting H3K9 and H3K27 promotes lymphoid potential of hematopoietic progenitors derived from pluripotent stem cells. The histone modifying enzymes are histone lysine methyltransferases. Post-translational modifications of histone proteins regulate chromatin compaction, mediate epigenetic regulation of transcription, and control cellular differentiation in health and disease. Methylation of histone tails is one of the fundamental events of epigenetic signaling. Tri-methylation of lysine 9 of histone H3 (H3K9) mediates chromatin recruitment of HP1, heterochromatin condensation and gene silencing. Similarly, methylation of H3K27 and H4K20 are associated with a repressed state of chromatin, whereas expressed genes are methylated at H3K4, H3K36 and H3K79. Methylation of H3K9 in humans relies mostly on members of the Suv39 family, namely EHMT1/GLP, EHMT2/G9a, SUV39H1, SUV39H2, SETDB1 and SETDB2, as well as then non-Suv39 enzymes PRDM2 and ASH1L (Hong Wu et al., Structural Biology of Human H3K9 Methyltransferases, 2010, PLoS ONE, 5(2): e8570. In contrast, the methylation of H3K27 is carry out by the polycomb repressive complex 2 (PRC2).

Di/trimethylation of H3K9 is mainly catalyzed by the conserved SUV39H1/2 histone methyltransferases, while the polycomb repressive complex 2 (PRC2) ensures di/trimethylation of H3K27 (Rea S, 2000. Nature 406:593-599; Margueron R, and Reinberg D. 2011. Nature 469:343-349. PRC2 comprises the EZH1/2 catalytic subunit, SUZ12, EED, and RBBP7/4 (Margueron R, and Reinberg D, 2011).

While wishing not to be bound by theory, inhibiting the histone lysine methyltransferases that target H3K9 and H3K27 relieves transcriptional repression that results from methylation of histone H3, and thereby promotes gene expression which facilitates cell differentiation.

In one embodiment of any method, cells, or composition described herein, the histone methyltransferase catalyzes the addition of methyl group to the histone H3 lysine residue 9 (H3K9) and/or histone H3 lysine residue 27 (H3K27).

In one embodiment of any method, cells, or composition described, the histone methyltransferase inhibitor inhibits the G9a/GLP heteromeric complex.

G9a (EC 2.1.1.43) (UniProtKB: Q96KQ7) is also known as EHMT2, (Euchromatic Histone-Lysine N-Methyltransferase 2), G9A Histone Methyltransferase and protein G9a.

GLP (EC 2.1.1.43) (UniProtKB: Q9H9B1) is also known as EHMT1 (Euchromatic Histone-Lysine N-Methyltransferase 1), G9a-Like Protein 1 and GLP1.

In one embodiment of any method, cells, or composition described, the histone methyltransferase inhibitor inhibits EZH1 (Enhancer Of Zeste 1 Polycomb Repressive Complex 2 Subunit).

In one embodiment of any method, cells, or composition described, the H3K27 histone methyltransferase is EZH1 (EC:2.1.1.43) (UniproKB Q92800-1).

In one embodiment of any method, cells, or composition described, the H3K27 histone methyltransferase is not EZH2 (EC:2.1.1.43) (Unipro Q15910-1).

In one embodiment of any method, cells, or composition described herein, the inhibitor of histone methyltransferase inhibits the gene expression or protein catalytic activity of the histone methyltransferase.

In one embodiment of any method, cells, or composition described herein, the histone methyltransferase H3K9 and/or H3K27 is inhibited by a small molecule or a nucleic acid or a CRISPR-mediated target genetic interference.

In one embodiment of any method, cells, or composition described, the histone methyltransferase small molecule inhibitor is a chemical agent including, but not limited to, peptides, peptidomimetics, amino acids, amino acid analogs, polynucleotides, polynucleotide analogs, aptamers, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. In some embodiments, the small molecule is a heterorganic compound or an organometallic compound.

In one embodiment of any method, cells, or composition described, the histone methyltransferase small molecule inhibitor include but are not limited to AMI-1, A-366, BIX-01294, BIX01338, BRD4770, chaetocin, UNC0224, UNC0631, UNC0638, UNC0642, UNC0646, EPZ5676, EPZ005687, GSK343, EPZ-6438, 3-deazaneplanocin A (DZNeP) HCl, UNC1999, MM-102, SGC 0946, Entacapone, EPZ015666, UNC0379, EI1, MI-2 (Menin-MLL Inhibitor), MI-3 (Menin-MLL Inhibitor), PFI-2, GSK126, EPZ004777, BRD4770, and EPZ-6438.

In one embodiment of any method, cells, or composition described, the histone methyltransferase small molecule inhibitor is selected from the group consisting of UNC0631, BRD4770, UNC1999, CPI-360, and BIX 01294.

In one embodiment of any method, cells, or composition described herein, the nucleic acid inhibitor is a nucleic acid targeting the expression of histone methyltransferase. For example, targeting the mRNA or primary transcript of the histone methyltransferase, EZH1, thereby inhibiting protein expression of the enzyme. Histone-lysine N-methyltransferase aka Enhancer Of Zeste 1 Polycomb Repressive Complex 2 Subunit (EZH1) or EC 2.1.1.43, is a component of a noncanonical Polycomb repressive complex-2 (PRC2) that mediates methylation of histone H3 (see MIM 602812) lys27 (H3K27) and functions in the maintenance of embryonic stem cell pluripotency and plasticity. The external identification for the human EZH1 gene are as follows: HGNC: 3526; Entrez Gene: 2145; Ensembl: ENSG00000108799; OMIM: 601674; UniProtKB: Q92800; EMBL: AB002386 mRNA and the corresponding mRNA translation: BAA20842.2; GENBANK: BT009782 mRNA and the corresponding mRNA translation: AAP88784.1.

In one embodiment, the nucleic acid inhibitor targets the human EZH1 mRNA.

In one embodiment of any method, cells, or composition described herein, the nucleic acid inhibitor is a RNA interference inhibitor or CRISPR-mediated genetic interference inhibitor. The RNA interference inhibitor can be designed using the predictor RNAi softwares found at the Whitehead Institute, MIT, sirna website, BLOCK-iT™ M RNAi Designer at Invitrogen/ThermoFisher, and other online siRNA design tools at The RNAi Web using the mRNA of EZH1 as the target.

Similarly, Crisper guide RNA can be designed using the Broad Institute (MIT) crispr software (see MIT website), dna20, Clontech, AddGene, e-crisp, and innovativegenomic using the mRNA or genomic gene of EZH1 as the target.

CRISPR (Clustered Regularly Interspaced Short Palindromic Repeats) Cas9-mediated gene disruption has been widely used in generating loss-of-function mutations in diverse organisms including mammals (Cong et al., 2013, Science, 339(6121):819-23; reviewed in Hsu et al., 2014, Cell, 157(6):1262-78)). Cas9-based knockout screens have been applied in identifying essential genes and genes involved in drug resistance in various cell lines. With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,999,641, 8,993,233, 8,945,839, 8,932,814, 8,906,616, 8,895,308, 8,889,418, 8,889,356, 8,871,445, 8,865,406, 8,795,965, 8,771,945 and 8,697,359; US Patent Publications US 2014-0310830, US 2014-0287938, US 2014-0273234, US2014-0273232, US 2014-0273231, US 2014-0256046, US 2014-0248702, US 2014-0242700, US 2014-0242699, US 2014-0242664, US 2014-0234972, US 2014-0227787, US 2014-0189896, US 2014-0186958, US 2014-0186919, US 2014-0186843, US 2014-0179770 and US 2014-0179006, US 2014-0170753; European Patents EP 2 784 162 B1 and EP 2 771 468 B1; European Patent Applications EP 2 771 468 (EP13818570.7), EP 2 764 103 (EP13824232.6), and EP 2 784 162 (EP14170383.5); and PCT Patent Publications WO 2014/093661, all of which are incorporated herein by reference in their entirety.

The CRISPR/Cas system envisaged for use in the context of the invention can make use of any suitable CRISPR enzyme. In some embodiments, the CRISPR enzyme is a type II CRISPR system enzyme. In some embodiments, the CRISPR enzyme is a Cas9 enzyme. In some embodiments, the Cas9 enzyme is *S. pneumoniae, S. pyogenes,* or *S. thermophilus* Cas9, and may include mutated Cas9 derived from these organisms. The enzyme may be a Cas9 homolog or ortholog. In some embodiments, the CRISPR enzyme is codon-optimized for expression in a eukaryotic cell.

As described herein, the CRISPR/Cas system is used to specifically target a multitude of sequences within the continuous genomic region of interest. The targeting typically comprises introducing into each cell of a population of cells a vector system of one or more vectors comprising an engineered, non-naturally occurring CRISPR-Cas system comprising: at least one Cas protein, and one or more guide RNAs of the guide RNA library described herein.

In these methods, the Cas protein and the one or more guide RNAs may be on the same or on different vectors of the system and are integrated into each cell, whereby each guide sequence targets a sequence within the continuous genomic region in each cell in the population of cells. The Cas protein is operably linked to a regulatory element to ensure expression in said cell, more particularly a promoter suitable for expression in the cell of the cell population. In particular embodiments, the promoter is an inducible promoter, such as a doxycycline inducible promoter. When transcribed within the cells of the cell population, the guide RNA comprising the guide sequence directs sequence-specific binding of a CRISPR-Cas system to a target sequence in the continuous genomic region. Typically binding of the CRISPR-Cas system induces cleavage of the continuous genomic region by the Cas protein.

RNA interference (RNAi) mediated by short interfering RNAs (siRNA) or microRNAs (miRNA) is a powerful method for post-transcriptional regulation of gene expression. RNAi has been extensively used for the study of biological processes in mammalian cells and could constitute a therapeutic approach to human diseases in which selective modulation of gene expression would be desirable. Depending on the degree of complementarity between miRNA and target mRNA sequences, loss of gene expression occurs by inducing degradation of the cognate mRNA or by translational attenuation. Endogenous miRNAs are transcribed as primary transcripts and subsequently processed by the RNAse III enzyme Drosha, (1) to create a stem loop structure. Nuclear export and cleavage by Dicer generates a mature short double stranded molecule (siRNA) that is separated into guide and passenger strands. The guide strand is loaded into the RNA induced silencing complex (RISC), the effector complex mediating cleavage of target mRNAs with the functional guide strand binding to RISC proteins while the passenger strand is degraded. The loading of guide versus passenger strands into RISC largely depends on the 5' end stability of the siRNA, with the less stable strand preferentially incorporated into RISC, although the exact regulation in mammalian cells is incompletely understood. The 5' end of the guide strand contains the "seed region," which is critical for target identification. Precise cleavage by Drosha and Dicer is critical for the generation of guide RNAs with defined seed regions that mediate efficient binding to the appropriate target mRNAs. Inaccurate processing results in binding to off-target molecules but a shift in cleavage sites also alters the nucleotide composition of duplex ends, which may have a profound effect on strand loading into RISC.

The inhibiting the expression of selected target polypeptides is through the use of RNA interference agents. RNA interference (RNAi) uses small interfering RNA (siRNA) duplexes that target the messenger RNA encoding the target polypeptide for selective degradation. siRNA-dependent post-transcriptional silencing of gene expression involves cleaving the target messenger RNA molecule at a site guided by the siRNA. RNAi is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) J. Virology 76(18):9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex (termed "RNA induced silencing complex," or "RISC") that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" includes any decrease in expression or protein activity or level of the target gene or protein encoded by the target gene as compared to a situation wherein no RNA interference has been induced. The decrease will be of at least 10%, at least 20%, at least 30%, at least 40%, at least 50%, at least 60%, at least 70%, at least 80%, at least 90%, at least 95%, at least 99%, or more as compared to the expression of a target gene or the activity or level of the protein encoded by a target gene which has not been targeted by an RNA interfering agent.

The terms "RNA interference agent" and "RNA interference" as they are used herein are intended to encompass those forms of gene silencing mediated by double-stranded RNA, regardless of whether the RNA interfering agent comprises an siRNA, miRNA, shRNA or other double-stranded RNA molecule. siRNA is defined as an RNA agent which functions to inhibit expression of a target gene, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) RNA April; 9(4):493-501, incorporated by reference herein in its entirety). The target gene or sequence of the RNA interfering agent may be a cellular gene or genomic sequence, e.g., the BCL11A sequence. An siRNA may be substantially homologous to the target gene or genomic sequence, or a fragment thereof. As used in this context, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence include RNA derivatives and analogs. Preferably, the siRNA is identical to its target. The siRNA preferably targets only one sequence. Each of the RNA interfering agents, such as siRNAs, can be screened for potential off-target effects by, for example, expression profiling. Such methods are known to one skilled in the art and are described, for example, in Jackson et al. Nature Biotechnology 6:635-637, 2003. In addition to expression profiling, one may also screen the potential target sequences for similar sequences in the sequence databases to identify potential sequences which may have off-target effects. For example, 15, or perhaps as few as 11 contiguous nucleotides, of sequence identity are sufficient to direct silencing of non-targeted transcripts. Therefore, one may initially screen the proposed siRNAs to avoid potential off-target silencing using the sequence identity analysis by any known sequence comparison methods, such as BLAST. siRNA sequences are chosen to maximize the uptake of the antisense (guide) strand of the siRNA into RISC and thereby maximize the ability of RISC to target G9a/GLP or EZH1 mRNA for degradation. This can be accomplished by scanning for sequences that have the lowest free energy of binding at the 5'-terminus of the antisense strand. The lower free energy leads to an enhancement of the unwinding of the 5'-end of the antisense strand of the siRNA duplex, thereby ensuring that the antisense strand will be taken up by RISC and direct the sequence-specific cleavage of the human G9a/GLP or EZH1 mRNA. siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function. Moreover, a non-natural linkage between nucleotide residues can be used, such as a phosphorothioate linkage. The RNA strand can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatizes with a variety of groups. Other useful RNA derivatives incorporate nucleotides having modified carbohydrate moieties, such as 2'O-alkylated residues or 2'-O-methyl ribosyl derivatives and 2'-O-fluoro ribosyl derivatives. The RNA bases may also be modified. Any modified base useful for inhibiting or interfering with the expression of a target sequence may be used. For example, halogenated bases, such as 5-bromouracil and 5-iodouracil can be incorporated. The bases may also be alkylated, for example, 7-methylguanosine can be incorporated in place of a guanosine residue. Non-natural bases that yield successful inhibition can also be incorporated. The most preferred siRNA modifications include 2'-deoxy-2'-fluorouridine or locked nucleic acid (LAN) nucleotides and RNA duplexes containing either phosphodiester or varying numbers of phosphorothioate linkages. Such modifications are known to one skilled in the art and are described, for example, in Braasch et al., Biochemistry, 42: 7967-7975, 2003. Most of the useful modifications to the siRNA molecules can be introduced using chemistries established for antisense oligonucleotide technology. Preferably, the modifications involve minimal 2'-O-methyl modification, preferably excluding such modification. Modifications also preferably exclude modifications of the free 5'-hydroxyl groups of the siRNA. The Examples herein provide specific examples of RNA interfering agents, such as shRNA molecules that effectively target mRNA.

In one embodiment, the nucleic acid is a G9a/GLP or EZH1 specific RNA interference agent or a vector encoding the RNA interference agent. In one embodiment, the RNA interference agent comprises one or more of the nucleotide sequences selected from the group consisting of CTATCTGGCAGTGCGAGAATG (SEQ. ID. NO: 1), AGACGTGCAAGCAGGTCTTTC (SEQ. ID. NO: 2), TGGATGACTTATGCGTGATTT (SEQ. ID. NO: 3), CAACAGAACTTTATGGTAGAA (SEQ. ID. NO: 4), CCGCCGTGGTTTGTATTCATT (SEQ. ID. NO: 5), GCTTCCTCTTCAACCTCAATA (SEQ. ID. NO: 27), CCGCCGTGGTTTGTATTCATT (SEQ. ID. NO: 28), GCTCTTCTTTGATTACAGGTA (SEQ. ID. NO: 29), and GCTACTCGGAAAGGAAACAAA (SEQ. ID. NO: 30).

In one embodiment of any method, cells, or composition described herein, the nucleic acid is selected from the group consisting of CTATCTGGCAGTGCGAGAATG (SEQ. ID. NO: 1), AGACGTGCAAGCAGGTCTTTC (SEQ. ID. NO: 2), TGGATGACTTATGCGTGATTT (SEQ. ID. NO: 3), CAACAGAACTTTATGGTAGAA (SEQ. ID. NO: 4), CCGCCGTGGTTTGTATTCATT (SEQ. ID. NO: 5), GCTTCCTCTTCAACCTCAATA (SEQ. ID. NO: 27), CCGCCGTGGTTTGTATTCATT (SEQ. ID. NO: 28), GCTCTTCTTTGATTACAGGTA (SEQ. ID. NO: 29), and GCTACTCGGAAAGGAAACAAA (SEQ. ID. NO: 30).

In one embodiment of any method, cells, or composition described herein, the multilineage hematopodetic progenitor cells are contacted with the viral vector or vector carrying a nucleic acid molecule comprising a nucleic acid sequence selected from a group consisting of SEQ ID NOS:1-5, 27-30.

In one embodiment of any method, cells, or composition described herein, the contacting with the histone methyltransferase inhibitor occurs more than once. For example, after the initial first contacting of the multilineage hematopodetic progenitor cell with the virus or vector carrying a nucleic acid molecule comprising a nucleic acid sequence selected from a group consisting of SEQ ID NOS:1-5, 27-30, or contacting with a small molecule inhibitor described herein, the contacted cell is washed, and the washed cell is then contacted for a second time with the same histone methyltransferase inhibitor used in the first contact.

It is contemplated herein that the Cas9/CRISPR system of genome editing be employed with the methods, cells and compositions described herein. Clustered regularly interspaced short palindromic repeats (CRISPR)/CRISPR-associated (Cas) systems is useful for RNA-programmable genome editing (see e.g., Jinek, M. et al. Science (2012) 337(6096):816-821).

Trans-activating crRNA (tracrRNA) is a small trans-encoded RNA. It was first discovered in the human pathogen *Streptococcus pyogenes*. (See Deltcheva E, et al. (2011). Nature 471 (7340): 602-7). In bacteria and archaea, CRISPR/Cas (clustered, regularly interspaced short palindromic repeats/CRISPR-associated proteins) constitute an RNA-mediated defense system which protects against viruses and plasmids. This defensive pathway has three steps. First a copy of the invading nucleic acid is integrated into the CRISPR locus. Next, CRISPR RNAs (crRNAs) are transcribed from this CRISPR locus. The crRNAs are then incorporated into effector complexes, where the crRNA guides the complex to the invading nucleic acid and the Cas proteins degrade this nucleic acid. (See Terns M P and Terns R M (2011). Curr Opin Microbiol 14 (3): 321-7). There are several pathways of CRISPR activation, one of which requires a tracrRNA which plays a role in the maturation of crRNA. TracrRNA is complementary to and base pairs with a pre-crRNA forming an RNA duplex. This is cleaved by RNase III, an RNA-specific ribonuclease, to form a crRNA/tracrRNA hybrid. This hybrid acts as a guide for the endonuclease Cas9, which cleaves the invading nucleic acid. (see Deltcheva E, et al. supra; Jinek M, et al. (2012), Science 337 (6096): 816-21; and Brouns S J (2012), Science 337 (6096): 808-9).

In some embodiments, Cas9/CRISPR system guide RNAs are designed to target the exon 3 of EZH1 gene, which is present in all transcripts of EZH1 known. Exon 3 sequence is ATTACAGCAAGATGGAAATACCAAATCCCCC-TACCTCCAAATGTATCACTTACTGGAAAAG
AAAAGTGAAATCTGAATA-
CATGCGACTTCGACAACT-
TAAACGGCTTCAGGCAAATATGGGT GCAAAG (SEQ ID NO:6).

Non-limiting exemplary gRNAs that target exon 3 are TCGACAACTTAAACGGCTTC (SEQ ID NO:7), TGCGACTTCGACAACTTAAA (SEQ ID NO:8), CCTC-CAAATGTATCACTTAC (SEQ ID NO:9), TAAACGGCTTCAGGCAAATA (SEQ ID NO:10) AAACGGCTTCAGGCAAATAT (SEQ ID NO:11), CAT-TTGGAGGTAGGGGGATT (SEQ ID NO:12), CCAGTAAGTGATACATTTGG (SEQ ID NO:13), GTGA-TACATTTGGAGGTAGG (SEQ ID NO:14), AAGTGATA-CATTTGGAGGTA (SEQ ID NO:15), AGTGATACAT-TTGGAGGTAG (SEQ ID NO:16), TTTCCAGTAAGTGATACATT (SEQ ID NO:17), and TAAGTGATACATTTGGAGGT (SEQ ID NO:18)

In other embodiments, Cas9/CRISPR system guide RNAs are designed to target the exon 4 of EZH1 gene, which is also present in all transcripts of EZH1 known. Exon 4 sequence is GCTTTGTATGTGGCAAAT-TTTGCAAAGGTTCAAGAAAAAACCCAGATCCT- CAATGAAGAAT GGAAGAAGCTTCGTGTC-CAACCTGTTCAGTCAATGAAGCCTGTGAGTGGACA CCCTTTTCTC AAAAAG (SEQ ID NO:19).

Non-limiting exemplary gRNAs that target exon 4 are GCTTCATTGACTGAACAGGT (SEQ ID NO:20), ACAGGCTTCATTGACTGAAC (SEQ ID NO:21), AGAAAAGGGTGTCCACTCAC (SEQ ID NO:22), TCCATTCTTCATTGAGGATC (SEQ ID NO:23), CCAT-TCTTCATTGAGGATCT (SEQ ID NO:24), CCCA-GATCCTCAATGAAGAA (SEQ ID NO:110), GTATGTGGCAAATTTTGCAA (SEQ ID NO:25), and CAGTCAATGAAGCCTGTGAG (SEQ ID NO:26).

In one embodiment of any method, cells, or composition described herein, a vector is used as a transport vehicle to introduce any of the herein described exogenous gene coding copies of transcription factors or reprogramming factors or nucleic acid inhibitor into the target cells selected from the disclosed myeloid progenitor cells or the disclosed reverse lineage multipotent hematopoietic progenitor cell.

In one embodiment of any method, cells, or composition described herein, a vector is used as a transport vehicle to introduce any of the herein described nucleic acid comprising the described exogenous gene coding copies of transcription factors or reprogramming factors or nucleic acid inhibitor into the target cells selected from the disclosed myeloid progenitor cells or the disclosed reverse lineage multipotent hematopoietic progenitor cell.

In one aspect, the present specification provides a vector or more, wherein the vector(s) collectively comprises an exogenous gene coding copies of each of the transcription factors or reprogramming factors or nucleic acid inhibitor described. The exogenous gene coding copy is for the expression of the transcription factors or reprogramming factors inside the cells. The in vivo expression of the nucleic acid inhibitor is for degrading the mRNA of the targeted histone methyltransferase such as G9a/GLP or EZH1 so as to reduce and inhibit the expression of the respective histone methyltransferase, with the goal being to reduce methylation of the histone H3 in the transfected cells and relief repression of gene expression therein. In one embodiment, each vector consists essentially of a transcription factors or reprogramming factor described herein. In one embodiment, each vector consists essentially of two or more of the described transcription factors or reprogramming factors.

In one aspect, the present specification provides a vector or more, wherein the vector(s) collectively comprises nucleic acids comprising the described exogenous gene coding copies of transcription factors or reprogramming factors or nucleic acid inhibitor. The nucleic acid is for the expression of the transcription factors or reprogramming factors inside the cells.

In one aspect, the present specification provides a vector or more, wherein the vector(s) collectively comprises an exogenous gene coding copy of each of the following transcription factors, ERG, HOXA9, and RORA described herein. For example, a single vector carrying the coding copies for all three transcription factors, ERG, HOXA9, and RORA. In another aspect, the vector(s) collectively further comprise an exogenous gene coding copy of SOX4 and MYB. For example, a single vector carrying the coding copies for both SOX4 and MYB. In another aspect, the vector(s) collectively further comprise an exogenous gene coding copy of DACH1 and NFIA. For example, a single vector carrying the coding copies for both DACH1 and NFIA.

In another aspect, the present disclosure also provides a host cell comprising a vector or more described herein or nucleic acid(s) of the transcription factors or reprogramming factors or both described herein.

In another aspect, the disclosure herein also provides a host cell comprising a vector or more described herein or nucleic acid(s) of the transcription factors, ERG, HOXA9, and RORA described herein.

In another aspect, the host cell further comprises a vector or more described herein or nucleic acid(s) of the transcription factors SOX4 and MYB.

In another aspect, the host cell further comprises a vector or more described herein or nucleic acid(s) of reprogramming factors or both described herein, OCT4, SOX2, and KLF4, and optionally with c-MYC or NANOG and LIN28, or the four reprogramming factors OCT4, SOX2, NANOG and LIN28

In one embodiment of any host cell described herein, the host cell is an embryonic stem cell, a somatic stem cell, a progenitor cell, a bone marrow cell, a hematopoietic stem cell, a hematopoietic progenitor cell, an immune cell such as a T cell or B cell, an erythrocyte, a fibroblast, a keratinocyte, or a myeloid progenitor cell. In one embodiment, the host cell is isolated from a subject. In one embodiment, the host cell is isolated from a subject who has been diagnosed with a hematological disease.

In one embodiment of any method, cells, or composition described herein, the vector further comprises a spleen focus-forming virus promoter, a tetracycline-inducible promoter, a Doxycycline (Dox)-inducible, or a β-globin locus control region and a β-globin promoter. In one embodiment, the promoter provide for targeted expression of the nucleic acid molecule therein. Other examples of promoters include but are not limited to the CMV promoter and EF1α promoters for the various transgenes, and U6 promoter for shRNAs targeting EZH1.

In one embodiment of any method, cells, or composition described herein, the vector is a virus or a non-viral vector. Non-limiting examples of viral vectors for gene delivery and expressions in cells are retrovirus, adenovirus (types 2 and 5), adeno-associated virus (AAV), Helper-dependent adenoviral vector (HdAd), hybrid adenoviral vectors, herpes virus, pox virus, human foamy virus (HFV), and lentivirus.

In one embodiment of any method, cells, or composition described herein, the vector is an episomal vector.

In one embodiment of any method, cells, or composition described herein, the vector is an intergrating vector.

In one embodiment of any method, cells, or composition described herein, the vector is a non-intergrating vector.

In one embodiment of any method, cells, or composition described herein, the vector is an excisable vector.

In one embodiment of any method, cells, or composition described herein, the in vivo expression of the described transcription factors are regulatable. That is, the promoters used in the vectors for gene expression are inducible.

In one aspect of any method, cells, or composition described herein, the lentivirus is selected from the group consisting of: human immunodeficiency virus type 1 (HIV-1), human immunodeficiency virus type 2 (HIV-2), caprine arthritis-encephalitis virus (CAEV), equine infectious anemia virus (EIAV), feline immunodeficiency virus (FIV), bovine immune deficiency virus (BIV), and simian immunodeficiency virus (SIV).

As used herein, the term "vector" refers to a nucleic acid molecule capable of transporting another nucleic acid to which it has been linked. One type of vector is a "plasmid", which refers to a circular double stranded DNA loop into which additional nucleic acid segments can be ligated. Another type of vector is a viral vector, wherein additional nucleic acid segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors", or more simply "expression vectors." In general, expression vectors of utility in recombinant DNA techniques are often in the form of plasmids. In the present specification, "plasmid" and "vector" can be used interchangeably as the plasmid is the most commonly used form of vector. However, the methods and compositions described herein can include such other forms of expression vectors, such as viral vectors (e.g., replication defective retroviruses, lentiviruses, adenoviruses and adeno-associated viruses), which serve equivalent functions.

Within an expression vector, "operably linked" is intended to mean that the nucleotide sequence of interest is linked to the regulatory sequence(s) in a manner which allows for expression of the nucleotide sequence (e.g., in an in vitro transcription/translation system or in a target cell when the vector is introduced into the target cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). Furthermore, the DNA-targeting endonuclease can be delivered by way of a vector comprising a regulatory sequence to direct synthesis of the DNA-targeting endonuclease at specific intervals, or over a specific time period. It will be appreciated by those skilled in the art that the design of the expression vector can depend on such factors as the choice of the target cell, the level of expression desired, and the like.

Suitable viral vectors include, but are not limited to, vectors based on RNA viruses, such as retrovirus-derived vectors (for example, Moloney murine leukemia virus (MLV)-derived vectors), and more complex retrovirus-derived vectors (such as Lentivirus-derived vectors); and vectors based on DNA viruses, such as adenovirus-based vectors and adeno-associated virus (AAV)-based vectors. In some embodiments, the polynucleotide delivery system comprises a retroviral vector, more preferably a lentiviral vector. Non-limiting examples of viral vector include lentivirus vectors derived from human immunodeficiency virus 1 (HIV-1), HIV-2, feline immunodeficiency virus (FIV), equine infectious anemia virus, simian immunodeficiency virus (SIV) and maedi/visna virus.

Induction of Lymphoid Potential and Lymphocyte Differentiation

In another embodiment, this disclosure provides an immune cell produced by a method described herein. These immune cells are genetically modified to have exogenous copies of ERG, HOXA9, and RORA compared to the original myeloid progenitor cells. These immune cells can also further have exogenous copies of SOX4, and MYB compared to the original myeloid progenitor cells. These immune cells can also further have exogenous copies of DACH1 and NFIA compared to the original myeloid progenitor cells.

In another embodiment, this disclosure provides an immune cell derived from a population of myeloid progenitor cells, wherein the immune cell comprises an exogenous copy of each of the following transcription factors ERG, HOXA9, and RORA.

In another embodiment, this disclosure provides an immune cell derived from a population of myeloid progenitor cells, wherein the immune cell comprises an exogenous gene coding copy of each of the following transcription factors ERG, HOXA9, and RORA, and an exogenous gene coding copy of each of the following reprogramming factors OCT4, SOX2, KLF4 and optionally c-MYC or NANOG and LIN28, or the four reprogramming factors OCT4, SOX2, NANOG and LIN28.

In one embodiment of any immune cell described, the immune cell further comprises an exogenous gene coding copy of SOX4 or MYB or both SOX4 and MYB.

In one embodiment of any immune cell described, the immune cell further comprises an exogenous gene coding copy of DACH1 or NFIA or both DACH1 and NFIA. DACH1 and NFIA enhance lymphoid potential in the reverse lineage MHPCs described herein.

In one embodiment of any immune cell described, the immune cell is a B-cell or a T-cell. In one embodiment of any immune cell described, the T-cell is a T regulatory ($T_{Reg}$) cell. In one embodiment of any immune cell described, the T-cell is a natural killer cell.

The reverse lineage multipotent hematopoietic progenitor cells are immortalized and they represent a useful platform amenable to further genetic modification such as removal of the native T cell receptor locus to enhance targeted specificity, deletion of class I and class II major histocompatibility complexes, and expression of non-canonical HLA-G and HLA-E to prevent NK cell-mediated lysis (Riolobos L et al. 2013), which can provide a source of universal T cells for immunotherapy, e.g., cancer immune therapy. In one embodiment of any immune cell described, the immune cell can undergo further genetic modification to edit endogenous HLA (please see Riolobos L et al. 2013), or the removal endogenous TCR for targeted specificity, chimeric antigen receptor (CAR) knock-in.

The reverse lineage MHPCs also retained their lymphoid potential after long term in vitro culture, producing ~$10^8$ T cells from an average of ~$10^4$ EB cells after 13 weeks of expansion and differentiation. See FIG. 1F.

In nature, the haematopoietic stem cells (HSCs) in the bone marrow give rise to multipotent progenitors (MPPs) before differentiating into common myeloid progenitors (CMPs) and common lymphoid progenitors (CLPs). CLPs migrate from the bone marrow to the thymus, where thymic epithelial cells that express Delta-like ligand 4 (DLL4) trigger canonical Notch 1 signalling in early thymic progenitors (ETPs). This Notch 1 signal is essential for T cell lineage commitment and is further required during early phases of thymocyte differentiation up to the double-negative 3 (DN3) stage. Active Notch signaling during these early stages of T cell development inhibits other lineage potentials, such as B cell and myeloid cell (including dendritic cell (DC)) potential. During β-selection, Notch signaling is turned off as a consequence of pre-T cell receptor signaling. Thus subsequent stages of T cell development exhibit very low levels of Notch signaling. Notch was also suggested to influence the development of regulatory T (T$_{Reg}$) cells (specifically, thymic T$_{Reg}$ cells). Notch signaling is mediated by the Notch 2 receptor. Notch signaling pathway is highly conserved in both vertebrate and invertebrate species and it regulates many different cell fate decisions. It is important for pattern formation during development such as neurogenesis, angiogenesis or myogenesis and regulates T cell development and stem cell maintenance. Notch signaling is also involved in cellular processes throughout adulthood. Signaling via Notch occurs between neighbouring cells and both the receptor and its ligands are transmembrane proteins. Schmitt T. M., Zúñiga-Pflucker J. C. (2002) Induction of T cell development from hematopoietic progenitor cells by delta-like-1 in vitro. Immunity 17:749-756; Mohtashami M. (2010) Direct Comparison of Dll1- and Dll4-Mediated Notch Activation Levels Shows Differential Lymphomyeloid Lineage Commitment Outcomes. J Immunol. 185(2):867-76; Ohishi K et al. Delta-1 enhances marrow and thymus repopulating ability of human CD34($^+$) CD38($^-$) cord blood cells. J Clin Invest. 2002 October; 110(8):1165-74; and Dallas M H et al. Density of the Notch ligand Delta1 determines generation of B and T cell precursors from hematopoietic stem cells J Exp Med. 2005 May 2; 201(9): 1361-1366.

Accordingly, to initiate differentiation in the lymphoid lineage and T cell lineage commitment in the histone methyltransferase inhibited multipotent hematopoietic progenitor cells, these cells are exposed to a Notch ligand to activate the Notch signaling pathway therein.

Notch ligands are single-pass transmembrane proteins with a DSL (Delta, Serrate, LAG-2)-domain and varying numbers of EGF-like repeats. There are two classes of canonical Notch ligands, the Delta/Delta-like and the Serrate/Jagged class. The later has an additional domain of cysteine rich repeats close to the transmembrane domain. There are 5 canonical Notch ligands in mammals: Jagged-1, Jagged-2, DLL1, DLL3 and DLL4. These can bind to the four Notch receptors Notch 1-4. DLL1, also known as Notch Delta ligand, Delta-like 1, is a protein which interacts with a NOTCH2 receptor. Shimizu K, et al., 2001, J. Biol. Chem. 276 (28): 25753-8; Blaumueller C M, et al., 1997, Cell 90 (2): 281-91; Shimizu K, et al., 2000, Mol. Cell. Biol. 20 (18): 6913-22. DLL1 is a protein that in humans is encoded by the DLL1 gene. DLL1 is a human homolog of the Notch Delta ligand.

There are several ways to provide a Notch ligand. These include but are not limited to co-culturing with stroma cells such as OP-9-DL1 or similar cells that express and display extracellular or secretes such a Notch ligand, and by providing a purified recombinant form of a Notch ligand or a Notch receptor-binding fragment, the receptor-binding fragment being sufficient to elicit cell signaling events in vivo upon contact and binding with the extracellular Notch receptors on these cells.

In one embodiment of any method, cells, or composition described herein, the histone methyltransferase inhibited multipotent hematopoietic progenitor cells of step (b) is co-culture with a stromal cell that express a Notch ligand.

In one embodiment of any method, cells, or composition described herein, the co-culturing of cells occurs in a medium comprising Flt-3L and IL-7.

In one embodiment of any method, cells, or composition described herein, the co-culturing of cells is performed in serum-free culture conditions.

In one embodiment of any method, cells, or composition described herein, the cell expressing the Notch ligand is an OP-9 cell. In one embodiment, the OP-9 cell expresses DLL1, otherwise referred to as OP9-DL1 cells. In another embodiment, the OP-9 cell expresses DLL4, otherwise referred to as OP9-DL4 cells.

In one embodiment of any method, cells, or composition described herein, the notch ligand is Delta-like-1 (DLL1), Delta-like-4 (DLL4), and immobilized Delta1$^{ext-IgG}$, consisting of the extracellular domain of human Delta-like-1 (DLL1) fused to the Fc domain of human IgG1. "Immobolized Deltalext-IgG" refers to recombinant Notch ligand made by fusing the extracellular domain of Delta-like 1 to the Fc domain of human IgG1. This is a synthetic way of providing a titratable dose of NOTCH ligand. Varnum-Finney B et al. Immobilization of Notch ligand, Delta-1, is required for induction of notch signaling. J Cell Sci. 2000, 23:4313-8. These references are incorporated herein by reference in their entirety. Recombinant Notch ligands and Fc-fusions are commercially available at AdipoGen™.

In one embodiment of any method, cells, or composition described herein, the DLL1 or DLL4 is supplied with co-culturing the multilineage hematopoietic progenitor cells with immobilized Delta1$^{ext-IgG}$, OP9-DL1 cells or OP9-DL4 cells. OP9-DL1 cells are a bone-marrow-derived stromal cell line that ectopically expresses the Notch ligand, Delta-like 1 (DLL1).

In one embodiment of any method, cells, or composition described herein, the Notch ligand is DLL1 or DLL4.

Method of differentiating progenitor cells to T-cells using the Notch signaling pathway and OP9-Notch ligand expressing cells are known in the art. Any method can be used herein to produce the engineered immune from the multilineage hematopoietic progenitor cells that had previously been inhibited with a histone methyltransferase inhibitor. For examples, as described in the Example section and also as described in U.S. Pat. Nos. 7,575,925, 8,772,028, 8,871,510, and 9,206,394 and US Patent Publication Nos: 20090217403, 20110123502, 20110052554 20110027881, 20110236363, 20120149100, 20130281304, 20140322808, 20140248248, and 20140037599. These references are incorporated herein by reference in their entirety.

For differentiation in the lymphoid lineage and B cell lineage commitment in the histone methyltransferase inhibited multipotent hematopoietic progenitor cells, these cells are exposed to (1) a B-cell priming factors; (2) co-culturing with supporting cells expressing one or more B-lineage growth factors; (3) co-culturing with supporting cells expressing CD40L in the absence or presence of one or more B-cell activators; (4) exposure to one or more B-cell activators; or a combination of (1)-(4) over period of time in culture.

In some embodiments, a B-cell priming factor can also be a B-lineage growth factor. In some embodiments, a B-lineage growth factor can also be a B-cell priming factor.

B-cell priming factors are known in the art. For examples, IL-3, Flt3 ligand, thrombopoietin, stem cell factor (SCF), granulocyte colony-stimulating factor (G-CSF), granulocyte colony-stimulating factor (GM-CSF), IL-7, and IL-11. As used herein, the term "B-cell priming factor" refers to any compounds that are capable of supporting or promoting the commitment of hematopoietic stem cells and/or lymphoid progenitor cells to B-lineage development. A compound can be a small molecule, a polypeptide, a protein, or a nucleic acid. Various B-cell priming factors can be used in the methods and systems described herein. Examples of B-cell priming factors include, but are not limited to, interleukin 3 (IL-3), Flt3 ligand, thrombopoietin, stem cell factor (SCF), granulocyte colony-stimulating factor (G-CSF), granulocyte macrophage colony-stimulating factor (GM-CSF), interleukin 7 (IL-7), interleukin 11 (IL-11), anti-phosphatase (Sbfl), and mechano growth factor (MGF). One of skill in the art will be able to select the amount of a B-cell priming factor to use based on the particular circumstances. Generally, from about 1 to about 1000 ng/ml of a B-cell priming factor can be used in the methods or systems described herein; however, in the typical situation from about 1 to about 100 ng/ml of a B-cell priming factor can be used. However, in some situations, more or less amount of a B-cell priming factor may be used. In situations where more than one B-cell priming factor is used, the amount of each B-cell priming factor may the same, or the amount of each B-cell priming factor may be different from each other.

B-cell activators are known in the art. For examples, CpG DNA, IL-2, IL-10, IL-15, IL-6, IFNα, and anti-CD40L. As used herein, the term "B-cell activator" refers to any compounds that are capable of promoting the activation of naïve B cells, preferably the antigen-independent activation of naïve B cells. B-cell activators can be small molecules, polypeptides, proteins or nucleic acids. Conventional methods can be used to determine if a compound has the ability of stimulating antigen-independent activation of naïve B cell. For example, the compound can be tested for the activation of naïve B cells isolated from human peripheral blood. Non-limiting examples of B-cell activators include CpG DNA; cytokines, such as IL-2, IL-3, IL-4, IL-6, IL-10, IL-15, IFNα; anti-CD40L; and lactic acid. One of skill in the art will be able to select the amount of a B-cell activator based on the particular circumstances. Generally, from about 1 to about 1000 ng/ml of a cytokine B-cell activator can be used in the methods or systems described herein; however, in the typical situation from about 1 to about 150 ng/ml, or about 1 to about 100 ng/ml of a cytokine B-cell activator can be used. However, in some situations, more or less amount may be used. Generally, from about 0.1 to about 5 µM CpG DNA can be used; however, in the typical situation from about 0.5 to about 4 µM, or about 1 to about 3.5 µM, or about 1.5 to about 3 µM, or about 2 to about 2.5 µM CpG DNA can be used. In situations where more than one B-cell activator is used, the amount of each B-cell activator may the same, or the amount of each B-cell activator may be different from each other.

B-lineage growth factors are known in the art. For examples, pre-pro-B cell growth-stimulating factor (PPBSF), insulin-like growth factor-1 (IGF-1), interleukin 3 (IL-3), Flt3 ligand, thrombopoietin, stem cell factor (SCF), granulocyte colony-stimulating factor (G-CSF), Granulocyte macrophage colony-stimulating factor (GM-CSF), interleukin 11 (IL-11), anti-phosphatase (Sbfl), and mechano growth factor (MGF). As used herein, the term "B-lineage growth factor" refers to any compounds that are capable of promoting one or more stages of B cell differentiation during B-lineage development. B-lineage growth factors can be small molecules, polypeptides, proteins, or nucleic acids. Non-limiting examples of the stages in B-lineage development include: the stage from progenitor B cells to early pro-B cells, the stage from early pro-B cells to late pro-B cells, the stage from late pro-B cells to large pre-B cells, the stage from large pre-B cells to small pre-B cells, the stage from small pre-B cells to immature B cells, and the stage from immature B cells to mature B cells. Examples of B-lineage growth factor include, but are not limited to, interleukin 7 (IL-7), pre-pro-B cell growth-stimulating factor (PPBSF), insulin-like growth factor-1 (IGF-1), interleukin 3 (IL-3), Flt3 ligand, thrombopoietin, stem cell factor (SCF), granulocyte colony-stimulating factor (G-CSF), granulocyte macrophage colony-stimulating factor (GM-CSF), interleukin 11 (IL-11), anti-phosphatase (Sbfl), and mechano growth factor (MGF). One of skill in the art will be able to select the amount of a B-lineage growth factor based on the particular circumstances. Generally, from about 1 to about 1000 ng/ml of a B-lineage growth factor can be used in the methods or systems described herein. However, in the typical situation from about 1 to about 300 ng/ml, about 20 to about 200 ng/ml, about 50 to about 150 ng/ml, about 80 to about 150 ng/ml of a cytokine B-cell activator can be used. However, in some situations, more or less amount of a B-lineage growth factor may be used. In situations where more than one B-lineage growth factor is used, the amount of each B-lineage growth factor may the same, or the amount of each B-lineage growth factor may be different from each other.

Supporting cells used in co-cultures for cell differentiation purposes are typically stromal cells. Various stromal cells can be used in the methods described herein. Examples of stromal cell lines include, but are not limited to murine MS5 stromal cell line; murine bone marrow-derived stromal cell lines, such as S10, S17, OP9 and BMS2 cell lines; human marrow stromal cell lines such as those described in U.S. Pat. No. 5,879,940. This reference is incorporated herein by reference in its entirety. The supporting cell or stromal cell expresses one or more B-lineage growth factors, for example, growth factors IL-7.

As used herein, the term "supporting cell or stromal cell" when used in the context of cell differentiation refers to any cells that are capable of creating, promoting, or supporting a microenvironment for the growth, proliferation, differentiation, or expansion of multipotent hematopoietic progenitor cells or T cells or B cells. Suitable supporting cells that can be used in the systems and methods disclosed herein include, but are not limited to, stromal cells and fibroblast cells.

In some embodiments, the histone methyltransferase inhibited multipotent hematopoietic progenitor cells are co-cultured with a population of first supporting cells expressing one or more B-lineage growth factors. In an embodiment, the first supporting cells can express IL-7. In another embodiment, the first supporting cells can express IL-7 and at least one B-lineage growth factor selected from pre-pro-B cell growth-stimulating factor (PPBSF), insulin-like growth factor-1 (IGF-1), interleukin 3 (IL-3), Flt3 ligand, thrombopoietin, stem cell factor (SCF), granulocyte colony-stimulating factor (G-CSF), Granulocyte macrophage colony-stimulating factor (GM-CSF), interleukin 11 (IL-11), anti-phosphatase (Sbfl), and mechano growth factor (MGF). In some embodiments, one or more B-lineage growth factors are from humans. In some embodiments, all B-lineage growth factors are from humans. In some embodiments, one or more B-lineage growth factors are from mammals other than humans. In some embodiments, all B-lineage growth factors are from mammals other than humans.

Entry and commitment to the B cell lineage can be monitored by the appearance of B cell specific markers. Many early B-lineage markers are known in the art. For instance, pro-B cells can be identified by CD19 and CD10 co-expression (CD19+CD10+) and the lack of for expression of surrogate light chains.

Methods of differentiating progenitor cells to B-cells are known in the art. Any method can be used herein to produce the engineered immune from the multilineage hematopoietic progenitor cells that had previously been inhibited with a histone methyltransferase inhibitor. For examples, U.S. Pat. Nos. 8,034,613, 8,133,727, and 8,206,979, and US Patent Publication Nos: 20030152558, 20040029271, 20050153443, 20100047854, 2012004036, 20120040362, and 20140273211. These references are incorporated herein by reference in their entirety.

Induced Pluripotent Stem Cells

In some embodiments, the pluripotent stem cells (PSCs) described herein are derived from isolated induced pluripotent stem cells (iPSCs). An advantage of using iPSCs is that the cells can be derived from the same subject to which the eventual immune cells would be reintroduced. That is, a somatic cell can be obtained from a subject, reprogrammed to an induced pluripotent stem cell, and then transfected and differentiated into a modified immune cell to be administered to the subject (e.g., autologous cells). Since the progenitors are essentially derived from an autologous source, the risk of engraftment rejection or allergic responses is reduced compared to the use of cells from another subject or group of subjects. In some embodiments, the cells for generating iPSCs are derived from non-autologous sources. In addition, the use of iPSCs negates the need for cells obtained from an embryonic source. Thus, in one embodiment, the PSCs used in the disclosed methods are not embryonic stem cells.

Although differentiation is generally irreversible under physiological contexts, several methods have been recently developed to reprogram somatic cells to induced pluripotent stem cells. Exemplary methods are known to those of skill in the art and are described briefly herein below.

As used herein, the term "reprogramming" refers to a process that alters or reverses the differentiation state of a differentiated cell (e.g., a somatic cell). Stated another way, reprogramming refers to a process of driving the differentiation of a cell backwards to a more undifferentiated or more primitive type of cell. It should be noted that placing many primary cells in culture can lead to some loss of fully differentiated characteristics. Thus, simply culturing such cells included in the term differentiated cells does not render these cells non-differentiated cells (e.g., undifferentiated cells) or pluripotent cells. The transition of a differentiated cell to pluripotency requires a reprogramming stimulus beyond the stimuli that lead to partial loss of differentiated character in culture. Reprogrammed cells also have the characteristic of the capacity of extended passaging without loss of growth potential, relative to primary cell parents, which generally have capacity for only a limited number of divisions in culture.

The cell to be reprogrammed can be either partially or terminally differentiated prior to reprogramming. In some embodiments, reprogramming encompasses complete reversion of the differentiation state of a differentiated cell (e.g., a somatic cell) to a pluripotent state or a multipotent state. In some embodiments, reprogramming encompasses complete or partial reversion of the differentiation state of a differentiated cell (e.g., a somatic cell) to an undifferentiated cell (e.g., an embryonic-like cell). Reprogramming can result in expression of particular genes by the cells, the expression of which further contributes to reprogramming. In certain embodiments described herein, reprogramming of a differentiated cell (e.g., a somatic cell) causes the differentiated cell to assume an undifferentiated state (e.g., is an undifferentiated cell). The resulting cells are referred to as "reprogrammed cells," or "induced pluripotent stem cells (iPSCs or iPS cells)."

Reprogramming can involve alteration, e.g., reversal, of at least some of the heritable patterns of nucleic acid modification (e.g., methylation), chromatin condensation, epigenetic changes, genomic imprinting, etc., that occur during cellular differentiation. Reprogramming is distinct from simply maintaining the existing undifferentiated state of a cell that is already pluripotent or maintaining the existing less than fully differentiated state of a cell that is already a multipotent cell (e.g., a common myeloid stem cell). Reprogramming is also distinct from promoting the self-renewal or proliferation of cells that are already pluripotent or multipotent, although the compositions and methods described herein can also be of use for such purposes, in some embodiments.

The specific approach or method used to generate pluripotent stem cells from somatic cells (broadly referred to as "reprogramming") is not critical to the claimed invention. Thus, any method that re-programs a somatic cell to the pluripotent phenotype would be appropriate for use in the methods described herein.

Reprogramming methodologies for generating pluripotent cells using defined combinations of transcription factors have been described to induce pluripotent stem cells from somatic cells. Yamanaka and Takahashi converted mouse somatic cells to ES cell-like cells with expanded developmental potential by the direct transduction of Oct4, Sox2, Klf4, and optionally c-Myc. See U.S. Pat. Nos. 8,058,065 and 9,045,738 to Yamanaka and Takahashi. iPSCs resemble ES cells as they restore the pluripotency-associated transcriptional circuitry and much of the epigenetic landscape. In addition, mouse iPSCs satisfy all the standard assays for pluripotency: specifically, in vitro differentiation into cell types of the three germ layers, teratoma formation, contribution to chimeras, germline transmission, and tetraploid complementation.

Subsequent studies have shown that human iPS cells can be obtained using similar transduction methods, and the transcription factor trio, OCT4, SOX2, and NANOG, has been established as the core set of transcription factors that govern pluripotency. The production of iPS cells can be achieved by the introduction of nucleic acid sequences encoding stem cell-associated genes into an adult, somatic cell, using viral vectors.

iPS cells can be generated or derived from terminally differentiated somatic cells, as well as from adult stem cells, or somatic stem cells. That is, a non-pluripotent progenitor cell can be rendered pluripotent or multipotent by reprogramming. In such instances, it may not be necessary to include as many reprogramming factors as required to reprogram a terminally differentiated cell. Further, reprogramming can be induced by the non-viral introduction of reprogramming factors, e.g., by introducing the proteins themselves, or by introducing nucleic acids that encode the reprogramming factors, or by introducing messenger RNAs that upon translation produce the reprogramming factors (see e.g., Warren et al., Cell Stem Cell, 2010 Nov. 5; 7(5):618-30, this reference is incorporated herein by reference in its entirety.). Reprogramming can be achieved by introducing a combination of nucleic acids encoding stem cell-associated genes including, for example Oct-4 (also known as Oct-3/4 or Pouf51), Sox1, Sox2, Sox3, Sox 15, Sox 18, NANOG, Klf1, Klf2, Klf4, Klf5, NR5A2, c-Myc, 1-Myc, n-Myc, Rem2, Tert, and LIN28. In one embodiment, reprogramming using the methods and compositions described herein can further comprise introducing one or more of Oct-3/4, a member of the Sox family, a member of the Klf family, and a member of the Myc family to a somatic cell. In one embodiment, the methods and compositions described herein further comprise introducing one or more of each of Oct 4, Sox2, Nanog, c-MYC and Klf4 for reprogramming. As noted above, the exact method used for reprogramming is not necessarily critical to the methods and compositions described herein. However, where cells differentiated from the reprogrammed cells are to be used in, e.g., human therapy, in one embodiment the reprogramming is not effected by a method that alters the genome. Thus, in such embodiments, reprogramming is achieved, e.g., without the use of viral or plasmid vectors.

The efficiency of reprogramming (i.e., the number of reprogrammed cells) derived from a population of starting cells can be enhanced by the addition of various small molecules as shown by Shi, Y., et al (2008) Cell-Stem Cell 2:525-528, Huangfu, D., et al (2008) Nature Biotechnology 26(7):795-797, and Marson, A., et al (2008) Cell-Stem Cell 3:132-135. This reference is incorporated herein by reference in its entirety. Thus, an agent or combination of agents that enhance the efficiency or rate of induced pluripotent stem cell production can be used in the production of patient-specific or disease-specific iPSCs. Some non-limiting examples of agents that enhance reprogramming efficiency include soluble Wnt, Wnt conditioned media, BIX-01294 (a G9a histone methyltransferase), PD0325901 (a MEK inhibitor), DNA methyltransferase inhibitors, histone deacetylase (HDAC) inhibitors, valproic acid, 5'-azacytidine, dexamethasone, suberoylanilide hydroxamic acid (SAHA), vitamin C, and trichostatin (TSA), among others.

Other non-limiting examples of reprogramming enhancing agents include: Suberoylanilide Hydroxamic Acid (SAHA (e.g., MK0683, vorinostat) and other hydroxamic acids), BML-210, Depudecin (e.g., (−)-Depudecin), HC Toxin, Nullscript (4-(1,3-Dioxo-1H,3H-benzo[de]isoquinolin-2-yl)-N-hydroxybutanamide), Phenylbutyrate (e.g., sodium phenylbutyrate) and Valproic Acid ((VPA) and other short chain fatty acids), Scriptaid, Suramin Sodium, Trichostatin A (TSA), APHA Compound 8, Apicidin, Sodium Butyrate, pivaloyloxymethyl butyrate (Pivanex, AN-9), Trapoxin B, Chlamydocin, Depsipeptide (also known as FR901228 or FK228), benzamides (e.g., CI-994 (e.g., N-acetyl dinaline) and MS-27-275), MGCD0103, NVP-LAQ-824, CBHA (m-carboxycinnaminic acid bishydroxamic acid), JNJ16241199, Tubacin, A-161906, proxamide, oxamflatin, 3-Cl-UCHA (e.g., 6-(3-chlorophenylureido) caproic hydroxamic acid), AOE (2-amino-8-oxo-9,10-epoxydecanoic acid), CHAP31 and CHAP 50. Other reprogramming enhancing agents include, for example, dominant negative forms of the HDACs (e.g., catalytically inactive forms), siRNA inhibitors of the HDACs, and antibodies that specifically bind to the HDACs. Such inhibitors are available, e.g., from BIOMOL International, Fukasawa, Merck Biosciences, Novartis, Gloucester Pharmaceuticals, Aton Pharma, Titan Pharmaceuticals, Schering AG, Pharmion, MethylGene, and Sigma Aldrich.

To confirm the induction of pluripotent stem cells for use with the methods described herein, isolated clones can be tested for the expression of a stem cell marker. Such expression in a cell derived from a somatic cell identifies the cells as induced pluripotent stem cells. Stem cell markers can be selected from the non-limiting group including SSEA3, SSEA4, CD9, Nanog, Fbx15, Ecat1, Esg1, Eras, Gdf3, Fgf4, Cripto, Dax1, Zpf296, Slc2a3, Rex1, Utf1, and Nat1. In one embodiment, a cell that expresses Oct4 or Nanog is identified as pluripotent. Methods for detecting the expression of such markers can include, for example, RT-PCR and immunological methods that detect the presence of the encoded polypeptides, such as Western blots or flow cytometric analyses. In some embodiments, detection does not involve only RT-PCR, but also includes detection of protein markers. Intracellular markers may be best identified via RT-PCR, while cell surface markers are readily identified, e.g., by immunocytochemistry.

The pluripotent stem cell character of isolated cells can be confirmed by tests evaluating the ability of the iPSCs to differentiate to cells of each of the three germ layers. As one example, teratoma formation in nude mice can be used to evaluate the pluripotent character of the isolated clones. The cells are introduced to nude mice and histology and/or immunohistochemistry is performed on a tumor arising from the cells. The growth of a tumor comprising cells from all three germ layers, for example, further indicates that the cells are pluripotent stem cells.

Many US Patents and Patent Application Publications teach and describe methods of generating iPSCs and related subject matter. For examples, U.S. Pat. Nos. 9,347,044, 9,347,042, 9,347,045, 9,340,775, 9,341,625, 9,340,772, 9,250,230, 9,132,152, 9,045,738, 9,005,975, 9,005,976, 8,927,277, 8,993,329, 8,900,871, 8,852,941, 8,802,438, 8,691,574, 8,735,150, 8,765,470, 8,058,065, 8,048,675, and US Patent Publication Nos: 20090227032, 20100210014, 20110250692, 20110201110, 20110200568, 20110306516, 20100021437, 20110256626, 20110044961, 20120276070, 20120263689, 20120128655, 20120100568, 20130295064, 20130029866, 20130189786, 20130295579, 20130130387, 20130157365, 20140234973, 20140227736, 20140093486, 20140301988, 20140170746, 20140178989, 20140349401, 20140065227, and 20150140662. These references are incorporated herein by reference in their entirety.

Somatic Cells for Reprogramming

Somatic cells, as that term is used herein, refer to any cells forming the body of an organism, excluding germline cells. Every cell type in the mammalian body-apart from the sperm and ova, the cells from which they are made (gametocytes) and undifferentiated stem cells—is a differentiated somatic cell. For example, internal organs, skin, bones, blood, and connective tissue are all made up of differentiated somatic cells.

Additional somatic cell types for use with the compositions and methods described herein include: a fibroblast (e.g., a primary fibroblast), a muscle cell (e.g., a myocyte), a cumulus cell, a neural cell, a mammary cell, an hepatocyte and a pancreatic islet cell. In some embodiments, the somatic cell is a primary cell line or is the progeny of a primary or secondary cell line. In some embodiments, the somatic cell is obtained from a human sample, e.g., a hair follicle, a blood sample, a biopsy (e.g., a skin biopsy or an adipose biopsy), a swab sample (e.g., an oral swab sample), and is thus a human somatic cell.

Some non-limiting examples of differentiated somatic cells include, but are not limited to, epithelial, endothelial, neuronal, adipose, cardiac, skeletal muscle, skin, immune cells, hepatic, splenic, lung, peripheral circulating blood cells, gastrointestinal, renal, bone marrow, and pancreatic cells. In some embodiments, a somatic cell can be a primary cell isolated from any somatic tissue including, but not limited to brain, liver, gut, stomach, intestine, fat, muscle, uterus, skin, spleen, endocrine organ, bone, etc. Further, the somatic cell can be from any mammalian species, with non-limiting examples including a murine, bovine, simian, porcine, equine, ovine, or human cell. In some embodiments, the somatic cell is a human somatic cell.

When reprogrammed cells are used for generation of thyroid progenitor cells to be used in the therapeutic treatment of disease, it is desirable, but not required, to use somatic cells isolated from the patient being treated. For example, somatic cells involved in diseases, and somatic cells participating in therapeutic treatment of diseases and the like can be used. In some embodiments, a method for selecting the reprogrammed cells from a heterogeneous population comprising reprogrammed cells and somatic cells they were derived or generated from can be performed by any known means. For example, a drug resistance gene or the like, such as a selectable marker gene can be used to isolate the reprogrammed cells using the selectable marker as an index.

Reprogrammed somatic cells as disclosed herein can express any number of pluripotent cell markers, including: alkaline phosphatase (AP); ABCG2; stage specific embryonic antigen-1 (SSEA-1); SSEA-3; SSEA-4; TRA-1-60; TRA-1-81; Tra-2-49/6E; ERas/ECAT5, E-cadherin; β-III-tubulin; α-smooth muscle actin (α-SMA); fibroblast growth factor 4 (Fgf4), Cripto, Dax1; zinc finger protein 296 (Zfp296); N-acetyltransferase-1 (Nat1); (ES cell associated transcript 1 (ECAT1); ESG1/DPPA5/ECAT2; ECAT3; ECAT6; ECAT7; ECAT8; ECAT9; ECAT10; ECAT15-1; ECAT15-2; Fthl17; Sal14; undifferentiated embryonic cell transcription factor (Utf1); Rex1; p53; G3PDH; telomerase, including TERT; silent X chromosome genes; Dnmt3a; Dnmt3b; TRIM28; F-box containing protein 15 (Fbx15); Nanog/ECAT4; Oct3/4; Sox2; Klf4; c-Myc; Esrrb; TDGF1; GABRB3; Zfp42, FoxD3; GDF3; CYP25A1; developmental pluripotency-associated 2 (DPPA2); T-cell lymphoma breakpoint 1 (Tcl1); DPPA3/Stella; DPPA4; other general markers for pluripotency, etc. Other markers can include Dnmt3L; Sox15; Stat3; Grb2; β-catenin, and Bmi1. Such cells can also be characterized by the down-regulation of markers characteristic of the somatic cell from which the induced pluripotent stem cell is derived.

Uses of the Engineered Immune Cells Derived from Pluripotent Stem Cells

In one embodiment, provided herein a population of engineered immune cells produced by a method described herein, where in the cell comprises an exogenous gene coding copy of each of the transcription factors: ERG, HOXA9, and RORA, and optionally, further comprising an exogenous gene coding copy of each of the transcription factors:SOX4, and MYB, or further comprising an exogenous gene coding copy of each of the transcription factors: DACH1 and NFIA, or further comprising an exogenous gene coding copy of each of the transcription factors: SOX4, MYB, DACH1 and NFIA, In one embodiment, the population of cells further comprises a pharmaceutically acceptable carrier. These engineered immune cells can be culture expanded to increase the number of cells for use.

The engineered immune cells described herein are useful in the laboratory for biological studies. For examples, these cells can be derived from an individual having a genetic disesase or defect, and used in the laboratory to study the biological aspects of the disesase or defect, and to screen and test for potential remedy for that disesase or defect.

Alternatively, the engineered immune cells described herein are useful in cellular replacement therapy and other medical treatment in subjects having the need. For example, patients who have undergone chemotherapy or irradiation or both, and manifest deficiencies in immune function and/or lymphocyte reconstitution, or in cancer immune therapy.

In various embodiments, the engineered immune cells described herein are administered (ie., implanted or transplanted) to a subject in need of cellular replacement therapy.

In one embodiment, provided herein is a method of cellular replacement therapy, or for the treatment of cancer, autoimmune disorders, hematological diseases, or other genetic diseases and disorders in a subject, comprising (a) providing a somatic cell from a donor subject, (b) generating multilineage hematopoietic progenitor cells from myeloid progenitor cells derived from the somatic cell as described in any of the preceding paragraphs; (c) inhibiting a histone methyltransferase in the resultant population of multilineage hematopoietic progenitor cells as described in any of the preceding paragraphs; (d) differentiating the resultant population of multilineage hematopoietic progenitor cells in the presence of a notch ligand or a stromal cell or both to promote differentiation into the lymphoid lineage as described in any of the preceding paragraphs, and (e) implanting or administering the resultant differentiated lymphoid cells into a recipient subject.

In one embodiment of the treatment method described above, the host subject and the recipient subject are the same individual.

In one embodiment of the treatment method described above, the host subject and the recipient subject are not the same individual, but are at least HLA compatible.

Hematologic diseases are disorders which primarily affect the blood. Non-limiting such diseases or disorders include myeloid derived disorders such as hemoglobinopathies (congenital abnormality of the hemoglobin molecule or of the rate of hemoglobin synthesis), examples, sickle-cell disease, thalassemia, and methemoglobinemia; Anemias (lack of red blood cells or hemoglobin), Pernicious anemia; disorders resulting in decreased numbers of cells, such as myelodysplastic syndrome, neutropenia (decrease in the number of neutrophils), and thrombotic thrombocytopenic purpura (TTP), thrombocytosis, tematological malignancies such as lymphomas, myelomas, and leukemia. Lymphomas such as Hodgkin's disease, Non-Hodgkin's lymphoma, Burkitt's lymphoma, Anaplastic large cell lymphoma, Splenic marginal zone lymphoma, Hepatosplenic T-cell lymphoma, and Angioimmunoblastic T-cell lymphoma (AILT); myelomas such as Multiple myeloma, Waldenström macroglobulinemia, Plasmacytoma; leukemias that increases defect WBC such as Acute lymphocytic leukemia (ALL), Chronic lymphocytic leukemia (CLL), Acute myelogenous leukemia (AML), Chronic Idiopathic Myelofibrosis (MF), Chronic myelogenous leukemia (CML), T-cell prolymphocytic leukemia (T-PLL), B-cell prolymphocytic leukemia (B-PLL), Chronic neutrophilic leukemia (CNL), Hairy cell leukemia (HCL), T-cell large granular lymphocyte leukemia (T-LGL), and Aggressive NK-cell leukemia.

Autoimmune diseases such as diabetes, rheumatoid arthritis and multiple sclerosis.

As used herein, the terms "administering," "introducing" and "transplanting" are used interchangeably in the context of the placement of described cells, e.g. hematopoietic progenitor cells, into a subject, by a method or route which results in at least partial localization of the introduced cells at a desired site, such as a site of injury or repair, such that a desired effect(s) is produced. The cells e.g. hematopoietic progenitor cells, or their differentiated progeny can be administered by any appropriate route which results in delivery to a desired location in the subject where at least a portion of the implanted cells or components of the cells remain viable.

In various embodiments, the engineered immune cells described herein are optionally expanded ex vivo prior to administration to a subject. In other embodiments, the engineered immune cells are optionally cryopreserved for a period, then thawed prior to administration to a subject.

The engineered immune cells used for cellular replacement therapy can be autologous/autogeneic ("self") or non-autologous ("non-self," e.g., allogeneic, syngeneic or xenogeneic) in relation to the recipient of the cells.

"Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In preferred embodiments, the cells of the invention are allogeneic.

In various embodiments, the engineered immune cell described herein that is to be implanted into a subject in need thereof is autologous or allogeneic to the subject.

In various embodiments, the engineered immune cell described herein can be derived from one or more donors, or can be obtained from an autologous source. In some embodiments of the aspects described herein, the engineered immune cells are expanded in culture prior to administration to a subject in need thereof.

In various embodiments, the engineered immune cell described herein can be derived from one or more donors, or can be obtained from an autologous source.

In various embodiments, prior to implantation, the recipient subject is treated with chemotherapy and/or radiation.

In one embodiment, the chemotherapy and/or radiation is to reduce endogenous stem cells to facilitate engraftment of the implanted cells.

In various embodiments, prior to implantation, the engineered immune cells or the inhibited, reverse-lineage multilineage hematopoietic progenitor cells are treated ex vivo with prostaglandin E2 and/or antioxidant N-acetyl-L-cysteine (NAC) to promote subsequent engraftment in a recipient subject.

In various embodiments, the receipient subject is a human.

In various embodiments, the subject is diagnosed with HIV or other viral disease, a hematological disease, or undergoing a cancer treatment.

In one aspect of any method, cells and composition described herein, a subject is selected to donate a somatic cell which would be used to produce iPSCs and an engineered immune cell described herein. In one embodiment, the selected subject has a genetic disease or defect.

In various embodiments, the donor subject is a human.

In various embodiments, the donor or the recipient subject is an animal, human or non-human, and rodent or non-rodent. For example, the subject can be any mammal, e.g., a human, other primate, pig, rodent such as mouse or rat, rabbit, guinea pig, hamster, cow, horse, cat, dog, sheep or goat, or a non-mammal such as a bird.

In various embodiments, the donor or the recipient subject is diagnosed with HIV, a hematological disease or cancer.

In one aspect of any method, cells and composition described herein, a biological sample or a population of embryonic stem cells, somatic stem cells, progenitor cells, bone marrow cells, hematopoietic stem cells, or hematopoietic progenitor cells is obtained from the donor subject.

In various embodiments, biological sample or a population of embryonic stem cells, somatic stem cells, progenitor cells, bone marrow cells, hematopoietic stem cells, or hematopoietic progenitor cells described herein can be derived from one or more donors, or can be obtained from an autologous source.

In one embodiment, the embryonic stem cells, somatic stem cells, progenitor cells, bone marrow cells, hematopoietic stem cells, or hematopoietic progenitor cells are isolated from the donor subject, transfected, cultured (optional), and transplanted back into the same subject, i. e. an autologous cell transplant. Here, the donor and the recipient subject is the same individual. In another embodiment, the embryonic stem cells, somatic stem cells, progenitor cells, bone marrow cells, hematopoietic stem cells, or hematopoietic progenitor cells are isolated from a donor who is an HLA-type match with a subject (recipient). Donor-recipient antigen type-matching is well known in the art. The HLA-types include HLA-A, HLA-B, HLA-C, and HLA-D. These represent the minimum number of cell surface antigen matching required for transplantation. That is the transfected cells are transplanted into a different subject, i.e., allogeneic to the recipient host subject. The donor's or subject's embryonic stem cells, somatic stem cells, progenitor cells, bone marrow cells, hematopoietic stem cells, or hematopoietic progenitor cells can be transfected with a vector or nucleic acid comprising the nucleic acid molecule(s) described herein, the transfected cells are cultured, inhibited, and differentiated as disclosed, optionally expanded, and then transplanted into the recipient subject. In one embodiment, the transplanted engineered immune cells engrafts in the recipient subject. In one embodiment, the transplanted engineered immune cells reconstitute the immune system in the recipient subject. The transfected cells can also be cryopreserved after transfected and stored, or cryopreserved after cell expansion and stored.

The engineered immune cells or the histone methyltransferase inhibited, reverse-lineage multilineage hematopoietic progenitor cells may be administered as part of a bone marrow or cord blood transplant in an individual that has or has not undergone bone marrow ablative therapy. In one embodiment, genetically modified cells contemplated herein are administered in a bone marrow transplant to an individual that has undergone chemoablative or radioablative bone marrow therapy.

In one embodiment, a dose of cells is delivered to a subject intravenously. In one embodiment, the cells are intravenously administered to a subject.

In particular embodiments, patients receive a dose of the modified cells described herein, e.g., engineered immune cells or the histone methyltransferase inhibited, reverse-lineage multilineage hematopoietic progenitor cells, of about $1\times10^5$ cells/kg, about $5\times10^5$ cells/kg, about $1\times10^6$ cells/kg, about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $5\times10^7$ cells/kg, about $1\times10^8$ cells/kg, or more in one single intravenous dose.

In certain embodiments, patients receive a dose of the modified cells described herein, e.g., engineered immune cells or the histone methyltransferase inhibited, reverse-lineage multilineage hematopoietic progenitor cells, of at least $1\times10^5$ cells/kg, at least $5\times10^5$ cells/kg, at least $1\times10^6$ cells/kg, at least $2\times10^6$ cells/kg, at least $3\times10^6$ cells/kg, at least $4\times10^6$ cells/kg, at least $5\times10^6$ cells/kg, at least $6\times10^6$ cells/kg, at least $7\times10^6$ cells/kg, at least $8\times10^6$ cells/kg, at least $9\times10^6$ cells/kg, at least $1\times10^7$ cells/kg, at least $5\times10^7$ cells/kg, at least $1\times10^8$ cells/kg, or more in one single intravenous dose.

In an additional embodiment, patients receive a dose of the modified cells described herein, e.g., engineered immune cells or the histone methyltransferase inhibited, reverse-lineage multilineage hematopoietic progenitor cells, of about $1\times10^5$ cells/kg to about $1\times10^8$ cells/kg, about $1\times10^6$ cells/kg to about $1\times10^8$ cells/kg, about $1\times10^6$ cells/kg to about $9\times10^6$ cells/kg, about $2\times10^6$ cells/kg to about $8\times10^6$ cells/kg, about $2\times10^6$ cells/kg to about $8\times10^6$ cells/kg, about $2\times10^6$ cells/kg to about $5\times10^6$ cells/kg, about $3\times10^6$ cells/kg to about 5×10⁶ cells/kg, about 3×10⁶ cells/kg to about 4×10⁸ cells/kg, or any intervening dose of cells/kg.

In general, the engineered immune cells or the histone methyltransferase inhibited, reverse-lineage multilineage hematopoietic progenitor cell described herein are administered as a suspension with a pharmaceutically acceptable carrier. For example, as therapeutic compositions. Therapeutic compositions contain a physiologically tolerable carrier together with the cell composition and optionally at least one additional bioactive agent as described herein, dissolved or dispersed therein as an active ingredient. In a preferred embodiment, the therapeutic composition is not substantially immunogenic when administered to a mammal or human patient for therapeutic purposes, unless so desired. One of skill in the art will recognize that a pharmaceutically acceptable carrier to be used in a cell composition will not include buffers, compounds, cryopreservation agents, preservatives, or other agents in amounts that substantially interfere with the viability of the cells to be delivered to the subject. A formulation comprising cells can include e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the cells as described herein using routine experimentation.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the methods described herein that will be effective in the treatment of a particular disorder or condition will depend on the nature of the disorder or condition, and can be determined by standard clinical techniques. Suitable pharmaceutical carriers are described in Remington's Pharmaceutical Sciences, A. Osol, a standard reference text in this field of art. For example, a parenteral composition suitable for administration by injection is prepared by dissolving 1.5% by weight of active ingredient in 0.9% sodium chloride solution.

In one embodiment, the "pharmaceutically acceptable" carrier does not include in vitro cell culture media.

In some embodiments, the composition of engineered immune cells described further comprises a pharmaceutically acceptable carrier. In one embodiment, the pharmaceutically acceptable carrier does not include tissue or cell culture media.

In various embodiments, a second or subsequent dose of cells is administered to the recipient subject. For example, second and subsequent administrations can be given between about one day to 30 weeks from the previous administration. Two, three, four or more total administrations can be delivered to the individual, as needed.

A cell composition can be administered by any appropriate route which results in effective cellular replacement treatment in the subject, i.e. administration results in delivery to a desired location in the subject where at least a portion of the composition delivered, i.e. at least 1×10⁴ cells are delivered to the desired site for a period of time. Modes of administration include injection, infusion, or instillation, "Injection" includes, without limitation, intravenous, intra-arterial, intraventricular, intracardiac injection and infusion. For the delivery of cells, administration by injection or infusion is generally preferred.

Efficacy testing can be performed during the course of treatment using the methods described herein. Measurements of the degree of severity of a number of symptoms associated with a particular ailment are noted prior to the start of a treatment and then at later specific time period after the start of the treatment.

The present invention can be defined in any of the following numbered paragraphs:

[1]. A method comprising:
  a. generating multilineage hematopoietic progenitor cells from myeloid progenitor cells;
  b. inhibiting a histone methyltransferase in the resultant population of multilineage hematopoietic progenitor cells; and
  c. differentiating the resultant population of multilineage hematopoietic progenitor cells in the presence of a notch ligand or a stromal cell or both to promote differentiation into the lymphoid lineage.

[2]. A method comprising:
  a. in vitro transfecting myeloid progenitor cells with an exogenous gene coding copy of each of the following transcription factors ERG, HOXA9, and RORA, wherein the transcription factors are expressed in the transfected cells to produce a population of multilineage hematopoietic progenitor cells that having myeloid and erythroid potential;
   b. inhibiting a histone methyltransferase in the resultant population of multilineage hematopoietic progenitor cells to expand lymphoid potential; and
   c. differentiating the resultant population of multilineage hematopoietic progenitor cells in the presence of a notch ligand or supportive stroma or both to promote differentiation into the lymphoid lineage.

[3]. The method of paragraph 1, wherein the multilineage hematopoietic progenitor cells are produced by introducing in vitro each of the following transcription factors ERG, HOXA9,RORA, in the myeloid progenitor cells.

[4]. The method of paragraph 2 or 3, further comprising transfecting the myeloid progenitor cells with an exogenous gene coding copy of the transcription factor, SOX4, and MYB.

[5]. The method of paragraph 2, 3, or 4, further comprising transfecting the myeloid progenitor cells with an exogenous gene coding copy of the transcription factor, NFIA and DACH1.

[6]. The method of any one of paragraphs 1-5, wherein the myeloid lineage progenitor cells are CD34+ CD45+.

[7]. The method of any one of paragraphs 1-6, wherein the multilineage hematopoietic progenitor cells are CD34+ CD38 negative/low.

[8]. The method of any one of paragraphs 1-7, wherein the myeloid lineage progenitor cells are embryoid body progenitor cells derived from a population of pluripotent stem cells.

[9]. The method of paragraph 8, wherein the population of pluripotent stem cells is induced pluripotent stem cells (iPS cells) or embryonic stem cells (ESC).

[10]. The method of paragraph 9, wherein the induced pluripotent stem cells are produced by introducing only reprogramming factors OCT4, SOX2, KLF4 and optionally c-MYC or nanog and LIN28 into mature cells.

[11]. The method of paragraph 10, wherein the mature cells are selected from the group consisting of B lymphocytes (B-cells), T lymphocytes, (T-cells), fibroblasts, and keratinocytes.

[12]. The method of paragraph 9, 10 or 11, wherein the induced pluripotent stem cells are produced by introducing the reprogramming factors two or more times into the mature cells.

[13]. The method of any one of paragraphs 1-12, wherein the notch ligand is selected from the group consisting of Delta-like-1, Delta-like-4, and immobilized Delta1$^{ext-IgG}$, which consisting of the extracellular domain of human Delta-like-1 fused to the Fc domain of human IgG1.

[14]. The method of paragraph 13, wherein the Delta-like-1 or Delta-like-4 is supplied with co-culturing the multilineage hematopoietic progenitor cells with immobolized Delta1$^{ext-IgG}$OP9-DL1 cells or OP9-DL4 cells.

[15]. The method of any one of paragraphs 1-14, wherein the histone methyltransferase catalyses the addition of methyl group to the histone H3 lysine residue 9 (H3K9) and/or histone H3 lysine residue 27 (H3K27).

[16]. The method of paragraph 15, wherein the histone methyltransferase H3K9 and/or H3K27 is inhibited by a small molecule or a nucleic acid.

[17]. The method of paragraph 16, wherein the histone methyltransferase H3K9 and/or H3K27 small molecule inhibitor is an organic or inorganic compound having a molecular weight of less than about 10,000 grams per mole or a salt, or ester or other pharmaceutically acceptable form of said compound, a peptide, a peptidomimetic, an amino acid, an amino acid analog, a nucleotide, or a nucleotide analog.

[18]. The method of paragraph 16 or 17, wherein the histone methyltransferase H3K9 and/or H3K27 small molecule inhibitor is a heterorganic compound or an organometallic compound.

[19]. The method of any one of claims 16-18, wherein the small molecule inhibitor is selected from the group consisting of BIX-01294, UNC0638, E72, BRD4770, A-366, chaetocin, UNC0224, UNC0631, UNC0646, EPZ005687, EPZ-6438 (E7438), 3-deazaneplanocin A (DZNep), EI1, GSK343, GSK126, and UNC1999.

[20]. The method of paragraph 16, wherein the nucleic acid inhibitor is a nucleic acid targeting the expression of histone methyltransferase.

[21]. The method of paragraph 16 or 17, wherein the nucleic acid inhibitor is a RNA interference inhibitor or agent.

[22]. The method of paragraph 21, wherein the nucleic acid inhibitor is a EZH1 specific nucleic acid that is selected from the group consisting of an aptamer that binds EZH1, a EZH1 specific RNA interference agent, or a vector encoding a EZH1 specific RNA interference agent, wherein the RNA interference agent comprises one or more of the nucleotide sequences selected from the group consisting of SEQ ID NO: 1-5, 27-30.

[23]. An immune cell produced by a method of any one of paragraphs 1-22.

[24]. An immune cell derived from a population of myeloid progenitor cells, wherein the immune cell comprises an exogenous copy of each of the following transcription factors ERG, HOXA9, and RORA.

[25]. The immune cell of paragraph 24, wherein the immune cell further comprises an exogenous copy of each of the following reprogramming factors SOX4, and MYB

[26]. The immune cell of paragraph 24 or 25, wherein the immune cell further comprises an exogenous copy of each of the following reprogramming factors NFIA and DACH1.

[27]. The immune cell of paragraph 24, 25 or 26, wherein the immune cell further comprises an exogenous copy of each of the following reprogramming factors OCT4, SOX2, KLF4 and optionally c-MYC.

[28]. The immune cell of any one of paragraphs 24-27, wherein the cell is further genetically modified remove of the native T cell receptor (TCR) locus, to deletion of class I or class II major histocompatibility complexes or both, to express of non-canonical HLA-G or HLA-E or both, or to edit endogenous HLA therein.

[29]. A composition comprising a population of immune cells of any one of paragraphs 23-28.

[30]. The composition of paragraph 29, further comprising a pharmaceutically acceptable carrier.

[31]. A pharmaceutical composition comprising a population of immune cells of any one of paragraphs 23-28 and a pharmaceutically acceptable carrier.

[32]. A pharmaceutical composition of paragraph 31 for use in cellular replacement therapy in a subject.

[33]. An ex vivo or in vitro method of improving in vivo engraftment of hematopoietic cells in a host comprising:
  a. generating multilineage hematopoietic progenitor cells from myeloid progenitor cells according to the method paragraphs 2-12;
  b. inhibiting a histone methyltransferase in the resultant population of multilineage hematopoietic progenitor cells according to the method paragraphs 15-22;
  c. differentiating the resultant population of multilineage hematopoietic progenitor cells in the presence of a notch ligand or supportive stroma or both to promote differentiation into the lymphoid lineage according to paragraphs 13-14, and
  d. transplanting said resultant multilineage hematopoietic progenitor cells into a host.

[34]. A method of cellular replacement therapy, or immunotherapy in a subject in need thereof, the method comprising administering a population of immune cells of paragraphs 23-28, or a composition of paragraph 29-30, or a pharmaceutical composition of paragraphs 31-32 to a recipient subject.

[35]. The method of cellular replacement therapy of paragraph 34, wherein the subject is a patient who has undergone chemotherapy or irradiation or both, and manifest deficiencies in immune function or lymphocyte reconstitution or both deficiencies in immune function and lymphocyte reconstitution.

[36]. The method of cellular replacement therapy of paragraph 34 or 35, wherein the subject prior to implantation, the immune cells are treated ex vivo with prostaglandin E2 and/or antioxidant N-acetyl-L-cysteine (NAC) to promote subsequent engraftment in a recipient subject.

[37]. The method of cellular replacement therapy of paragraph 34 or 35, wherein the immune cells are autologous to the recipient subject or at least HLA type matched with the recipient subject.

[38]. A modified or an engineered myeloid progenitor cell having reversed lineage that include increased lymphoid lineage potential.

[39]. A composition comprising modified or engineered myeloid progenitor cell having reversed lineage that include increased lymphoid lineage potential.

[40]. A modified myeloid progenitor cell or a composition comprising modified or engineered myeloid progenitor cell, the modified myeloid progenitor cell having reversed lineage and has increased lymphoid lineage potential, for use in the manufacture/production of described modified immune cells, wherein the modified myeloid progenitor cell comprises an exogenous gene coding copy of each of the following transcription factors: ERG, HOXA9, and RORA.

[41]. A modified myeloid progenitor cell or a composition comprising modified or engineered myeloid progenitor cell, the modified myeloid progenitor cell having reversed lineage and has increased lymphoid lineage potential, for use in cellular replacement therapy, or for the treatment of cancer, autoimmune disorders, hematological diseases, or other genetic diseases and disorders, wherein the modified myeloid progenitor cell comprises an exogenous gene coding copy of each of the following transcription factors: ERG, HOXA9, and RORA.

[42]. The modified myeloid progenitor cell of paragraphs 38-41 further comprises an exogenous gene coding copy of SOX4, or MYB, or both SOX4 and MYB.

[43]. The modified myeloid progenitor cell of paragraphs 38-42 further comprises an exogenous gene coding copy of DACH1, or NFIA, or both DACH1 and NFIA.

[44]. The modified myeloid progenitor cell of paragraphs 38-43 are derived from lineage-restricted CD34$^+$ CD45$^+$ myeloid precursor cells.

[45]. The modified myeloid progenitor cell of paragraphs 38-44 further comprises an exogenous copy of each of the following reprogramming factors OCT4, SOX2, KLF4 and optionally c-MYC.

[46]. A method of cellular replacement therapy, or for the treatment of cancer, autoimmune disorders, hematological diseases, or other genetic diseases and disorders in a subject, comprising (a) providing a somatic cell from a donor subject, (b) generating multilineage hematopoietic progenitor cells from myeloid progenitor cells derived from the somatic cell as described in any of the preceding paragraphs; (c) inhibiting a histone methyltransferase in the resultant population of multilineage hematopoietic progenitor cells as described in any of the preceding paragraphs; (d) differentiating the resultant population of multilineage hematopoietic progenitor cells in the presence of a notch ligand or a stromal cell or both to promote differentiation into the lymphoid lineage as described in any of the preceding paragraphs, and implanting the resultant differentiated lymphoid cells into a recipient subject.

[47]. The method of paragraph 46, wherein the host subject and the recipient subject are the same individual.

[48]. The method of paragraph 46, wherein the host subject and the recipient subject are not the same individual, but are at least HLA compatible.

This invention is further illustrated by the following example which should not be construed as limiting. The contents of all references cited throughout this application, as well as the figures and table are incorporated herein by reference.

Those skilled in the art will recognize, or be able to ascertain using not more than routine experimentation, many equivalents to the specific embodiments of the invention described herein. Such equivalents are intended to be encompassed by the following claims.

EXAMPLE

Experimental Procedures hIPSC culture. All experiments were performed using MSC-IPS1 (Park et al., 2008), CD34-IPS and CD45-IPS. Human IPS cells were maintained on mouse embryonic fi-broblasts (GlobalStem) feeders in DMEM/F12+20% KnockOut-Serum Replacement (Invitrogen™), 1 mM L-glutamine, 1 mM NEAA, 0.1 mM β-mercaptoethanol, and 10 ng/ml bFGF. Media was changed daily, and cells were passaged 1:4 onto fresh feeders every 7 days using standard clump passaging with collagenase IV.

EB differentiation. EB differentiation was performed as previously described (Chadwick et al., 2003). Briefly, hPSC colonies were scraped into non-adherent rotating 10 cm plates at the ratio of 2:1. The EB media was KO-DMEM+ 20% FBS (Stem Cell Technologies), 1 mM L-glutamine, 1 mM NEAA, penicillin/streptomycin, 0.1 mM β-mercaptoethanol, 200 µg/ml h-transferrin, and 50 µg/ml ascorbic acid. After 24 hrs, media was changed by allowing EBs to settle by gravity, and replaced with EB media supplemented with growth factors: 50 ng/ml BMP4 (R&D Systems), 200 ng/ml SCF, 200 ng/ml FLT3, 50 ng/ml G-CSF, 20 ng/ml IL-6, 10 ng/ml IL-3 (all Peprotech). Media was changed on day 5, and day 10. EBs were dissociated on day 14 by digesting with collagenase B (Roche) for 2 hrs, followed by treatment with enzyme-free dissociation buffer (Gibco), and filtered through an 80 μm filter. Dissociated EBs were frozen in 10% DMSO, 40% FBS freezing solution.

Progenitor sorting. Dissociated EB cells were thawed following the Lonza Poietics protocol which can be found at the website of Lonza, under the section of manuals and instructions for the procedure for thawing poietics cells. The thawed cells are resuspended at $1\times10^6$ per 100 μl staining buffer (PBS+2% FBS). CD34+ cells were sorted from bulk EB culture using human CD34 microbeads (Miltenyi Biotec) and run through a magnetic column separator (MACS) as per manufacturer's instructions.

Lentiviral and shRNA library plasmids. 5F lentiviral plasmids: HOXA9, ERG, RORA, SOX4, and MYB were cloned into pInducer-21 Dox-inducible lentiviral vector. Four shRNAs for each epigenetic modifier and three shRNAs for luciferase were obtained from the Broad Institute RNAi Consortium in pLKO.1 or pLKO.5 lentiviral vectors. Lenti-viral particles were produced by transfecting 293T-17 cells (ATCC) with the lentiviral plasmids and 3rd-generation packaging plasmids. Virus was harvested 24 hours after transfection and concentrated by ultracentrifugation at 23,000 rpm for 3 hrs. All viruses were titered by serial dilution on 293T cells. All TRC numbers for shRNAs used in this study are provided in Table 1.

5F gene transfer and 5F culture. MACS separated CD34$^+$ EB progenitors were seed-ed on retronectin-coated (10 μg/cm$^2$) 96 well plates at a density of $2-5\times10^4$ cells per well. The infection media was SFEM (StemCell) with 50 ng/ml SCF, 50 ng/ml FLT3, 50 ng/ml TPO, 50 ng/ml IL6, 10 ng/ml IL3 (all R&D Systems). Lentiviral infections were car-ried out in a total volume of 150 μl. The multiplicity of infection (MOI) for the factors was MOI=5 for ERG and HOXA9, MOI=3 for RORA, SOX4, MYB, and MOI=2 for all shRNAs. Virus was concentrated onto cells by centrifuging the plate at 2300 rpm for 30 min at RT. Infections were carried out for 24 hrs. After gene transfer, 5F cells were cultured in SFEM with 50 ng/ml SCF, 50 ng/ml FLT3, 50 ng/ml TPO, 50 ng/ml IL6, and 10 ng/ml IL3 (all R&D Systems). Dox was added at 2 μg/ml (Sigma). Cultures were main-tained at a density of $<1\times10^6$ cells/ml, and media were changed every 3-4 days. After 14 days of culture, 5F were plated in the T cell differentiation protocol.

Co-cultures with Notch ligand delta like 1-expressing OP9 (OP9-DL1) cell lines. The OP9-DL1 cells were cul-tured as monolayers in OP9 media, which is α-MEM supplemented with FCS (20% final conc.), 2-mercaptoetha-nol (0.1 mM final conc.), nonessential amino acids (0.1 mM final conc,), sodium pyruvate (1 mM final conc.), penicillin (10 U/ml final conc.), L-glutamine (1 mM final conc.), streptomycin (100 μg/ml final conc.), and sodium bicarbon-ate (2.2 g/liter final conc.).

Reverse lineage, multipotent hematopoietic progenitor cells (also known as the EB-derived progenitors described above) were plated on the monolayers of OP9-DL1 at a density of $1-6\times10^5$ cells per well of a 6-well or 100-mm non-treated dish. The culture media contained SCF (30 ng/ml final conc.; R&D systems), Flt3 ligand and IL-7 (5 ng/ml final conc. each; R&D systems). On day 7 of culture, loosely adherent hematopoietic cells were harvested by gentle pipetting. Every 5 days thereafter, non-adherent iPS cell-derived hematopoietic cells were collected by vigorous pipetting, filtered through a 70-μm nylon mesh, and trans-ferred onto OP9-DL1 monolayers in OP9 media. All cyto-kines were added at all subsequent passages.

By day 14 of co-culture with OP9-DL1 cells, the reverse lineage, multipotent hematopoietic progenitor cells were transformed into lymphocyte-like cells. These cells expressed CD25 and/or CD44 by day 14 of coculture, and are considered to have been differentiated into T lineage in the same way that progenitor cells differentiate in the thymus. Phycoerythrin-conjugated anti-CD8 antibody (clone 53-6.7), anti-CD19 antibody (clone 1D3) and anti-CD25 antibody (clone 7D4), and allophycocyanin-conju-gated anti-CD4 antibody (clone GK1.5), anti-CD11b anti-body (clone M1/70) and anti-CD44 antibody (clone IM7) (all from Biolegend (Tokyo)) were used to verify expression of the CD cell surface markers.

Rearrangement at the TCRβ locus (Tcrb) is a hallmark of T cell lineage commitment and is essential for the progres-sion of CD4/CD8 double negative thymocytes to the double positive stage during normal αβ T cell development. To determine whether the T cells that develop from reverse lineage, multipotent hematopoietic progenitor cells cultured on OP9-DL1 cells undergo normal rearrangement of the TCRβ locus, the differentiated cells were stained at day 30 with various antibodies against TCRβ chain. Fluorescein isothiocyante-conjugated TCR panel (BD biosciences) was used.

It is expected that a diverse patterns of TcrVβ gene expression be detected in the differentiated reverse lineage, multipotent hematopoietic progenitor cells. The diversity can be confirmed by genomic PCR. OP9-DL1 cells and mouse adult thymocytes can be used as positive controls for the genomic PCR-based analysis. Previously-reported PCR primers are used for the analysis of Tcr gene rearrangement (Ikawa T, Kawamoto H, Wright L Y et al., "Long-term cultured E2A-deficient hematopoietic progenitor cells are pluripotent", Immunity, Vol. 20, pp. 349-360.; Kawamoto H, Ohmura K, Fujimoto S et al., "Extensive proliferation of T cell lineage-restricted progenitors in the thymus: an essential process for clonal expression of diverse T cell receptor beta chains" Eur. J. Immunol., Vol. 33, pp. 606-615.).

During normal thymocyte development, T cells bearing TCRαβ or TCRγδ develop in the thymus. To determine whether both populations of T cells develop from reverse lineage, multipotent hematopoietic progenitor cells cultured on OP9-DL1 cells, the differentiated reverse lineage, mul-tipotent hematopoietic progenitor cells were analyzed for surface expression of TCRαβ or TCRγδ using allophyco-cyanin-conjugated anti-TCRβ antibody (clone H57-597), and phycoerythrin-conjugated anti-TCRγδ antibody (clone GL3). It is expected that both αβ T cells and γδ T cells were generated from differentiated cells in this coculture system.

Similarly, after day 20 co-culture, the differentiated cells are CD4/CD8 double positive cells and CD8 single positive cells.

Confirmation of functional TCRs expressed on the co-culture differentiated cells. The CD4+CD8+ differentiated cells in this coculture system were sorted from the cultures at day 21, and $7.5\times10^4$ T cells were stimulated for 3 days with plate-bound anti-CD3 antibody (10 μg/ml final conc.; clone 145-2C11) in the differentiation medium in the pres-ence of IL-2 (1 ng/ml final conc.) and anti-CD28 antibody (1 μg/ml final conc.; clone 37.51). After that, PMA/Iono-mycin was added to the culture and the cell were exposed to the added PMA/Ionomycin for a further 6 hour. Intracellular staining for IFN-γ was done with Cytofix/Cytoperm® and GolgiStop® (BD Biosciences) according to the manufactur-er's instructions. Phycoerythrin-conjugated anti-CD8 antibody (clone 53-6.7) and phycoerythrin-conjugated anti-IFN-γ antibody (clone XMG1.2) were used for IFN-γ production analysis. The stained cells were analyzed by flow cytometry. It is expected that the CD4−CD8+ differentiated cells in this coculture system would produce IFN-γ in response to the TCR stimulation by anti-CD3 antibody and anti-CD28 antibody, and this indicate functional TCRs are expressed in the differentiated cells from reverse lineage, multipotent hematopoietic progenitor cells.

Additionally, the $7.5 \times 10^4$ of the CD4+CD8+ differentiated cells in this co-culture system were cultured for 2 days with plate-bound anti-CD3 antibody (10 μg/ml final conc.; clone 145-2C11) in differentiation medium in the presence of IL-2 (2 ng/ml final conc.) and TGF-β1 (5 ng/ml final conc.). It is expected that there will be enhanced the population of Foxp3-positive cells, which is the hallmark of regulatory T cells, as observed in naïve T cells derived from normal adult lymphoid tissue (Chen W, Jin W, Hardegen N et al., "Conversion of peripheral CD4+CD25− naive T cells to CD4+CD25+ regulatory T cells by TGF-β induction of transcription factor Foxp3", J. Exp. Med., Vol. 198, pp. 1875-1886.). These data indicate that the iPS cell-derived T cells generated in this coculture can respond to stimulation via TCR or cytokine receptors.

T cell differentiation. After 14 days of respecification, $1 \times 10^5$ 5F were plated in OP9-DL1 stromal co-culture. Cells were cultured in α-MEM (Gibco), 1% penicil-lin/streptomycin, 20% FBS (Gemini), 1 mM L-glutamine with 30 ng/mL SCF, 5 ng/mL FLT3, 5 ng/mL (all R&D Systems) for 20 days with 2 ug/mL Dox followed by Dox re-moval. Cells were harvested by mechanical dissociation and filtered through a 40 uM cap and passaged onto fresh stroma every 5-7 days. T cell development was assessed after 35 days using CD45, CD7, CD3, CD4 and CD8.

Mouse YS or AGM cells were dissociated to single cells for 30 minutes in EB dissociation media containing 250 mg Collagenase IV, 100 mg Hyaluronidase V, 6.8 mg DNase I in 50 mL DMEM (10×) diluted to IX with IMDM. Cells across multiple embryos were pooled and counted. 75K cells were seeded onto one confluent well of OP9-DL1 in a 6-well plate. Cells were cultured in aMEM, 20% serum, 1% Pen/Strep/L-glutamine, 5 ng/mL mIL-7 (R&D) and 5 ng/mL hFLT3 (R&D) for 12 days.

B cell differentiation. After 14 days of respecification, $5 \times 10^4$ 5F were plated into a single well of MS-5 stroma in a 6-well plate. Cells were cultured in Myelocult H5100 (Stem Cell Technologies) supplemented with 1% penicillin/streptomycin 50 ng/mL SCF (R&D), 10 ng/mL FLT3 (R&D), 25 ng/mL IL7 (R&D) and 25 ng/mL TPO (R&D) for 10 days with 2 ug/mL Dox followed by Dox removal.

For murine B cell differentiation, YS or EP pooled from multiple embryos of the same genotype were dissociated to single cells and 75K cells were seeded onto a confluent well of OP9 stroma in a 6-well plate. Cells were cultured in aMEM, 10% serum, $5 \times 10^{-5}$ M B-mercaptoethanol, 1% PSG, 50 U/mL mIL7 (R&D) and 10 ng/mL hFLT3 (R&D).

For the class-switching assay, B cell progenitors were purified using the B220 MACS or CD19 MACS microbead enrichment kit (Miltenyi Biotec) as per manufacturer's recommendations. $5 \times 10^5$ B220+ or $5 \times 10^5$ CD19+ cells were plated into one well of a 6-well plate in complete RPMI media supplemented with 0.5 ug/mL anti-CD40 (Ebioscience, Cat. #16-0402-86) and 25 ng/mL IL4 (Ebioscience, Cat. #14-8041). Class-switching was analyzed by flow on day 4.

Colony assays. After 14 days of respecification, $5 \times 10^4$ cells were plated into 3 ml of complete methylcellulose H3434 (StemCell Technologies) supplemented with 10 ng/ml IL6 (Peprotech), 10 ng/ml FLT3 (R&D), and 50 ng/ml TPO (R&D). The mixture was dis-tributed into two 60 mm dishes and maintained in a humidified chamber for 14 days.

Mouse transplantation. NOD/LtSz-scidIL2Rgnull (NSG) (Jackson Labs) mice were bred and housed at the Boston Children's Hospital animal care facility. Animal experiments were performed in accordance to institutional guidelines approved by BCH ani-mal care committee. Intravenous transplants have been previously described. Briefly, 6-10 week old mice were irradiated (275 rads) 24 hrs before transplant. To ensure con-sistency between experiments, only female mice were used. Cells were transplanted in a 100 uL volume using a 28.5 g insulin needle. Sulfatrim was administered in drinking water to prevent infections after irradiation.

Flow cytometry. The following antibodies were used for human cells: CD45 APC-Cy7 (557833, BD Biosciences), CD4 PE-Cy5 (IM2636U, Beckman Coulter Immunotech), CD8 BV421 (RPA-T8, BD Horizon), CD5 BV510 (UCHT2, BD Biosciences), TCRgd APC (555718, BD Biosciences), TCRab BV510 (T10B9.1A-31, BD Biosciences), CD3 PE-Cy7 (UCHT1, BD Pharmigen), CD7 PE (555361, BD Pharmigen), CD1a APC (559775, BD Pharmigen) for T cell staining. For B cell staining: CD45 PE-Cy5 (IM2652U, Beckman Coulter Immunotech), CD19 PE (4G7, BD), CD56 V450 (B159, BD Biosciences), CD1 lb APC-Cy7 (557754, BD Biosciences), For HSC/Progenitor sorting: CD34 PE-Cy7 (8G12, BD), CD45 (557833, BD Biosciences), CD38 PE-Cy7 (IM2651 U, BD), DAPI. For myeloid and erythroid staining: CD11b APC-Cy7 (557754, BD Bio-sci-ences), GLYA PE-Cy7 (A71564, Beckman Coulter), CD71 PE (555537, BD Bioscienc-es), CD45 PE-Cy5 (IM2652U, Beckman Coulter Immunotech). All stains were per-formed with <1×106 cells per 100 μl staining buffer (PBS+2% FBS) with 1:100 dilution of each antibody, 30 min at RT in dark. Compensation was performed by automated compensation with anti-mouse Igk and negative beads (BD). All acquisition was per-formed on BD Fortessa or BD Aria cytometer.

The following antibodies were used for mouse cells: CD45.2 PE-Cy7 (104, eBioscience), CD45.1 FITC (A20, eBioscience), B220 PB (RA3-6B2, BD Biosciences), Ter119 PE-Cy5 (Ter 119, eBioscience), GR1 (RB6-8C5, BD Bio-science), CD3 APC (145-2C11, eBioscience), CD19 APC-Cy7 (1D3, BD Bioscience), MAC1 A700 (M1/70, BD Biosci-ence) for engraftment analyses. For HSC/progenitor staining: CD45.2 APC-Cy7 (104, BioLegend), Sca1 PE-Cy7 (D7, BD Bioscience), CD34 AF700 (RAM34, eBioscience), CD48 FITC (BioLegend), CD150 PE-Cy5 (TC15-12F12.2, BioLegend), cKit APC (2B8, eBioscience), Fcγ PE (93, eBioscience). For RNA seq sort: CD16/32

(93, Bio-legend), Ter119 Biotin (Ter119, eBioscience), GR1 Biotin (RB6-8C, eBioscience), CD3 Biotin (17A2, eBioscience), CD5 Biotin (53-6.7, eBioscience), CD19 Bio-tin (eBio1D3, eBioscience), Streptavidin EF450 (eBiosci-ence), CD45 PerCP-Cy5.5 (30-F11, eBiosci-ence), CD144 EF660 (eBioBV13, eBioscience), CD117 APC-EF780 (2B8, eBioscience), CD41 PE-Cy7 (eBioMWReg30, eBiosci-ence). For B cell staining: CD45.2 APC-CY7 (104, BioLe-gend), CD23 PE-Cy7 (B3B4, eBioscience), Ter119 PE-Cy5 (Ter 119, eBioscience), IgM EF660 (eB121-15F9, eBiosci-ence), MAC1 A700 (M1/70, BD Bioscience), CD5 BV510 (53-7.3 BD Biosciences), IgM (11/41, eBioscience), IgG1 FITC (A85-1, BD), B220 PE Cy5 (RA3-6B2, BD Biosci-ences). For T cell staining: CD45.2 APC-CY7 (104, BioLe-gend), TCRb PE-Cy5 (H57-597, BD Biosciences), CD8

APC-EF780 (53-6.7, eBioscience), CD4 APC (GK1.5, eBioscience), CD3 AF700 (17A2, BioLegend), TCRgd FITC (GL3, BD Biosciences). All stains were performed with <1×106 cells per 100 μl staining buffer (PBS+2% FBS) with 1:100 dilution of each antibody, 30 min on ice in dark. Compensation was performed by automated compensation with anti-mouse Igk and negative beads (BD). All acquisition was performed on BD Fortessa or BD Aria cytometer.

Results

Figures 7A, 7B:
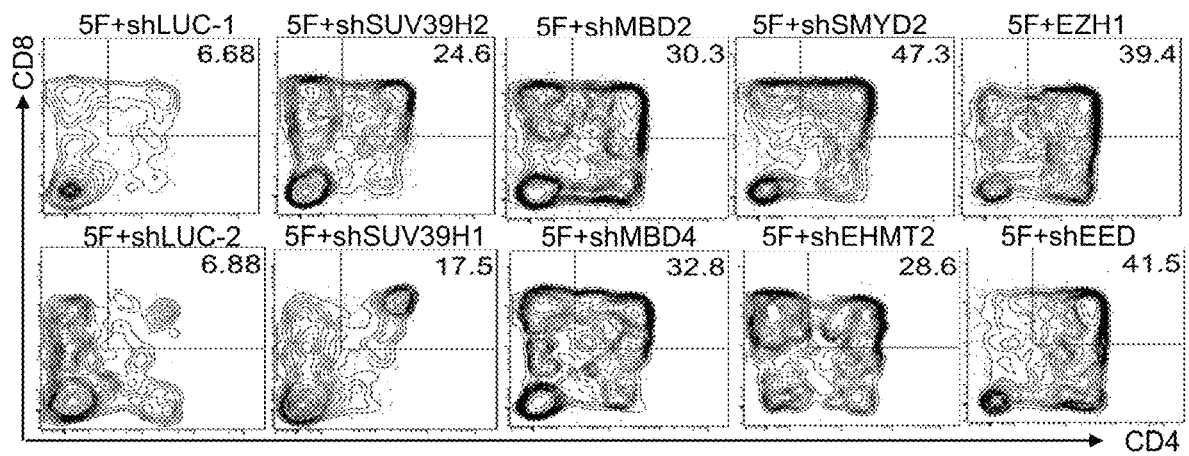
FIGS. 7A-7B collectively show that the screening for epigenetic modifiers that can restrict T cell potential.
Figure 8:
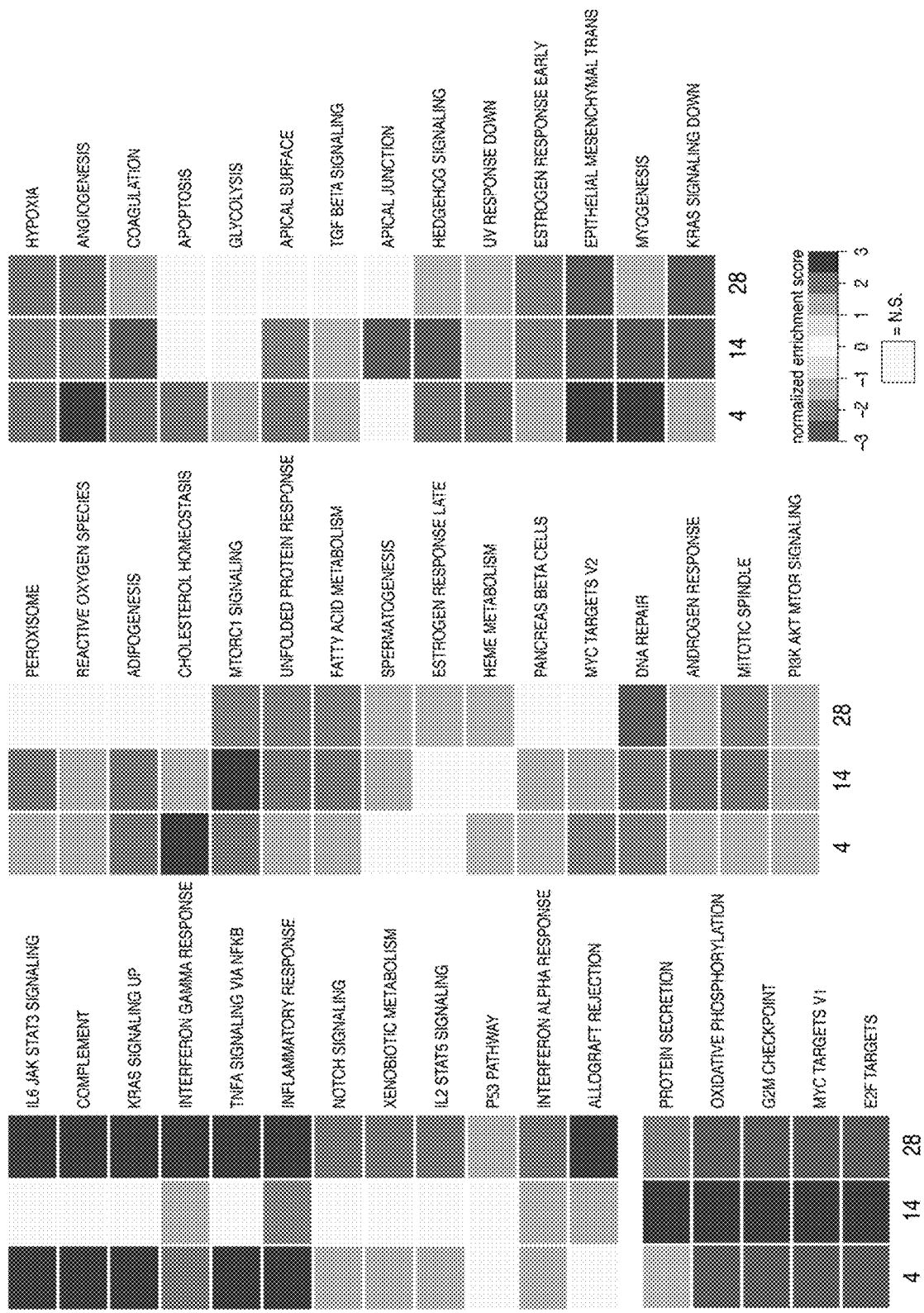
FIG. 8 shows the significantly enriched GSEA networks. Statistically significant upregulated or downregulated pathways on day 4, 14 or 28 after EZH1 knockdown in 5F cells assessed by RNA sequencing.
Figure 10A:
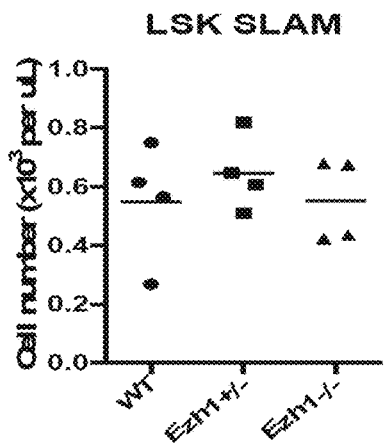
Figure 10B:
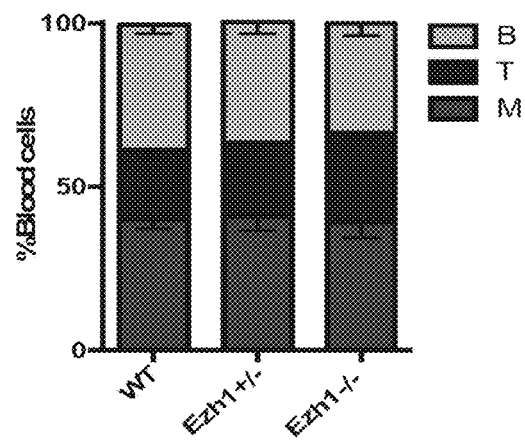
FIG. 10B shows the lineage distribution of WT, Ezh1+/− and Ezh1−/− adult mice (8-12 weeks old). n=3 mice per genotype.
Figure 10C:
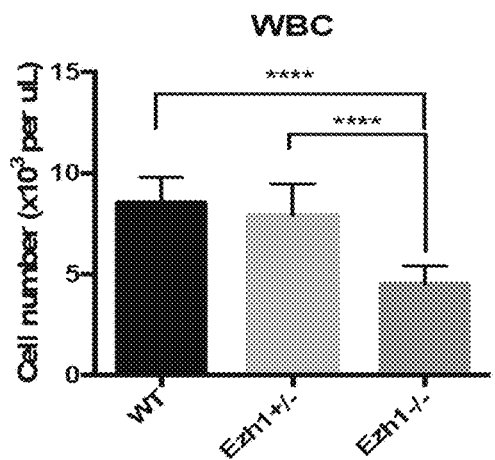
FIG. 10C shows the WBC counts in peripheral blood.
Figure 10D:
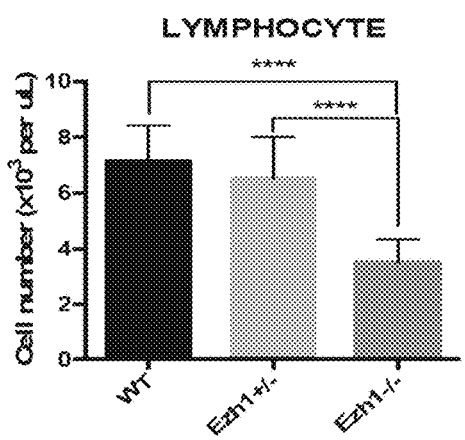
FIG. 10D shows the lymphocyte counts in peripheral blood.
Figure 10E:
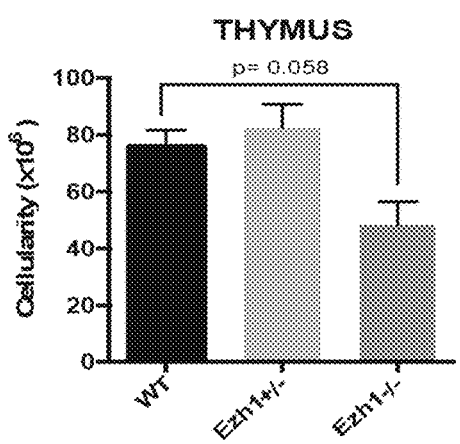
FIG. 10E shows the absolute cell numbers in the thymus.
Figure 10F:
FIG. 10F shows the representative image of two thymuses from WT, Ezh1+/− and Ezh1−/− mice. ****P<0.0001.

The inventors have previously demonstrated that it is possible to respecified primitive progenitors with limited lymphoid differentiation potential. To expand the selection of candidate factors, the inventors screened epigenetic modifiers to provide an additional regulatory layer for the respecification. The inventors employed a library of short hairpin RNAs (shRNAs) from the Broad RNAi Consortium to target 20 genes in DNA and histone methylation pathways (FIG. 7A) previously used in the lab to enhance efficiency of reprogramming to pluripotency (Onder T. et al. 2012).

Using the established respecification platform, the inventors differentiated two iPSC lines (MSC-IPS, CD45-IPS) into embryoid bodies (EB) under hematopoietic promoting conditions to generate CD34$^+$CD45$^+$ myeloid progenitors. The inventors then transduced EB-derived progenitors with the five transcription factors (5F cocktail: ERG, HOXA9, RORA, SOX4 and MYB) and infected with individual shRNAs targeting each epigenetic modifier and screened for T lymphoid potential using the established OP9-DL1 co-culture system. The results from three independent screens are summarized in FIGS. 1A-1F. After validation of top hits, the lead candidate was EZH1.

EZH1 is a Critical Repressor of Definitive Potential.

Figure 1B:
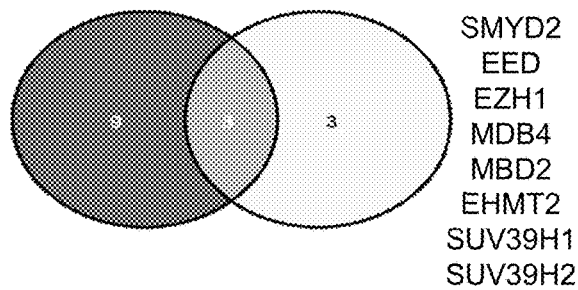
Figure 1C:
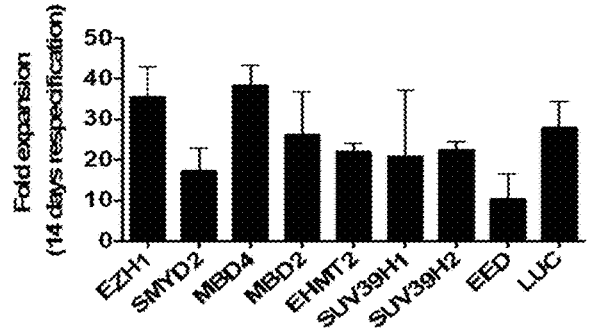
Figure 1D:
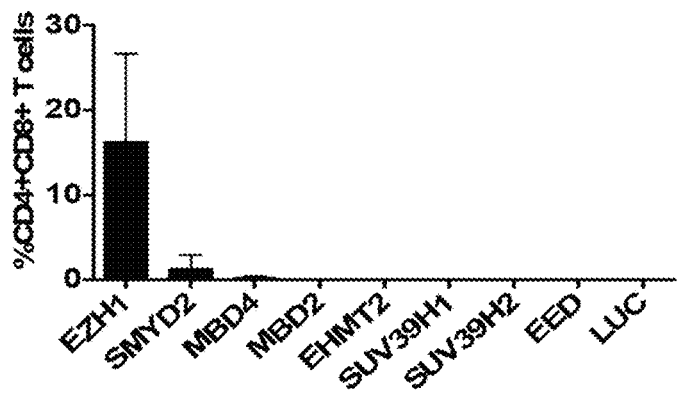
Figure 1E:
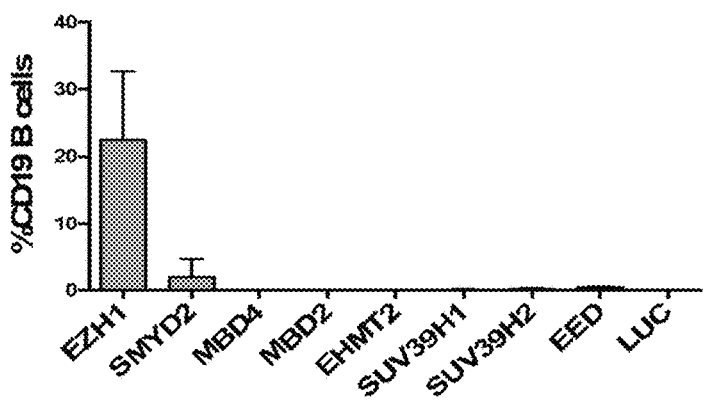
Figure 1F:
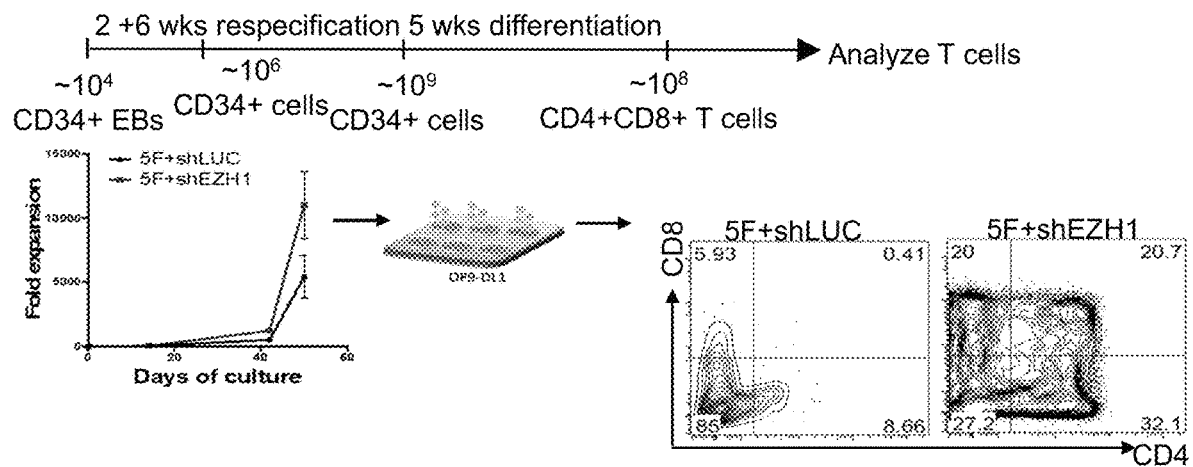

To test the hypothesis that epigenetic factors act as barriers to definitive potential, the inventors adopted a loss-of-function phenotypic screen using an shRNA library targeting 20 DNA and histone methylation factors previously shown to affect somatic cell reprogramming (FIG. 7A) (Onder et al. 2012). The inventors introduced the library into primitive CD34$^+$ progenitors derived from embryoid body differentiation. To facilitate phenotypic screening, the inventors expanded these primitive progenitors using a defined set of 5 transcription factors (5F) (Doulatov et al 2013). Expanded progenitors retained embryonic features, including lack of B and T cell potential, and expression of embryonic globins. The inventors transduced 5F cells the individual hairpins (4× hairpins per gene), and screened for the emergence of T cell potential using the OP9-DL1 co-culture system (Holmes and Zúñiga-Pflücker 2009) (FIGS. 1A and 1F). After five weeks of co-culture, T cell potential was analyzed by flow cytometry for CD7, CD3, CD4 and CD8. The inventors found that knockdown of eight epigenetic regulators enhanced CD4$^+$CD8$^+$ T cell potential from primitive 5F cells (FIG. 1B). Among the top hits were several members of the methylated DNA binding proteins, histone H3 lysine 9 (H3K9) methyltransferases, PRC2 components, and SMYD2, a SET domain-containing methyltransferase (FIG. 1C). H3K9 and H3K27 methyltransferases have been previously linked to lineage commitment and self-renewal in fetal and adult HSCs (Ugarte et al. 2015, Chen et al. 2012, Xie et al. 2014, Hidalgo et al. 2012, Lee et al. 2015).

Figure 2A:
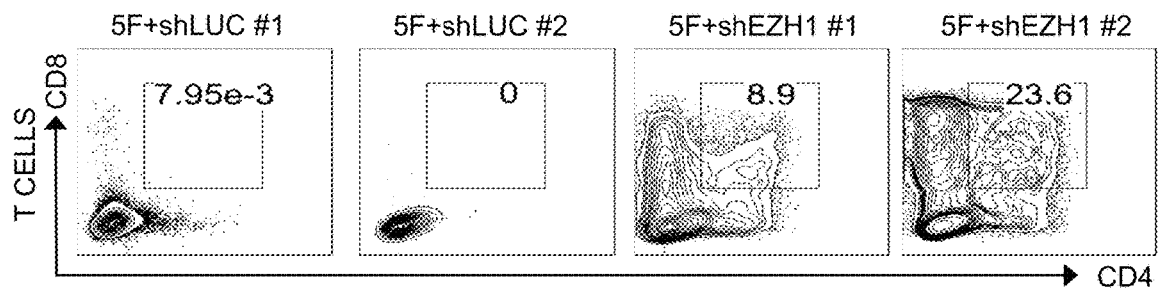
Figure 2B:
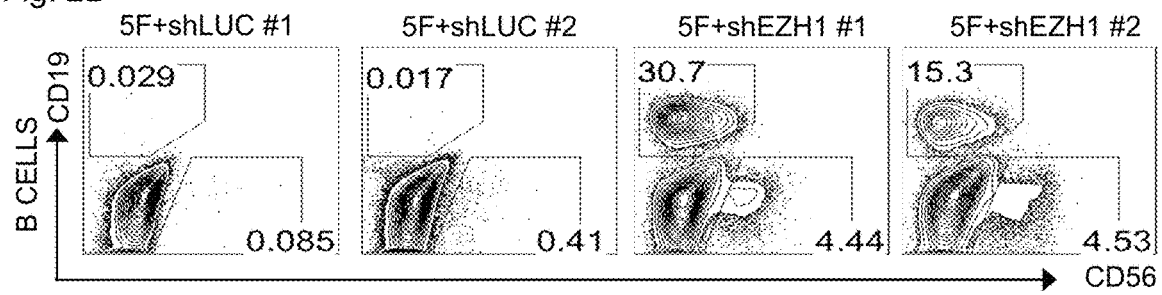
Figure 2C:
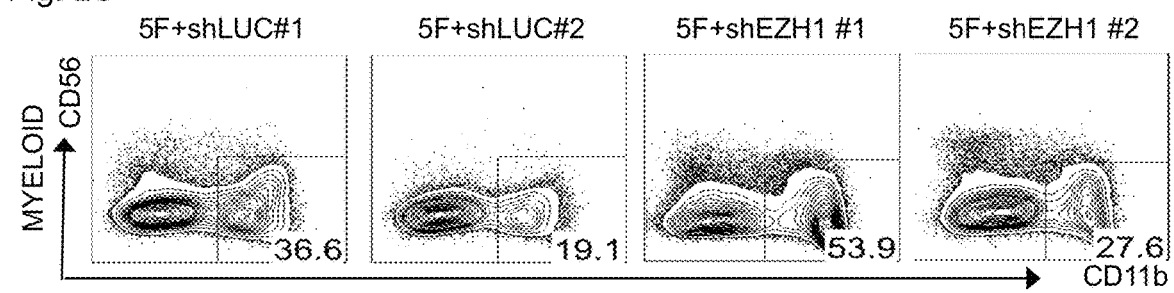
Figure 2D:
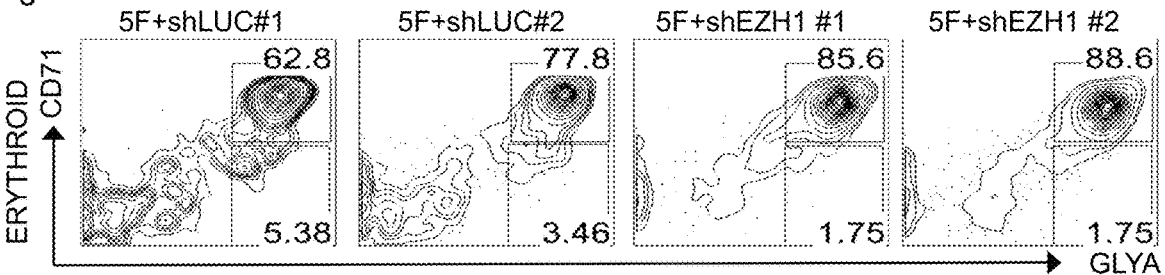

To prospectively validate these top candidates, the inventors analyzed T cell potential of 5F cells transduced with shRNAs (2× per gene) targeting these 8 factors. Independently, the inventors tested their B lymphoid potential using co-culture with MS-5, a murine bone marrow-derived stroma that supports B cell differentiation (Nishihara et al. 1998, Ohkawara et al. 1998). 5F cells transduced with multiple shRNAs targeting a control luciferase gene displayed none or negligible (interval, with standard deviations) levels of T and B cell potential. Of the tested candidates, only knockdown of EZH1 elicited robust T and B cell potential across independent hairpins and iPSC lines (FIGS. 2A, 2B, 2E). Myelo-erythroid differentiation potential of progenitors transduced with shRNAs for EZH1 (5F+shEZH1) was largely unchanged as compared to shRNAs targeting luciferase (5F+shLUC), by flow cytometry (FIGS. 2C, 2D) and colony-forming assays (FIG. 2F). These findings indicate that loss of EZH1 uncovers multi-lymphoid potential in primitive hematopoietic progenitors.

Other PRC2 Components do not Phenocopy EZH1.

EZH1 is a member of the Polycomb group proteins. Polycomb repressive complex 2 (PRC2) mediates methylation on histone H3 lysine 27 (H3K27) and plays critical roles in transcriptional regulation and stem cell development. EZH1 and EZH2 are closely related enzymatic subunits of PRC2. The well-characterized canonical PRC2 is comprised of EZH2, EED and SUZ (Onder T. et al., 2012). EZH1 was identified as a homolog of EZH2 and an interacting partner to EED (Jones C A et al. 1998 and Shen X. et al. 2008) and believed to play redundant or compensatory roles for EZH2. Recent work, however, has uncovered novel gene activating roles for EZH1 in addition to its transcriptional repression functions (Mousavi K. et al. 2012 and Xu J. et al. 2015).

EZH1 is a homolog of *Drosophila* Enhancer of zeste E(z) (Abel et al. 1996), a catalytic component of PRC2 (Laible et al. 1997, Jones et al. 1998, Shen et al. 2008). PRC2 is comprised of E(z), Eed and Suz12, which mediate epigenetic silencing at developmentally regulated genes (Muller et al. 2002, Sparmann and van Lohuizen 2006, Simon and Kingston 2009). While EZH2 is the primary catalytic component of PRC2, EZH1 can functionally substitute for Ezh2 (Shen et al. 2008), although Ezh1 has a weaker methyltransferase activity (Magueron et al. 2008) and can promote RNA polymerase elongation (Mousavi et al. 2012). Accumulating evidence indicates that EZH1 and EZH2 have distinct molecular functions. Ezh1, unlike Ezh2, is most frequently found by itself or in complex with nucleosome-recognizing protein Suz12. By contrast, Ezh2 is almost always complexed with Suz12 and scaffold protein Eed. In addition, while EZH2 is required for somatic reprogramming, loss of EZH1 enhances reprogramming (Onder et al. 2012, Cacchiarelli et al. 2015). These studies illustrate a complex mode of epigenetic regulation by PRC2 depending on subunit interactions and holoenzyme composition.

Figure 3A:
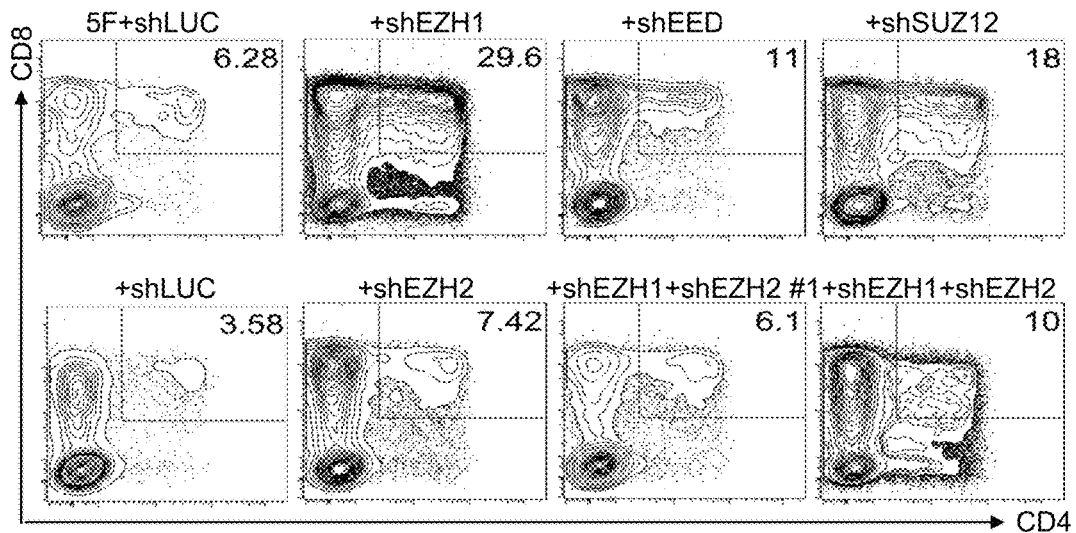
FIGS. 3A-3J collectively show that the repression of canonical PRC2 subunits does not unlock robust lymphoid potential.
Figure 3B:
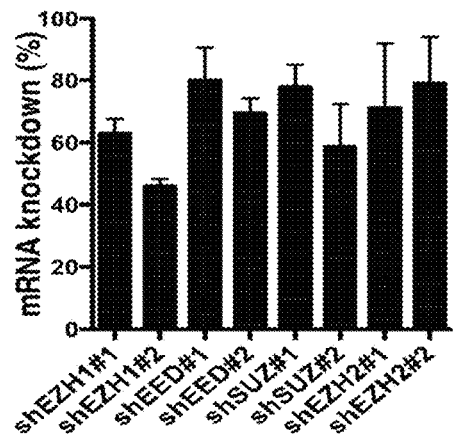
Figure 3C:
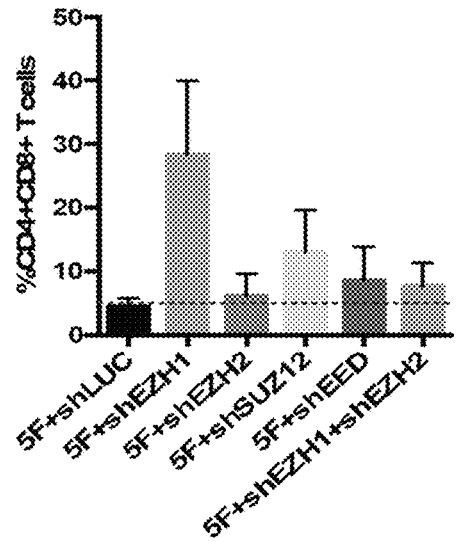

To dissect the importance of PRC2 in definitive hematopoietic potential, the inventors knocked down each component of PRC2 (2 shRNAs per gene) in 5F cells and assessed T cell differentiation. The inventors confirmed efficient knockdown by each shRNA (FIG. 3A). EZH1 knockdown dramatically enhanced the percentage of CD4$^+$CD8$^+$ T cells (5-fold vs shLUC). Knockdown of SUZ12 also enhanced T cell potential, albeit to a lesser extent. However, knockdown of EED and EZH2 did not affect T cell potential (FIGS. 3A and 3C). EZH1 and EZH2 dual knockdown phenocopied EZH2 depletion, indicating that EZH2 is epistatic to EZH1 (FIG. 3B). Thus, loss of EZH2 does not phenocopy EZH1 in restoring definitive potential. To validate this finding, the inventors used an EZH2/EZH1 dual inhibitor, GSK126, that has 150-fold higher selectivity for EZH2 over EZH1 (McCabe et al. 2012) (FIGS. 3G, 3I and 3J). At 3 uM of GSK126, the inventors observed markedly reduced global H3K27me3 with partial toxicity, as assessed by colony-forming assays (FIGS. 3I, 3J). To test the effect of EZH2 inhibition on T cell potential, the inventors generated definitive hemogenic endothelium (HE) from hPSCs with T lymphoid potential via inhibition of Activin/Nodal signaling at the early stage of mesoderm differentiation (Kennedy et al. 2012). In DMSO-treated cells, the inventors observed a robust CD4+CD8+ T cell population, which was abrogated upon treatment with 3 uM GSK126, indicating that EZH2 unlike EZH1 is required for T cell differentiation (FIG. 3H).

Figure 3D:
Figure 3E:
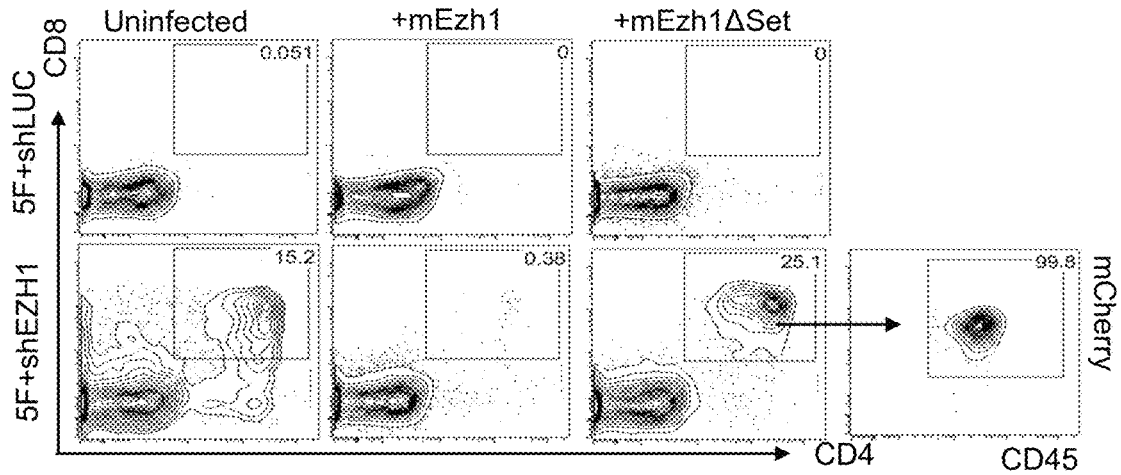
Figure 3F:
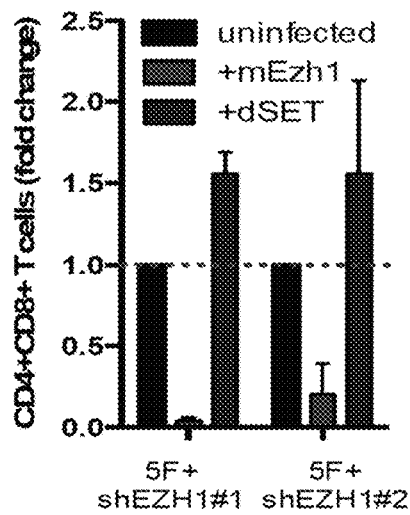
Figure 3G:
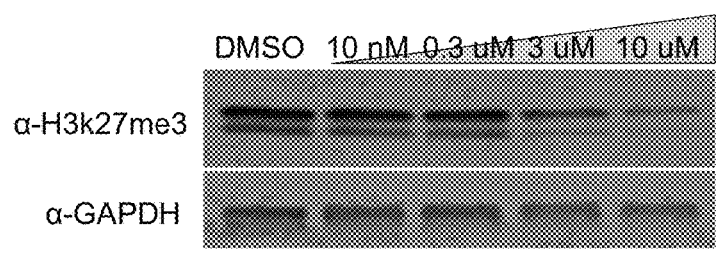
Figure 3H:
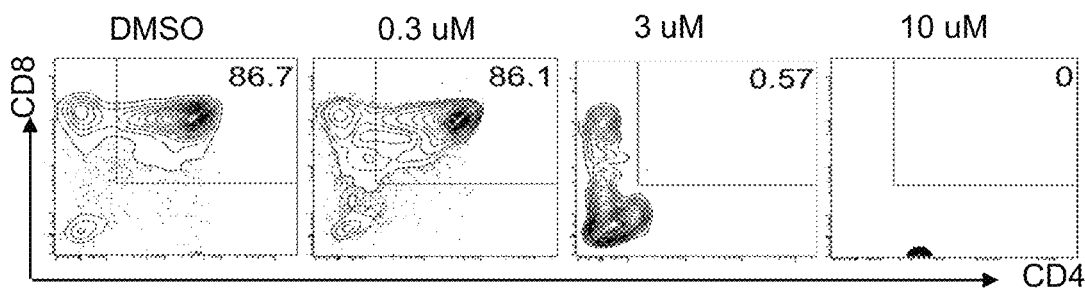
Figure 3I:
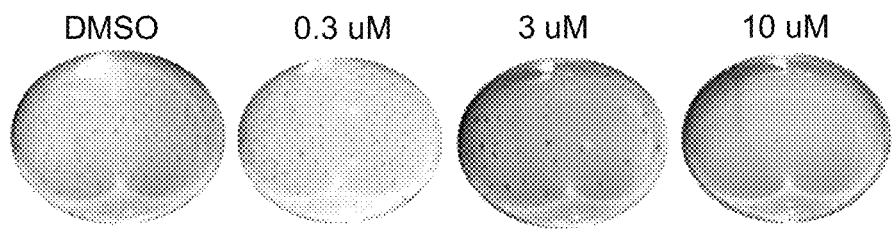
Figure 3J:
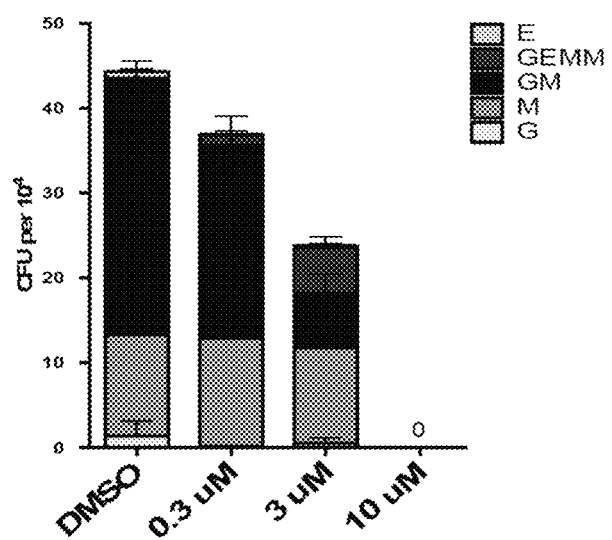

To determine whether the catalytic SET domain of EZH1 was required to restrict definitive hematopoietic potential, the inventors performed rescue experiments with the full-length murine Ezh1 open reading frame (ORF) (mEzh1) or Ezh1 with the catalytic SET domain deleted (mEzh1$\Delta$SET) to escape targeting by shRNAs targeting human EZH1 (FIG. 3D). The inventors observed no T cells in any condition with 5F+shLUC, and a robust population of CD4+CD8+ T cells in 5F+shEZH1, as before (FIG. 3E, 3F). Co-expression of mEzh1 completely abrogated T cell potential of 5F+shEZH1 cells (FIG. 3E, 3F), indicating that the murine ORF is sufficient to functionally restrict definitive hematopoietic potential. By contrast, expression of mEzh1$\Delta$SET did not repress T cell potential (FIG. 3E, 3F). Taken together, these data indicate that specific EZH1 inhibition rather than general PRC2 inhibition unlocks definitive hematopoietic potential and the catalytic SET domain is required to restrict this potential.

Figure 4A:
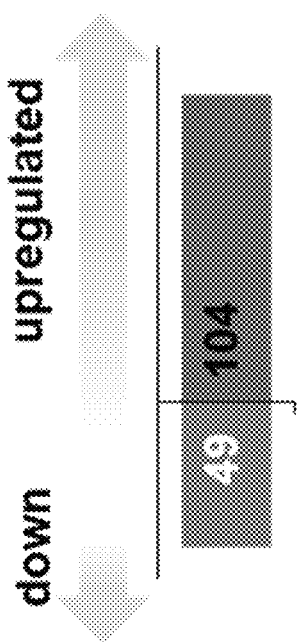
Figure 4B:
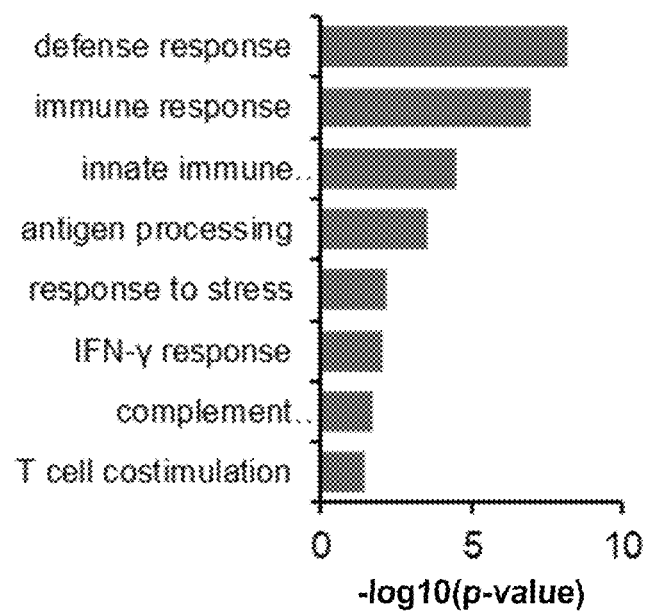
Figure 4D:
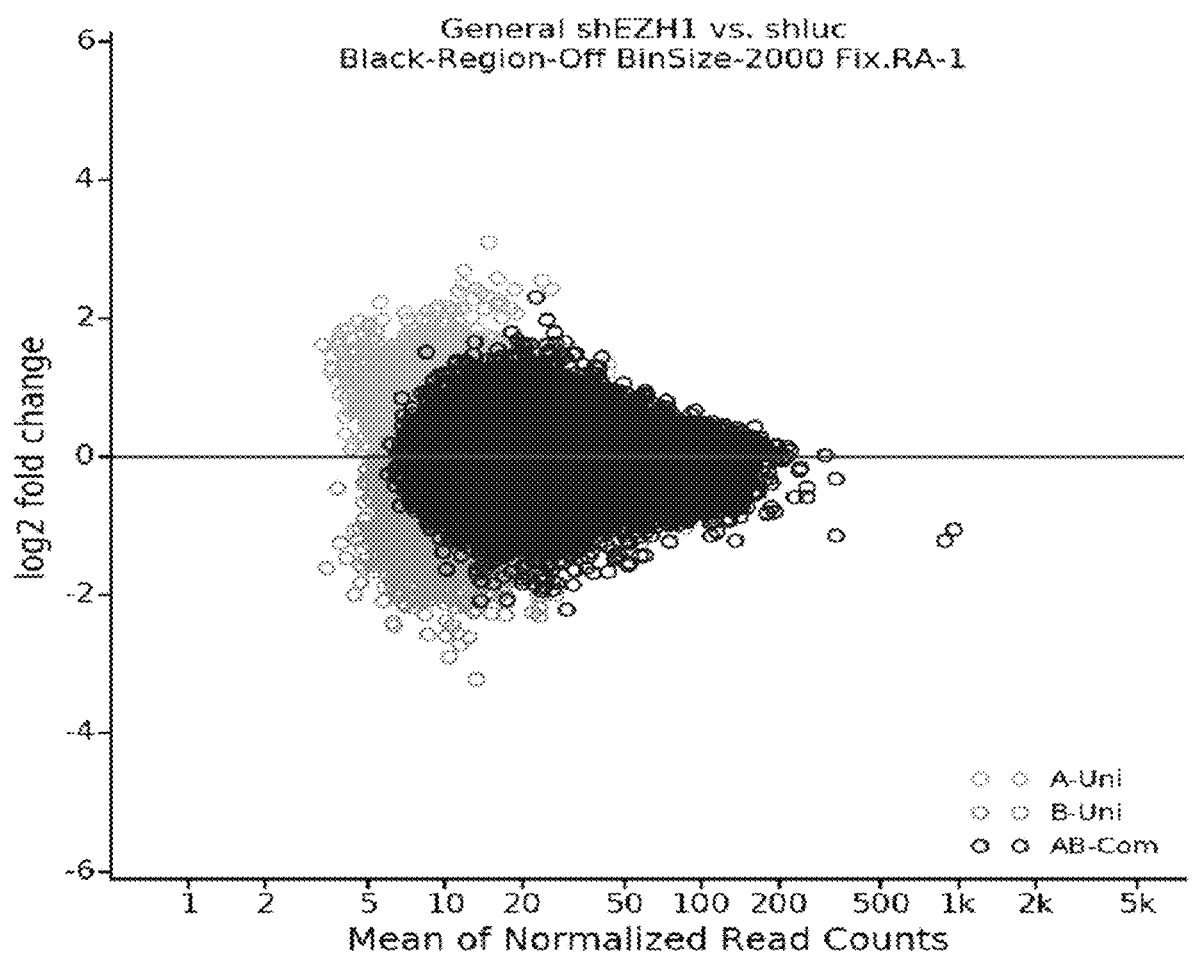
Figure 4H:
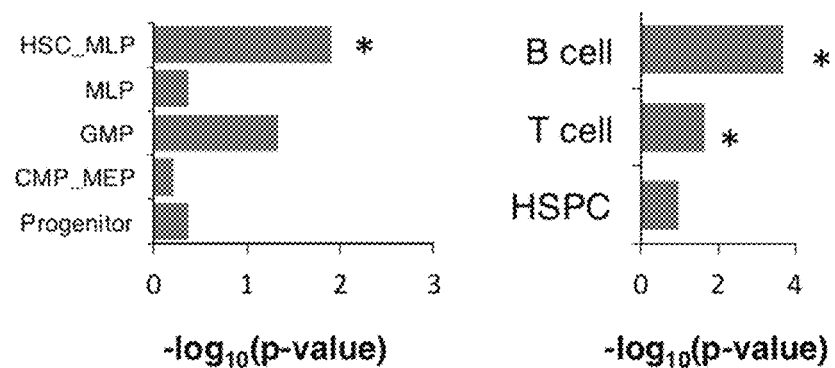

EZH1 directly regulates HSC and lymphoid genes. To understand the molecular basis for enhanced definitive potential, the inventors performed RNA sequencing analysis of $CD34^+CD38^-$ 5F+shLUC and 5F+shEZH1 cells. Genes significantly upregulated following EZH1 knockdown (104 genes, >2-fold, t-test, p<0.1) were enriched for gene ontology (GO) terms defense response, immune response and T cell costimulation (FIGS. 4A, 4B). To specifically analyze the transcriptional changes associated with the human HSPC hierarchy, the inventors performed GSEA using the six signatures that capture earliest patterns of lineage commitment (Doulatov et al. 2010): HSC, MLP (early lymphoid), HSC_MLP (stem and lymphoid), GMP (myeloid), CMP_MEP (erythroid) and Progenitor (all progenitors). HSC_MLP and MLP signatures were highly enriched in 5F+shEZH1 (FIG. 4C), consistent with acquisition of lymphoid potential.

The inventors next performed ATAC-sequencing to identify differential regions of chromatin accessibility (Buenrostro et al. 2013). Unbiased GREAT analysis (McLean et al. 2010) of the 1500 ATAC peaks significantly upregulated upon EZH1 knockdown revealed en-richment in pathways related to T cell development, lymphocyte activation and immune response (FIG. 4E, FIG. 9A). Conversely, downregulated peaks were enriched in pathways related to other cell developmental processes such as re-productive process, neural and lung development, and importantly embryonic hemato-poiesis (FIG. 4G, FIG. 9B). Furthermore, HSC, HSC/MLP, B and T cell signatures were all significantly enriched among upregulated ATAC peaks (FIG. 4F, FIG. 9C), indicating that EZH1 knockdown induces epigenetic remodeling to unlock accessibility to HSC and lymphoid-associated genes.

Figure 5A:
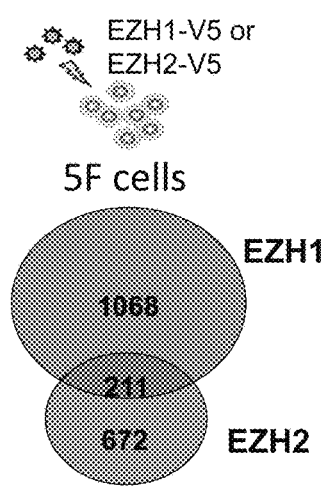
FIGS. 5A-5H collectively show that EZH1 directly binds and regulates HSC and lymphoid gene networks.
Figure 5B:
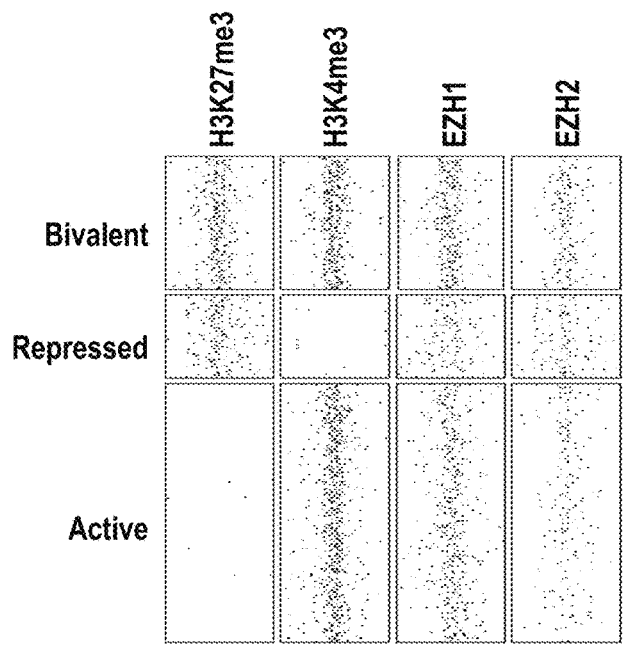
Figure 5C:
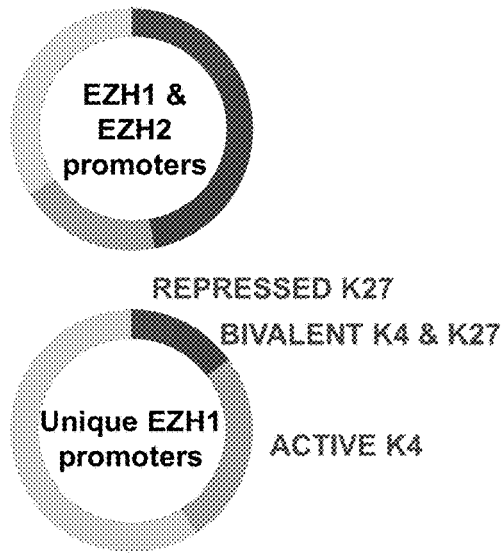
Figure 5D:
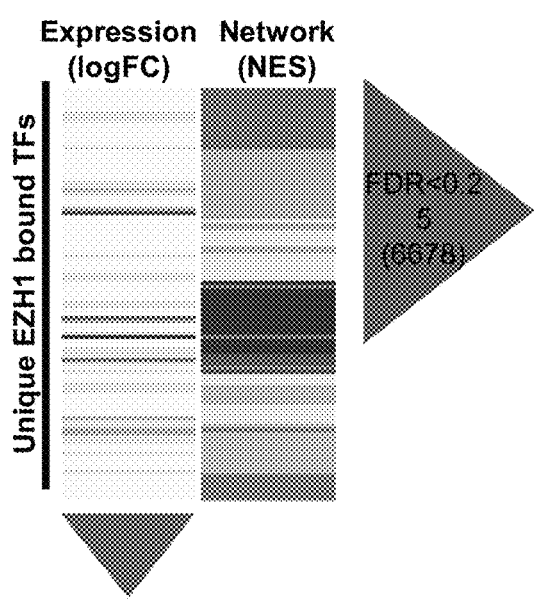
Figure 5E:
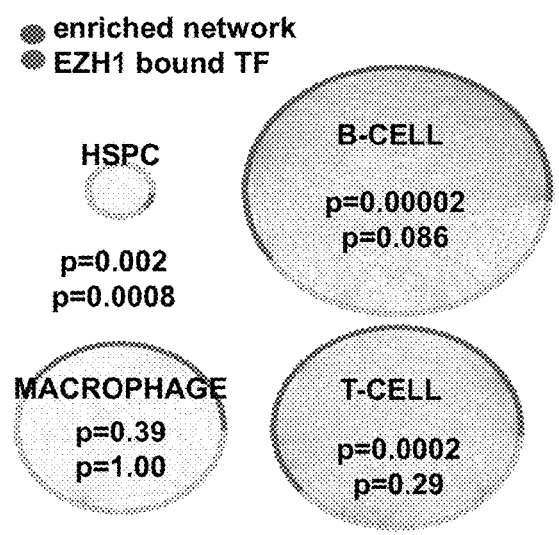
Figure 5F:
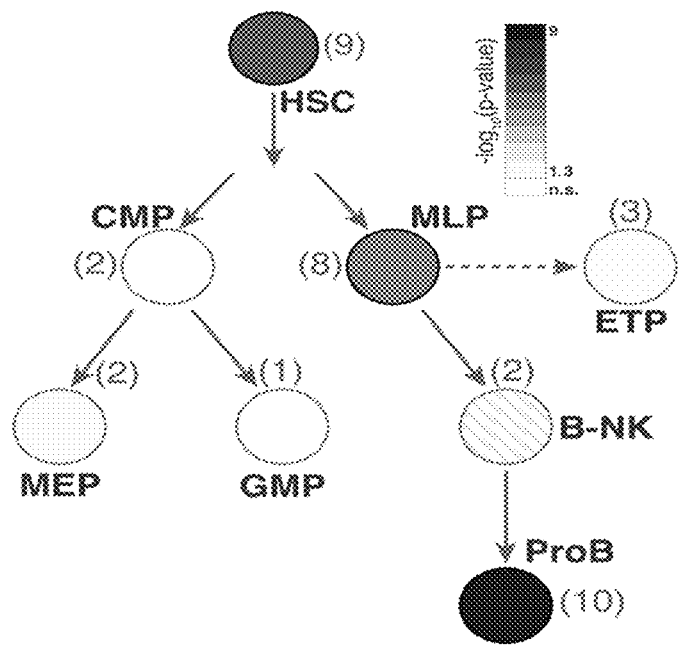
Figure 5G:
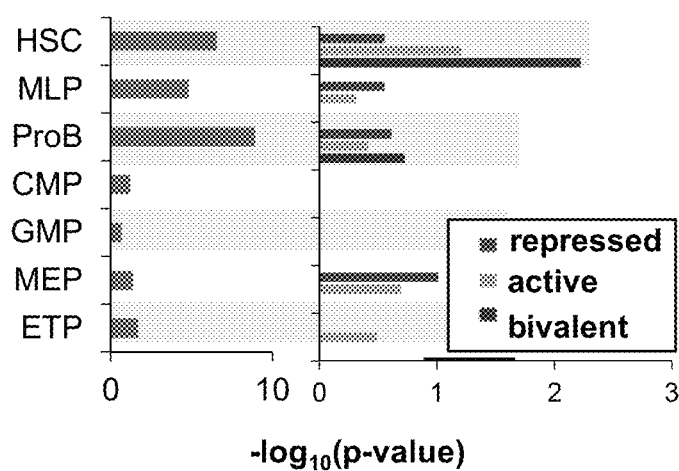
Figure 5H:
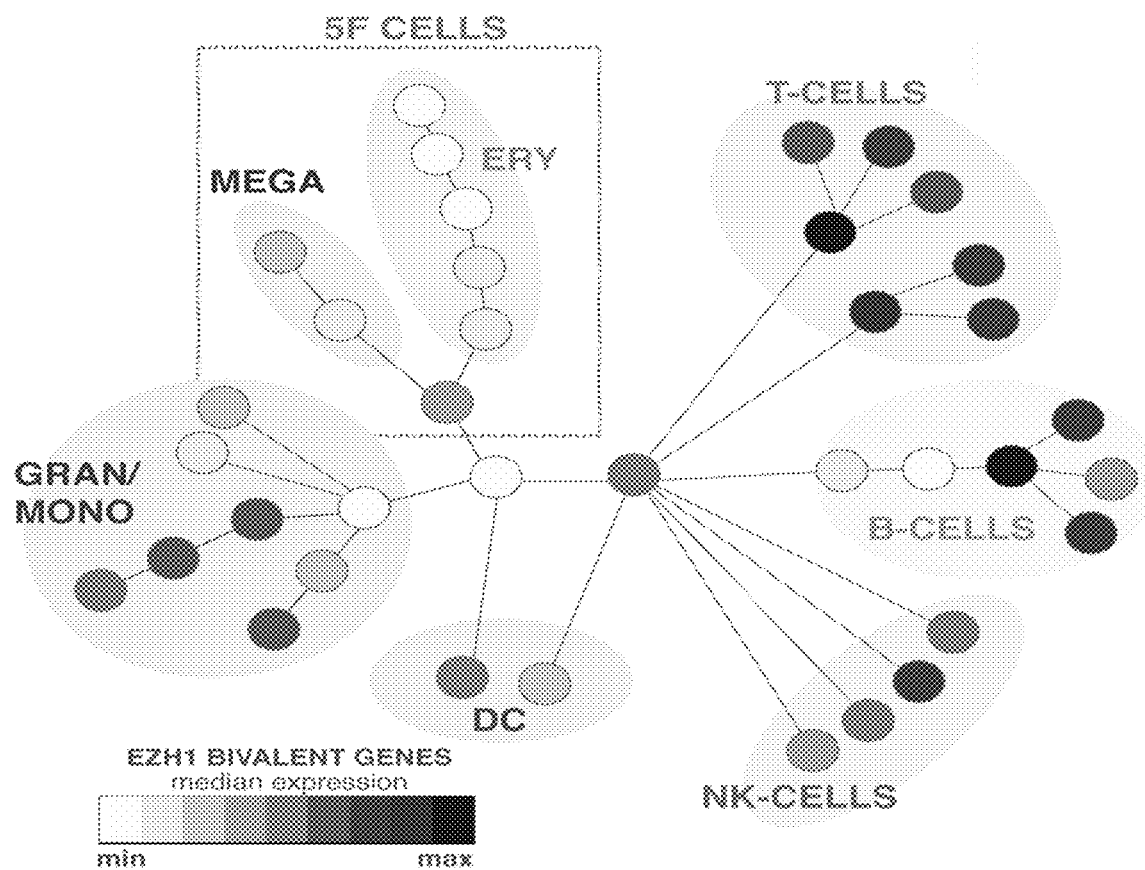

To determine if the changes in chromatin accessibility and gene expression were directly induced by EZH1, the inventors defined its genome-wide occupancy by overexpressing an epitope-tagged EZH1 or EZH2 in 5F cells followed by ChIP-sequencing. Comparison of EZH2 and EZH1 binding sites at promoter regions identified 1069 unique EZH1 binding sites (FIG. 5A) that were associated with repressive, bivalent and active marks (FIGS. 5B, 5C). To better annotate these EZH1 binding sites, the inventors defined the transcriptions factors (TF, 152 out of 1069 genes) that were uniquely bound and compared them to the TF signatures of early HSPC hierarchy (Laurenti et al. 2013). Strikingly, EZH1-bound TFs were highly enriched in HSC, MLP and Pro-B populations (FIGS. 5D and 5F), and a large number of these were bivalently marked (FIG. 5G). Of all the EZH1-bound bivalent genes, a significant number of genes are annotated as granulocyte/macrophage, NK-, T- and B-cell specific genes (Novershtern et al. 2011) (FIG. 5H). Although EZH1-bound TFs did not show significant alterations in expression, the regulated networks controlled by each EZH1-bound TF defined by CellNet were significantly changed (FIG. 5D). Specifically, the EZH1-bound TFs and their networks were significantly enriched in the HSPC, B and T cell GRNs (FIG. 5E). The networks of EZH1-bound TFs such as STAT5A, YAP1, NLRC5, ZNF697 and BACH2 were all significantly upregulated in B and T cell GRNs (Data not shown). Taken together, these data provide compelling evidence that EZH1 directly binds to HSC and MLP transcription factors, and inhibition of EZH1 unlocks definitive hematopoietic potential by de-repressing stem and lymphoid gene regulatory networks.

Figure 6A:
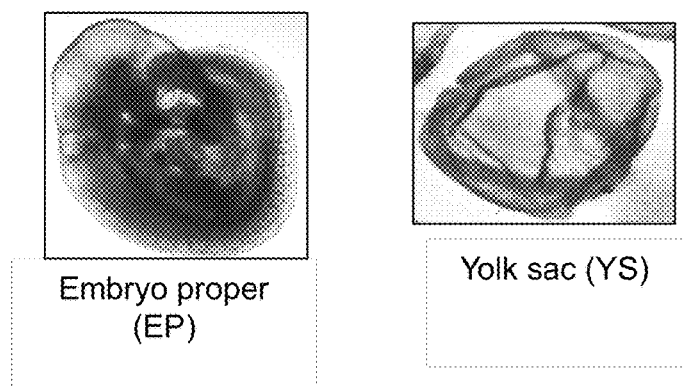
FIGS. 6A-6N collectively show that Ezh1 deficiency increases lymphoid potential and engraftment of embryonic hematopoietic stem/progenitor cells.
Figure 6B:
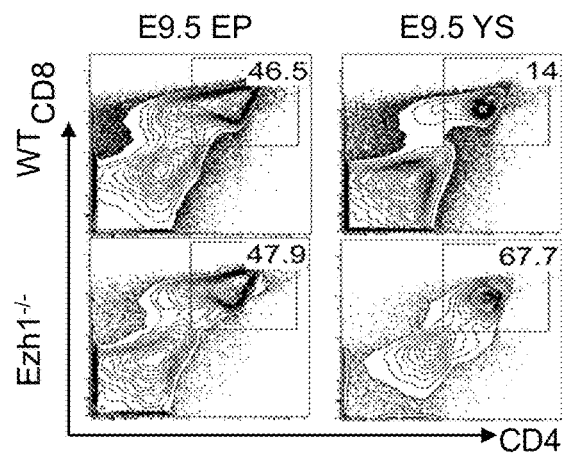
FIG. 6B shows the representative flow plots of T cell analysis from E9.5 WT or Ezh1−/− EP and YS. YS and EP were dissociated into single cells and plated into OP9-DL1 stromal co-culture supplemented with 5 ng/ml IL-7 and 5 ng/mL FLT3. After 12 days of stromal co-culture, cells were harvested and analyzed for T cell development by the markers CD4 and CD8. All plots are gated on CD45.
Figure 6C:
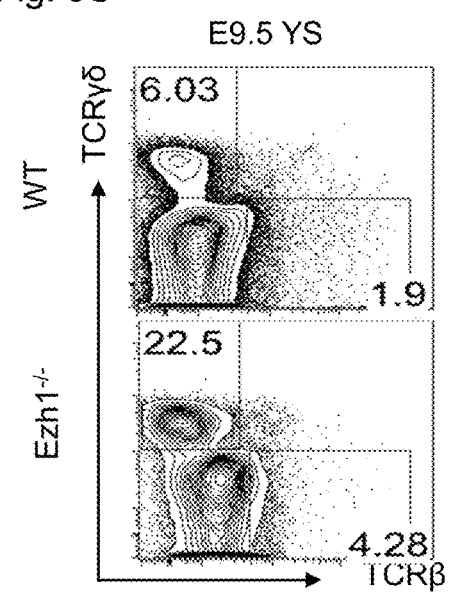
FIG. 6C shows the representative flow analysis of TCRγδ and TCRβ from WT or Ezh1−/− EP and YS.
Figure 6D:
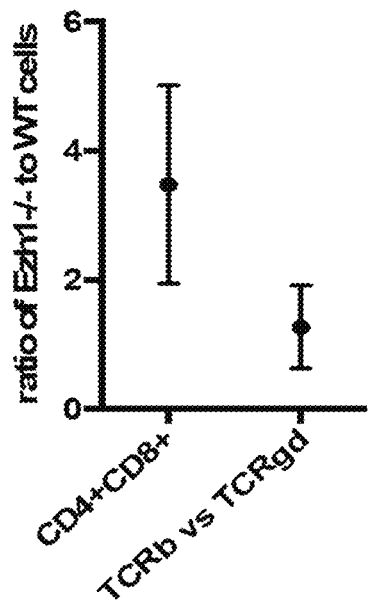
FIG. 6D shows the quantitation of the ratio of CD4+CD8+ T cells or TCRβ versus TCRγδ from Ezh1−/− YS compared to WT from three independent experiments.
Figure 11A:
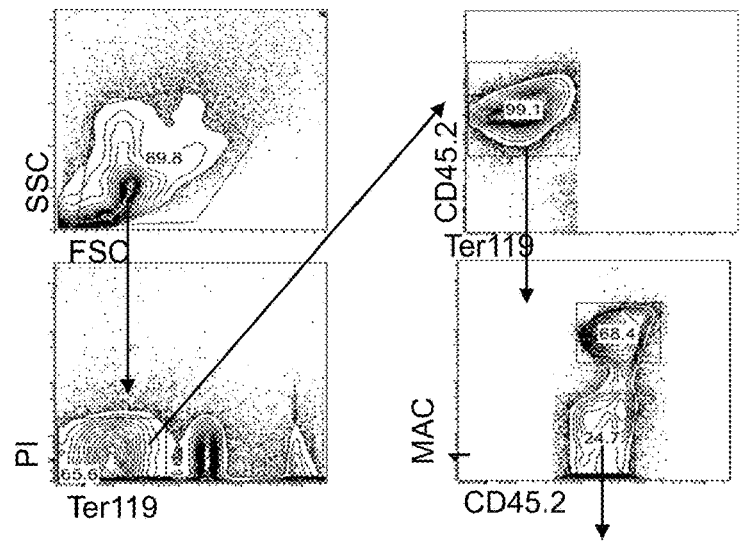
FIGS. 11A-11C collectively show the lineage analysis of hematopoietic populations in E9.5 YS.
Figure 11B:
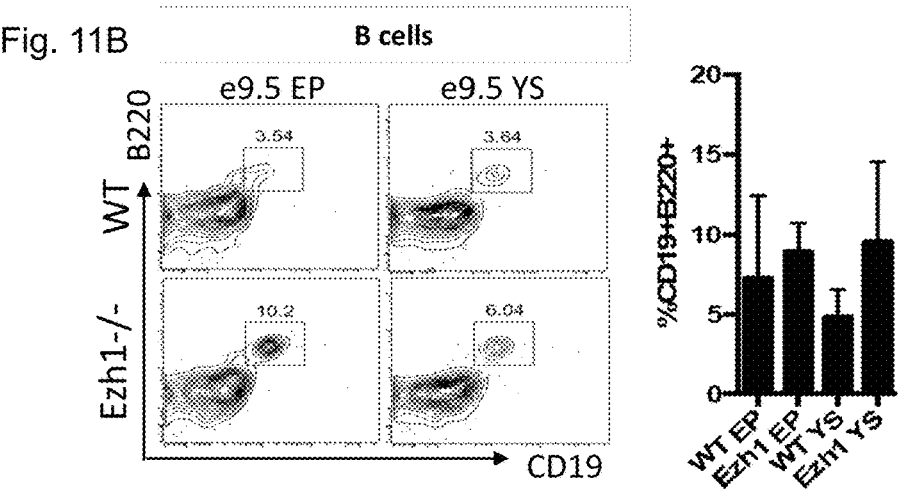
Figure 11C:
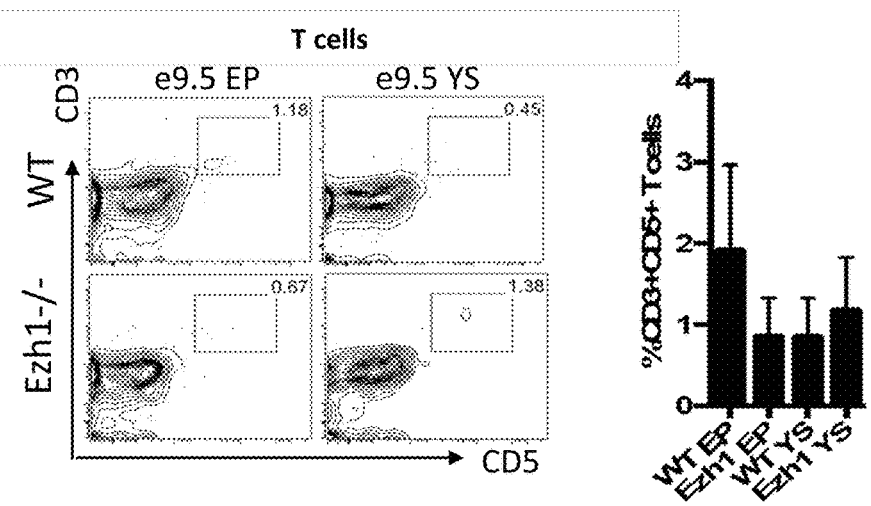
Figure 12A:
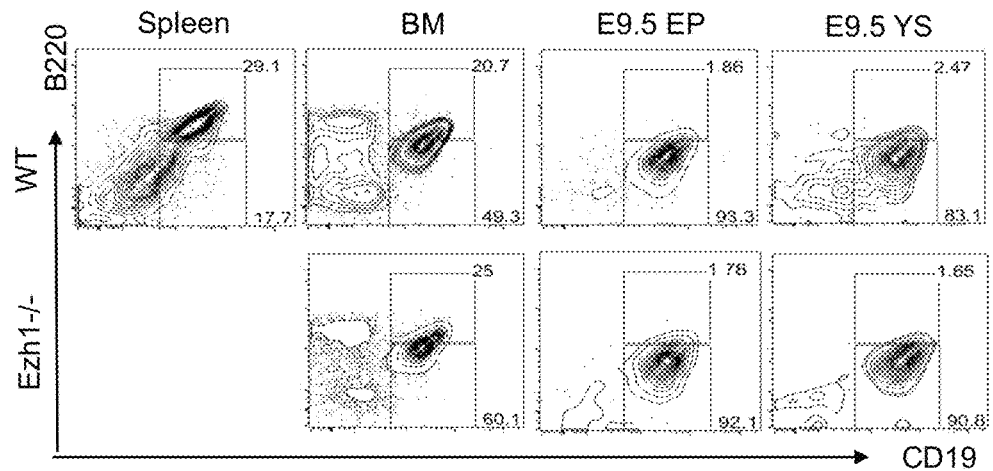
FIGS. 12A-12C collectively show the in vitro B cell differentiation potential of E9.5 EP and YS.
Figure 12B:
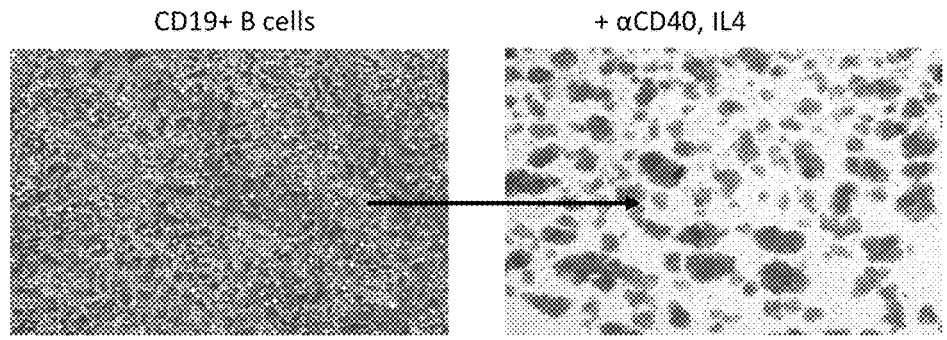
Figure 12C:
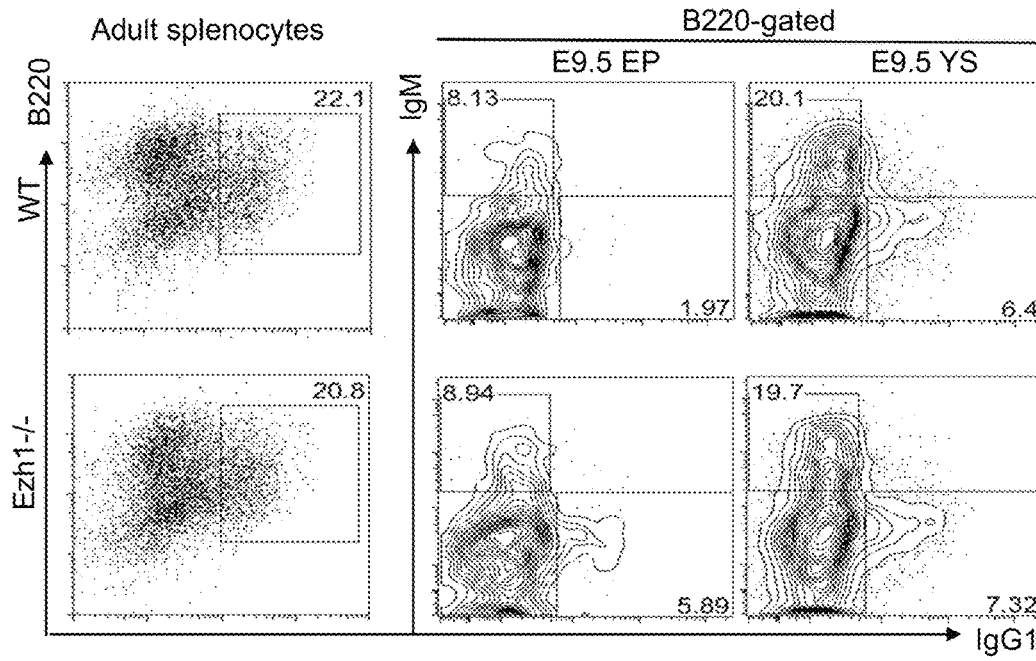

Ezh1 deficiency enhances embryonic lymphopoiesis in vivo. To interrogate the role of Ezh1 in vivo, the inventors first investigated early lymphoid development in murine embryos. The extra-embryonic yolk sac (YS) is the earliest site of hematopoiesis and was thought to generate only primitive erythroid and myelo-erythroid progenitors (Dzierzak and Speck 2008). However, recent studies have reported lymphoid potential in the yolk sac before definitive HSC emergence (Boiers et al. 2013, Yoshimoto et al. 2012, Yoshimoto et al. 2011). To determine whether Ezh1 deficiency can enhance this early lymphoid potential, the inventors performed lineage analysis of E9.5 yolk sac (YS) from wild-type (WT) and Ezh1 knockout (Ezh1−/−) embryos. The inventors detected a small population of $CD19^+B220^+$ B cells (3.64%) as well as $CD3^+CD5^+$ T cells (0.45%) (FIGS. 11A-11C) in the WT YS. These lymphoid populations trended toward higher frequencies in Ezh1−/− YS, although this increase was not significant (FIGS. 11B and 11C). Furthermore, the inventors could not rule out the possibility of circulating maternal blood confounding our lineage analysis. Therefore, the inventors dissected yolk sac away from E9.5 WT and Ezh1−/− embryo proper and performed in vitro lymphoid differentiation. The inventors detected a robust population of embryonic B cells (B-1 subtype; $AA4.1^+CD19^+B220^{lo-neg}$), and few adult-like B-2 cells ($AA4.1^+CD19^+B220^+$) consistent with previous findings (Yoshimoto et al. 2012) (FIG. 12A). The inventors did not find significant differences in B cell potential between WT and Ezh1$^{-/-}$ cells, but note an increase in class-switching from germline IgM to IgG1 (FIG. 12C). Similarly, the inventors did not observe differences in T cell potential between WT and Ezh1$^{-/-}$ in the embryo proper (EP) (FIGS. 6A and 6B). By contrast, Ezh1$^{-/-}$ YS progenitors generated 2-5-fold more $CD4^+CD8^+$ T cells (FIGS. 6B and 6D). These early T cells predominantly expressed fetal TCRγδ, though a small proportion expressed adult-type TCRβ (FIGS. 6C and 6D). These data demonstrate that Ezh1-deficiency enhances lymphoid potential of YS progenitors. Taken together, the findings thus far propose a role for EZH1 in repressing lymphoid lineage fate, as a surrogate measure of definitive potential.

Figure 6E:
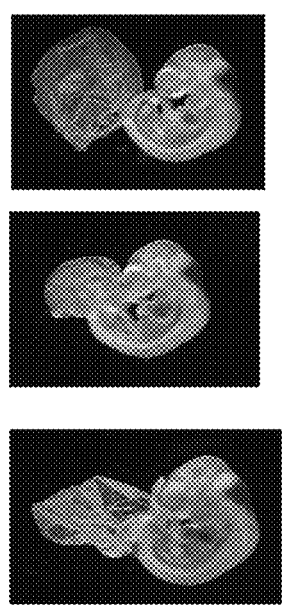
FIG. 6E shows the representative images of E10.5 embryos.
Figure 6F:
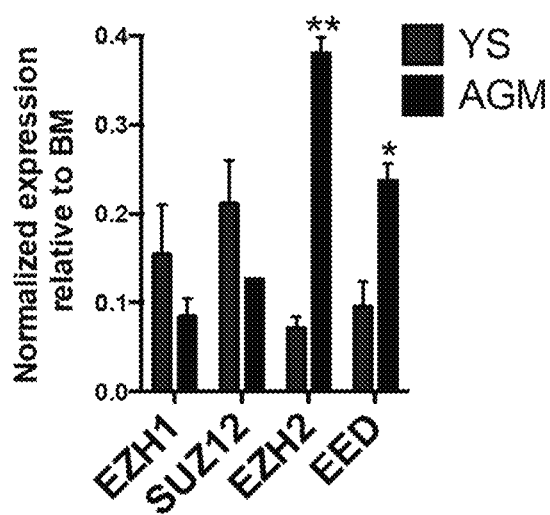
FIG. 6F shows the quantitative PCR of each PRC2 subunit in YS and AGM from E10.5 WT embryos as mean±SEM of three replicates.
Figure 6G:
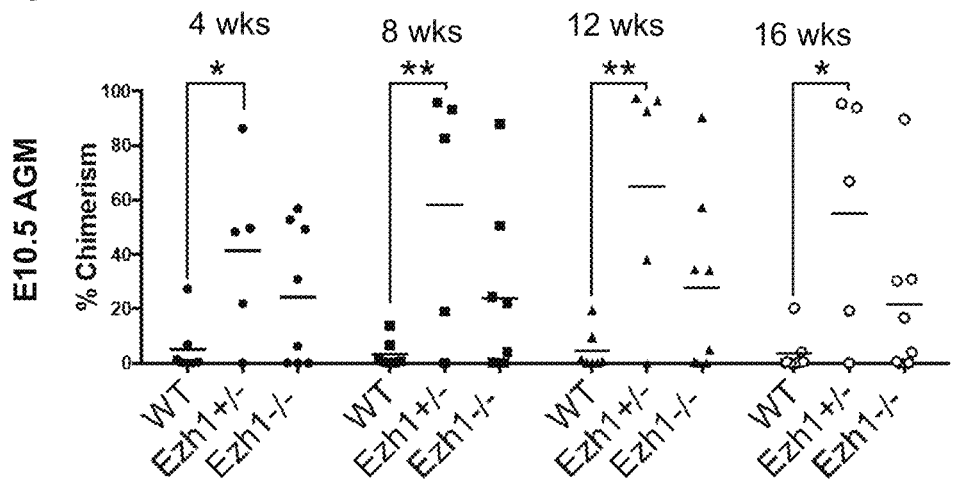
FIG. 6G shows the sublethally-irradiated adult NSG females transplanted intravenously with 3.5 ee of whole E10.5 AGM. Mice were bled retroorbitally every 4 weeks to monitor donor chimerism up to 16 weeks post-transplantation. Each dot represents a single transplant recipient.
Figure 6H:
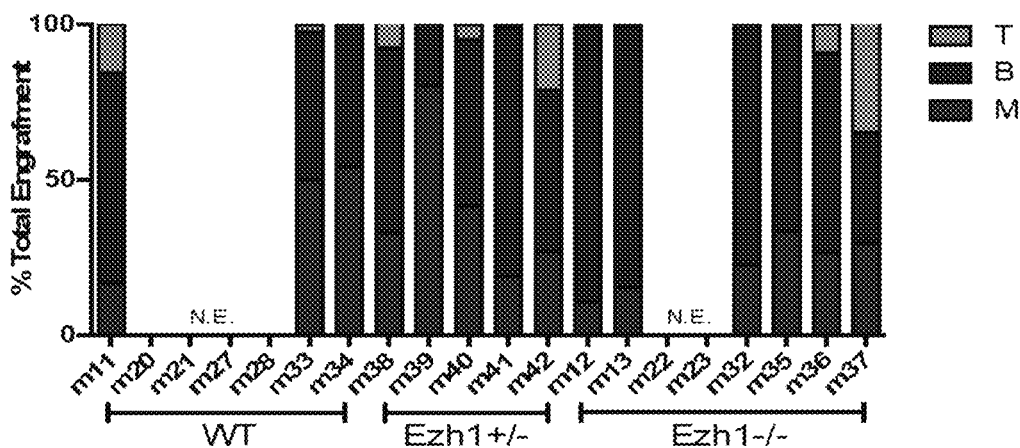
FIG. 6H shows the lineage distribution of engrafted mice in FIG. 6G.

Ezh1 haploinsufficiency promotes generation of HSCs in ontogeny. The emergence of bona fide HSCs, defined by the capacity to repopulate adult recipients, marks the transition from embryonic to definitive hematopoiesis. If EZH1 acts as a gatekeeper of definitive potential, the inventors predicted that HSCs may emerge earlier and dis-play enhanced repopulating potential. While HSCs appear in the AGM around 10.5 dpc (Boisset et al. 2010), they are extremely rare (~1 HSC/embryo) and do not robustly support engraftment of adult hosts (Bertrand et al. 2005, Muller et al. 1994, North et al. 2002). Thus, focusing on this transitional time point, the inventors isolated AGM and YS from E10.5 WT, Ezh1$^{+/-}$ and Ezh1$^{-/-}$ embryos (FIG. 6E). Expression of Ezh1 and Suz12 decreased from YS to AGM, while Ezh2 and Eed were higher in the AGM (FIG. 6F). The inventors transplanted whole AGM (3.5 embryo equivalents (ee)) or YS (5 ee) into sub-lethally irradiated adult NOD/SCID-IL2Rγ$^{null}$ (NSG) mice and monitored hematopoietic reconstitution. Engraftment from WT AGM was observed in 3/7 mice (11.9±13.6%) after 4 weeks, but decreased over time, with 2/7 mice engrafted (12.2±11.4%) after 16 weeks (FIG. 6G). This corresponds to 1 repopulating unit in ~10.4 embryo equivalents (ee). Only 1/7 WT AGM-transplanted mice displayed long-term multi-lineage chimerism, consistent with HSCs being exceedingly rare at this time. By contrast, 5/8 mice transplanted with Ezh1$^{-/-}$ AGM-derived cells were engrafted after 4 weeks (36.7±20.9%) and retained stable chimerism over time (16 weeks; 34.3±32.9%). Even more notably, mice transplanted with Ezh1+/− cells had the highest initial chimerism (41.2±29.2%; 4/5 engrafted), which increased over time (68.9±35.6%), and was predominantly multi-lineage (3/5 mice). (FIGS. 6G and 6H). This corresponds to 1 repopulating unit in 3.6 Ezh1−/− and 2.2 Ezh1+/− embryo equivalents, a nearly 5-fold increase in frequency of HSCs.

Figure 6I:
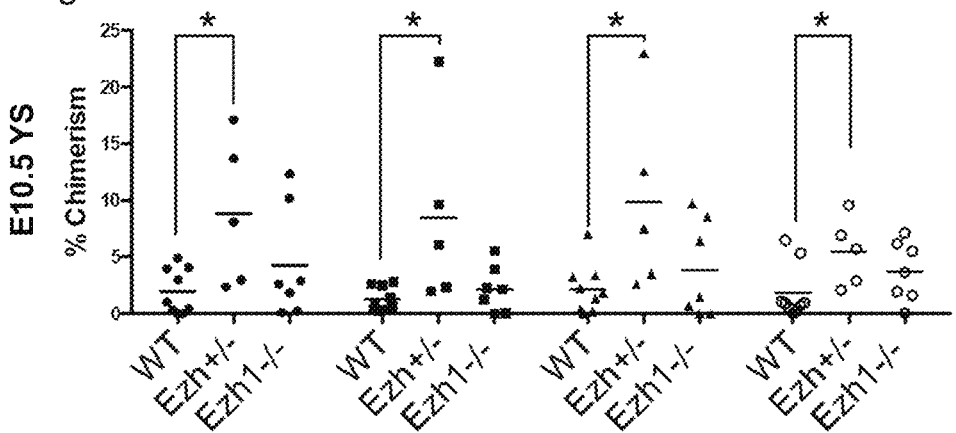
FIG. 6I shows the sublethally-irradiated adult NSG females transplanted via tail vein injections with 5 ee of whole E10.5 YS.
Figure 6J:
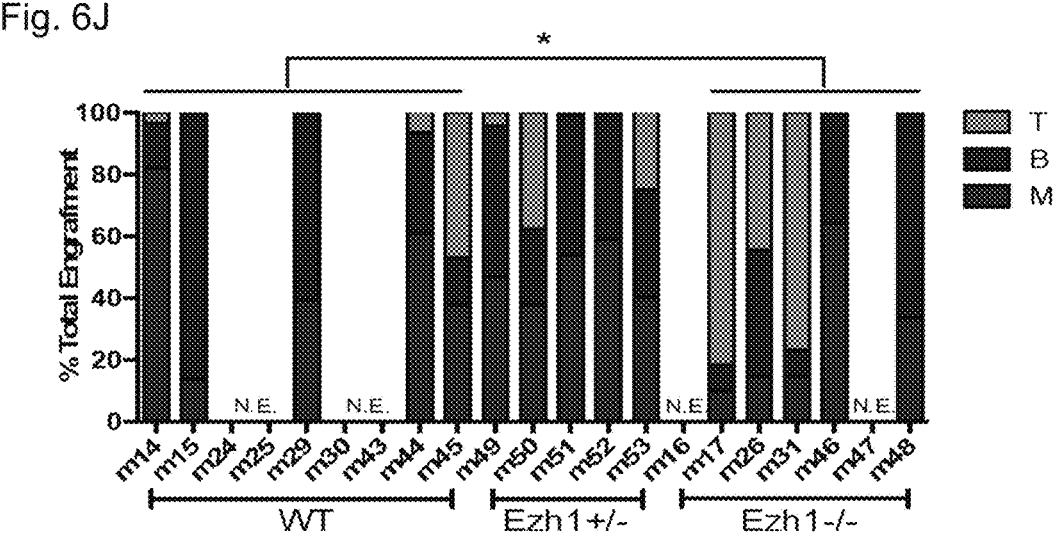
FIG. 6J shows the lineage distribution of engrafted mice in (FIG. 6I).
Figure 6K:
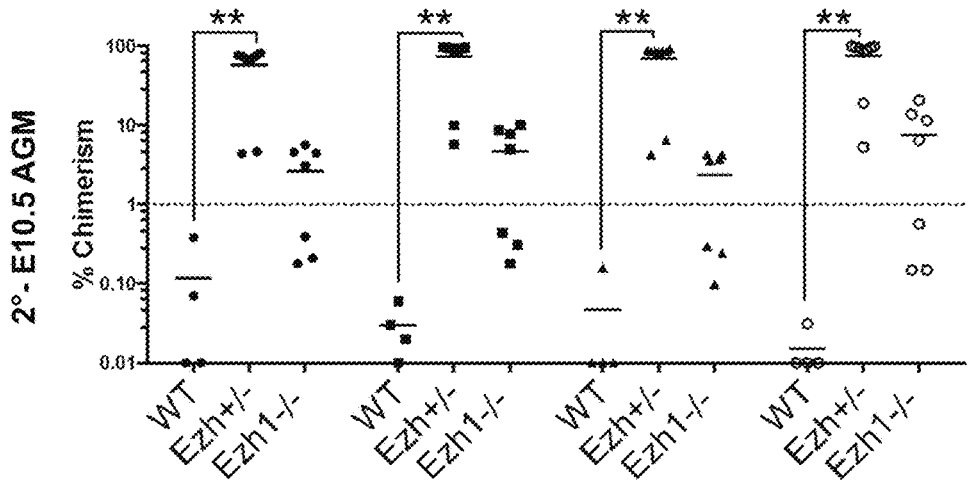
FIG. 6K shows the whole marrow from primary recipients in FIG. 6G transplanted into secondary recipients 24 weeks after primary transplantation. Two to five primary recipients from each group were sacrificed and 4×10$^6$ whole bone marrow cells were transplanted into 1-3 secondary recipients.
Figure 6L:
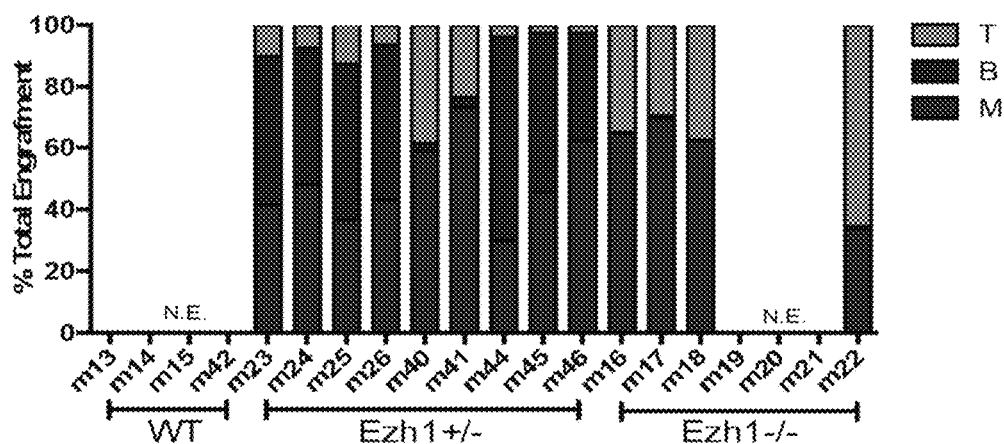
FIG. 6L shows the lineage distribution of secondary recipients in FIG. 6K.
Figure 6M:
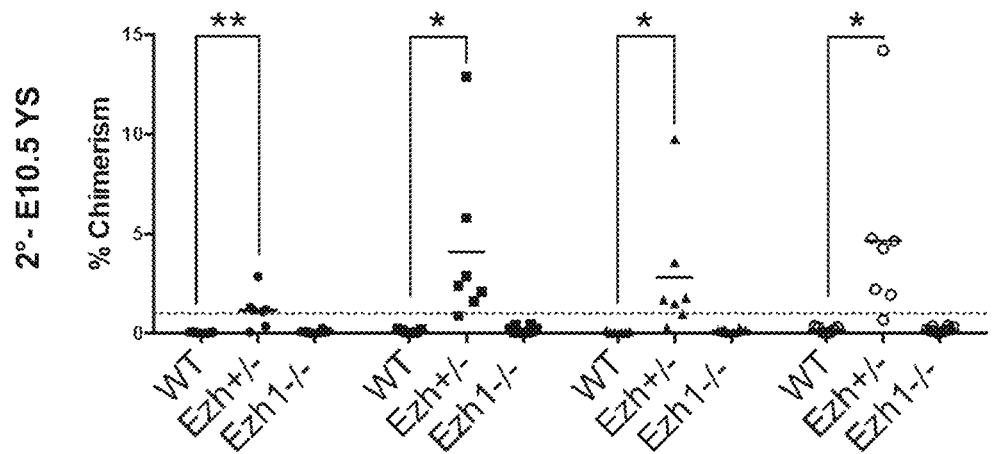
FIG. 6M shows the secondary transplantation of primary recipients in FIG. 6I.
Figure 13A:
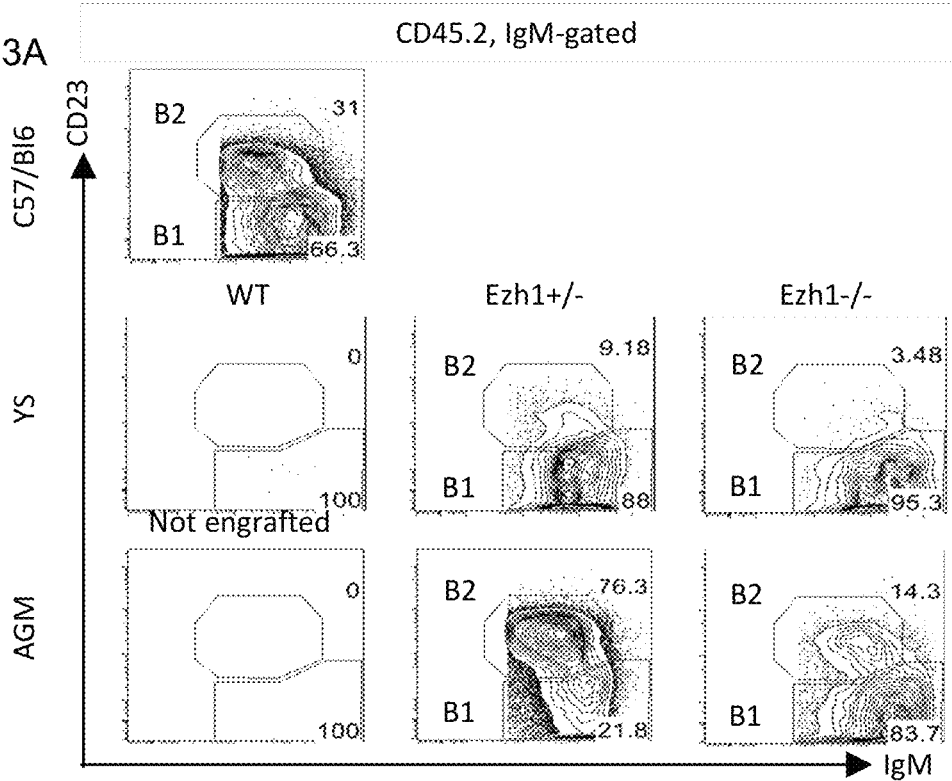
FIGS. 13A-13B collectively show that Ezh1-deficient embryonic HSPCs contribute to adult-type lymphopoiesis in vivo.
Figure 13B:
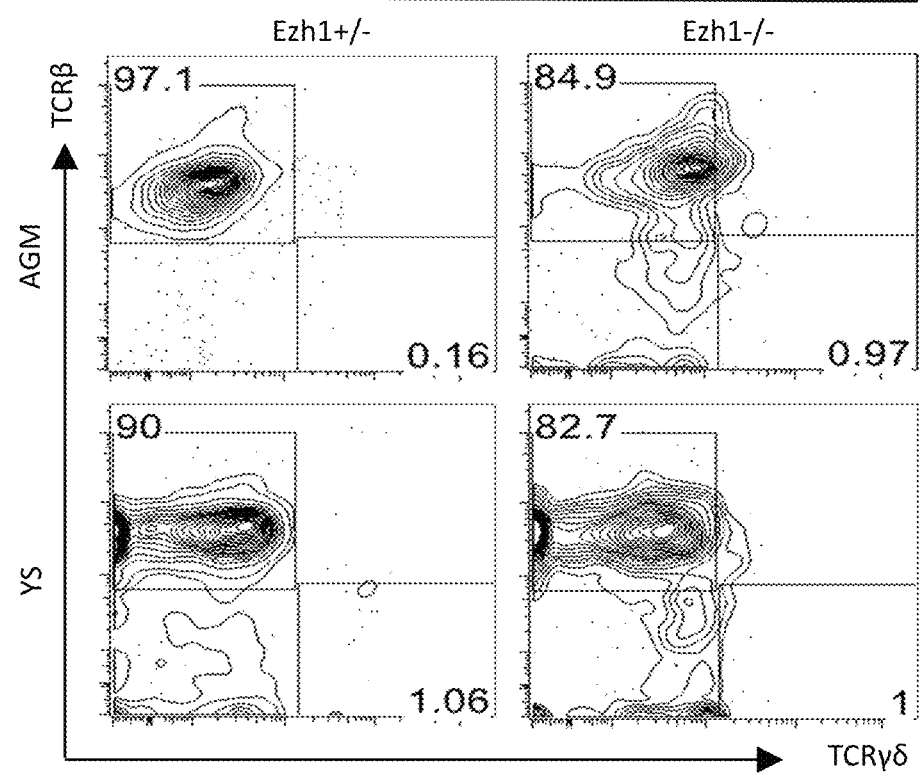
Figure 14D:
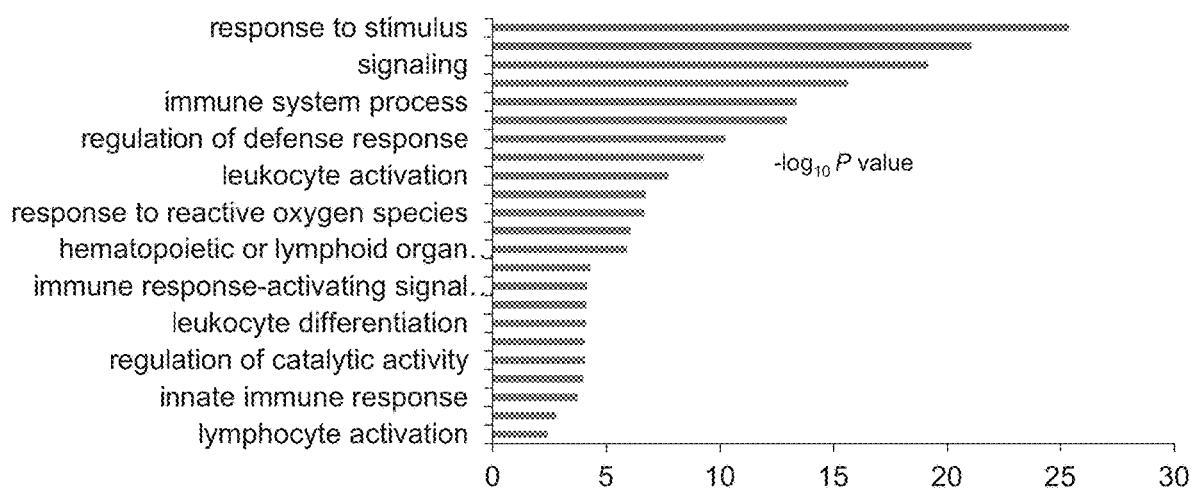
Figure 15:
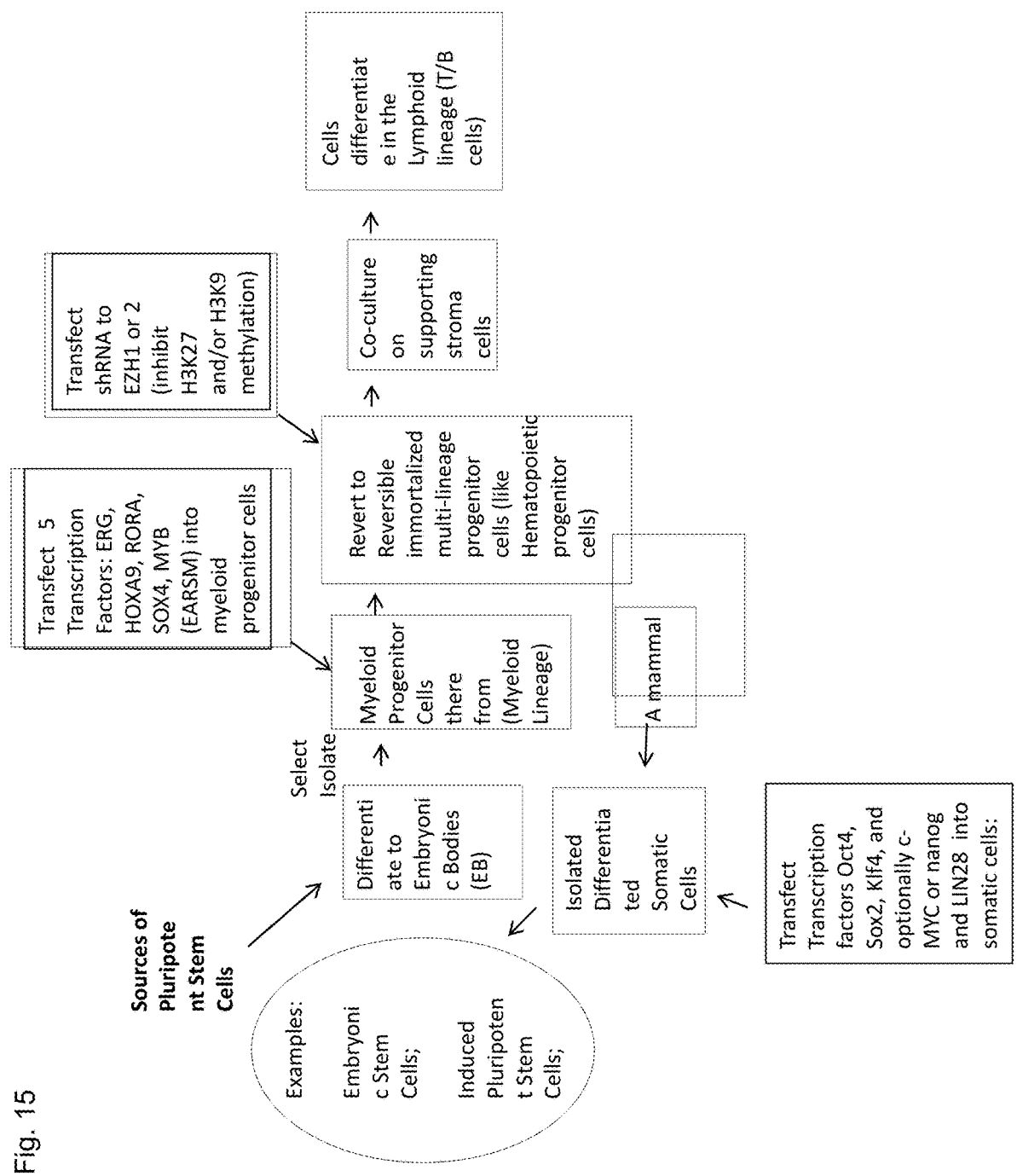
FIG. 15 is a schematic diagram showing an embodiment production of various myeloid, erythroid, and immune cells from pluripotent hematopoietic stem cells.

Similarly to the AGM, YS at E10.5 contains few if any HSCs. Consistent with this, we detected low level engraftment of WT YS cells in 5/7 recipients after 4 weeks (3.4±1.5%), but only 3/9 mice after 16 weeks (4.3±2.9%) (FIG. 6I). By contrast, most Ezh1−/− (6.0±4.9%, 5/7 engrafted), and all of Ezh1+/− YS-transplanted mice (8.8±6.5%, 5/5 engrafted), showed stable long-term engraftment (FIGS. 6I and 6M). The number of repopulating units was similar to the AGM (~1 in 8.9 ee WT; 1 in 4 Ezh1−/−, 1 in <2 Ezh1+/−). All engrafted mice were reconstituted with myeloid and lymphoid lineages (FIG. 6J). The inventors observed a significant increase in the T cell graft of Ezh1−/− AGM transplant recipients compared with WT AGM recipients (FIG. 6J). Up to 80% of B cells in the peritoneal cavity of Ezh1+/− AGM-engrafted mice were of the adult-like B-2, as opposed to the embryonic B-1 cells (FIG. 13A). Furthermore, >90% of donor-derived CD45.2+CD3+ T cells expressed adult-type TCRβ, as opposed to embryonic TCRγδ configuration, in Ezh1−/− and Ezh1+/− AGM and YS engrafted mice (FIG. 13B). These data provide compelling evidence that Ezh1 deficiency, and especially haploinsufficiency, stimulates generation of definitive HSCs and adult-like lymphopoiesis.

Figure 6N:
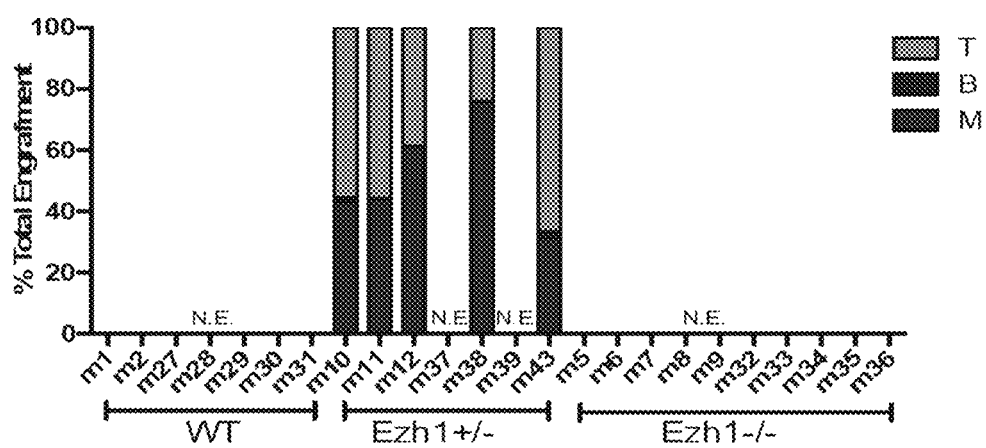

To determine the extended self-renewal potential of Ezh1-deficient HSCs, the inventors performed secondary transplantation. Using 1% as the cutoff for engraftment, the inventors did not detect any donor contribution in mice transplanted with WT AGM (0/4 mice) or YS (0/7 mice) in the peripheral blood after 4 weeks. By contrast, 4/7 Ezh1−/− (4.4±1.0%) and 9/9 Ezh1+/− (57.8±30.6%) AGM-transplanted secondary recipients were engrafted. (FIGS. 6K and 6L). While no Ezh1$^{-/-}$ YS mice (0/10) were engrafted, the inventors observed chimerism from Ezh1$^{+/-}$ YS cells (5/7 mice engrafted, 1.5±0.7%), which increased by 16 weeks post-transplantation (6/7 mice engrafted, 5.3 =4.5%) (FIGS. 6M and 6N). Notably, all of the secondary recipients of Ezh1-deficient AGM and YS displayed multi-lineage engraftment with B, T, and myeloid lineages. (FIGS. 6L and 6N) Taken together, Ezh1 uniquely represses definitive potential during ontogeny, and Ezh1-deficiency promotes long-term, multilineage differentiation and self-renewal potential of embryonic stem and progenitor cells.

The references cited herein and throughout the specification are incorporated herein by reference.

REFERENCES

1. Dzierzak E and Speck N A. Of lineage and legacy: the development of mammalian hematopoietic stem cells. Nat Immunol. 2008 February; 9(2):129-36.
2. Baron M H and Fraser S T. The specification of early hematopoiesis in the mammal. Curr Opin Hematol. 2005 May; 12(3):217-21.
3. Tavian M and Péault B. The changing cellular environments of hematopoiesis in human devel-opment in utero. Exp Hematol. 2005 September; 33(9):1062-9.
4. Ferkowicz M J and Yoder M C. Blood island formation: longstanding observations and modern in-terpretations. Exp Hematol. 2005 September; 33(9):1041-7.
5. Kennedy M et al. T lymphocyte potential marks the emergence of definitive hematopoietic progenitors in human pluripotent stem cell differentiation cultures. Cell Rep. 2012 Dec. 27; 2(6):1722-35.
6. Sturgeon C M et al. Wnt signaling controls the specification of definitive and primitive hematopoiesis from human pluripotent stem cells. Nat Biotechnol. 2014 June; 32(6):554-61.
7. Ditadi A et al. Human definitive haemogenic endothelium and arterial vascular endothelium represent distinct lineages. Nat Cell Biol. 2015 May; 17(5):580-91.
8. Böiers C et al. Lymphomyeloid contribution of an immune-restricted progenitor emerging prior to definitive hematopoietic stem cells. Cell Stem Cell. 2013 Nov. 7; 13(5):535-48.
9. Yoshimoto M et al. Autonomous murine T-cell progenitor production in the extra-embryonic yolk sac before HSC emergence. Blood. 2012 Jun. 14; 119(24):5706-14.
10. Yoshimoto M et al. Embryonic day 9 yolk sac and intra-embryonic hemogenic endothelium independently generate a B-1 and marginal zone progenitor lacking B-2 potential. Proc Natl Acad Sci USA. 2011 Jan. 25; 108(4):1468-73.
11. McKinney-Freeman S et al. The transcriptional landscape of hematopoietic stem cell ontogeny. Cell Stem Cell. 2012 Nov. 2; 11(5):701-14.
12. Miranda-Saavedra D et al. BloodExpress: a database of gene expression in mouse haematopoiesis. Nucleic Acids Res. 2009 January; 37(Database issue):D873-9.
13. Sauvageau G et al. Differential expression of homeobox genes in functionally distinct CD34+ subpopulations of human bone marrow cells. Proc Natl Acad Sci USA. 1994 Dec. 6; 91(25):12223-7.
14. McGrath K E and Palis J. Expression of homeobox genes, including an insulin promoting factor, in the murine yolk sac at the time of hematopoietic initiation. Mol Reprod Dev. 1997 October; 48(2):145-53.
15. Doulatov S et al. Induction of multipotential hematopoietic progenitors from human pluripotent stem cells via respecification of lineage-restricted precursors. Cell Stem Cell. 2013 Oct. 3; 13(4):459-70.

16. Ramos-Mejia V et al. HOXA9 promotes hematopoietic commitment of human embryonic stem cells. Blood. 2014 Nov. 13; 124(20):3065-75.
17. Dou D R et al. Medial HOXA genes demarcate haematopoietic stem cell fate during human devel-opment. Nat Cell Biol. 2016 June; 18(6):595-606.
18. Dambacher S et al. Epigenetic regulation of development by histone lysine methylation. Heredity (Edinb). 2010 July; 105(1):24-37.
19. Majewski I J et al. Polycomb repressive complex 2 (PRC2) restricts hematopoietic stem cell activity. PLoS Biol. 2008 Apr. 15; 6(4):e93.
20. Majewski I J et al. Opposing roles of polycomb repressive complexes in hematopoietic stem and progenitor cells. Blood. 2010 Aug. 5; 116(5):731-9.
21. Mochizuki-Kashio M et al. Dependency on the polycomb gene Ezh2 distinguishes fetal from adult hematopoietic stem cells. Blood. 2011 Dec. 15; 118(25):6553-61.
22. Hidalgo I et al. Ezh1 is required for hematopoietic stem cell maintenance and prevents senes-cence-like cell cycle arrest. Cell Stem Cell. 2012 Nov. 2; 11(5):649-62.
23. Xie H et al. Polycomb repressive complex 2 regulates normal hematopoietic stem cell function in a developmental-stage-specific manner. Cell Stem Cell. 2014 Jan. 2; 14(1):68-80.
24. Kinkel S A et al. Jarid2 regulates hematopoietic stem cell function by acting with polycomb repressive complex 2. Blood. 2015 Mar. 19; 125(12):1890-900.
25. Lee S C et al. Polycomb repressive complex 2 component Suz12 is required for hematopoietic stem cell function and lymphopoiesis. Blood. 2015 Jul. 9; 126(2):167-75.
26. Ikeda K et al. Maintenance of the functional integrity of mouse hematopoiesis by EED and promotion of leukemogenesis by EED haploinsufficiency. Sci Rep. 2016 Jul. 19; 6:29454.
27. Onder T T et al. Chromatin-modifying enzymes as modulators of reprogramming. Nature. 2012 Mar. 4; 483(7391):598-602.
28. Holmes R and Znniga-Pflücker J C. The OP9-DL1 system: generation of T-lymphocytes from em-bryonic or hematopoietic stem cells in vitro. Cold Spring Harb Protoc. 2009 February; 2009(2):pdb.prot5156.
29. Ugarte F et al. Progressive Chromatin Condensation and H3K9 Methylation Regulate the Differentiation of Embryonic and Hematopoietic Stem Cells. Stem Cell Reports. 2015 Nov. 10; 5(5):728-40.
30. Chen X et al. G9a/GLP-dependent histone H3K9me2 patterning during human hematopoietic stem cell lineage commitment. Genes Dev. 2012 Nov. 15; 26(22):2499-511.
31. Nishihara M et al. A combination of stem cell factor and granulocyte colony-stimulating factor enhances the growth of human progenitor B cells supported by murine stromal cell line MS-5. Eur J Immunol. 1998 March; 28(3):855-64.
32. Ohkawara J I et al. Culture system for extensive production of CD19+IgM+ cells by human cord blood CD34+ progenitors. Leukemia. 1998 May; 12(5):764-71.
33. Abel K J et al. Characterization of EZH1, a human homolog of Drosophila Enhancer of zeste near BRCA1. Genomics. 1996 Oct. 15; 37(2):161-71.
34. Laible G et al. Mammalian homologues of the Polycomb-group gene Enhancer of zeste mediate gene silencing in Drosophila heterochromatin and at S. cerevisiae telomeres. EMBO J. 1997 Jun. 2; 16(11):3219-32.
35. Jones C A et al. The Drosophila esc and E(z) proteins are direct partners in polycomb group-mediated repression. Mol Cell Biol. 1998 May; 18(5):2825-34.
36. Shen X et al. EZH1 mediates methylation on histone H3 lysine 27 and complements EZH2 in maintaining stem cell identity and executing pluripotency. Mol Cell. 2008 Nov. 21; 32(4):491-502.
37. Muller J et al. Histone methyltransferase activity of a Drosophila Polycomb group repressor complex. Cell. 2002 Oct. 18; 111(2):197-208.
38. Sparmann and van Lohuizen 2006. Polycomb silencers control cell fate, development and cancer. Nat Rev Cancer. 2006 November; 6(11):846-56.
39. Simon J A and Kingston R E. Mechanisms of polycomb gene silencing: knowns and unknowns. Nat Rev Mol Cell Biol. 2009 October; 10(10):697-708.
40. Margueron R et al. Ezh1 and Ezh2 maintain repressive chromatin through different mechanisms. Mol Cell. 2008 Nov. 21; 32(4):503-18.
41. Mousavi K et al. Polycomb protein Ezh1 promotes RNA polymerase II elongation. Mol Cell. 2012 Jan. 27; 45(2):255-62.
42. Cacchiarelli D et al. Integrative Analyses of Human Reprogramming Reveal Dynamic Nature of Induced Pluripotency. Cell. 2015 Jul. 16; 162(2):412-24.
43. McCabe M T et al. EZH2 inhibition as a therapeutic strategy for lymphoma with EZH2-activating mutations. Nature. 2012 Dec. 6; 492(7427):108-12.
44. Doulatov S et al. Revised map of the human progenitor hierarchy shows the origin of macrophages and dendritic cells in early lymphoid development. Nat Immunol. 2010 July; 11(7):585-93.
45. Buenrostro J et al. Transposition of native chromatin for fast and sensitive epigenomic profiling of open chromatin, DNA-binding proteins and nucleosome position. Nat Methods. 2013 December; 10(12):1213-8.
46. McLean C Y et al. GREAT improves functional interpretation of cis-regulatory regions. Nat Biotechnol. 2010 May; 28(5):495-501.
47. Laurenti E et al. The transcriptional architecture of early human hematopoiesis identifies multilevel control of lymphoid commitment. Nat Immunol. 2013 July; 14(7):756-63.
48. Novershtern N et al. Densely interconnected transcriptional circuits control cell states in human hematopoiesis. Cell. 2011 Jan. 21; 144(2):296-309.
49. Boisset J C et al. In vivo imaging of haematopoietic cells emerging from the mouse aortic endothelium. Nature. 2010 Mar. 4; 464(7285):116-20.
50. Bertrand J Y et al. Characterization of purified intraembryonic hematopoietic stem cells as a tool to define their site of origin. Proc Natl Acad Sci USA. 2005 Jan. 4; 102(1):134-9.
51. Müller A M et al. Development of hematopoietic stem cell activity in the mouse embryo. Immunity. 1994 July; 1(4):291-301.
52. North T E et al. Runx1 expression marks long-term repopulating hematopoietic stem cells in the midgestation mouse embryo. Immunity. 2002 May; 16(5):661-72.
53. Rowe R G et al. Engineering Hematopoietic Stem Cells: Lessons from Development. Cell Stem Cell. 2016 Jun. 2; 18(6):707-20.
54. Vo L T and Daley G Q. De novo generation of HSCs from somatic and pluripotent stem cell sources. Blood. 2015 Apr. 23; 125(17):2641-8.

55. Pereira C F, Lemischka I R and Moore K. 'From blood to blood': de-differentiation of hematopoietic progenitors to stem cells. EMBO J. 2014 Jul. 17; 33(14): 1511-1513.
56. Kyba M, Perlingeiro R C and Daley G Q. HoxB4 confers definitive lymphoid-myeloid engraftment potential on embryonic stem cell and yolk sac hematopoietic progenitors. Cell. 2002 Apr. 5; 109(1):29-37.
57. Chanda B et al. Retinoic acid signaling is essential for embryonic hematopoietic stem cell devel-opment. Cell. 2013 Sep. 26; 155(1):215-27.
58. Orkin S H and Zon L I. Hematopoiesis: an evolving paradigm for stem cell biology. Cell. 2008 Feb. 22; 132(4):631-44.
59. Doulatov S et al. Hematopoiesis: a human perspective. Cell Stem Cell. 2012 Feb. 3; 10(2):120-36.
60. Huang H T et al. A network of epigenetic regulators guides developmental haematopoiesis in vivo. Nat Cell Biol. 2013 December; 15(12):1516-25.
61. Abdalkader L et al. Aberrant differential expression of EZH1 and EZH2 in Polycomb repressive complex 2 among B- and T/NK-cell neoplasms. Pathology. 2016 August; 48(5):467-82.
62. Bachmann I M et al. EZH2 expression is associated with high proliferation rate and aggressive tumor subgroups in cutaneous melanoma and cancers of the endometrium, prostate, and breast. J Clin Oncol. 2006 Jan. 10; 24(2): 268-73.
63. Varambally S et al. The polycomb group protein EZH2 is involved in progression of prostate cancer. Nature. 2002 Oct. 10; 419(6907):624-9.
64. Yu J et al. Integrative genomics analysis reveals silencing of beta-adrenergic signaling by polycomb in prostate cancer. Cancer Cell. 2007 November; 12(5):419-31.
65. Wang C G et al. EZH2 and STAT6 expression profiles are correlated with colorectal cancer stage and prognosis. World J Gastroenterol. 2010 May 21; 16(19):2421-7.
66. Abd Al Kader L et al. In aggressive variants of non-Hodgkin lymphomas, Ezh2 is strongly expressed and polycomb repressive complex PRC1.4 dominates over PRC1.2. Virchows Arch. 2013 November; 463(5):697-711.
67. Morin R D et al. Somatic mutations altering EZH2 (Tyr641) in follicular and diffuse large B-cell lymphomas of germinal-center origin. Nat Genet. 2010 February; 42(2):181-5.
68. Yap D B et al. Somatic mutations at EZH2 Y641 act dominantly through a mechanism of selectively altered PRC2 catalytic activity, to increase H3K27 trimethylation. Blood. 2011 Feb. 24; 117(8):2451-9.
69. Xu J et al. Developmental control of polycomb subunit composition by GATA factors mediates a switch to non-canonical functions. Mol Cell. 2015 Jan. 22; 57(2):304-16.
70. June C H, Riddell S R and Schumacher T N. Adoptive cellular therapy: a race to the finish line. Sci Transl Med. 2015 Mar. 25; 7(280):280ps7.
71. Themeli M, Riviere I and Sadelain M. New cell sources for T cell engineering and adoptive immu-notherapy. Cell Stem Cell. 2015 Apr. 2; 16(4):357-66.
72. Timmermans F et al. Generation of T cells from human embryonic stem cell-derived hematopoietic zones. J Immunol. 2009 Jun. 1; 182(11):6879-88.
73. Themeli M et al. Generation of tumor-targeted human T lymphocytes from induced pluripotent stem cells for cancer therapy. Nat Biotechnol. 2013 October; 31(10): 928-33.
74. Riolobos L et al. HLA engineering of human pluripotent stem cells. Mol Ther. 2013 June; 21(6):1232-41.
75. Fazi F et al. A minicircuitry comprised of microRNA-223 and transcription factors NFI-A and C/EBPalpha regulates human granulopoiesis. Cell. 2005 Dec. 2; 123 (5):819-31.
76. Starnes L M et al. NFI-A directs the fate of hematopoietic progenitors to the erythroid or granulocytic lineage and controls beta-globin and G-CSF receptor expression. Blood. 2009 Aug. 27; 114(9):1753-63.
77. Lee J W et al. DACH1 regulates cell cycle progression of myeloid cells through the control of cyclin D, Cdk 4/6 and p21Cip1. Biochem Biophys Res Commun. 2012 Mar. 30; 420(1):91-5.
78. Lee J W et al. Regulation of HOXA9 activity by predominant expression of DACH1 against C/EBPα and GATA-1 in myeloid leukemia with MLL-AF9. Biochem Biophys Res Commun. 2012 Sep. 28; 426(3):299-305

TABLE 1

Candidate target transcription factors for RNA interference and the corresponding shRNA

| Clone ID | Symbol | NCBI Gene ID | Taxon ID | Preferred Gene Name | Region | Target Seq | SEQ. ID. NO.: |
|---|---|---|---|---|---|---|---|
| TRCN0000355903 | NM_024670.3 | SUV39H2 | 79723 | 9606 | 3UTR | TAATGGAAGGCAGACTATTTA | 31 |
| TRCN0000355904 | NM_024670.3 | SUV39H2 | 79723 | 9606 | CDS | CTCTAATGACAAGCATAATTA | 32 |
| TRCN0000355905 | NM_024670.3 | SUV39H2 | 79723 | 9606 | 3UTR | TCAAGGTTCTACCTATGTTAA | 33 |
| TRCN0000011057 | NM_024670.3 | SUV39H2 | 79723 | 9606 | CDS | GCCCACCTTCAGACTTCTATT | 34 |
| TRCN0000275322 | NM_003173.2 | SUV39H1 | 6839 | 9606 | CDS | GTACGTGGGAGAGATCATTAC | 35 |
| TRCN0000275321 | NM_003173.2 | SUV39H1 | 6839 | 9606 | CDS | GACTGAGTCCTGCCGCAAATA | 36 |
| TRCN0000275372 | NM_003173.2 | SUV39H1 | 6839 | 9606 | CDS | AGTCGAGTACCTGTGCGATTA | 37 |
| TRCN0000158337 | NM_003173.1 | SUV39H1 | 6839 | 9606 | 3UTR | CGTTGGGATTCATGGCCTATT | 38 |
| TRCN0000040076 | NM_004456.3 | EZH2 | 2146 | 9606 | CDS | CGGAAATCTTAAACCAAGAAT | 39 |
| TRCN0000010475 | NM_004456.3 | EZH2 | 2146 | 9606 | 3UTR | GAAACAGCTGCCTTAGCTTCA | 40 |
| TRCN0000018365 | NM_004456.3 | EZH2 | 2146 | 9606 | CDS | TATGATGGTTAACGGTGATCA | 41 |

TABLE 1-continued

Candidate target transcription factors for RNA interference and the corresponding shRNA

| Clone ID | Symbol | NCBI Gene ID | Taxon ID | Preferred Gene Name | Region | Target Seq | SEQ. ID. NO.: |
|---|---|---|---|---|---|---|---|
| TRCN0000040073 | NM_004456.3 | EZH2 | 2146 | 9606 | 3UTR | TATTGCCTTCTCACCAGCTGC | 42 |
| TRCN0000276085 | NM_020197.2 | SMYD2 | 56950 | 9606 | CDS | CGGCAAAGATCATCCATATAT | 43 |
| TRCN0000276083 | NM_020197.2 | SMYD2 | 56950 | 9606 | CDS | GcTGTGAAGGAGTTTGAATCA | 44 |
| TRCN0000276154 | NM_020197.2 | SMYD2 | 56950 | 9606 | CDS | GCTCTGTGTTTGAGGACAGTA | 45 |
| TRCN0000276155 | NM_020197.2 | SMYD2 | 56950 | 9606 | 3UTR | ACTTAGTTCAGAAACCTTAAA | 46 |
| TRCN0000036056 | NM_024757.3 | EHMT1 | 79813 | 9606 | CDS | GCAACGGATACATCTTAAATA | 47 |
| TRCN0000036057 | NM_024757.3 | EHMT1 | 79813 | 9606 | CDS | CCTCGGTTCTGAGTCGTATAA | 48 |
| TRCN0000217965 | NM_024757.3 | EHMT1 | 79813 | 9606 | CDS | TCGAGAAGCTAGAGATCATAA | 49 |
| TRCN0000218919 | NM_024757.3 | EHMT1 | 79813 | 9606 | CDS | ACCTCTTTGATCTCGACAATA | 50 |
| TRCN0000115668 | NM_025256.4 | EHMT2 | 10919 | 9606 | CDS | CCTCTTCGACTTAGACAACAA | 51 |
| TRCN0000115867 | NM_025256.4 | EHMT2 | 10919 | 9606 | 3UTR | CACACATTCCTGACCAGAGAT | 52 |
| TRCN0000115670 | NM_025256.4 | EHMT2 | 10919 | 9606 | CDS | CGAGAGAGTTCATGGCTCTTT | 53 |
| TRCN0000115669 | NM_025256.4 | EHMT2 | 10919 | 9606 | CDS | GCTCCAGGAATTTAACAAGAT | 54 |
| TRCN0000148112 | NM_012432.2 | SETDB1 | 9869 | 9606 | CDS | GCTCAGATGATAACTTCTGTA | 55 |
| TRCN0000072261 | promegaLuc.1 | LUCIFERASE | -14 | CONTROL | CDS | CACTCGGATATTTGATATGTG | 56 |
| TRCN0000276105 | NM_012432.2 | SETD81 | 9869 | 9606 | CDS | AGTTAGAGACATGGGTAATAC | 57 |
| TRCN0000276106 | NM_012432.2 | SETDB1 | 9869 | 9606 | CDS | CGTGACTTCATAGAGGAGTAT | 58 |
| TRCN0000276103 | NM_012432.2 | SETDB1 | 9869 | 9606 | 3UTR | ATCCCTCCCATCCCATATTTG | 59 |
| TRCN0000297828 | NM_003927.3 | MBD2 | 8932 | 9606 | CDS | GTAGCAATGATGAGACCCTTT | 60 |
| TRCN0000013319 | NM_003927.3 | MBD2 | 8932 | 9606 | CDS | GCCTAGTAAATTACAGAAGAA | 61 |
| TRCN0000297830 | NM_003927.3 | MBD2 | 8932 | 9606 | CDS | GTACGCAAGAAATTGGAAGAA | 62 |
| TRCN0000013322 | NM_003927.3 | MBD2 | 8932 | 9606 | CDS | CTTGAATACAACATTGCCAAT | 63 |
| TRCN0000358468 | NM_002384.2 | MBD1 | 4152 | 9606 | 3UTR | GCCCTTCCTCACAGAGTTAAA | 64 |
| TRCN0000072256 | promegaLuc.1 | LUCIFERASE | -14 | CONTROL | CDS | ACGCTGAGTACTTCGAAATGT | 65 |
| TRCN0000358382 | NM_002384.2 | MBD1 | 4152 | 9606 | CDS | GATGATTCTGCCTCCAAATTG | 56 |
| TRCN0000015429 | NM_002384.1 | MBD1 | 4152 | 9606 | CDS | CCGGGAACAGAGAATGTTAA | 67 |
| TRCN0000329862 | NM_002384.2 | MBD1 | 4152 | 9606 | CDS | CACCCGTGATCACGGAGATTT | 68 |
| TRCN0000355735 | NM_001991.3 | EZH1 | 2145 | 9606 | CDS | CTATCTGGCAGTGCGAGAATG | 1 |
| TRCN0000355734 | NM_001991.3 | EZH1 | 2145 | 9606 | CDS | AGACGTGCAAGCAGGTCTTTC | 2 |
| TRCN0000378151 | NM_001991.3 | EZH1 | 2145 | 9606 | 3UTR | TGGATGACTTATGCGTGATTT | 3 |
| TRCN0000002442 | NM_001991.2 | EZH1 | 2145 | 9606 | CDS | CAACAGAACTTTATGGTAGAA | 4 |
| TRCN0000021208 | NM_003797.2 | EED | 8726 | 9606 | CDS | CCAGTGAATCTAATGTGACTA | 69 |
| TRCN0000021205 | NM_003797.2 | EED | 8726 | 9606 | CDS | CCAGAGACATACATAGGAATT | 70 |
| TRCN0000381067 | NM_003797.2 | EED | 8726 | 9606 | CDS | GTGCGATGGTTAGGCGATTTG | 71 |
| TRCN0000021204 | NM_003797.2 | EED | 8726 | 9606 | CDS | GCAAACTTTATGTTTGGGATT | 72 |
| TRCN0000280721 | NM_002931.3 | RING1 | 6015 | 9606 | CDS | CTGGAGCTGGTGAATGAGAAA | 73 |
| TRCN0000021989 | NM_002931.2 | RING1 | 6015 | 9606 | CDS | GCCCTGATCTCTAAGATCTAT | 74 |
| TRCN0000280798 | NM_002931.3 | RING1 | 6015 | 9606 | CDS | GTCAGATCAGACCACAACGAT | 75 |

TABLE 1-continued

Candidate target transcription factors for RNA interference and the corresponding shRNA

| Clone ID | Symbol | NCBI Gene ID | Taxon ID | Preferred Gene Name | Region | Target Seq | SEQ. ID. NO.: |
|---|---|---|---|---|---|---|---|
| TRCN0000352834 | NM_002931.3 | RING1 | 6015 | 9606 | CDS | AGACGAGGTATGTGAAGACAA | 75 |
| TRCN0000229416 | NM_005180.5 | BMI1 | 648 | 9606 | CDS | ATTGATGCCACAACCATAATA | 77 |
| TRCN0000218869 | NM_005180.5 | BMI1 | 648 | 9606 | CDS | CAGATTGGATCGGAAAGTAAA | 78 |
| TRCN0000020156 | NM_005180.5 | BMI1 | 648 | 9606 | CDS | CCTAATACTTTCCAGATTGAT | 79 |
| TRCN0000229418 | NM_005180.5 | BMI1 | 648 | 9606 | CDS | TAATGGATATTGCCTACATTT | 80 |
| TRCN0000274442 | NM_003926.5 | MBD3 | 53615 | 9606 | CDS | CAAGATGCTGATGAGCAAGAT | 81 |
| TRCN0000285209 | NM_003926.5 | MBD3 | 53615 | 9606 | CDS | CGGCCTGAACGCCTTCGACAT | 82 |
| TRCN0000358524 | NM_003926.5 | MBD3 | 53615 | 9606 | CDS | GACCTGAGCACCTTCGACTTC | 83 |
| TRCN0000274441 | NM_003926.5 | MBD3 | 53615 | 9606 | CDS | GCCGGTGACCAAGATTACCAA | 84 |
| TRCN0000298921 | NM_015355.2 | SUZ12 | 23512 | 9606 | CDS | GCTGACAATCAAATGAATCAT | 85 |
| TRCN0000331118 | NM_015355.2 | SUZ12 | 23512 | 9606 | CDS | CGGAATCTCATAGCACCAATA | 86 |
| TRCN0000038725 | NM_015355.1 | SUZ12 | 23512 | 9606 | CDS | GCTTACGTTTACTGGTTTCTT | 87 |
| TRCN0000038726 | NM_015355.1 | SUZ12 | 23512 | 9606 | CDS | CCAAACCTCTTGCCACTAGAA | 88 |
| TRCN0000034269 | NM_003925.1 | MBD4 | 8930 | 9606 | 3UTR | GCCTAGTGTGTGTGCTTTCTT | 89 |
| TRCN0000342754 | NM_003925.1 | MBD4 | 8930 | 9606 | CDS | GCAACGACTCTTACCGAATTT | 90 |
| TRCN0000342688 | NM_003925.1 | MBD4 | 8930 | 9606 | CDS | CCCACGACGTAAAGCCTTTAA | 91 |
| TRCN0000342752 | NM_003925.1 | MBD4 | 8930 | 9606 | CDS | GCCAAGTAGTAGTTCAGAGTT | 92 |
| TRCN0006021891 | NM_001379.1 | DNMT1 | 1786 | 9606 | CDS | GCCCAATGAGACTGACATCAA | 93 |
| TRCN0000072250 | promegaLuc.1 | LUCIFERASE | -14 | CONTROL | CDS | AGAATCGTCGTATGCAGTGAA | 94 |
| TRCN0000021893 | NM_001379.1 | DNMT1 | 1786 | 9606 | CDS | CGACTACATCAAAGGCAGCAA | 95 |
| TRCN0000232751 | NM_001379.1 | DNMT1 | 1786 | 9606 | 3UTR | GAGGTTCGCTTATCAACTAAT | 96 |
| TRCN0000232748 | NM_001379.1 | DNMT1 | 1786 | 9606 | CDS | CCCGAGTATGCGCCCATATTT | 97 |
| TRCN0000236345 | NM_032482.2 | DOT1L | 84444 | 9606 | CDS | TCGCCAACACGAGTGTTATAT | 98 |
| TRCN0000020210 | NM_032482.1 | DOT1L | 84444 | 9606 | CDS | CCGCAAGAAGAAGCTAAACAA | 99 |
| TRCN0000236342 | NM_032482.2 | DOT1L | 84444 | 9606 | CDS | CACATTGGAGAGAGGCGATTT | 100 |
| TRCN0000020211 | NM_032482.1 | DOT1L | 84444 | 9606 | CDS | CCCGGATCTCAAGCTCGCTAT | 101 |
| TRCN0000035757 | NM_022552.3 | DNMT3A | 1788 | 9606 | CDS | CCAGATGTTCTTCGCTAATAA | 102 |
| TRCN0000035756 | NM_022552.3 | DNMT3A | 1788 | 9606 | CDS | GCCTCAGAGCTATTACCCAAT | 103 |
| TRCN0000035754 | NM_022552.3 | DNMT3A | 1788 | 9606 | CDS | CCCAAGGTCAAGGAGATTATT | 104 |
| TRCN0000035758 | NM_022552.3 | DNMT3A | 1788 | 9606 | CDS | CCACCAGAAGAAGAGAAGAAT | 105 |
| TRCN0000021242 | NM_004992.2 | MECP2 | 4204 | 9606 | CDS | CGTCTGCAAAGAGGAGAAGAT | 106 |
| TRCN0000330971 | NM_004992.3 | MECP2 | 4204 | 9606 | CDS | GAGAGCGCAAAGACATTGTTT | 107 |
| TRCN0000021241 | NM_004992.2 | MECP2 | 4204 | 9605 | CDS | CTGGGAAGTATGATGTGTATT | 108 |
| TRCN0000380871 | NM_004992.3 | MECP2 | 4204 | 9605 | CDS | ACCACCTAAGAAGCCCAAATC | 109 |

What is claimed:

1. A method of producing T lymphocytes or B lymphocytes from multilineage hematopoietic progenitor cells (MHPC), the method comprising:
   a) inhibiting Enhancer of Zeste Homolog 1 (EZH1) expression in the MHPC, wherein MHPC are differentiated from CD34+ hemogenic endothelium cells generated from induced pluripotent stem (iPS) cells; and
   b) contacting the MHPC with a notch ligand or a stromal cell or both to promote differentiation into the lymphoid lineage and production of T lymphocytes or B lymphocytes.

2. A method of producing T lymphocytes or B lymphocytes from myeloid progenitor cells, the method comprising:
   a) in vitro transfecting myeloid progenitor cells that are CD34+CD45+ with an exogenous gene coding copy of each of the following transcription factors: ETS-related gene (ERG), homeobox A9 (HOXA9), and retinoic acid receptor (RAR)-related orphan receptor alpha (RORA), wherein the transcription factors are expressed in the transfected cells to produce a population of multilineage hematopoietic progenitor cells that have myeloid and erythroid potential and have no lymphoid potential or lymphoid potential that is less than 5%;
   b) inhibiting Enhancer of Zeste Homolog 1 (EZH1) expression in the resultant population of multilineage hematopoietic progenitor cells to expand lymphoid potential; and
   c) differentiating the resultant population of multilineage hematopoietic progenitor cells in the presence of a notch ligand or supportive stroma or both to promote differentiation into the lymphoid lineage and production of T lymphocytes or B lymphocytes.

3. The method of claim 2, further comprising transfecting the myeloid progenitor cells with an exogenous gene coding copy of the transcription factor, SOX4, and MYB.

4. The method of claim 2, further comprising transfecting the myeloid progenitor cells with an exogenous gene coding copy of the transcription factor, NFIA and DACH1.

5. The method of claim 2, wherein the myeloid progenitor cells are embryoid body progenitor cells isolated from a population of pluripotent stem cells.

6. The method of claim 5, wherein the population of pluripotent stem cells is induced pluripotent stem cells (iPS cells) or embryonic stem cells (ESC).

7. The method of claim 6, wherein the induced pluripotent stem cells are produced by introducing only reprogramming factors OCT4, SOX2, KLF4 and optionally c-MYC or nanog and LIN28 into mature cells, wherein the mature cells are selected from the group consisting of B lymphocytes (B-cells), T lymphocytes, (T-cells), fibroblasts, and keratinocytes.

8. The method of claim 1, wherein the notch ligand is selected from the group consisting of Delta-like-1, Delta-like-4, and immobilized Delta1$^{ext\text{-}IgG}$ wherein Delta1$^{ext\text{-}IgG}$ consists of the extracellular domain of human Delta-like-1 fused to the Fc domain of human IgG1.

9. The method of claim 8, wherein the Delta-like-1 or Delta-like-4 is supplied with co-culturing the multilineage hematopoietic progenitor cells with immobilized Delta1$^{ext\text{-}IgG}$ OP9-DL1 cells or OP9-DL4 cells.

10. The method of claim 1, wherein EZH1 catalyses the addition of methyl group to the histone 3 lysine residue 27 (H3K27 histone methyltransferase).

11. The method of claim 10, wherein EZH1 is inhibited by a small molecule or a nucleic acid.

12. The method of claim 11, wherein the small molecule that inhibits EZH1 is a heterorganic compound or an organometallic compound.

13. The method of claim 11, wherein the small molecule that inhibits EZH1 is selected from the group consisting of UNC0224, 3-deazaneplanocin A (DZNep) and UNC1999.

14. The method of claim 11, wherein the nucleic acid that inhibits EZH1 is a nucleic acid targeting the expression of EZH1.

15. The method of claim 14, wherein the nucleic acid is EZH1 specific RNA interference agent, wherein the RNA interference agent comprises one or more of the nucleotide sequences selected from the group consisting of SEQ ID NO: 1-5, 27-30.

16. The method of claim 14, wherein the nucleic acid is an aptamer that binds EZH1.

17. The method of claim 14, wherein the nucleic acid is a vector encoding an EZH1 specific RNA interference agent.

18. The method of claim 1, wherein EZH1 is inhibited by an inhibitor that is specific to EZH1 and not to EZH2.

19. The method of claim 2, wherein EZH1 is inhibited by an inhibitor that is specific to EZH1 and not to EZH2.

* * * * *